US011685741B2

(12) United States Patent
Guo

(10) Patent No.: US 11,685,741 B2
(45) Date of Patent: Jun. 27, 2023

(54) FLUORESCENT PROBES

(71) Applicant: University of Massachusetts, Boston, MA (US)

(72) Inventor: Maolin Guo, Dartmouth, MA (US)

(73) Assignee: University of Massachusetts, Boston, MA (US)

(*) Notice: Subject to any disclaimer, the term of this patent is extended or adjusted under 35 U.S.C. 154(b) by 804 days.

(21) Appl. No.: 16/485,469

(22) PCT Filed: Feb. 1, 2018

(86) PCT No.: PCT/US2018/016453
§ 371 (c)(1),
(2) Date: Aug. 13, 2019

(87) PCT Pub. No.: WO2018/151949
PCT Pub. Date: Aug. 23, 2018

(65) Prior Publication Data
US 2022/0009940 A1 Jan. 13, 2022

Related U.S. Application Data

(60) Provisional application No. 62/458,831, filed on Feb. 14, 2017.

(51) Int. Cl.
G01N 31/00 (2006.01)
C07D 491/107 (2006.01)
C07D 491/22 (2006.01)
G01N 21/64 (2006.01)
G01N 33/52 (2006.01)

(52) U.S. Cl.
CPC ....... *C07D 491/107* (2013.01); *C07D 491/22* (2013.01); *G01N 21/643* (2013.01); *G01N 33/52* (2013.01)

(58) Field of Classification Search
CPC .................................. C07D 491/107
USPC ....................................... 436/172
See application file for complete search history.

(56) References Cited

U.S. PATENT DOCUMENTS

2016/0077077 A1  3/2016  Shi et al.

FOREIGN PATENT DOCUMENTS

CN          104860957      8/2015
WO     WO 2015-052731     4/2015

OTHER PUBLICATIONS

Xie et al. "Near-Infrared Fluorescent Probe with High Quantum Yield and Its Application in the Selective Detection of Glutathione in Living Cells and Tissues" Anal. Chem. 2016, 88, 9746-9752 (Year: 2016).*
Aydin, Z. et al., "An "off-on" optical sensor for mercury ion detection in aqueous solution and living cells", Inorganic Chemistry Communications, 2014, vol. 50, pp. 84-87.

(Continued)

*Primary Examiner* — Christine T Mui
*Assistant Examiner* — Emily R. Berkeley
(74) *Attorney, Agent, or Firm* — Fish & Richardson P.C.

(57) ABSTRACT

The present disclosure relates to compounds of Formula I, II, or III and compositions of the same, which are reversible off-on or ratiometric fluorescent iron sensors and are useful in live-cell imaging of labile iron ions and their quantification in subcellular compartments, as well as treatment of diseases associated with iron dyshomoestasis.

3 Claims, 81 Drawing Sheets

(56) References Cited

OTHER PUBLICATIONS

Aydin, Z., et al., "A highly selective rhodamine based turn-on optical sensor for Fe3+", Inorganic Chemistry Communications, 2012, vol. 20, pp. 93-96.

Bag, B. et al., "Alteration of selectivity in rhodamine based probes for Fe(III) and Hg(II) ion induced dual mode signalling responses", Org. Biomol. Chem., 2012, vol. 10, pp. 2733-2738.

Kumar, M. et al., "FRET-induced nanomolar detection of $Fe^{2+}$ based on cinnamaldehyde-rhodamine derivative", Tetrahedron Letters, 2011, vol. 52, pp. 4333-4336.

Lee, M. H. et al., "A fluorescent probe for the $Fe^{3+}$ ion pool in endoplasmic reticulum in liver cells", Dyes and Pigments, 2016, vol. 130, pp. 245-250.

Ozdemir et al., "A highly selective "off-on" fluorescent sensor for subcellular visualization of labile iron(III) in living cells", Inorganic Chemistry Communications, 2018, vol. 90, pp. 73-77.

PCT International Search Report in International Application No. PCT/US2018/016453, dated May 11, 2018, 5 pages.

PCT Written Opinion in International Application No. PCT/US2018/016453, dated May 11, 2018, 10 pages.

Wei, Y. et al., "A novel profluorescent probe for detecting oxidative stress induced by metal and H2O2 in living cells", Chemical Communications, 2010, vol. 46, pp. 4472-4474.

Wei, Y. et al., "A Turn-on Fluorescent Sensor for Imaging Labile Fe3+ in Live Neuronal Cells at Subcellular Resolution", ChemBioChem, 2012, vol. 13, pp. 1569-1573.

Xie, P. et al., "A new chemosensor based on rhodamine 101 hydrazone for Cu(II) in the red region", Can. J. Chem., 2011, vol. 89, pp. 1364-1369.

Xie, P. et al., "A rhodamine-dansyl conjugate as a FRET based sensor for $Fe^{3+}$ in the red spectral region", Journal of Luminescence, 2014, vol. 145, pp. 849-854.

\* cited by examiner

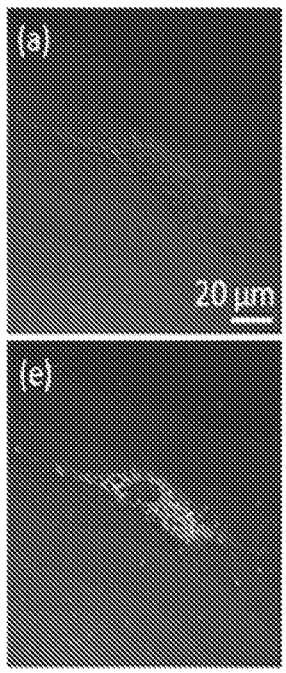
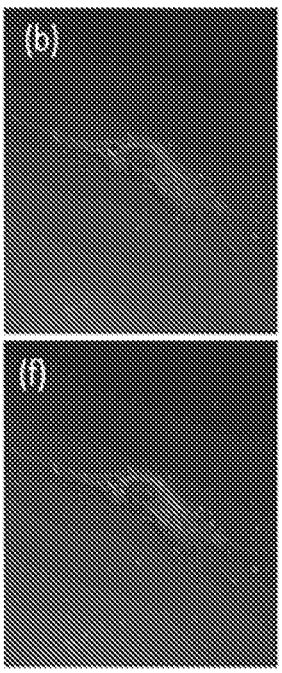
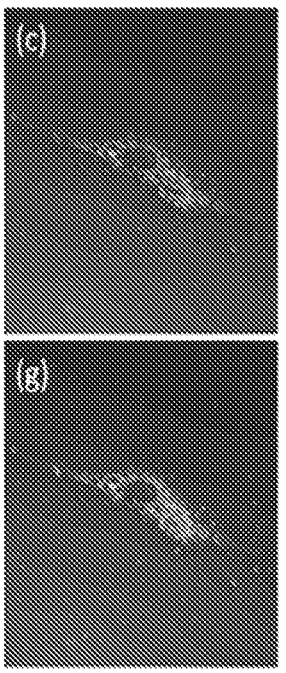
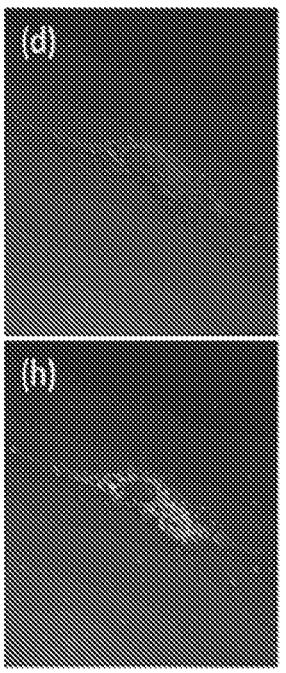
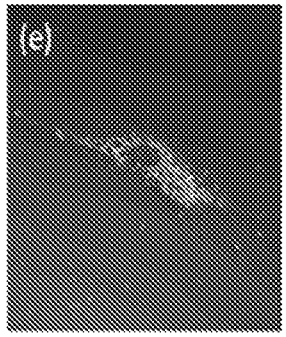
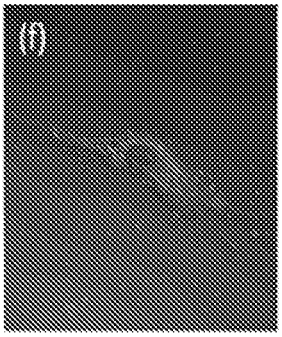
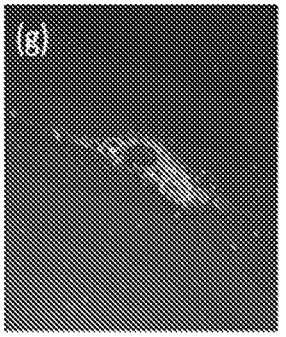
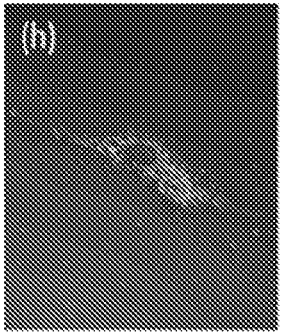
FIG. 20A  FIG. 20B  FIG. 20C  FIG. 20D
FIG. 20E  FIG. 20F  FIG. 20G  FIG. 20H FIG. 35A 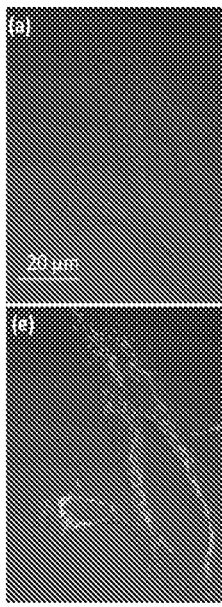 FIG. 35B 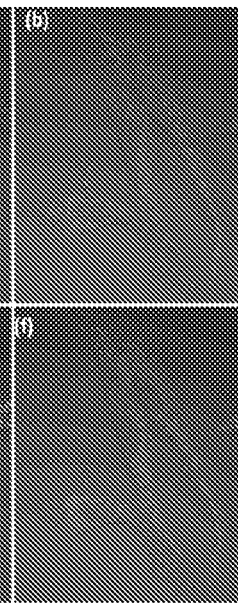 FIG. 35C 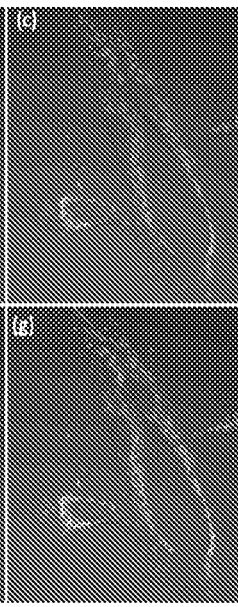 FIG. 35D 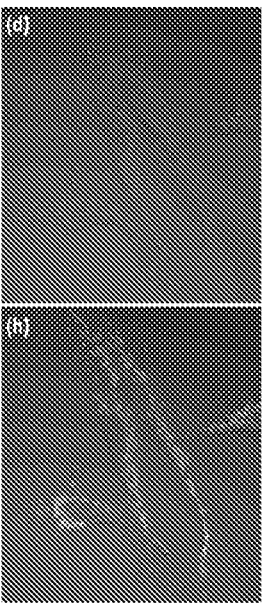
FIG. 35E　　　FIG. 35F　　　FIG. 35G　　　FIG. 35H FIG. 46A        FIG. 46B        FIG. 46C
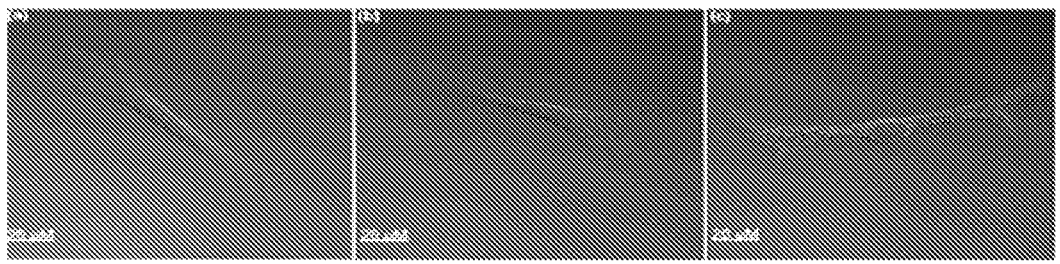
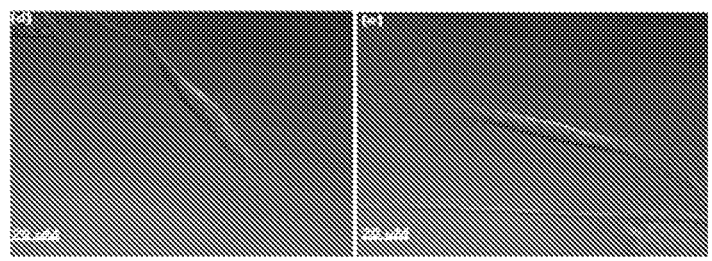
FIG. 46D        FIG. 46E

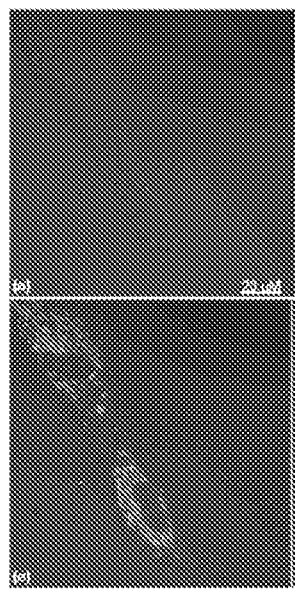 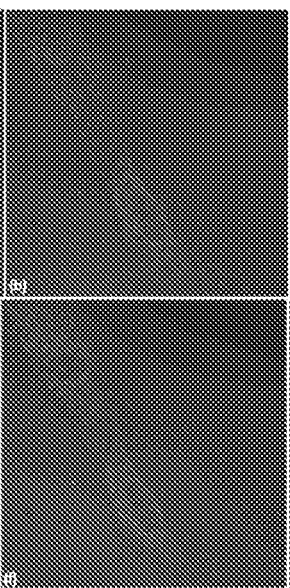 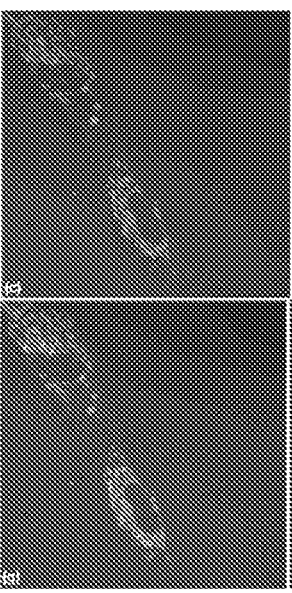 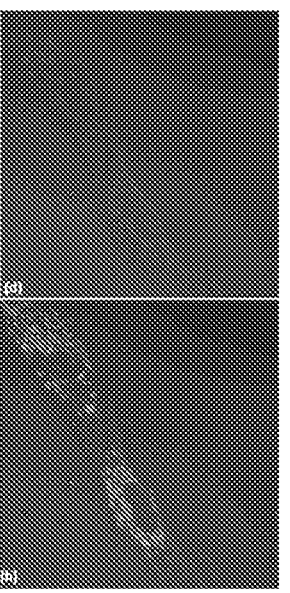
FIG. 47A  FIG. 47B  FIG. 47C  FIG. 47D
FIG. 47E  FIG. 47F  FIG. 47G  FIG. 47H FIG. 51A-L
| Cell Bright Images | $F_{red}$ | $F_{orange}$ | Ratio ($F_{orange}/F_{red}$) |
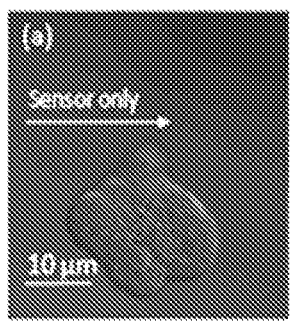 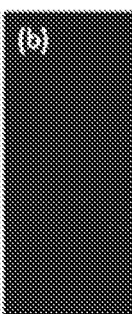 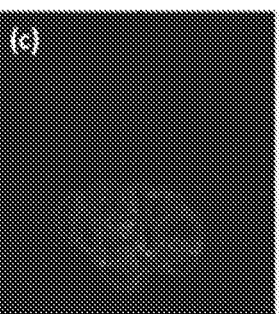 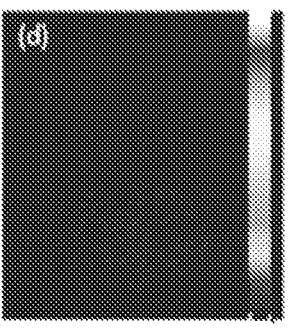
FIG 51A     FIG. 51B     FIG. 51C     FIG. 51D
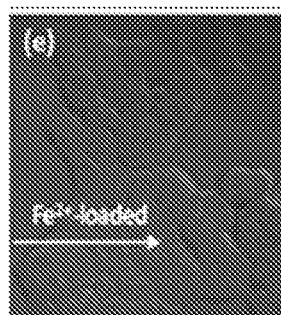 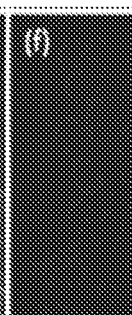 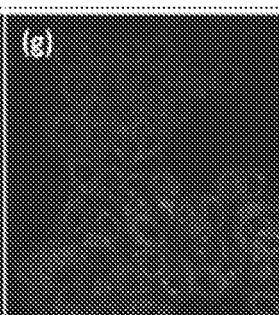 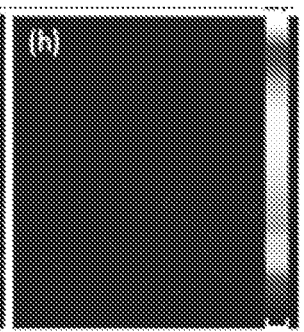
FIG 51E     FIG. 51F     FIG. 51G     FIG. 51H
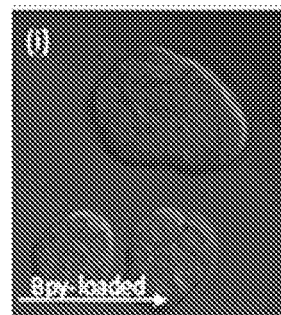 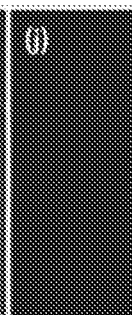 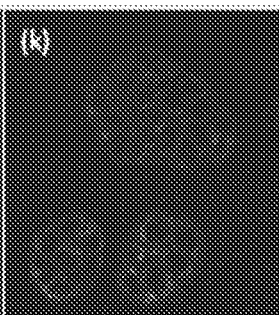 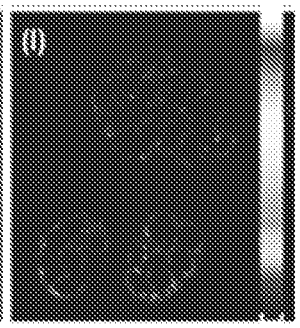
FIG 51I     FIG. 51J     FIG. 51K     FIG. 51L FIG. 63A    FIG. 63B    FIG. 63C
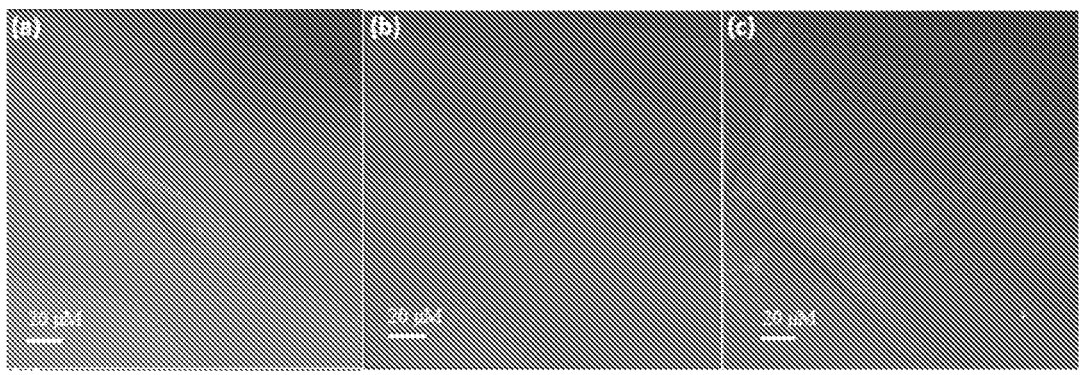
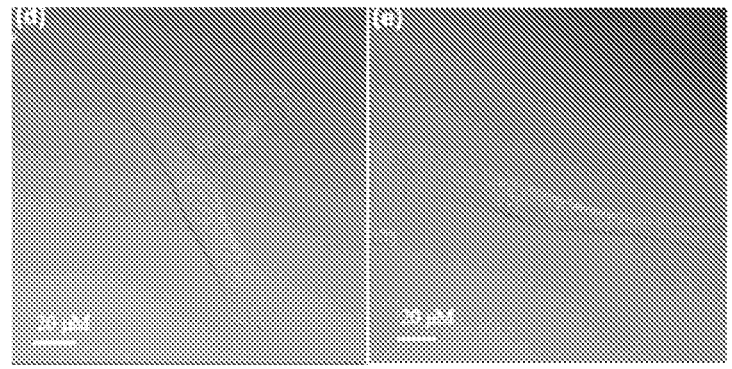
FIG. 63D    FIG. 63E FIG. 65A  FIG. 65B  FIG. 65C
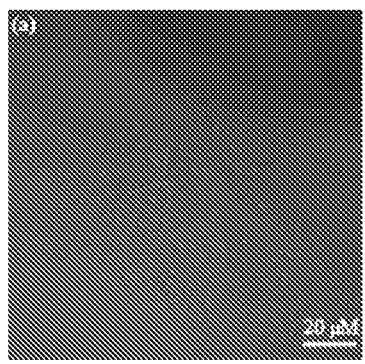 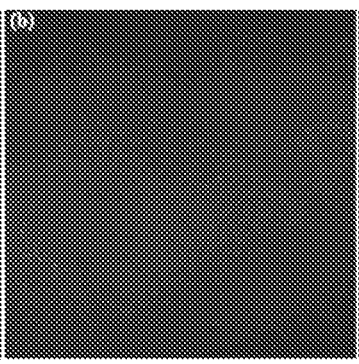 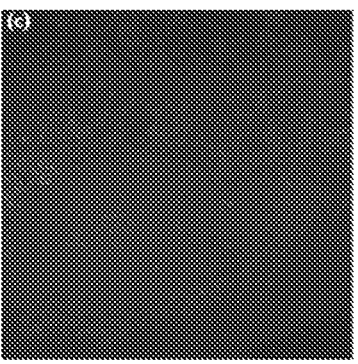
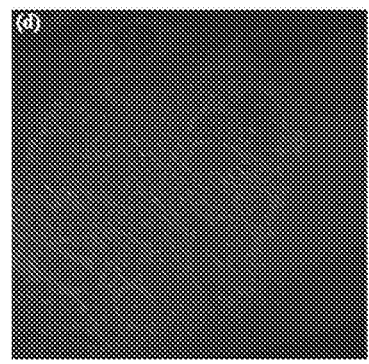 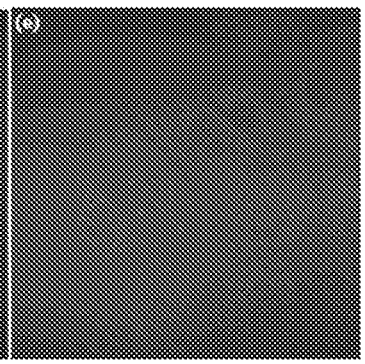
FIG. 65D  FIG. 65E FIG. 72 A-L
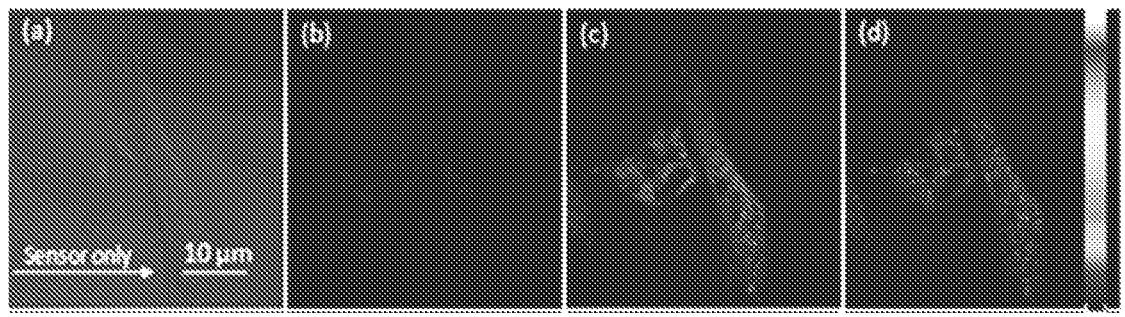
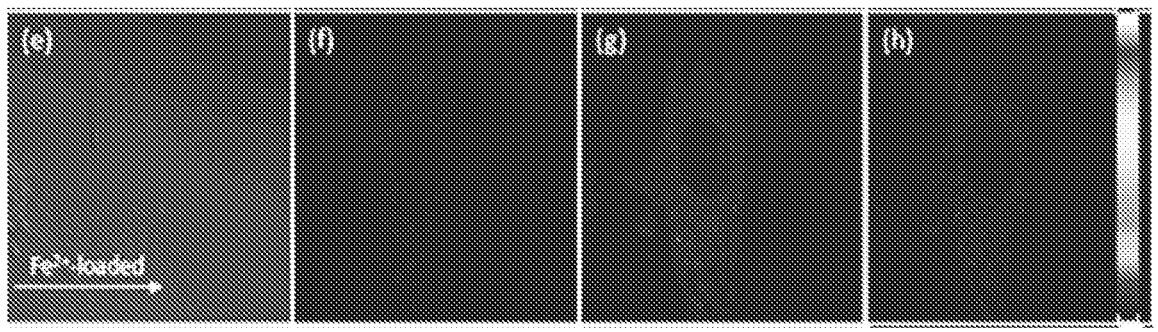
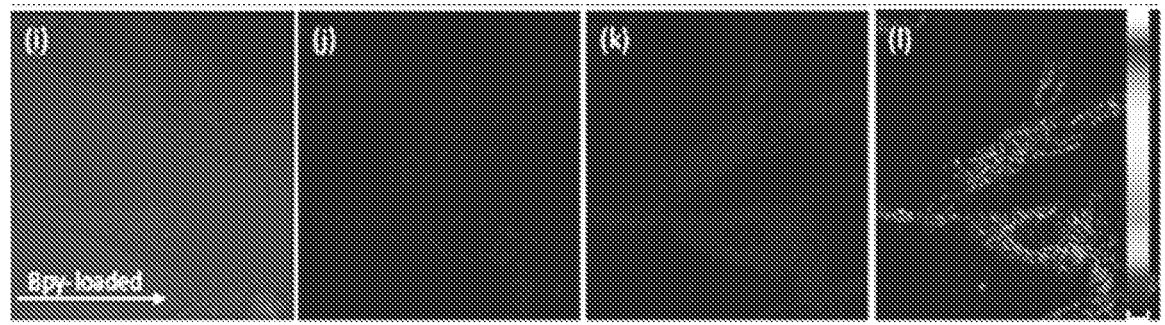

FIG. 73 A-L
| Cell Bright Images | $F_{red}$ | $F_{orange}$ | Ratio ($F_{orange}/F_{red}$) |
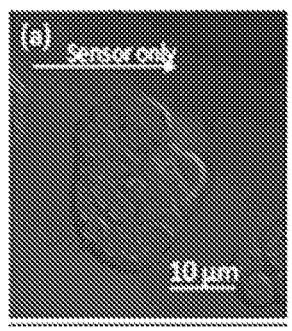 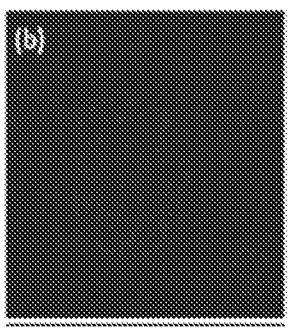 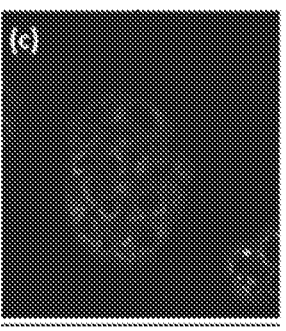 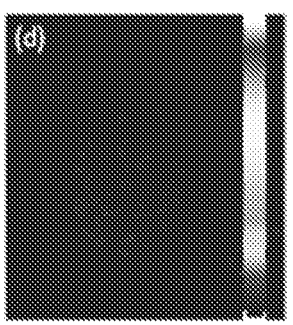
FIG 73A     FIG. 73B     FIG. 73C     FIG. 72D
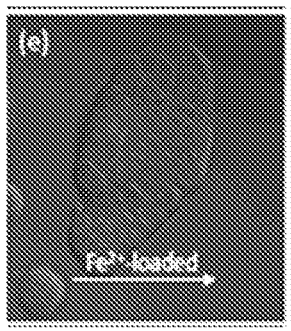 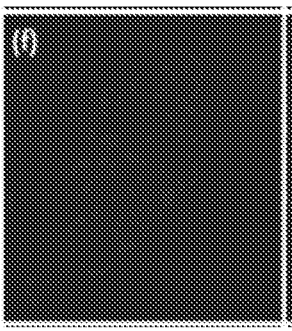 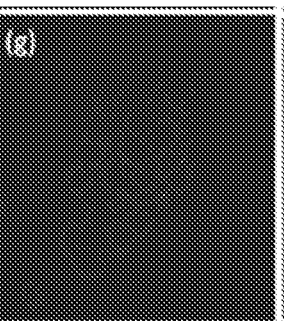 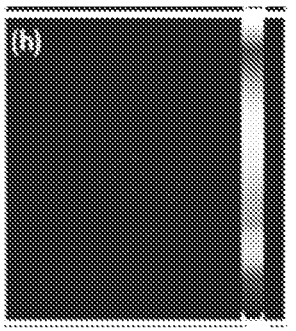
FIG 73E     FIG. 73F     FIG. 73G     FIG. 3H
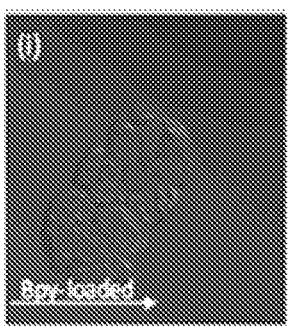 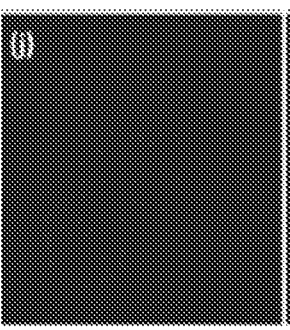 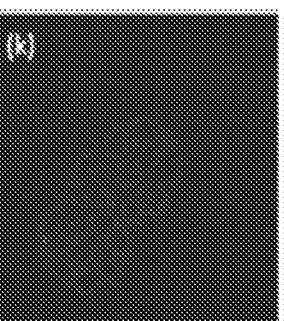 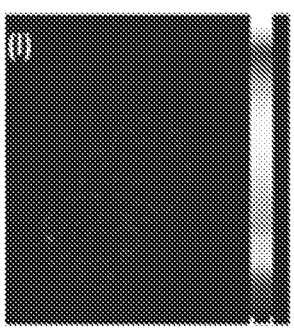
FIG 73I     FIG. 73J     FIG. 73K     FIG. 73L

FLUORESCENT PROBES

CROSS REFERENCE TO RELATED APPLICATION

This application is a national phase application under 35 U.S.C. § 371 of PCT International Application number PCT/US2018/016453, filed Feb. 1, 2018, which claims the benefit of priority under 35 U.S.C. § 119(e) to U.S. Application No. 62/458,831 filed Feb. 14, 2017, the disclosures of which are incorporated herein in their entirety.

STATEMENT REGARDING FEDERALLY SPONSORED RESEARCH OR DEVELOPMENT

This invention was made with government support under CHE-1213838 awarded by the National Science Foundation. The government has certain rights in the invention.

FIELD OF THE INVENTION

The present disclosure relates to compounds and compositions of the same, which are reversible off-on or ratiometric fluorescent iron sensors and are useful, e.g., in live-cell imaging of labile iron ions and their quantification in sub-cellular compartments, and treatment of diseases associated with iron dyshomoestasis.

BACKGROUND OF THE INVENTION

As the most abundant nutritionally essential transition metal in biological systems, iron plays crucial roles in many fundamental physiological processes. Iron dyshomeostasis, either deficiency or overload, is linked to various disease conditions. It has been well demonstrated that iron is involved in the development and progression of many diseases, including anemia, hemochromatosis, metabolic syndrome, atherosclerosis and other cardiovascular diseases, cancer, type 2 diabetes and related microvascular damage leading to end stage kidney disease, osteoporosis and osteopenia, hepatocellular carcinoma with or without cirrhosis of the liver, sarcopenia (muscle wasting), hepatitis C, non-alcoholic fatty liver disease (NAFLD), non-alcoholic steatohepatitis (NASH), Alzheimer's and other neurodegenerative diseases. Furthermore, iron is a well-known metal cofactor in the prosthetic group in heme containing proteins as well as non-heme iron containing proteins (such as Fe—S clusters) and thereby plays important roles in various biological processes such as oxygen delivery, electron transport, enzymatic reactions and DNA synthesis and repair, all of which are critical for proper cellular function. In living systems, iron can be found in ferrous ($Fe^{2+}$) or ferric ($Fe^{3+}$) forms because iron is a transition metal and thus can serve as an electron acceptor or donor and has favorable redox potential to switch between Fe (II) and Fe (III).

Although iron is an essential element for the body, free iron ions ($Fe^{2+}$ and $Fe^{3+}$) are toxic and damaging to cells as they catalyze the production of reactive oxygen species (ROS) via the Haber-Weiss reaction or the Fenton reaction, causing harmful oxidative stress leading to cell damage, lipid peroxidation and DNA mutagenesis. Excess iron can accelerate the aging process and adversely affect many chronic diseases.

The major fraction of iron in biological systems is tightly associated with enzymes and specialized iron transport and storage proteins. A distinct, minor fraction is bound comparatively loosely to a heterogeneous population of poorly defined anions, collectively defined as labile iron pools (LIP), which are associated with important physiological/pathological functions. LIP provide readily available sources of iron for incorporation into proteins/enzymes; however, they are also the forms of iron that promote ROS formation, which is responsible for iron toxicity. Moreover, pharmacologically, LIP are targets for chelators or metal scavengers for treating diseases related to iron dyshomeostasis. To monitor irons in living systems, e.g., determining concentration and/or subcellular localization of iron, e.g., $Fe^{2+}$ or $Fe^{3+}$ could help determine the effectiveness of treatment of diseases related to iron dyshomeostasis. Most of the currently available molecular and supramolecular probes for $Fe^{2+}$ or $Fe^{3+}$ are not suitable to be used in biological systems due to the challenge of overcoming cell permeability, specificity, solubility issues or inappropriate optical properties.

SUMMARY OF THE INVENTION

Selective and sensitive sensing systems for live-cell $Fe^{2+}$ and $Fe^{3+}$-imaging are lacking. Probes (or sensors) for non-invasive $Fe^{3+}$ quantification in cells are not available. Based on a few fluorescent scaffolds, multiple molecular probes for the detection of and qualifying ferrous or ferric ions in living systems have been developed and described here. Provided herein are selective, sensitive and reversible off-on fluorescent $Fe^{2+}$ and $Fe^{3+}$ sensors. The iron probes can selectively image native $Fe^{2+}$ or $Fe^{3+}$ in live cells. The reversible "turn-on" property and sensitivity of the iron probes allows viewing of the exchangeable $Fe^{2+}$ and $Fe^{3+}$ pools at subcellular resolution in multiple live human or animal cells. A few of the ratiometric probes can also qualify ferrous or ferric ions in subcellular compartments in living cells. The near infrared probes disclosed herein can also be used as fluorescent sensors for the detection of iron ions in a living animal.

The present disclosure relates to a compound of Formula I, Formula II, or Formula III:

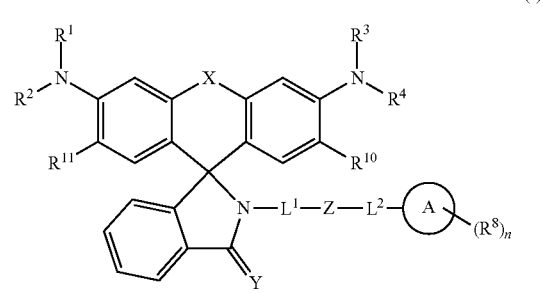

(I)

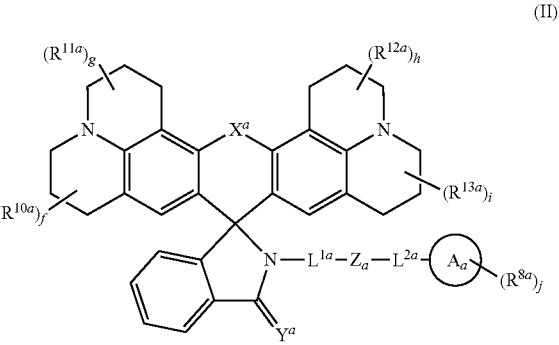

(II)

-continued (III)

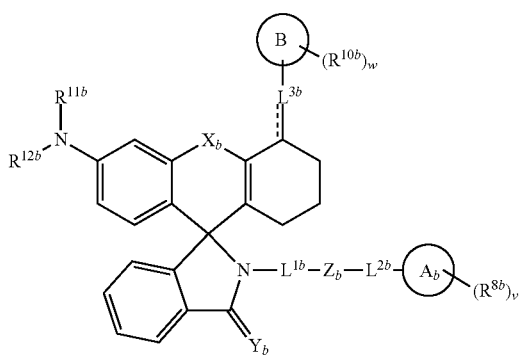

or a pharmaceutically acceptable salt thereof, wherein the variables are as described herein.

Provided herein are also compositions comprising a compound of Formula I, Formula II, or Formula III and one or more excipient or carrier.

The present disclosure also provides methods of monitoring iron, e.g., determining concentration and/or subcellular localization of iron, e.g., $Fe^{2+}$ and $Fe^{3+}$, in living cells comprising contacting said cells with an effective amount of a compound provided herein or a pharmaceutically acceptable salt thereof.

Further, the present disclosure provides methods of treating disease associated with iron dyshomoestasis comprising administering an effective amount of an agent suitable for treating said disease and a compound described herein or a pharmaceutically acceptable salt thereof.

BRIEF DESCRIPTION OF THE DRAWINGS

FIG. 17A is Rh-PK-$Fe^{3+}$ fluorescence intensity collected at 547-703 nm (red). FIG. 17B is the MitoTracker fluorescence intensity collected at 492-548 nm (green). FIG. 17C is a confocal microscopy image of FIG. 17A and FIG. 17B merged together.

FIG. 18A is a DIC image of cells with 10 µm scale bar. FIG. 18B is the Rh-PK-$Fe^{3+}$ fluorescence intensity collected at 547-703 nm (red). FIG. 18C is the MitoTracker fluorescence intensity collected at 492-548 nm (green). FIG. 18D is the LysoTracker fluorescence intensity collected at 409-484 nm (blue). FIG. 18E is a DIC image of FIG. 18A and fluorescence images of FIG. 18B and FIG. 18C merged together. FIG. 18F is a DIC image of FIG. 18A and fluorescence images of FIG. 18B and FIG. 18D merged together. FIG. 18G is an image of FIG. 18 A to FIG. 18D merged together. FIG. 18H is an image of FIG. 18A, FIG. 18C and FIG. 18D merged together.

FIG. 19A is the image of cell only. FIG. 19B is image where the cells were treated with the sensor after 30 min incubation. FIG. 19C is the image where the cells were incubated with 10 µM $Fe^3$ for 30 min and then RhHPA was added. FIG. 19D is the image where the cells were incubated with 10 µM $Fe^3$ for 30 min and then SIH was added, and incubated overnight. FIG. 19E is the image of the cells incubated with SIH ($Fe^{3+}$-chelator, 100 µM) overnight and then sensor was added.

FIG. 20A to FIG. 20H are representative confocal images of intracellular colocalization studies of 10 µM RhHPA incubated with live BAEC cells co-labeled with MitoTracker Green (100 nM) and LysoTracker Blue DND-22 (50 nM). FIG. 20A is a DIC image of cells with 10 µm scale bar. FIG. 20B is the RhHPA-$Fe^{3+}$ fluorescence collected at 547-703 nm (red). FIG. 20C is the MitoTracker fluorescence collected at 492-548 nm (green). FIG. 20D is the LysoTracker fluorescence collected at 409-484 nm (blue). FIG. 20E is a DIC image of FIG. 20A and fluorescence images of FIG. 20B and FIG. 20C merged together.

FIG. 20F is an image of FIG. 20A and fluorescence images of FIG. 20B and FIG. 20D merged together. FIG. 20G is an image of FIG. 20A to FIG. 20D merged together. FIG. 20H is an image of FIG. 20A, FIG. 20C and FIG. 20D merged together.

FIG. 21A is a DIC image of cells with 10 μm scale bar. FIG. 21B is the RhHPA-$Fe^{3+}$ fluorescence collected at 547-703 nm (red). FIG. 21C is the MitoTracker fluorescence collected at 492-548 nm (green). FIG. 21D is the LysoTracker fluorescence collected at 409-484 nm (blue). FIG. 21E is a DIC image of FIG. 21A and fluorescence images of FIG. 21B and FIG. 21C merged together. FIG. 21F is a DIC image of FIG. 21A and fluorescence images of FIG. 21B and FIG. 21D merged together. FIG. 21G is an image of FIG. 21A to FIG. 21D merged together. FIG. 21H is an image of FIG. 21A, FIG. 21C, and FIG. 21D merged together.

FIG. 34A is a DIC image of cells with 20 μm scale bar. FIG. 34B is a DIC image of cells treated with 10 μM Rh6GD at 37° C. for 30 min. FIG. 34C is a DIC image of cells treated with 100 μM $Fe^{2+}$ at 37° C. for overnight and then treated with 10 μM Rh6GD at 37° C. for 30 min. FIG. 34D is a DIC image of cells treated with 100 μM $Fe^{2+}$ at 37° C. for overnight and then 1 mM 2,2'-bipyridyl(Bpy) for 30 min at 37° C. and then treated with 10 μM Rh6GD at 37° C. for 30 min. FIG. 34E is a DIC image of cells treated with 1 mM 2,2'-bipyridyl (Bpy) for 30 min at 37° C. and then treated with 10 μM Rh6GD at 37° C. for 30 min.

FIG. 35A to FIG. 35H are representative confocal images of intracellular colocalization studies of 10 μM Rh6GD incubated with live human ws1 fibroblast cells co-labeled with MitoTracker Green (100 nM) and LysoTracker Deep Red (50 nM). FIG. 35A is a DIC image of cells with 20 μm scale bar. FIG. 35B is Rh6GD-$Fe^{2+}$ fluorescence collected at 545-625 nm (red). FIG. 35C is MitoTracker fluorescence collected at 492-535 nm (green). FIG. 35D is LysoTracker fluorescence collected at 650-800 nm (blue). FIG. 35E is a DIC image of FIG. 35A and fluorescence images of FIG. 35B and FIG. 35C were merged together. Colocalization regions are in yellow and non-overlapping regions remain in red. FIG. 35F is a DIC image of FIG. 35A and fluorescence images of FIG. 35B and FIG. 35D were merged together. Overlapping regions are in purple and non-overlapping regions remain in red. FIG. 35G is a DIC image of FIGS. 35A, 35B, 35C, and 35D were merged together, revealing that the Rh6GD-$Fe^{2+}$ images are 100% colocalized with the sum of those of MitoTracker and LysoTracker. FIG. 35H is a DIC image of FIGS. 35A, 35C, and 35D were merged together, showing no overlapping region between lysosomes and mitochondria.

FIGS. 46A-E shows the confocal microscopy images (with DIC) of live bovine aortic endothelial cells (BAEC). FIG. 46A is a DIC image of cells with 20 μm scale bar. FIG. 46B is a DIC image of cells treated with 10 μM Rh101D at 37° C. for 30 min. FIG. 46C is a DIC image of cells treated with 100 μM $Fe^{2+}$ at 37° C. for overnight and then treated with 10 μM Rh101D at 37° C. for 30 min. FIG. 46D is a DIC image of cells treated with 100 μM $Fe^{2+}$ at 37° C. for overnight and then 1 mM 2,2'-bipyridyl(Bpy) for 30 min at 37° C. and then treated with 10 μM Rh101D at 37° C. for 30 min. FIG. 46E is a DIC image of cells treated with 1 mM 2,2'-bipyridyl(Bpy) for 30 min at 37° C. and then treated with 10 μM Rh101D at 37° C. for 30 min.

FIGS. 47A-H shows representative confocal images of intracellular colocalization studies of 10 μM Rh101D incubated with live human bovine aortic endothelial cells (BAEC) co-labeled with MitoTracker Green (100 nM) and LysoTracker Deep Red (50 nM). FIG. 47A is a DIC image of cells with 20 μm scale bar. FIG. 47B is a DIC image of cells treated with Rh101D-$Fe^{2+}$ fluorescence collected at 545-625 nm (red). FIG. 47C is a DIC image of cells treated with MitoTracker fluorescence collected at 492-535 nm (green). FIG. 47D is a DIC image of cells treated with LysoTracker fluorescence collected at 650-800 nm (blue). FIG. 47E is an image of image of FIG. 47A and fluorescence images of FIG. 47B and FIG. 47C merged together. Colocalization regions are in yellow and non-overlapping regions remain in red. FIG. 47F is an image of FIG. 47A and fluorescence images of FIG. 47B and FIG. 47D merged together. Overlapping regions are in purple and non-overlapping regions remain in red. FIG. 47G is an image of FIGS. 47A, B, C, and D merged together, revealing that the Rh101D-$Fe^{2+}$ images are 100% colocalized with the sum of those of MitoTracker and LysoTracker. FIG. 47H is an image of FIGS. 47A, C, and D merged together, showing separate regions of lysosomes and mitochondria.

FIGS. 51A-L shows the confocal microscopy images (with DIC) of HCT-116 treated with (b,c) 20 μM Rh101D sensor after 30 min incubation; (f,g) the cells were incubated with $Fe^{2+}$ (20 μM) for 1 h then incubate with the sensor for 30 min.; (j,k) the cells were incubated with Bpy (100 μM) for 8 h then incubate with the sensor for 30 min (excitation wavelength was 543 nm for b,f,j and 405 nm for c,g,k); (d,h,l) ratio images of b,c; f,g; j,k. Confocal fluorescence ratiometric images are the average ratio in regions of interest.

FIGS. 63A-E show confocal microscopy images (with DIC) of live human bovine aortic endothelial cells (BAEC). FIG. 63A is a DIC image of cells with 20 μm scale bar.

FIG. 63B is a DIC image of cells treated with 10 μM NIRh-Fret at 37° C. for 30 min. FIG. 63C is a DIC image of cells treated with 100 μM $Fe^{2+}$ at 37° C. for overnight and then treated with 10 μM NIRh-Fret at 37° C. for 30 min. FIG. 63D is a DIC image of cells treated with 100 μM $Fe^{2+}$ at 37° C. for overnight and then 1 mM 2,2'-bipyridyl(Bpy) for 30 min at 37° C. and then treated with 10 μM NIRh-Fret at 37° C. for 30 min. FIG. 63E is a DIC image of cells treated with 1 mM 2,2'-bipyridyl(Bpy) for 30 min at 37° C. and then treated with 10 μM NIRh-Fret at 37° C. for 30 min.

FIG. 64A is a DIC image of cells with 20 μm scale bar. FIG. 64B is a DIC image of cells treated with NIRh-Fret-$Fe^{2+}$ fluorescence collected at 650-850 nm (red). FIG. 64C is a DIC image of cells treated with MitoTracker fluorescence collected at 492-535 nm (green). FIG. 64D is a DIC image of cells treated with LysoTracker fluorescence collected at 550-625 nm (blue). FIG. 64E is an image of FIG. 64A and fluorescence images of FIG. 64B and FIG. 64C merged together. Colocalization regions are in yellow and non-overlapping regions remain in red. FIG. 64F is an image of FIG. 64A and fluorescence images of FIG. 64B and FIG. 64D merged together. Overlapping regions are in purple and non-overlapping regions remain in red. FIG. 64G is an image of FIGS. 64A, B, C, and D merged together, revealing that the NIRh-Fret-$Fe^{2+}$ images are 100% colocalized with the sum of those of MitoTracker and LysoTracker. FIG. 64H is an image of FIGS. 64A, C, and D merged together, showing no overlapping region between lysosomes and mitochondria.

FIGS. 65A-E show confocal microscopy images (with DIC) of live human colon epithelial cancer cells (Caco-2). FIG. 65A is a DIC image of cells with 20 μm scale bar. FIG. 65B is a DIC image of cells treated with 10 μM NIRh-Fret at 37° C. for 30 min. FIG. 65C is a DIC image of cells treated with 100 μM $Fe^{2+}$ at 37° C. for 6 h and then treated with 10 μM NIRh-Fret at 37° C. for 30 min. FIG. 65D is a DIC image of cells treated with 100 μM of ferrous ammonium sulfate (Fe (NH4)2(SO4)2) for 1 h, followed by addition of 0.5 μM hepcidin and then incubated for another 5 h and then treated with 10 μM NIRh-Fret at 37° C. for 30 min. FIG. 65E is a DIC image of cells treated with 100 μM $Fe^{2+}$ and hepcidin for 6 and 5 h, respectively, and followed by a 40 min treatment with 1 mM of 2,2-bipyridyl (Bpy) and then treated with 10 μM NIRh-Fret at 37° C. for 30 min.

FIGS. 72A-L show confocal microscopy images (with DIC) of ws1 treated with (b,c) 20 μM NIRh-FRET sensor after 30 min incubation; (f,g) the cells were incubated with $Fe^{2+}$ (20 μM) for 1 h then incubate with the sensor for 30 min.; (j,k) the cells were incubated with Bpy (100 μM) for 8 h then incubate with the sensor for 30 min (Excitation wavelength was 633 nm for b,f,j and 405 nm for c,g,k); (d,h,l) ratio images of b,c; f,g; j,k. Confocal fluorescence ratiometric images are the average ratio in regions of interest.

FIGS. 73A-L show confocal microscopy images (with DIC) of HT 29 treated with (b,c) 20 μM NIRh-FRET sensor after 30 min incubation; (f,g) the cells were incubated with $Fe^{2+}$ (20 μM) for 1 h then incubate with the sensor for 30 min.; (j,k) the cells were incubated with Bpy (100 μM) for 8 h then incubate with the sensor for 30 min (Excitation wavelength was 633 nm for b,f,j and 405 nm for c,g,k); (d,h,l) ratio images of b,c; f,g; j,k. Confocal fluorescence ratiometric images are the average ratio in regions of interest.

DETAILED DESCRIPTION

Probes for $Fe^{3+}$

Figure 1:
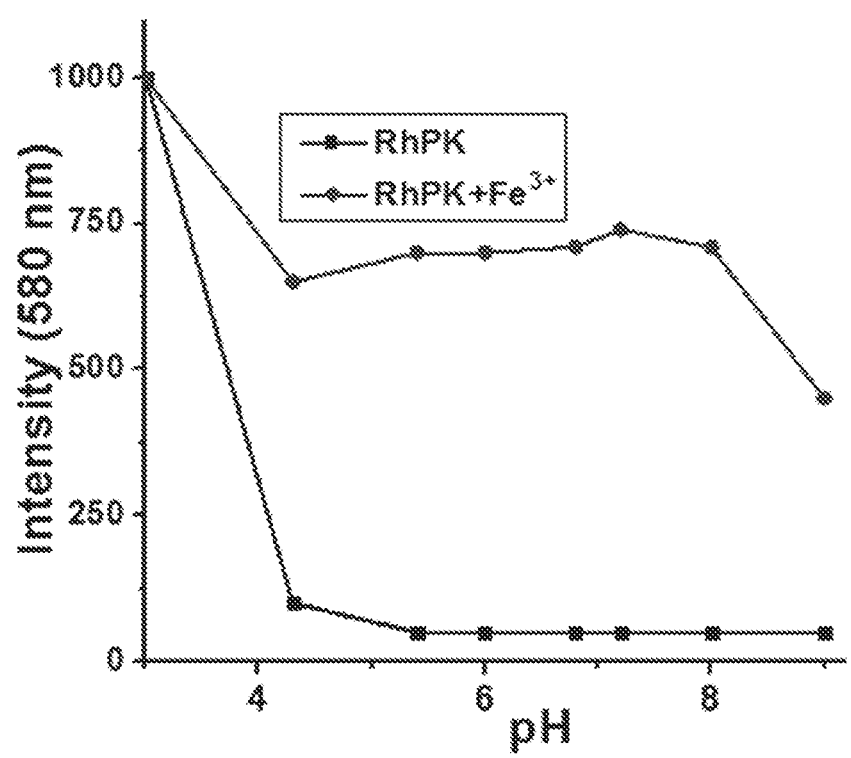
FIG. 1 is a graph showing the variation of fluorescence intensity of Rh-PK and Rh-PK+$Fe^{3+}$ at different pH values.

The vast majority of the currently available molecular and supramolecular probes for $Fe^{3+}$ are not suitable to be used in biological systems due to the challenge of overcoming cell permeability, specificity, solubility issues or inappropriate optical properties. The currently known fluorescent sensors that are capable of cellular iron imaging are largely limited to "turn-off" type, providing useful information but suffering from poor sensitivity, or interference from other metal ions. J. L. Bricks, et al., J. Am. Chem. Soc. 2005, 127, 13522-13529; S. Fakih, et al., J. Pharm. Sci., 2009, 98, 2212; and D. En, et al., RSC Adv., 2014, 4, 248. Recently, a few interesting "turn-on" iron sensors have been reported but their capabilities in detection of native cellular iron pools have yet to be established, due to various intrinsic drawbacks of the sensors. M. Zhang, et al., Tetrahedron Lett. 2007, 48, 3709-3712; N. C. Lim, et al., Inorg. Chem. 2009, 48, 1173-1182; M. H. Lee, et al., Chem. Commun. 2010, 46, 1047-1049; B. Wang, et al., Angew. Chem. Int. Ed. 2010, 49, 4576-4579; S. Wang, et al., Tetrahedron Lett. 2011, 52, 2840-2843; Z. Hu, et al., Sensors and Actuators B 2011, 156, 428-432; Z. Yang, et al., J. Org. Chem. 2012, 77, 1143-1147. For example, a $Fe^{3+}$-catalyzed hydrolysis reaction of rhodamine 6G Schiff base has been harnessed for selective detection of $Fe^{3+}$, but it cannot monitor the dynamic changes in $Fe^{3+}$ due to the irreversible nature of the catalytic hydrolysis reaction. M. H. Lee, et al., Chem. Commun. 2010, 46, 1047-1049. Rhodamine 6G-modified $Fe_3O_4$ nanoparticles can selectively detect $Fe^{3+}$ and $Cr^{3+}$; however, these $Fe_3O_4$ nanoparticles introduce exogeneous iron species into the systems to be analyzed. B. Wang, et al., Angew. Chem. Int. Ed. 2010, 49, 4576-4579. A FRET-based sensor for both $Fe^{3+}$ and $Cr^{3+}$ showed fluorescent responses to $Fe^{3+}$-loaded HeLa cells, but failed to detect the native cellular $Fe^{3+}$ pools, presumably due to the sensor's low affinity for $Fe^{3+}$ (K~8.75×$10^3$ $M^{-1}$ for 2:1 complex). S. Wang, et al., Tetrahedron Lett. 2011, 52, 2840-2843. A similar problem is seen in other low affinity sensors, including the recently reported Y3 which has a detection limit of 5 μM. M. Zhang, et al., Tetrahedron Lett. 2007, 48, 3709-3712; S. Wang, et al., Tetrahedron Lett. 2011, 52, 2840-2843; and Z. Hu, et al., Sensors and Actuators B 2011, 156, 428-432. A recent FRET-based ratiometric sensor RNP1 that was located in mitochondria could detect exogenously loaded $Fe^{3+}$ in mitochondria, but again could not detect the native cellular $Fe^{3+}$ pools. S. Sen, et al., Analyst, 2012, 137, 3335. The biological applications of these probes have been mostly limited to detection of exogenously added $Fe^{3+}$ in cells. W. D. Chen, et al., Dalton Trans., 2013, 42, 10093; and C. Kar, S. Samanta, et al., New J. Chem., 2014, 38, 2660. None of the current $Fe^{3+}$-detection systems is capable of detect native $Fe^{3+}$ in live cells or at subcellular resolution.

Good methods to monitor LIP are still absent. Several approaches have been used to identify labile iron pools in cells, but each one of these approaches has many disadvantages. Although traditional magnetic resonance imaging (MRI) technology can provide the overall total iron distribution in the body, it cannot deliver the cellular or subcellular resolution necessary for an understanding at the cellular or molecular level, nor any information on LIP. Radioactive $^{59}Fe$ has been used to provide important information on iron trafficking, but it cannot distinguish the oxidation states of iron in cells or the binding states of iron (e.g., protein-bound or in LIP). Moreover, the ionizing radiation form $^{59}Fe$ is highly toxic to the cells. Other radiation-involving methods such as X-ray absorption fine structure (EXAFS), X-ray fluorescence, and laser microprobe mass analysis (LAMMA) can provide oxidation states of Fe in biological samples but they destroy the sample as well as cannot be used in live cell imaging. Another method is using chelators such as deferrioxamine (DFO) to detect LIP in living cells with the help of electron paramagnetic resonance (EPR), which cannot distinguish the oxidation states of iron and requires cell disruption. Other traditional methods such as histochemical staining with Perl's method or the Turnbukk method have the ability to study labile iron ($Fe^{2+}$ and $Fe^{3+}$) qualitatively in tissue samples. However, these methods suffer from poor sensitivity and toxicity, and the need to use fixed samples limits their use in living cells.

Fluorescent probes are attractive tools to visualize the distribution and speciation of labile iron. Ideally, such probes should be able to selectively respond to either $Fe^{2+}$ or $Fe^{3+}$, and quantify the levels of each in living systems.

One major challenge with detection of iron using fluorescent sensors is the paramagnetic quenching nature of both ions; as such, many early probes for iron exhibit "turn off" fluorescence response to iron binding which has poor sensitivity and provides only indirect measure of iron in cells in most cases. Moreover, probes must be able to distinguish the two oxidation states of iron. Therefore, the development of iron-selective fluorescent probes is of great interest and could prove indispensable for monitoring the dynamic changes of iron in cells and other biological systems, as well as elucidating the mechanisms of iron trafficking. Highly sensitive, selective and reversible turn-on or ratiometric fluorescent sensors capable of subcellular iron imaging are in high demand, but are still lacking due to the challenge of overcoming cell permeability, specificity, solubility and paramagnetic quenching issues of iron ions.

Provided herein are compounds suitable as molecular probes for the detection of ferric ion in living systems. The compounds provided herein can be stable in low pH's such as pH of about 4-9 or about 5-9. Unexpectedly, cell imaging studies (as shown in the Examples) indicate that the compounds described herein are capable of detecting basal levels of $Fe^{3+}$ as well as dynamic changes in $Fe^{3+}$ levels in live cells at subcellular resolution.

Furthermore, the compounds provided herein are suitable for sensitive and specific ratiometric probes for the quantification of labile ferric ions in living systems. The ratiometric probes enables the determination of the absolute concentrations of labile ferric ions in living cells. The sensitivity of the sensors allows the determination of labile ferric ion concentration at subcellular resolution.

The compounds provided herein are non-toxic and thus can be useful in studying $Fe^{3+}$ in living systems as well as diseases related on abnormal iron metabolism and various other diseases that are found to have alterations in iron levels or localization. The compounds provided herein are also useful for biomedical research and monitoring diseases and drug effectiveness.

Probes for $Fe^{2+}$

There are very few fluorescent sensors available for the detection of $Fe^{2+}$ due to fluorescent quenching upon binding to iron ions as well as interference from other metal ions. For example, turn off sensor calcein consists of a fluorescein fluorophore with a EDTA-like binding moiety is more selective for $Fe^{2+}$ over $Fe^{3+}$ but also gives response to other metals, including $Ni^{2+}$, $Co^{2+}$, and $Cu^{2+}$. Another turn off sensor, Phen Green SK is another sensor that responds to both major oxidation states of iron, providing a 93% turn-off response to $Fe^{2+}$ and a 51% turn-off response to $Fe^{3+}$. It is also a fluorescein-based sensor linked to phenanthroline as the iron-binding moiety. It also gives response to other metal ions as well. Few $Fe^{2+}$ sensors have been reported. For example, dihydrorhodamine 123 has shown indirect and non-selective turn on response to iron (II) as it detects reactive oxygen species (ROS) produced by iron (II)-catalyzed Fenton reaction.

An example of fluorescent probe for $Fe^{2+}$ detection in live HL-7702 and Hep G2 cells have previously been reported but the probe suffers from quenching effects of iron (II) through Chelation. (P. Li, L. Fang, H. Zhou, W. Zhang, X. Wang, N. Li, H. Zhong, B. Tang, Chem.-Eur. J., 2011, 17, 10520-3). Pyrene-TEMPO is a reaction-based fluorescent turn on fluorescent sensor; however, it suffers from limitations such as the reaction is pH-dependent (favored at low pH's) and the sensor can also be reduced by other radicals and other biological relevant reductants. DansSQ is another $Fe^{2+}$-selective sensor which consists of a dansyl group-linked styrylquinoline which shows a 15-fold increase in fluorescence at 460 nm when it binds with $Fe^{2+}$. However, this sensor suffers from interference from other metal ions as well as it is only soluble in organic solvents and thus is not suitable for bioimaging. AGD is a coumarin-based $Fe^{2+}$ selective turn-off fluorescent sensor, in which the coumarin fluorophore linked to binding moiety 2-amino-2-(hydroxylmethyl) propane-1,3-diol when binds with $Fe^{2+}$, the fluorescence decreases. The sensor can only detect change in $Fe^{2+}$ concentration in cell membrane, as it cannot penetrate through it. Another $Fe^{2+}$-selective turn-on sensor is rhodamine based fluorescent sensor, RhoNox-1 that has an N-oxide group on the tertiary amine of the sensor. Upon binding with $Fe^{2+}$, fluorescence is increased due to the reduction of the N-oxide group. The sensor RhoNox-1 is capable to detect endogenous $Fe^{2+}$ in the Golgi apparatus rather than mitochondria, which is believed to be the major organelle store $Fe^{2+}$. RhoNox-1 also suffers from two limitations such as the mechanism of sensing is not known as well as it is not reversible and thereby binding with $Fe^{2+}$ is unknown. Another reaction-based $Fe^{2+}$ selective sensor IP1 is a fluorescein based turn-on fluorescent sensor, which is selective for $Fe^{2+}$ and can detect endogenous levels of labile $Fe^{2+}$ in liver cells. However, like RhoNox-1, it is a reaction-based sensor and it does not show reversible response to $Fe^{2+}$ as well as it displayed rather weak signal with poor spatial resolution, presumably due to the diffusive nature of the fluorophore liberated after reaction with $Fe^{2+}$.

Highly selective and sensitive sensing systems for live-cell $Fe^{2+}$-imaging are still lacking. Probes for non-invasive $Fe^{2+}$ quantification in cells have not been available. Selective, sensitive and turn-on fluorescent $Fe^{2+}$ sensors have previously been reported (S. Maiti, Z. Aydin, Y. Zhang, M. Guo, Dalton Trans., 2015, 44, 8942-8949). The Rh-T probe can selectively image $Fe^{2+}$ in mitochondria in live cells. However, it is limited in mitochondria only and cannot quantifying the $Fe^{2+}$ level.

Provided herein are multiple molecular probes for the detection of ferrous ion in living systems. These sensors can undergo a coordination-induced fluorescence activation (CIFA) process. In the absence of ferrous ion ($Fe^{2+}$), these fluorescent probes can have little to no fluorescent signal after being excited by a proper light source. However, in the presence of ferrous ion ($Fe^{2+}$), a unique novel coordination between ferrous ion ($Fe^{2+}$) and the probe can occur and thus activates the fluorescence of the probe. These fluorescent probes can have an increase in fluorescent signal following proper excitation by a light source. The sensors can distinguish the oxidation states of iron and have response to only ferrous ions. The fluorescence triggered by $Fe^{2+}$ is reversible. When the $Fe^{2+}$ level is lowered, the fluorescence is decreased (activated by $Fe^{2+}$ deactivated by remove of $Fe^{2+}$). Moreover, the sensors can have rapid fluorescence responses to $Fe^{2+}$ and monitor $Fe^{2+}$ in real time in living systems as well as the intracellular trafficking of $Fe^{2+}$ in live cells.

Certain sensors can absorb and emit light in the visible region, and there are also those that can absorb and emit in the near-infrared (NIR) region. The ones that absorb and emit in the near-infrared region are capable for in vivo imaging because they circumvent issues of autofluorescence and signal attenuation by biological tissues. A few of these NIR probes have been used to detect labile ferrous ions in zebrafish. The use of the NIR Fe(II) probes is the first example of using fluorescent sensors for the detection of iron ions in a living animal. The sensors provided herein have specificity and sensitivity labile ferric ions detection at subcellular resolution in living cells with two high level pools of labile Fe²⁺ located in mitochondria and lysosomes and a low level labile Fe²⁺ located in the cytosol in various cell lines (e.g., cancer cells) and primary cells from human and animals.

Provided herein are also sensitive and specific ratiometric probes for the quantification of labile ferrous ions in living systems. The ratiometric probes provided herein can determine the absolute concentrations of labile ferric ions in living cells at subcellular resolution. The sensitivity of the sensors allows for the determination of labile ferrous ion concentration at subcellular resolution.

The probes provided herein can be useful for studying the roles that iron plays in living systems under various circumstances, such as dietary changes, excises and under medication, as well as the roles iron plays in the development and progression of many diseases, including anemia, hemochromatosis, metabolic syndrome, atherosclerosis (ALS) and other cardiovascular diseases, cancer, type 2 diabetes and related microvascular damage leading to end stage kidney disease, osteoporosis and osteopenia, hepatocellular carcinoma with or without cirrhosis of the liver, sarcopenia (muscle wasting), hepatitis C, non-alcoholic fatty liver disease (NAFLD), non-alcoholic steatohepatitis (NASH). The probes provided herein are nontoxic and thus, are useful in diagnose diseases or determine efficacy of treatments for various diseases such as chelation therapy in human.

Compounds

The compounds provided herein are useful as probes for Fe²⁺ and Fe³⁺. This disclosure provides compounds of Formula I.

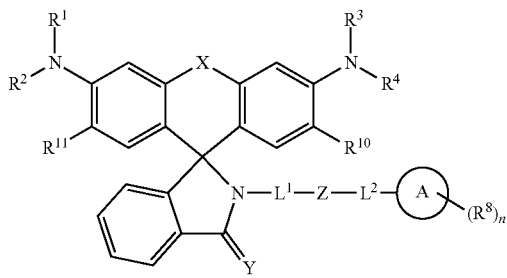

I or a pharmaceutically acceptable salt thereof, wherein
X is O, S, NR⁵, or CR⁶R⁷;
Y is O or S;
$L^1$ and $L^2$ are each independently selected from a bond, $(CR^xR^y)_t$ and $(CR^z)_u$;
Z is O, S, N, or NR⁹;
ring A is selected from $C_{6-10}$ aryl, $C_{3-10}$ cycloalkyl, and 5-10 membered heteroaryl;
$R^x$, $R^y$, and $R^z$ are each independently selected from H, halo, $C_{1-6}$ alkyl, $C_{2-6}$ alkenyl, $C_{2-6}$ alkynyl, $C_{1-6}$ haloalkyl, $C_{1-6}$ alkoxy, CN, and OH;
$R^1$, $R^2$, $R^3$, $R^4$, $R^5$, $R^9$, $R^{10}$, and $R^{11}$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 4-10 membered heterocycloalkyl; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^a$;

$R^6$, $R^7$, and $R^8$ are each independently selected from H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^1$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $S(O)R^1$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, OH, and $O(C_{1-6}$ alkyl);

$R^a$ is each independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, NO₂, OH, $O(C_{1-6}$ alkyl), $S(C_{1-6}$ alkyl), $C(O)(C_{1-6}$ alkyl), $C(O)NH(C_{1-6}$ alkyl), $C(O)N(C_{1-6}$ alkyl)₂, $C(O)O(C_{1-6}$ alkyl), $OC(O)(C_{1-6}$ alkyl), $OC(O)NH(C_{1-6}$ alkyl), $OC(O)N(C_{1-6}$ alkyl)₂, NH₂, $NH(C_{1-6}$ alkyl), $N(C_{1-6}$ alkyl)₂, and $NHC(O)(C_{1-6}$ alkyl);

$R^{a1}$, $R^{b1}$, $R^{c1}$, and $R^{d1}$ are each independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, NO₂, OH, $O(C_{1-6}$ alkyl), $S(C_{1-6}$ alkyl), $C(O)(C_{1-6}$ alkyl), $C(O)NH(C_{1-6}$ alkyl), $C(O)N(C_{1-6}$ alkyl)₂, $C(O)O(C_{1-6}$ alkyl), $OC(O)(C_{1-6}$ alkyl), $OC(O)NH(C_{1-6}$ alkyl), $OC(O)N(C_{1-6}$ alkyl)₂, NH₂, $NH(C_{1-6}$ alkyl), $N(C_{1-6}$ alkyl)₂, and $NHC(O)(C_{1-6}$ alkyl);

n is 1, 2, 3, 4, or 5;
t is 1, 2, 3, 4, or 5; and
u is 1, 2, 3, 4, or 5.

In some embodiments, X is O. In some embodiments, Y is O.

In some embodiments, $L^1$ is a bond or $(CR^xR^y)_t$. In some embodiments, $L^1$ is a bond or $(CH_2)_2$. In some embodiments, $L^1$ is a bond.

In some embodiments, $L^2$ is $(CR^z)_u$. In some embodiments, $L^2$ is CH, $(CH)_3$, or $C(CH_3)$.

In some embodiments, Z is N.

In some embodiments, ring A is 5-10 membered heteroaryl. In some embodiments, ring A is phenyl, pyridyl, pyrimidinyl, pyrazinyl, pyridazinyl, pyrrolyl, or pyrazolyl. In some embodiments, ring A is pyridyl or phenyl. In some embodiments, ring A is pyridyl. In some embodiments, ring A is phenyl.

In some embodiments, $R^8$ is H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^1$, $C(O)NR^{c1}R^{d1}$, $C(O)OR^{a1}$, or $NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, OH, and $O(C_{1-6}$ alkyl). In some embodiments, $R^8$ is $NR^{c1}R^{d1}$, $C(O)R^1$ or $C_{1-6}$ alkyl optionally substituted with OH or $O(C_{1-6}$ alkyl). In some embodiments, $R^8$ is hydroxymethyl, acetyl, or dimethylamino. In some embodiments, $R^8$ is hydroxymethyl or acetyl.

In some embodiments, $R^{10}$ is $C_{1-6}$ alkyl. In some embodiments, $R^{10}$ is methyl. In some embodiments, $R^{11}$ is $C_{1-6}$ alkyl. In some embodiments, $R^{11}$ is methyl. In some embodiments, $R^{10}$ is H. In some embodiments $R^{11}$ is H. In some embodiments, $R^{10}$ and $R^{11}$ are both H.

In some embodiments, $R^1$, $R^2$, $R^3$, and $R^4$ are each independently selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2, 3, 4, or 5 substituents independently selected from $R^a$. In some embodiments, $R^1$, $R^2$, $R^3$, and $R^4$ are $C_{1-6}$ alkyl.

In some embodiments:
X is O or S;
Y is O or S;
$L^1$ and $L^2$ are each independently selected from a bond, $(CR^xR^y)_t$ and $(CR^z)_u$;
Z is N, or $NR^9$;
ring A is $C_{6-10}$ aryl or, 5-10 membered heteroaryl;
$R^x$, $R^y$, and $R^z$ are each independently selected from H, halo, $C_{1-6}$ alkyl, $C_{2-6}$ alkenyl, and $C_{2-6}$ alkynyl;
$R^1$, $R^2$, $R^3$, $R^4$, and $R^9$ are each independently selected from H, $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2, 3, 4, or 5 substituents independently selected from $R^a$;
each $R^8$ is independently selected from H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, and $NR^{c1}C(O)OR^{a1}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, OH, and $O(C_{1-6}$ alkyl);
$R^a$ is each independently selected from halo, $C_{1-6}$ alkyl, $C_{2-6}$ alkenyl, $C_{2-6}$ alkynyl, $C_{1-6}$ haloalkyl, CN, $NO_2$, OH, $O(C_{1-6}$ alkyl), $S(C_{1-6}$ alkyl), $C(O)(C_{1-6}$ alkyl), $C(O)NH(C_{1-6}$ alkyl), $C(O)N(C_{1-6}$ alkyl)$_2$, $C(O)O(C_{1-6}$ alkyl), $OC(O)(C_{1-6}$ alkyl), $OC(O)NH(C_{1-6}$ alkyl), $OC(O)N(C_{1-6}$ alkyl)$_2$, $NH_2$, $NH(C_{1-6}$ alkyl), $N(C_{1-6}$ alkyl)$_2$, and $NHC(O)(C_{1-6}$ alkyl);
$R^{a1}$, $R^{b1}$, $R^{c1}$, and $R^{d1}$ are each independently selected from halo, $C_{1-6}$ alkyl, $C_{2-6}$ alkenyl, $C_{2-6}$ alkynyl, $C_{1-6}$ haloalkyl, CN, $NO_2$, OH, $O(C_{1-6}$ alkyl), $S(C_{1-6}$ alkyl), $C(O)(C_{1-6}$ alkyl), $C(O)NH(C_{1-6}$ alkyl), $C(O)N(C_{1-6}$ alkyl)$_2$, $C(O)O(C_{1-6}$ alkyl), $OC(O)(C_{1-6}$ alkyl), $OC(O)NH(C_{1-6}$ alkyl), $OC(O)N(C_{1-6}$ alkyl)$_2$, $NH_2$, $NH(C_{1-6}$ alkyl), $N(C_{1-6}$ alkyl)$_2$, and $NHC(O)(C_{1-6}$ alkyl)
n is 1, 2, 3, 4, or 5;
t is 1, 2, 3, 4, or 5; and
u is 1, 2, 3, 4, or 5.
In some embodiments:
X is O or S;
Y is O or S;
$L^1$ and $L^2$ are each independently selected from a bond, $(CR^xR^y)_t$ and $(CR^z)_u$;
Z is N, or $NR^9$;
ring A is $C_{6-10}$ aryl or 5-10 membered heteroaryl;
$R^x$, $R^y$, and $R^z$ are each independently selected from H, halo and $C_{1-6}$ alkyl;
$R^1$, $R^2$, $R^3$, $R^4$, and $R^9$ are each independently selected from H and $C_{1-6}$ alkyl;
each $R^8$ is independently selected from H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^{b1}$, and $NR^{c1}R^{a1}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, OH, and $O(C_{1-6}$ alkyl);
$R^{a1}$, $R^{b1}$, $R^{c1}$ and $R^{d1}$ are each independently selected from halo, $C_{1-6}$ alkyl, $C_{2-6}$ alkenyl, $C_{2-6}$ alkynyl, $C_{1-6}$ haloalkyl, CN, $NO_2$, OH, $O(C_{1-6}$ alkyl), and $S(C_{1-6}$ alkyl);
n is 1, 2, or 3;
t is 1, 2, or 3; and
u is 1, 2, or 3.
In some embodiments:
X is O;
Y is O;
$L^1$ and $L^2$ are each independently selected from a bond, $(CR^xR^y)_t$ and $(CR^z)_u$;
Z is N;

ring A is $C_{6-10}$ aryl or 5-10 membered heteroaryl;
$R^x$, $R^y$, and $R^z$ are each independently H or $C_{1-6}$ alkyl;
$R^1$, $R^2$, $R^3$, $R^4$, and $R^9$ are each independently H or $C_{1-6}$ alkyl;
each $R^8$ is independently selected from H, halo, $C_{1-6}$ alkyl, $C(O)R^{b1}$, and $NR^{c1}R^{d1}$; wherein said $C_{1-6}$ alkyl is optionally substituted with 1 or 2 substituents selected from OH and $O(C_{1-6}$ alkyl);
$R^{a1}$, $R^{b1}$, $R^{c1}$ and $R^{d1}$ are each independently selected from $C_{1-6}$ alkyl and OH;
n is 1 or 2;
t is 1, 2, or 3; and
u is 1, 2, or 3.
In some embodiments:
X is O;
Y is O;
$L^1$ and $L^2$ are each independently selected from a bond, $(CR^xR^y)_t$ and $(CR^z)_u$;
Z is N;
ring A is $C_{6-10}$ aryl;
$R^x$, $R^y$, and $R^z$ are each independently H or $C_{1-6}$ alkyl;
$R^1$, $R^2$, $R^3$, $R^4$, and $R^9$ are each independently H or $C_{1-6}$ alkyl;
each $R^8$ is independently selected from H, halo, $C_{1-6}$ alkyl, $C(O)R^{b1}$, and $NR^{c1}R^{d1}$; wherein said $C_{1-6}$ alkyl is optionally substituted with 1 or 2 substituents selected from OH and $O(C_{1-6}$ alkyl); $R^{a1}$, $R^{b1}$, $R^{c1}$ and $R^{d1}$ are each independently selected from $C_{1-6}$ alkyl and OH;
n is 1 or 2;
t is 1, 2, or 3; and
u is 1, 2, or 3.
In some embodiments:
X is O;
Y is O;
$L^1$ and $L^2$ are each independently selected from a bond, $(CR^xR^y)_t$ and $(CR^z)_u$;
Z is N;
ring A is $C_{6-10}$ aryl;
$R^x$, $R^y$, and $R^z$ are each independently H or $C_{1-6}$ alkyl;
$R^1$, $R^2$, $R^3$, $R^4$, and $R^9$ are each independently H or $C_{1-6}$ alkyl;
each $R^8$ is independently selected from H, halo, $C_{1-6}$ alkyl, $C(O)R^1$, and $NR^{c1}R^{d1}$; wherein said $C_{1-6}$ alkyl is optionally substituted with 1 or 2 substituents selected from OH and $O(C_{1-6}$ alkyl);
$R^{a1}$ and $R^{b1}$ are each independently selected from $C_{1-6}$ alkyl and OH;
n is 1 or 2;
t is 1, 2, or 3; and
u is 1, 2, or 3.
Provided herein also are compounds of Formula II.

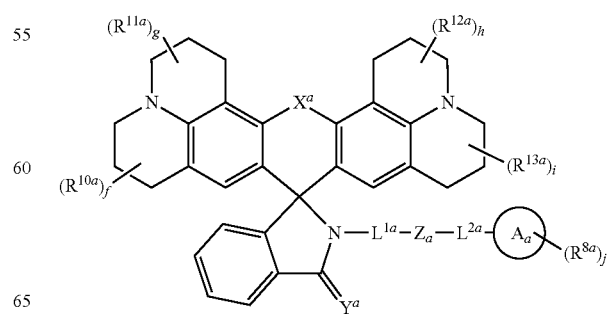

or a pharmaceutically acceptable salt thereof, wherein $X_a$ is O, S, $NR^{5a}$, or $CR^{6a}R^{7a}$;

$Y_a$ is O or S;

$L^{1a}$ and $L^{2a}$ are each independently selected from a bond, $(CR^xR^y)_t$, and $(CR^z)_u$;

$Z_a$ is O, S, N, or $NR^{9a}$;

ring $A_a$ is selected from $C_{6-10}$ aryl, $C_{3-10}$ cycloalkyl, 5-10 membered heteroaryl, and 4-10 membered heterocycloalkyl;

$R^x$, $R^y$, and $R^z$ are each independently selected from H, halo, $C_{1-6}$ alkyl, $C_{2-6}$ alkenyl, $C_{2-6}$ alkynyl, $C_{1-6}$ haloalkyl, $C_{1-6}$ alkoxy, CN, and OH;

$R^{5a}$, $R^{6a}$, $R^{7a}$, $R^{9a}$, $R^{10a}$, $R^{11a}$, $R^{12a}$, and $R^{13a}$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 4-10 membered heterocycloalkyl; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^a$;

$R^{8a}$ is selected from H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $S(O)R^{b1}$, $S(O)NR^{c1}R^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, OH, and $O(C_{1-6}$ alkyl);

$R^a$ is each independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, OH, $O(C_{1-6}$ alkyl), $S(C_{1-6}$ alkyl), $C(O)(C_{1-6}$ alkyl), $C(O)NH(C_{1-6}$ alkyl), $C(O)N(C_{1-6}$ alkyl)$_2$, $C(O)O(C_{1-6}$ alkyl), $OC(O)(C_{1-6}$ alkyl), $OC(O)NH(C_{1-6}$ alkyl), $OC(O)N(C_{1-6}$ alkyl)$_2$, $NH_2$, $NH(C_{1-6}$ alkyl), $N(C_{1-6}$ alkyl)$_2$, and $NHC(O)(C_{1-6}$ alkyl);

$R^{a1}$, $R^{b1}$, $R^{c1}$, and $R^{d1}$ are each independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, OH, $O(C_{1-6}$ alkyl), $S(C_{1-6}$ alkyl), $C(O)(C_{1-6}$ alkyl), $C(O)NH(C_{1-6}$ alkyl), $C(O)N(C_{1-6}$ alkyl)$_2$, $C(O)O(C_{1-6}$ alkyl), $OC(O)(C_{1-6}$ alkyl), $OC(O)NH(C_{1-6}$ alkyl), $OC(O)N(C_{1-6}$ alkyl)$_2$, $NH_2$, $NH(C_{1-6}$ alkyl), $N(C_{1-6}$ alkyl)$_2$, and $NHC(O)(C_{1-6}$ alkyl);

f is 1, 2, 3, 4, or 5;
g is 1, 2, 3, 4, or 5;
h is 1, 2, 3, 4, or 5;
i is 1, 2, 3, 4, or 5;
j is 1, 2, 3, 4, or 5;
t is 1, 2, 3, 4, or 5; and
u is 1, 2, 3, 4, or 5.

In some embodiments, $X_a$ is O.

In some embodiments, $Y_a$ is O.

In some embodiments, $L^{1a}$ is a bond or $(CR^xR^y)_t$. In some embodiments, $L^{1a}$ is a bond.

In some embodiments, $L^{2a}$ is $(CR^z)_u$. In some embodiments, $L^{2a}$ is $(CH)_3$.

In some embodiments, $Z_a$ is N.

In some embodiments, ring $A_a$ is $C_{6-10}$ aryl. In some embodiments, ring $A_a$ is phenyl.

In some embodiments, $R^{8a}$ is selected from H, halo, $C_{1-6}$ alkyl, $C_{2-6}$ alkenyl, $C_{2-6}$ alkynyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, and $NR^{c1}C(O)OR^{a1}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, OH, and $O(C_{1-6}$ alkyl). In some embodiments, $R^{8a}$ is $NR^{c1}R^{d1}$, $NR^{c1}C(O)R^{b1}$, or $NR^{c1}C(O)OR^{a1}$. In some embodiments, $R^{8a}$ is $NR^{c1}R^{d1}$. In some embodiments, $R^{8a}$ is $N(CH_3)_2$.

In some embodiments, $R^{10a}$ is H. In some embodiments, $R^{11a}$ is H. In some embodiments, $R^{12a}$ is H. In some embodiments, $R^{13a}$ is H.

Provided herein are also compounds of Formula III:

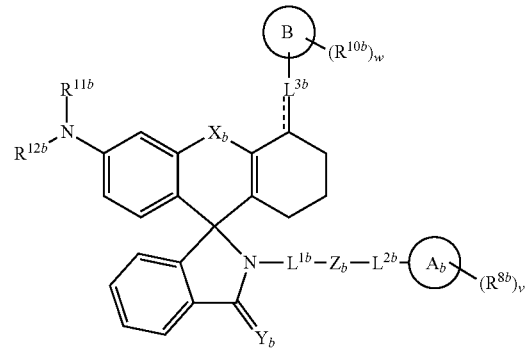

III or a pharmaceutically acceptable salt thereof, wherein

----- is a single or double bond;

$X_b$ is O, S, $NR^{5b}$, or $CR^{6b}R^{7b}$;

$Y_b$ is O or S;

$L^{1b}$ and $L^{3b}$ are each independently selected from a bond, $(CR^xR^y)_t$, and $(CR^z)_u$;

$L^{2b}$ is $(CH)_3$;

$Z_b$ is O, S, N, or $NR^{9b}$;

ring $A_b$ and ring B are each independently selected from $C_{6-10}$ aryl, $C_{3-10}$ cycloalkyl, 5-10 membered heteroaryl, and 4-10 membered heterocycloalkyl;

$R^x$, $R^y$, and $R^z$ are each independently selected from H, halo, $C_{1-6}$ alkyl, $C_{2-6}$ alkenyl, $C_{2-6}$ alkynyl, $C_{1-6}$ haloalkyl, $C_{1-6}$ alkoxy, CN, and OH;

$R^{5b}$ and $R^{9b}$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, and 4-10 membered heterocycloalkyl; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from $R^a$;

$R^{6b}$, $R^{7b}$, $R^{8b}$, $R^{10b}$, $R^{11b}$, and $R^{12b}$ are each independently selected from H, halo, $C_{1-6}$ alkyl, $C_{2-6}$ alkenyl, $C_{2-6}$ alkynyl, $C_{1-6}$ haloalkyl, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $S(O)R^{b1}$, $S(O)NR^{c1}R^{d1}$, $S(O)_2R^{b1}$, and $S(O)_2NR^{c1}R^{a1}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, OH, and $O(C_{1-6}$ alkyl);

$R^a$ is each independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, OH, $O(C_{1-6}$ alkyl), $S(C_{1-6}$ alkyl), $C(O)(C_{1-6}$ alkyl), $C(O)NH(C_{1-6}$ alkyl), $C(O)N(C_{1-6}$ alkyl)$_2$, $C(O)O(C_{1-6}$ alkyl), $OC(O)(C_{1-6}$ alkyl), $OC(O)NH(C_{1-6}$ alkyl), $OC(O)N(C_{1-6}$ alkyl)$_2$, $NH_2$, $NH(C_{1-6}$ alkyl), $N(C_{1-6}$ alkyl)$_2$, and $NHC(O)(C_{1-6}$ alkyl);

$R^{a1}$, $R^{b1}$, $R^{c1}$, and $R^{d1}$ are each independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, OH, $O(C_{1-6}$ alkyl), $S(C_{1-6}$ alkyl), $C(O)(C_{1-6}$ alkyl), $C(O)NH(C_{1-6}$ alkyl), $C(O)N(C_{1-6}$ alkyl)$_2$, $C(O)O(C_{1-6}$ alkyl), $OC(O)(C_{1-6}$ alkyl), $OC(O)NH(C_{1-6}$ alkyl), $OC(O)N(C_{1-6}$ alkyl)$_2$, $NH_2$, $NH(C_{1-6}$ alkyl), $N(C_{1-6}$ alkyl)$_2$, and $NHC(O)(C_{1-6}$ alkyl);

t is 1, 2, 3, 4, or 5;
u is 1, 2, 3, 4, or 5;
v is 1, 2, 3, 4, or 5; and
w is 1, 2, 3, 4, or 5.

In some embodiments, $X_b$ is O.
In some embodiments, $Y_b$ is O.
In some embodiments, $L^{1b}$ is a bond or $(CR^xR^y)_t$. In some embodiments, $L^{1b}$ is a bond.
In some embodiments, $Z_b$ is N.
In some embodiments, ring $A_b$ is $C_{6-10}$ aryl. In some embodiments, ring $A_b$ is phenyl.
In some embodiments, $R^{8b}$ is selected from H, halo, $C_{1-6}$ alkyl, $C_{2-6}$ alkenyl, $C_{2-6}$ alkynyl, $C_{1-6}$ haloalkyl, $OR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, and $NR^{c1}C(O)OR^{a1}$; wherein said $C_{1-6}$ alkyl, $C_{2-6}$ alkenyl, and $C_{2-6}$ alkynyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, OH, and $O(C_{1-6}$ alkyl). In some embodiments, $R^{8b}$ is $NR^{c1}R^{d1}$, $NR^{c1}C(O)R^{b1}$, or $NR^{c1}C(O)OR^{a1}$. In some embodiments, $R^{8b}$ is $NR^{c1}R^{d1}$. In some embodiments, $R^{8b}$ is $N(CH_3)_2$.

In some embodiments, $L^{3b}$ is $(CR^z)_u$. In some embodiments, $L^{3b}$ is $(CH)_2$.

In some embodiments, $R^{10b}$ is $C_{1-6}$ alkyl. In some embodiments, $R^{10b}$ is methyl.

In some embodiments, $R^{11b}$ is $C_{1-6}$ alkyl. In some embodiments, $R^{11b}$ is ethyl.

In some embodiments, $R^{12b}$ is $C_{1-6}$ alkyl. In some embodiments, $R^{12b}$ is ethyl.

In some embodiments, the compound provided herein is complexed to a transition metal. In some embodiments, the transition metal is iron. In some embodiments, the iron is $Fe^{2+}$ or $Fe^{3+}$.

Provided herein includes a compound of the structure:

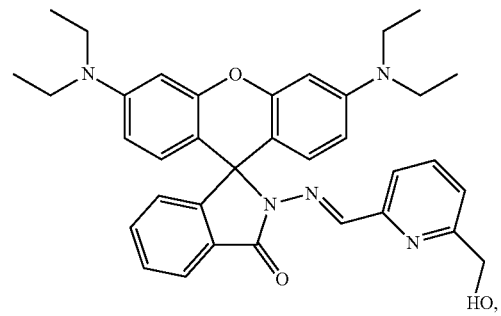

which can also be referred to by its chemical name: (E)-2-(2-((1-(6-acetylpyridin-2-yl)ethylidene)amino)ethyl)-3',6'-bis(diethylamino)spiro[isoindoline-1,9'-xanthen]-3-one or as Rh-PK.

Rh-PK can be a $Fe^{3+}$ probe as it can produce fluorescence when it complexes or chelates to Fe(III). The compound can be stable in low pH's and cell imaging studies (as shown in the Examples) indicate that the compound is capable of detecting basal level $Fe^{+3}$ as well as the dynamic changes in $Fe^{+3}$ levels in live cells at subcellular resolution, with two labile $Fe^{+3}$ pools identified in mitochondria and lysosomes in human primary fibroblast (ws1) cells. The compound exhibits selectivity and sensitivity toward $Fe^{3+}$ as shown in the Examples described herein and rapid fluorescence response with nearly a 12-fold increase in fluorescence emission intensity upon addition of one equivalent $Fe^{3+}$ ion at pH 7.3. Rh-PK is a fluorescent chemosensor that has selective "off-on" fluorescence changes for the detection of $Fe^{3+}$ in solution and in living cells. Rh-Pk exhibits selectivity and sensitivity for $Fe^{3+}$ with an ideal working pH range of 4-9 that covers the desired physiological pH range. The sensor binds to $Fe^{3+}$ at 1:1 (Rh-Pk/$Fe^{3+}$) with relatively high affinity. Complex formation between Rh-PK and $Fe^{3+}$ was found 1:1 ratio with an apparent binding constant $1.54 \times 10^7$ $M^{-1}$. Rh-PK has excellent cell permeability and is non-toxic for cells in the culture experiments as shown in the Examples below. These data are unexpected.

Provided herein includes a compound of the structure:

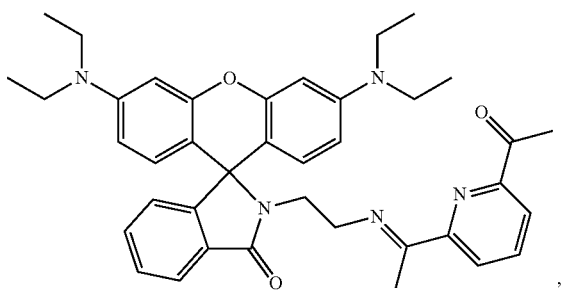 [SMILES: CCN(CC)c1ccc2c(c1)Oc1cc(N(CC)CC)ccc1C21c2ccccc2C(=O)N1CC/N=C(\C)c1cccc(C(C)=O)n1]

which can also be referred to by its chemical name: (E)-3',6'-bis(diethylamino)-2-(((6-(hydroxymethyl)pyridin-2-yl)methylene)amino)spiro[isoindoline-1,9'-xanthen]-3-one or as RhHPA.

RhHPA is a compound that exhibits selectivity and sensitivity toward $Fe^{3+}$. Nearly a 20-fold increase in fluorescence emission intensity was determined upon addition of one equivalent $Fe^{3+}$ in ACN/Tris-HCl buffer at pH 7.3. Complex formation between RhHPA and $Fe^{3+}$ was found 1:1 ratio with an apparent binding constant $1.27 \times 10^7$ $M^{-1}$. The sensor is stable in low pH's and cell imaging studies demonstrated that the sensor is capable of detecting basal level $Fe^{+3}$ as well as the dynamic changes in $Fe^{+3}$ levels in live cells at subcellular resolution, with two labile $Fe^{+3}$ pools identified in mitochondria and lysosomes in bovine aortic endothelial cells (BAEC). RhHPA is a fluorescent chemosensor RhHPA displaying selective "off-on" fluorescence changes for the detection of $Fe^{3+}$ in solution and in primary living cells. RhHPA exhibits selectivity and sensitivity for $Fe^{3+}$ with an improved working pH profile (pH 5-9) that covers most of the physiological pH range. RhHPA has excellent cell permeability and is non-toxic for cells in the culture experiments. See Examples provided herein. These data are unexpected.

Provided herein includes a compound of the structure:

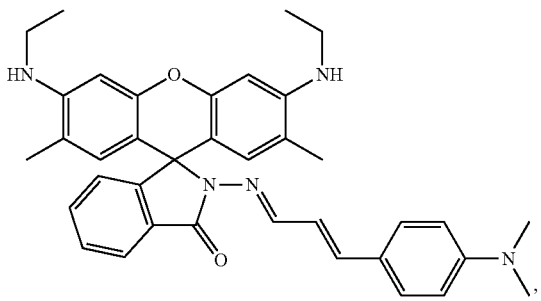

which can also be referred to by its chemical name: 2-(((1E, 2E)-3-(4-(dimethylamino)phenyl)allylidene)amino)-3',6'-bis(ethylamino)-2',7'-dimethylspiro[isoindoline-1,9'-xanthen]-3-one or as Rh6GD.

Rh6GD was developed using rhodamine as the fluorophore and N,N-dimethylaminocinnamaldehyde (DMACA) as the binding moiety for $Fe^{2+}$ ion. The sensor gives distinct rapid and reversible 3-fold fluorescence enhancement response to $Fe^{2+}$ with little interference from other biologically relevant metal ions. The sensor forms a 2:1 complex with $Fe^{2+}$ in solution with an apparent binding constant $1.8 \times 10^{11}$ $M^{-2}$ 2D NMR and FT-IR studies suggest a novel $Fe^{2+}$ coordination mode for the sensor Rh6GD which may explain its excellent selectivity for $Fe^{2+}$. This coordination involves O, N and C=C ($\eta$-2 $\pi$-coordination) as the donor atoms from the sensor that coordinate with $Fe^{2+}$, with the formation of a 5-membered chelating ring and a 5.5-membered chelating ring. As $Fe^{2+}$ is a borderline Lewis acid in the "HSAB" (hard, soft acid and base) classification, this combination of ligands (O, N and C=C $\pi$-coordination) provide a borderline Lewis base to match the borderline Lewis acid $Fe^{2+}$. Metal-$\pi$ bond coordination is less common however it has been known in transition metal alkene complexes and $\pi$-coordinated $Fe^{2+}$-diene complexes have been observed. This coordination involving a $\eta$-2 $\pi$-binding is unlikely to occur with $Fe^{3+}$ or other physiologically relevant metal ions thus the sensor has selectivity for $Fe^{2+}$. Confocal experiments with live human fibroblast ws1 cells demonstrated that Rh6GD has the capability of detecting endogenous basal level $Fe^{2+}$, as well as the dynamic changes in cellular $Fe^{2+}$ levels, i.e., externally supplemented $Fe^{2+}$ or under $Fe^{2+}$ depleting conditions. Colocalization experiments demonstrate that Rh6GD detects labile $Fe^{2+}$ pools in mitochondria and lysosomes of ws1 cells and no significant $Fe^{2+}$ ions are detected in the cytosol. This novel $Fe^{2+}$-sensor is useful for studying the cell biology of $Fe^{2+}$ in live cells.

Provided herein includes a compound of the structure:

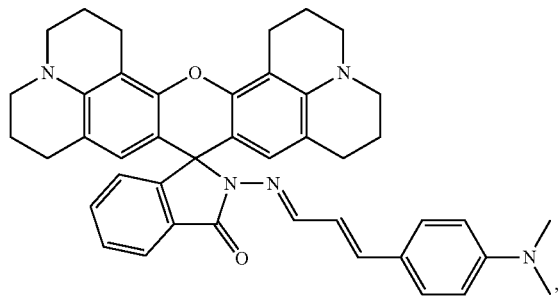 [SMILES: CN(C)c1ccc(/C=C/C=N/N2C(=O)c3ccccc3C23c2cc4c5c(c2Oc2c3cc3c6c2CCCN6CCC3)CCCN5CCC4)cc1]

which can also be referred to as Rh101D.

Rh101D gives a rapid distinct and reversible fluorescence response upon the alteration of intracellular $Fe^{2+}$ levels with little interference from other biologically relevant metal ions. As the same $Fe^{2+}$-binding moiety was used as that of in Rh6GD, Rh101D adopts the same coordination mode with $Fe^{2+}$, however, in contrast to the 2:1 (sensor to Fe) stoichiometry found in the low-spin Fe(II)-complex with Rh6GD, the Fe(II)-complex of Rh101D is 1:1 (sensor to Fe) stoichiometry. It is likely that the bulky ring system in the Rh101 moiety prevents it from forming a 2:1 complex and the remaining coordination sites on FeII is filled with small ligands (DMSO, Tris, $NH_4^+$, $H_2O$, $OH^-$, etc) in the solution. These oxygen/nitrogen-based small ligands are not able to provide a strong enough ligand field as that from the pair of N and C=C donors, the Fe(II) thus could adopt a paramagnetic high-spin state. Confocal experiments with live bovine aortic endothelial cells (BAEC) cells demonstrated that Rh101D has the capability of detecting endogenous basal level $Fe^{2+}$, as well as the dynamic changes in cellular $Fe^{2+}$ levels, i.e., externally supplemented $Fe^{2+}$ or under $Fe^{2+}$ depleting conditions. Colocalization experiments showed that the labile $Fe^{2+}$ pools detected by Rh101D are located in mitochondria and lysosomes of BAEC cells. The ratiometric sensor Rh101D enables the direct determination of endogenous labile $Fe^{2+}$ concentration in HCT-116 cells for the first time, with a value of ~10±1 μM determined in the mitochondria of untreated cells, 14±1 μM in the mitochondria of Fe (II) treated cells, and 7±1 μM in the mitochondria of Fe(II)-chelator Bpy treated cells and ~8±1 μM determined in the lysosomes of untreated cells, 11±1 μM in the lysosomes of Fe (II) treated cells, and 5±1 μM in the lysosomes of Bpy treated cells.

Provided herein includes a compound of the structure:

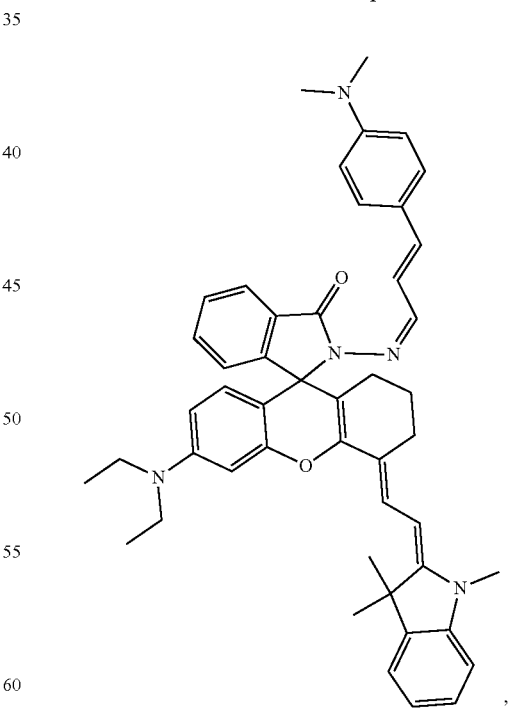

which can also be referred to by its chemical name: (E)-6'-(diethylamino)-2-(((1Z,2E)-3-(4-(dimethylamino)phenyl) allylidene)amino)-4'-(2-((E)-1,3,3-trimethylindolin-2-ylidene)ethylidene)-1',2',3',4'-tetrahydrospiro[isoindoline-1, 9'-xanthen]-3-one or as NIRh-Fret.

NIRh-Fret is a near infrared sensor that can absorb and emit in the near infrared region thus display low auto fluorescence background, deeper penetration to tissues and cause less damage to biological samples. The NIRh-Fret sensor gives a distinct rapid and reversible 10 times fluorescence enhancement response upon the alteration of intracellular $Fe^{2+}$ levels with little interference from other biologically relevant metal ions. Confocal experiments with live bovine aortic endothelial cells (BAEC) cells demonstrated that NIRh-Fret has the capability of detecting endogenous basal level $Fe^{2+}$, as well as the dynamic changes in cellular $Fe^{2+}$ levels with labile $Fe^{2+}$ pools located in mitochondria and lysosomes of BAEC cells. The ratiometric sensor NIRh-Fret enables the direct determination of endogenous labile $Fe^{2+}$ concentration ws1 cells, with a value of ~8±1 µM determined in the mitochondria of untreated cells, 12±1 µM in mitochondria of Fe (II) treated cells, and 5±1 µM in the mitochondria of Bpy treated cells. Lysosomal $Fe^{2+}$ levels were determined as 7±1 µM in untreated cells, 10±1 µM in Fe (II) treated cells, and 5±1 µM in Bpy treated cells. Cytosol $Fe^{2+}$ levels are low but are significantly higher than that of the background. Below 1 µM was determined in the cytosol of untreated cells, 3-4 µM in the cytosol of Fe (II) treated cells, and ~0 µM in the cytosol of Bpy treated cells. Labile $Fe^{2+}$ concentrations in HT-29 cells were determined to be ~11±1 µM in the mitochondria of untreated cells, 15±1 µM in the mitochondria of Fe (II) treated cells, and 9±1 µM in the mitochondria of Bpy treated cells. Lysosomal $Fe^{2+}$ levels were determined as ~9±1 µM determined in untreated cells, 13±1 µM in Fe (II) treated cells, and 6±1 µM in Bpy treated cells. Again, below 1 µM determined in the cytosol of untreated HT-29 cells, 4-5 µM in the cytosol of Fe (II) treated cells, and 0 µM in the cytosol of Bpy treated cells.

Certain features of the disclosure, for clarity, which described in the context of separate embodiments, can also be provided in combination in a single embodiment. Conversely, various features of the disclosure which are, for brevity, described in the context of a single embodiment, can also be provided separately or in any suitable subcombination.

At various places in the present disclosure, substituents of compounds are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present disclosure, various aryl, heteroaryl, cycloalkyl, and heterocycloalkyl rings are described. Unless otherwise specified, these rings can be attached to the rest of the molecule at any ring member as permitted by valency. For example, the term "a pyridine ring" may refer to a pyridin-2-yl, pyridin-3-yl, or pyridin-4-yl ring.

The term "n-membered" where n is an integer is used herein to describe the number of ring-forming atoms in a group where the number of ring-forming atoms is n.

When a variable for compounds provided herein appears more than once, the variable can be a different moiety independently selected from the group defining the variable. For example, where a formula is described as having two R groups that are simultaneously present on the same compound, the two R groups can represent different moieties independently selected from the group defined for R.

As used herein, "alkyl" refers to branched and straight-chain saturated hydrocarbon groups. For example, $C_{1-6}$ alkyl refers to an alkyl group having one to six carbon atoms. Examples of alkyl include, but are not limited to, methyl, ethyl, n-propyl, isopropyl, n-butyl, isobutyl, sec-butyl, t-butyl, n-pentyl, 2-methyl-1-butyl, 3-pentyl, n-hexyl, etc.

As used herein, "alkenyl" refers to straight or branched hydrocarbon chains having one or more carbon-carbon double bonds. For example, $C_{2-6}$ alkenyl refers to an alkenyl group having two to six carbon atoms. Examples of alkenyl include, but are not limited to, ethenyl, n-propenyl, isopropenyl, n-butenyl, etc.

As used herein, "alkynyl" refers to straight or branched hydrocarbon chains having one or more carbon-carbon triple bonds. For example, $C_{2-6}$ alkynyl refers to an alkynyl group having two to six carbon atoms. Examples of alkynyl include, but are not limited to, ethynyl, propynyl, etc.

As used herein, "halo" refers to halogen includes fluoro, chloro, bromo, and iodo. In certain embodiments, halo is fluoro or chloro.

As used herein, "haloalkyl" refers to branched or straight-chain saturated hydrocarbon groups substituted with one or more halogen, which may either be the same or different. Examples of haloalkyl groups include trifluoromethyl, difluoromethyl, pentafluoroethyl, trichloromethyl, etc.

As used herein, "alkoxy" refers to an alkyl group attached through an oxygen atom (—O-alkyl). Examples of alkoxy groups include methoxy, ethoxy, propoxy, t-butoxy, etc.

As used herein, "cycloalkyl" refers to a non-aromatic cyclic hydrocarbon groups. Cycloalkyl groups can include mono- or polycyclic (e.g., fused, bridged, or spiro) ring systems. Cycloalkyl groups can also include one or more aromatic rings fused to the cycloalkyl ring. The ring-forming carbon atoms of a cycloalkyl group can be optionally substituted by oxo. In certain embodiments, the cycloalkyl group is monocyclic. Examples of cycloalkyl groups include cyclopropyl, cyclobutyl, cyclopentyl, cyclohexyl, cycloheptyl, cyclopentenyl, cyclohexenyl, etc. As used herein, "heterocycloalkyl" refers to a non-aromatic ring, which has at least one heteroatom ring member independently selected from nitrogen, sulfur, and oxygen. Heterocycloalkyl groups can include mono- or polycyclic (e.g., fused, bridged, or spiro) ring systems. Heterocycloalkyl also includes one or more aromatic rings fused to the non-aromatic heterocycloalkyl ring. The ring-forming carbon atoms of a heterocycloalkyl group can be optionally substituted by oxo. The ring-forming heteroatoms of the heterocycloalkyl group can be oxidized to form an N-oxide or a sulfonyl group. Examples of heterocycloalkyl group include morpholine ring, pyrrolidine ring, piperazine ring, piperidine ring, tetrahydropyran ring, tetrahyropyridine, azetidine ring, tetrahydrofuran, etc.

As used herein, "aryl" refers to a monocyclic or polycyclic aromatic hydrocarbon rings. Examples of aryl include phenyl and naphthyl, etc.

As used herein, "heteroaryl" refers to a monocyclic or polycyclic aromatic hydrocarbon ring with one or more heteroatom ring members independently selected from nitrogen, sulfur and oxygen. Examples of heteroaryl include pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, etc. The ring-forming carbon atoms of a heteroaryl group can be optionally substituted by oxo; the ring-forming heteroatoms of the heteroaryl group can be oxidized to form an N-oxide or a sulfonyl group, provided the aromaticity of the ring is preserved.

The compounds provided herein can include one or more isotopes. Isotopes include those atoms having the same atomic number but different mass numbers. For example, isotopes of hydrogen include tritium and deuterium. Isotopes of carbon include $^{13}C$ and $^{14}C$. Compounds of presented herein can be substituted with e.g., one or more deuterium atoms.

As used herein, "pharmaceutically acceptable" refers to compounds, materials, compositions, and/or dosage forms which are, within the scope of sound medical judgment, suitable for administration to a human, e.g., use in contact with the tissues of human beings and animals without excessive toxicity, irritation, allergic response, or other problem or complication, commensurate with a reasonable benefit/risk ratio.

As used herein, "salt" refer compound that is modified by making acid or base salts thereof. The term "pharmaceutically acceptable salts" refers to salts of the compounds provided herein that are suitable for administration to a human or animals. Examples of salts e.g., pharmaceutically acceptable salts, include mineral or organic acid salts of basic residues such as amines; alkali or organic salts of acidic residues such as carboxylic acids; and the like. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

As used herein, "treating" or "treatment" refers to (a) inhibiting the disease, condition, or disorder in an individual; and/or (b) ameliorating the disease, condition, or disorder in an individual, i.e., causing regression of the disease, condition, or disorder.

Pharmaceutical Formulation and Administration

The compounds provided herein can be useful in studying $Fe^{3+}$ in living systems as well as diseases related to abnormal iron metabolism and various other diseases that are associated with alterations in iron levels or localization. The compounds provided herein are also useful for biomedical research and monitoring diseases and drug effectiveness. The compounds provided herein can be incorporated into any suitable carrier prior to use. The dose of the compound, mode of administration and choice and use of suitable carriers will depend upon the intended recipient and target organism.

Provided herein are compositions comprising a compound described herein and one or more excipient or carrier. The excipient and carrier are "acceptable" or "pharmaceutically acceptable" in that they are compatible with the other ingredients of the formulations and not harmful to the recipient. Some examples of suitable excipients and carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose.

A composition described herein should be formulated to be compatible with its intended route of administration. Examples of routes of administration include oral, parenteral, for example, intravenous, intradermal, inhalation, transdermal (topical), transmucosal, and rectal administration.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Formulations can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Compositions can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). Suitable carriers include physiological saline, bacteriostatic water, Cremophor EL™ (BASF, Parsippany, N.J.) or phosphate buffered saline (PBS).

Compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals. The compositions can be formulated in a unit dosage form, each dosage containing from about 1 to about 1000 mg, more usually about 10 to about 500 mg, of the compound provided herein.

Uses of the Compounds

A method of monitoring iron, e.g., determining concentration and/or subcellular localization of iron, e.g., $Fe^{2+}$, in living cells comprising contacting said cells with an effective amount of a compound provided herein or a pharmaceutically acceptable salt thereof. The compound provided herein can complexed (chelated) to the iron in the cell and the resulting complex can produce fluorescence (e.g., upon exposure to a light source). The fluorescence can be reversible. These compounds or sensors are all based in a "coordination-induced fluorescence activation (CIFA)" process. In the absence of ferrous ion ($Fe^{2+}$), these fluorescent probes have little to no fluorescent signal after being excited by a proper light source. However, in the presence of ferrous ion ($Fe^{2+}$), a coordination between ferrous ion ($Fe^{2+}$) and the probe occurs and thus activates the fluorescence of the probe. These fluorescent probes have an increase in fluorescent signal following proper excitation by a light source. The sensors are able to distinguish the oxidation states of iron and have response to only ferrous ions. The fluorescence triggered by $Fe^{2+}$ is reversible. Upon the $Fe^{2+}$ level is lowered, the fluorescence is decreased (activated by $Fe^{2+}$ deactivated by remove of $Fe^{2+}$). Moreover, the sensors have rapid fluorescence responses to $Fe^{2+}$ and is capable of monitor $Fe^{2+}$ in real time in living systems as well as the intracellular trafficking of $Fe^{2+}$ in live cells. Similarly, the $Fe^{3+}$ sensors have response to only ferric ions and are capable of monitor $Fe^{3+}$ in real time in living systems as well as the intracellular trafficking of $Fe^{3+}$ in live cells.

A few of the developed sensors absorb and emit light in the visible region while a few others absorb and emit in the near-infrared (NIR) region. The ones that absorb and emit in the near-infrared region are capable of use for in vivo imaging because they circumvent issues of auto fluorescence and signal attenuation by biological tissues. A few of these NIR probes have been used to detect labile ferrous ions in zebrafish. The currently available probes have been mostly limited to detection of exogenously added $Fe^{2+}$ in cells. None of the current $Fe^{2+}$-detection systems is capable of detecting native $Fe^{2+}$ in live cells or at subcellular resolution, nor of determining the concentration of labile $Fe^{2+}$ in cells. Moreover, there are no NIR iron sensors, which are needed for detection in animals. Use of the present NIR Fe(II) probes is the first example of the use of fluorescent sensors for the detection of iron ions in a living animal. The sensors have specificity and sensitivity that can detect labile ferric ions at subcellular resolution in living cells with two pools of labile $Fe^{2+}$ located in mitochondria and lysosomes in various cell lines (including cancer cells) and primary cells from human and animals.

The compounds provided herein can be stable in low pH's such as pH of about 4-9 or about 5-9. Unexpectedly, cell imaging studies (as shown in the Examples) indicate that the compounds described herein are capable of detecting basal levels of $Fe^{2+}$ (or $Fe^{+3}$) as well as dynamic changes in $Fe^{2+}$ (or $Fe^{+3}$) levels in live cells at subcellular resolution.

The compounds provide herein are useful for studying or monitoring the roles that iron plays in living systems under various circumstances, such as dietary changes, excises and under medication, as well as the roles iron plays in the development and progression of many diseases. The monitoring of irons in cells and in subjects can be carried out using laser confocal microscopy (see Examples). For example, the monitoring of irons in zebrafish can be imaged by a LSM710 confocal microscope (see Examples). The compounds provided herein are nontoxic, they can be used in humans to diagnose diseases or determine efficacy of treatments for various diseases such as chelation therapy. The compounds provided herein can be Fe(III) and Fe(II) chelators and the chelation can be reversible and thus, the compounds provided herein can also be useful to regulate the level of Fe(III) and Fe(II) in a subject. The compounds provided herein can be used to treat diseases associated with iron imbalance.

The compound provided herein can also be useful in treating a disease associated with iron dyshomoestasis, which includes administering an effective amount of an agent suitable for treating said disease and a compound provided herein or a pharmaceutically acceptable salt thereof to monitor the effectiveness of said treatment. For example, the compounds provided herein can be used in monitoring the effectiveness of deferoxamine, deferiprone and deferasirox (Exjade), which are used for the treatment of patients with iron overload or thalassemia syndromes. Examples of diseases associated with iron dyshomoestasis include anemia, hemochromatosis, metabolic syndrome, atherosclerosis, cardiovascular diseases, cancer, type 2 diabetes, kidney disease, osteoporosis, osteopenia, hepatocellular carcinoma, liver disease, sarcopenia, hepatitis C, non-alcoholic fatty liver disease (NAFLD), non-alcoholic steatohepatitis (NASH), Alzheimer's, and neurodegenerative disease.

Furthermore, the compounds provided herein are suitable for sensitive and specific ratiometric probes for the quantification of labile ferric ions in living systems. The ratiometric probes enables the determination of the absolute concentrations of labile ferrous or ferric ions in living cells. The sensitivity of the sensors allows the determination of labile ferrous or ferric ion concentration at subcellular resolution.

The compounds provided herein are non-toxic and thus can be useful in studying $Fe^{3+}$ (or $Fe^{2+}$) in living systems as well as diseases related on abnormal iron metabolism and various other diseases that are found to have alterations in iron levels or localization. The compounds provided herein are also useful for biomedical research and monitoring diseases and drug effectiveness.

Kits

The present disclosure also provides kits, e.g., pharmaceutical kits useful in live-cell imaging and treatment of disease associated with iron dyshomoestasis, which include one or more containers containing a composition comprising an effective amount of a compound of the provided herein. The kits can further include one or more of various conventional kit components, e.g., containers with one or more carriers, additional containers, etc. The kit can also instructions (e.g., as inserts or as labels) indicating quantities of the components to be administered, guidelines for administration, and/or guidelines for mixing the components.

EXAMPLES

The invention will be described in greater detail by specific examples. The following examples are offered for illustrative purposes, and are not intended to limit the invention in any manner. Those of skill in the art will readily recognize a variety of non-critical parameters which can be changed or modified to yield essentially the same results.

Example 1. Synthesis of Rh-PK

Materials and Methods

The following materials and methods were used in the Examples set forth below.

Rhodamine B base was purchased from Sigma-Aldrich and the other chemicals and solvents that used in the experiments were purchase commercially. Rhodamine B ethylenediamine was synthesized according to the published procedure in Z. Ma, et al., Tetrahedron Letters, 2013, 54, 6504-6506. Rhodamine hydrizide and 6-hydroxymetyl-pyridine-2-aldehyde were synthesized according to literature methods. V. Dujols, et al., Journal of American Chemical Society 119(1997) 7386.

The characterization of the synthesized fluorescent sensor Rh-PK was based on analysis of $^1H$, $^{13}C$ NMR, ESI-MS, Fluorescence spectra and UV/Vis spectra. $^1H$ and $^{13}C$ NMR spectra were recorded on a Bruker DRX-300 spectrometer at ambient probe temperature, 298 K. Chemical shifts are reported in delta (δ) unit per million (ppm) downfield tetramethylsilane. Splitting patterns are abbreviated as follows: s, singlet; d, doublet; t, triplet; q, quartet; m, multiplet; br, broad. ESI-MS analyses were performed on a PerkinElmer API 150EX mass spectrometer. UV/Vis spectra were recorded on a Perkin-Elmer Lambda 25 spectrometer at 298

K. Fluorescence spectra were recorded on a Perkin-Elmer LS55 luminescence spectrometer at 298 K. Excitation and emission slit was 5.0 nm and emission spectra were collected 530 nm-700 nm after excited at 510 nm. The pH measurements were carried out on a Corning pH meter equipped with a Sigma-Aldrich micro combination electrode calibrated with standard buffer solution. The fluorescence response of the probe in living cells was investigated under a Zeiss LSM 710 laser scanning confocal microscope.

The characterization of the synthesized fluorescent sensor RhHPA was based on the analysis of $^1$H NMR, $^{13}$C NMR, ESI-MS, Fluorescence spectra and UV/Vis spectra. The NMR spectra were recorded on a Bruker Ascend 400 MHz digital spectrometer (Bruker Daltonics GmbH, Switzerland) using $CDCl_3$ as the solvent and tetramethylsilane (TMS) as an internal standard. The electron impact (ESI) mass spectra (70 eV) were obtained on a Perkin-Elmer system. Fluorescence measurements were performed on a Perkin Elmer LS-55 luminescence spectrophotometer. The absorbance was measured at PerkinElmer LAMBDA 25 UV/Vis.

To record pH measurements, PHS-SC instrument was used. To prepare the solutions of metal ions, the nitrate or chloride salts of $Na^+$, $K^+$, $Ca^+$, $Mg^{2+}$, $Cr^{3+}$, $Hg^{2+}$, $Cu^{2+}$, $Pb^{2+}$, $Zn^{2+}$, $Co^{2+}$, $Ni^{2+}$, $Cd^{2+}$, and $Ag^+$ dissolved in the distilled water were employed, respectively. $Fe^{3+}$, $Fe^{2+}$ solutions were prepared freshly from ferric chloride, ferrous ammonium sulfate (FAS, Fe $(NH_4)_2(SO_4)_2$, respectively in 0.01 M HCl.

2,6-diacetyl pyridine (200 mg, 1.23 mmol) was dissolved in ethanol (20 ml). Rhodemine B ethylene diamine (200 mg, 0, 48 mmol) dissolved in ethanol (40 ml) was added dropwise to the 2,6-diacetyl pyridine solution over 2 h. The mixture was refluxed and stirred overnight. After the mixture was cooled to room temperature, the solvent was evaporated and resulting crude product purified via column chromatography using an ethyl acetate/hexane (2;1) to obtain the sensor, Rh-PK (91 mg, 35% yield). $^1$H NMR ($CDCl_3$, 300 MHz) δ(ppm): 8.68 (d, 1H), 8.15 (d, 1H), 7.80-7.11 (m, 8H), 6.92-6.60 (m, 3H), 5.50 (s, 1H), 3.62 (d, 3H), 2.71 (t, 2H), 2.46-2.30 (m, 4H), 1.82 (s, 8H), 1.28 (t, 12H). $^{13}$C NMR ($CDCl_3$, 75 MHz) δ(ppm): 200.1, 199.3, 168.2, 166.7, 156.5, 153.8, 153.3, 152.6, 151.9, 148.7, 137.9, 136.9, 132.3, 131.1, 128.02, 124.7, 124.3, 123.7, 122.7, 121.7, 108.04, 105.6, 97.7, 64.8, 58.1, 50.5, 44.3, 40.9, 25.5, 18.4, 13.4, 12.5. ESI-MS. found: m/z=630.2 $[M+1]^+$, calcd for $C_{39}H_{43}N_5O_3$=629.4

Example 2. Cell Culture and Confocal Studies

Human SH-SY5Y neuroblastoma cells and primary fibroblast ws1 cells were obtained from ATCC (American Type Culture Collection). Cells were maintained in a 1:1 mixture of Eagle's Minimal Essential medium (ATCC) and Ham's F12 medium (ATCC) supplemented with 10% fetal bovine serum (FBS, ATCC) without antibiotics and incubated at 37° C. in a humidified 5% $CO_2$ atmosphere. The cells were routinely sub-cultured using 0.05% trypsin-EDTA solution (ATCC). The cells were seeded onto 2-chamber slides for 48 h at 5×10$^4$ cells/chamber and grown until each chamber was 20-30% confluent. A stock solution of Rh-PK (10 mm in DMS) was diluted to a concentration of 10 mm in culture medium without FBS. Cell culture medium was removed from the chambers and replaced with fresh medium containing Rh-PK (5-10 mm). The fluorescence responses of the sensor in living cells were measured under a Zeiss LSM 710 laser scanning confocal microscope. For images with the Rh-PK sensor, the excitation wavelength of the laser was 543 nm and emission was integrated over the range 547-703 nm. For images with MitoTracker Green FM, LysoTracker BlueDND-22 and Hoechst 33258, the excitation wavelengths recommended by the manufacturer were used (490 nm for MitoTracker, 373 nm for LysoTracker and 350 nm for Hoechst 33258). Emissions were integrated at 492-548 nm (MitoTracker), 409-484 nm (LysoTracker) and 426-535 nm (Hoechst 33258), respectively. The REUSE function controlled by Zeiss software was applied to guarantee that all spectra were recorded under the same instrumental conditions.

Example 3. Spectroscopic Studies

One of the disadvantages of Rhodamine-based sensors is that spirolactone of sensors gives response to hydrogen ions. The pH response of Rh-PK in ACN/water solution (3/1) was evaluated and the data are shown in FIG. 1, which shows the variation of fluorescence intensity of Rh-PK and Rh-PK+ $Fe^{3+}$ (100 μM, the absorption intensity was measured at 580 nm) at various pH values in $ACN/H_2O$ (3/1, v/v) solution. pH was adjusted by HCl and NaOH. The acid-base UV-Vis and fluorescent experiments revealed that Rh-PK did not show any obvious changes in UV-Vis or fluorescence (excited 510 nm) in the pH range 4 to 9, suggesting that it can be studied in biological pH with a very low background fluorescence. ACN/Tris-HCl buffer (10 mM, pH 7.3, v/v 3;1) was used for in vitro experiments.

Figure 2:
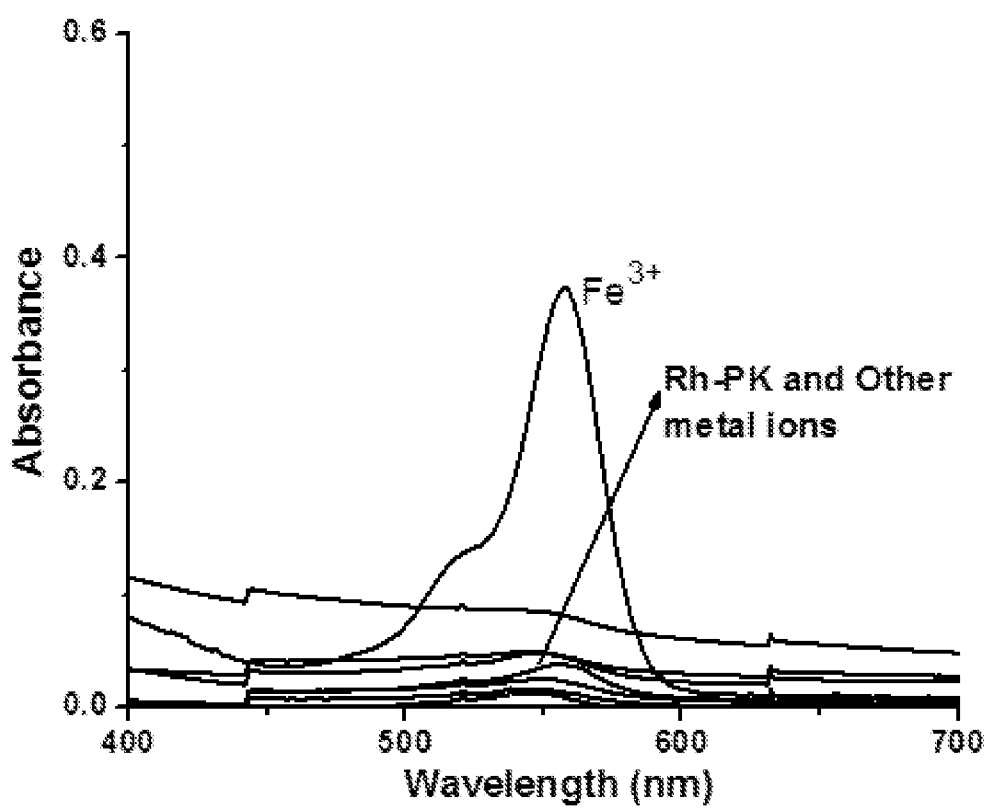
FIG. 2 shows absorbance spectra of 100 µM Rh-PK sensor with various metal ions in the ACN/Tris buffer.

The spectroscopic properties of Rh-PK and its interactions with various metal ions were evaluated in acetonitrile (ACN)/Tris-HCl buffer (10 mM, pH 7.3, v/v, 3:1). The colorless compound Rh-PK displays almost no absorption peak in the visible wavelength range (>400 nm). The changes in UV-Vis spectra after the addition of various ions are shown in FIG. 2, which is an absorbance spectrum of 100 μM sensor with various metal ions (100 μM for $Ni^{+2}$, $Cu^+$, $Cu^{+2}$, $Zn^{+2}$, Pb, $Fe^{+2}$, $Fe^{+3}$, $Cr^{+3}$, $Hg^{+2}$, $Mn^{+2}$, $Ag^+$, and $Co^{+2}$; 200 μM for $K^+$, $Na^+$, $Ca^{2+}$ and $Mg^{2+}$) in the ACN/Tris buffer (10 mM, pH 7.3, v/v 3:1). Only the addition of $Fe^{3+}$ to the solution of Rh-PK showed an obvious red color with an absorption peak at 555 nm (ε=3.2×10$^3$ M$^{-1}$ cm$^{-1}$ and (Φ=0.173) in ACN/Tris-HCl buffer (10 mM, pH 7.3, v/v 3:1). Compared with that of $Fe^{3+}$, other metal ions, $Zn^{2+}$, $Cr^{3+}$, $Ni^{2+}$, $Hg^{2+}$, $Mn^{2+}$, $Ag^+$, $Pb^{2+}$, $Fe^{2+}$, $Cu^+$, $Cu^{2+}$, $Co^{2+}$, $Na^+$, $K^+$, $Mg^{2+}$ and $Ca^{2+}$ did not induce any changes in UV-Vis absorption.

Figure 3:
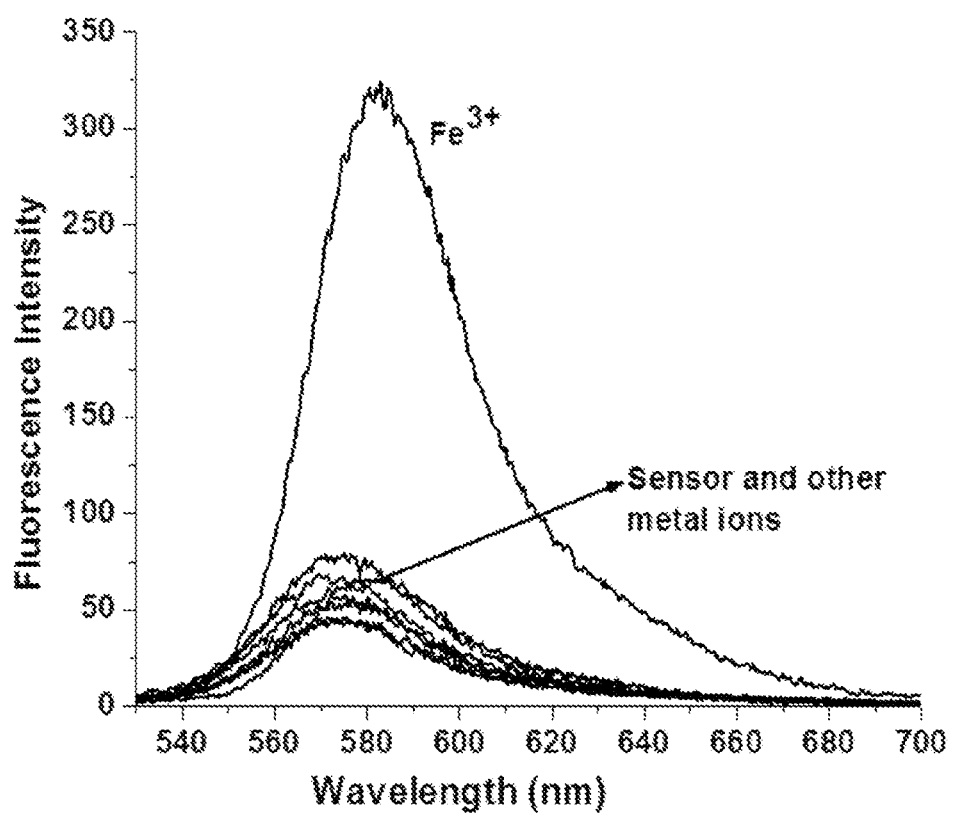
FIG. 3 shows fluorescence spectra of 100 µM Rh-PK sensor with various metal ions in the ACN/Tris buffer.

The fluorescence responses of Rh-PK to different metal ions are shown in FIG. 3, which shows a fluorescence response ($\lambda_{Ex}$ 510 nm) of 100 μM sensor with various metal ions (100 μM for $Ni^{+2}$, $Cu^+$, $Cu^{+2}$, $Zn^{+2}$, Pb, $Fe^{+2}$, $Fe^{+3}$, $Cr^{+3}$, $Hg^{+2}$, $Mn^{+2}$, $Ag^+$, and $Co^{+2}$; 200 μM for $K^+$, $Na^+$, $Ca^{2+}$ and $Mg^{2+}$) in the ACN/Tris buffer (10 mM, pH 7.3, v/v 3:1). The colorless sensor Rh-PK shows very weak fluorescence at 580 nm in the absence of metal ions. When $Fe^{3+}$ was added into the solution of Rh-PK, a significant enhancement of fluorescence (>12-fold with 1.0 equiv of $Fe^{3+}$) was observed. These data demonstrate that Rh-PK is a highly specific turn-on fluorescent sensor for $Fe^{3+}$.

Figure 4:
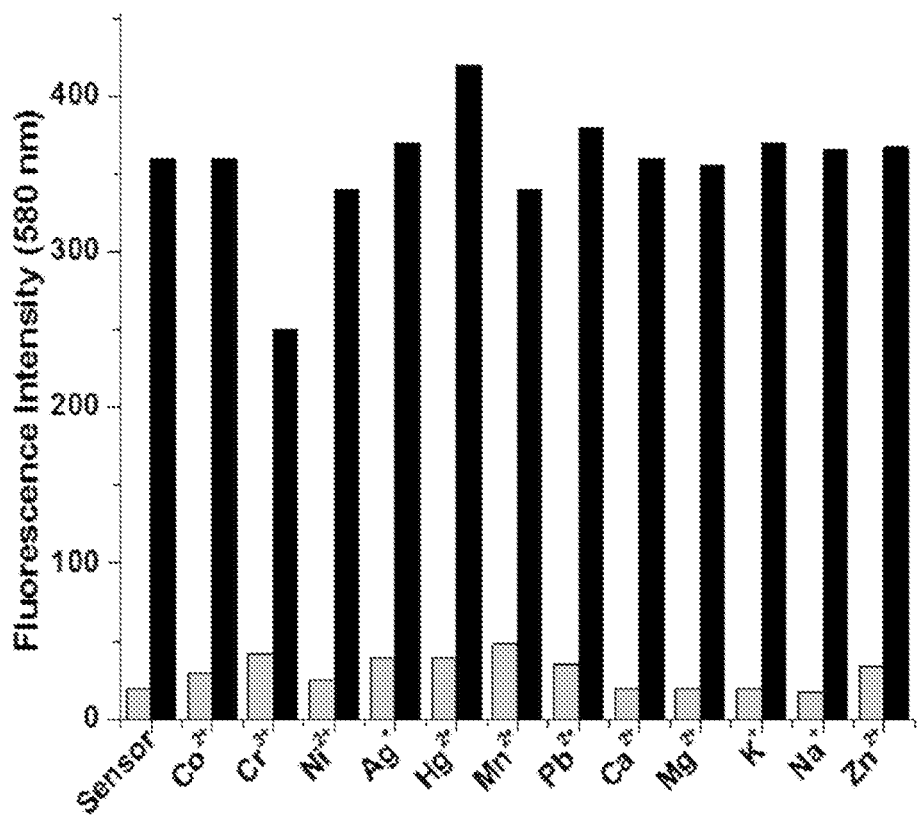
FIG. 4 is a bar graph showing the fluorescence responses of 100 µM Rh-PK sensor in the presence of various metal ions (gray bar) and the subsequent addition of $Fe^{3+}$ (black bar) in ACN/Tris-HCl buffer.

The interferences from the other metal ions with Rh-PK in its response to $Fe^{3+}$ was examined. The 12 metal ions tested do not turn-on the color or the fluorescence of Rh-PK. Each of the 12 metal ions was pre-incubated with Rh-PK before 1 equiv. of $Fe^{3+}$ was added, the fluorescence response was then measured. FIG. 4 shows the fluorescence responses of 100 μM sensor in the presence of various metal ions (gray bar) and the subsequent addition of $Fe^{3+}$ (black bar) in ACN/Tris-HCl buffer (10 mM, pH 7.3, v/v 3:1); the bars represent the fluorescence intensity at 580 nm. As shown in FIG. 4, the fluorescent intensity of Rh-PK with $Fe^{3+}$ is not affected significantly in the presence of any of the other metal ions tested, demonstrating little interferences from the other metal ions.

Example 4. Binding Studies

Job's method and UV-vis spectra were applied to study the binding stoichiometry between Rh-PK and $Fe^{3+}$ and monitored by the absorbance at 555 nm. The titration curve (a plot of Rh-PK versus $Fe^{3+}$ concentration) increased linearly and plateaued at 1:1 ratio of the sensor and $Fe^{3+}$, suggesting the formation of a 1:1 $Fe^{3+}$—Rh-PK complex. The binding constant of this complex was calculated following a method reported previously (G. E. Tumambac, et al., Tetrahedron 2004, 60, 11293-11297), using absorption values at 713 nm by the equations described below, and was determined to be $1.54 \times 10^7$ $M^1$.

The apparent binding constant K can then be calculated from $$K = \frac{F_c}{1-F_c} \times \frac{1}{[S]_e}$$

The Job's plot using a total concentration of 100 µM Rh-PK and $Fe^{3+}$ in ACN/Tris-HCl buffer (10 mM, pH 7.32, v/v 3:1) solution exhibited a maximum absorbance when the molecular fractions of $Fe^{3+}$ and Rh-PK were close to 50% suggesting a 1:1 stoichiometry for the binding of Rh-PK and $Fe^{3+}$. Reversibility experiments were carried out by adding EDTA to the complex in ACN/Tris-HCl buffer (10 mM, pH 7.3, v/v 3:1). In the absence of EDTA, the complex was colorful and fluorescent. After adding EDTA, the absorption of the complex decreased in intensity and finally, disappeared, suggesting a reversible binding between Rh-PK and $Fe^{3+}$. A possible mechanism for the reaction and the binding mode are shown in Scheme 1 (proposed 1:1 binding mode of Rh-PK with Fe3+ in ACN/Tris-HCl buffer (10 mM, pH 7.3, v/v 3:1)).

Scheme 1

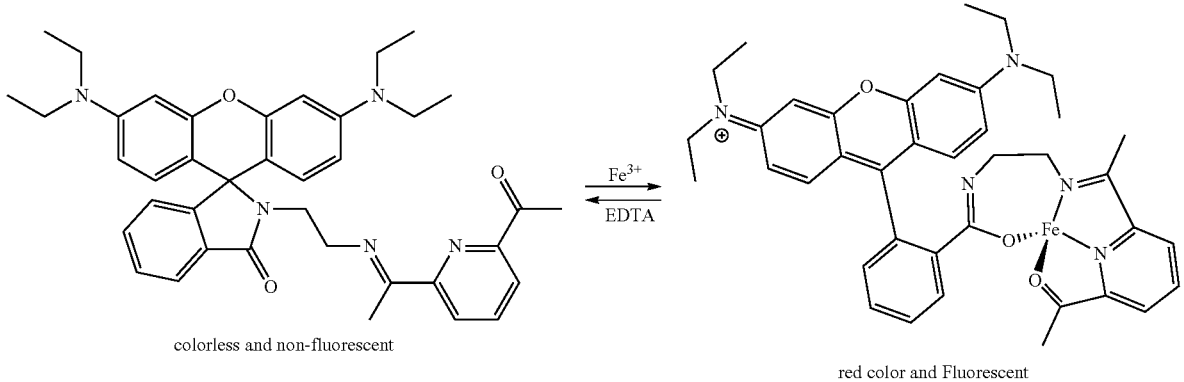

colorless and non-fluorescent red color and Fluorescent

The equations below was used to calculate the binding constants with stoichiometry of 1:1.

$$L + S \leftrightarrow LS$$

where L=sensor, S=Fe3+ and LS=sensor-$Fe^{3+}$ complex. The apparent binding constant is given by $$K = \frac{[LS]}{[L][S]}$$

Here, the concentrations are at equilibrium.

$$F_c = \frac{A_u - A_m}{A_u - A_c} = \frac{[LS]_e}{[L]_0}$$

Fe is the fraction of L that formed a complex, $[LS]_e$ is concentration at equilibrium, $[L]_0$ is the initial concentration. $A_u$, $A_m$, and $A_c$ are the absorbances of solutions of L (before any $Fe^{3+}$ was added), during the titration and at saturation, respectively. The concentration of free $Fe^{3+}$ at equilibrium, $[S]_e$, is found with the following identity.

$$[S]_e = [S]_o - [LS]_e = [S]_o - F_c[L]_o$$

Example 5. Cell Imaging Studies

The ability of Rh-PK to track $Fe^{3+}$ in live human fibroblast cells (ws1) was tested via a laser scanning confocal microscope (Zeiss LSM 710). 10 µM Rh-PK was incubated with the cells for 30 min, then scanned by a laser confocal microscopy. Turn on fluorescence was observed, which is likely being triggered by endogenous labile $Fe^{3+}$. Another possibility might be the acidic environment of certain intracellular orgenules (e.g., lysosomes/endosomes), as low pH can also trigger the turn-on response of spicro-lactone based sensors. J. D. Chartres, et al., Inorg. Chem. 2011, 50, 9178-9183. These possibilities were investigated. Two approaches were tested: first, loading the cells with $Fe^{3+}$ and second, depletion of $Fe^{3+}$ by cell permeable $Fe^{3+}$-specific chelator.

The fluorescence changes under both conditions were carefully monitored.

Figure 16A:
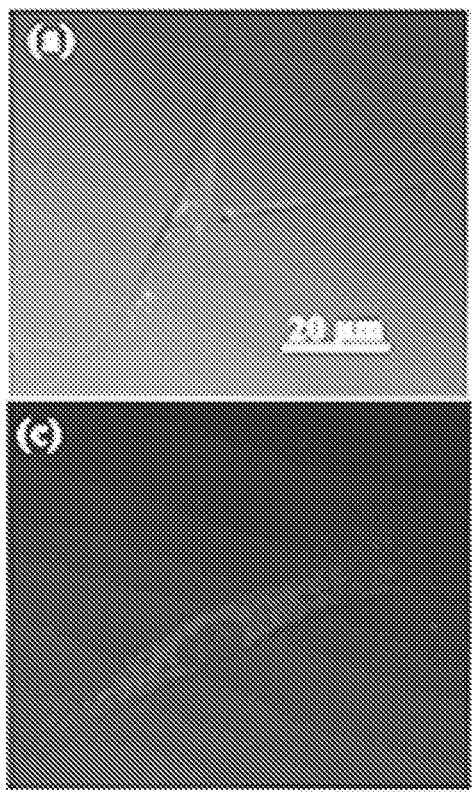
FIG. 16A is a confocal microscopy image (with DIC (differential interference contrast)) of ws1 cells only.
Figure 16B:
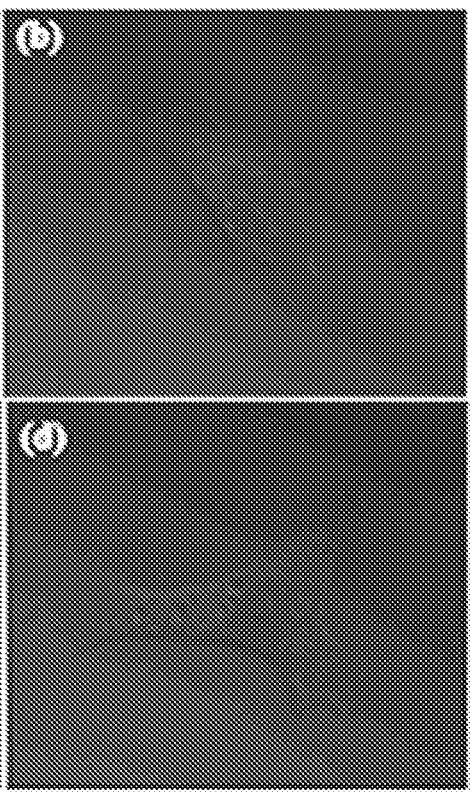
FIG. 16B is a confocal microscopy image (with DIC) of ws1 cells (primary human skin fibroblast cells) 10 µM Rh-PK sensor after 30 min incubation.
Figure 16C:
FIG. 16C is a confocal microscopy image (with DIC) of ws1 cells 10 µM Rh-PK sensor after 30 min incubation and then incubated with 50 µM $Fe^{3+}$ for 30 min.
Figure 16D:
FIG. 16D is a confocal microscopy image (with DIC) of ws1 cells incubated with SIH (salicylaldehydeisonicotinoyl hydrazone, an $Fe^{3+}$-chelator) (100 µM) overnight then sensor was added. Fluorescence intensity was collected at 547-703 nm for Rh-PK.

Comparing the confocal fluorescence images of Rh-PK in fibroblast (ws1) cells before and after being loaded with 50 µM $Fe^{3+}$, the $Fe^{3+}$-loaded fibroblast (ws1) cells clearly showed brighter and more widely distributed fluorescence signals in localized areas within the cytosol, suggesting a positive response of Rh-PK to elevated labile $Fe^{3+}$ levels in the $Fe^{3+}$-loaded cells. To deplete labile $Fe^{3+}$ from cells, if the cellular labile $Fe^{3+}$ were pre-depleted (by overnight incubation with a cell permeable $Fe^{3+}$-chelator salicylaldeheisonicotinoyl hydrazone (SIH) J. L. Buss, et al., Biochem. Pharmacol. 2003, 65, 349-360; A. D. Sheftel, et al., Blood 2007, 110, 125-132; D. R. Richardson, et al., Proc. Natl. Acad. Sci. USA 2010, 107, 10775-10782), treating the cells with Rh-PK revealed weaker fluorescence response. See FIG. 16A to FIG. 16D: confocal microscopy images (with DIC) of ws1 cells treated with (FIG. 16A) cells only; (FIG. 16B) 10 μM Rh-PK sensor after 30 min incubation; (FIG. 16C) the cells were then incubated with 50 μM Fe3 for 30 min.; (FIG. 16D) the cells were incubated with SIH (Fe3+-chelator) (100 μM) overnight then sensor was added Fluorescence intensity was collected at 547-703 nm (for Rh-PK). These data, together with those from $Fe^{3+}$-loaded cells demonstrate that the fluorescence response of Rh-PK in cells is triggered by cellular chelatable $Fe^{3+}$, not by acidic pH, thus confirming that Rh-PK can detect not only endogenous labile $Fe^{3+}$ in the cells but also the dynamic changes of $Fe^{3+}$ in the cells.

Figures 17A, 17B, 17C:
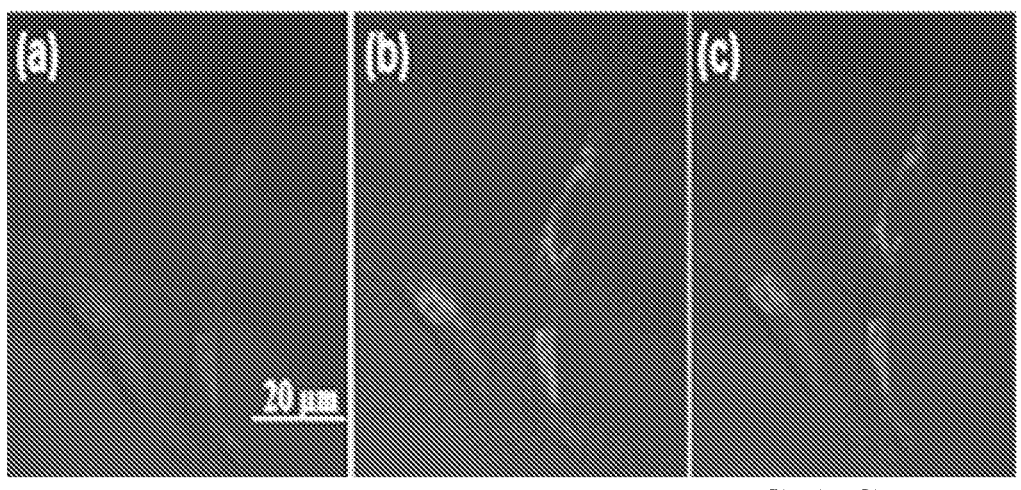
FIG. 17A to FIG. 17C are representative confocal microscopy images of intracellular colocalization studies of 10 µM Rh-PK incubated with $Fe^{3+}$-loaded ws1.

FIG. 17A to FIG. 17C show the distribution of exchangeable $Fe^{3+}$ pools in live fibroblast cells (ws1). The sensor Rh-PK-Fe(III) complex gives red fluorescent images and is shown in FIG. 17A, and FIG. 17B shows the MitoTracker dyed mitochondria in live fibroblast cells (ws1). As shown in FIG. 17C, there is a complete colocalization between Rh-PK-Fe(III) and MitoTracker (red+green=yellowish-orange). There was no colocalization observed between ws1-$Fe^{3+}$ and the lysosomes (results not shown). More specifically, FIG. 17A to FIG. 17C are representative confocal microscopy images of intracellular colocalization studies of 10 μM Rh-PK incubated with $Fe^{3+}$-loaded ws1 (pre-implemented with 50 μM $Fe^{3+}$) co-labeled with MitoTracker Green FM (100 nM, incubated for 30 min). FIG. 17A is the Rh-PK-Fe3+ fluorescence intensity collected at 547-703 nm (red). Stronger fluorescence suggests elevated $Fe^{3+}$ levels in $Fe^{3+}$-loaded human cells. FIG. 17B is the MitoTracker fluorescence intensity collected at 492-548 nm (green). FIG. 17C is a DIC image of FIG. 17A and fluorescence images of FIG. 17B merged together. Colocalization regions are in orange and non-overlapping regions remain in red, revealing that Rh-PK-$Fe^{3+}$ is partially colocalized with mitochondria.

The ability of the sensor RPE to detect $Fe^{3+}$ in human SH-SY5Y neuroblastoma cells have previously been reported (Y. Wei, et al., ChemBioChem, 2012, 13, 1569-1573). The results showed that chelatable iron pools in human SH-SY5Y neuroblastoma cells are in mitochondria and lysosomes. However, here, the sensor Rh-Pk detected chelatable $Fe^{3+}$ in mitochondria only in human primary fibroblast ws1 cells, not in lysosomes. To verify whether Rh-Pk has the capability to detect lysosomal $Fe^{3+}$ ions, Rh-PK was used to detect $Fe^{3+}$ ions in human SH-SY5Y neuroblastoma cells with colocalization experiments. The SH-SY5Y cells were pre-incubated with $Fe^{3+}$ ions, then incubated with Rh-PK, mito-tracker and lyso-tracker. The same results was observed as previously using RPE probe. Free $Fe^{3+}$ ions were located by Rh-PK in mitochondria and lysosomes in human SH-SY5Y neuroblastoma cells. See FIG. 18A to FIG. 18H. These results demonstrate that the Rh-PK is capable detecting $Fe^{3+}$ ions in both mitochondria and lysosomes, however, human primary fibroblast ws1 cells appears do not have a $Fe^{3+}$ pool in lysosomes, suggesting different cells may handle iron differently.

Figures 18A, 18B, 18C, 18D, 18E, 18F, 18G, 18H:
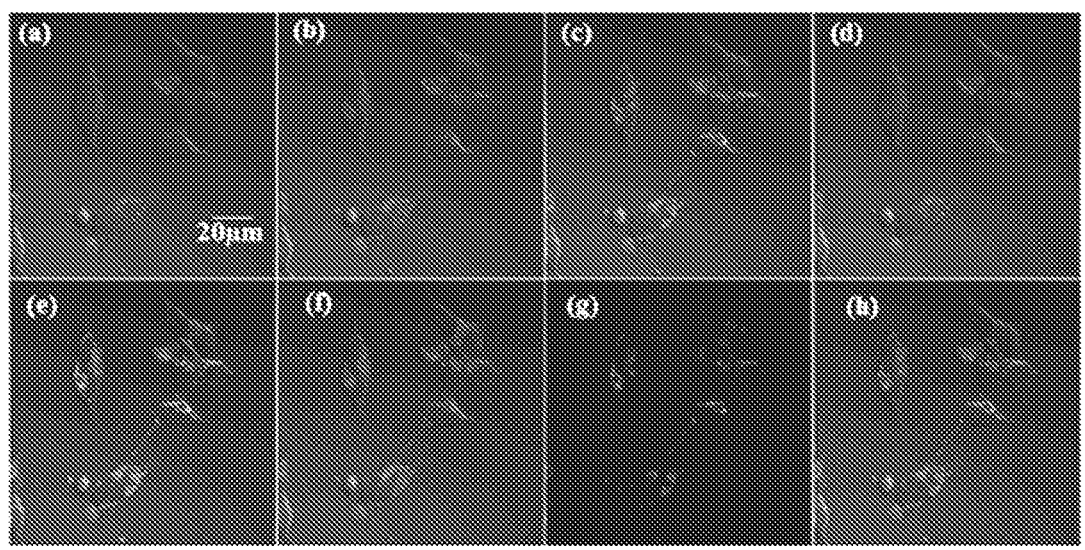
FIG. 18A to FIG. 18H are representative confocal microscopy images of intracellular colocalization studies of 10 µM Rh-PK incubated with $Fe^{3+}$-loaded human SH-SY5Y cells.

FIG. 18A to FIG. 18H are representative confocal microscopy images of intracellular colocalization studies of 10 μM Rh-PK incubated with $Fe^{3+}$-loaded human SH-SY5Y cells (pre-implemented with 10 μM $Fe^{3+}$) co-labeled with MitoTracker Green FM (100 nM, incubated for 30 min) and LysoTracker Blue DND-22 (50 nM, incubated for 120 min). FIG. 18A is an DIC image of cells with 10 μm scale bar. FIG. 18B is the Rh-PK-$Fe^{3+}$ fluorescence intensity collected at 547-703 nm (red). Stronger fluorescence suggests elevated $Fe^{3+}$ levels in $Fe^{3+}$-loaded human SH-SY5Y cells. FIG. 18C is the MitoTracker fluorescence intensity collected at 492-548 nm (green). FIG. 18D is the LysoTracker fluorescence intensity collected at 409-484 nm (blue). FIG. 18E is a DIC image of FIG. 18A and fluorescence images of FIG. 18B and FIG. 18C merged together. Colocalization regions are in yellow and non-overlapping regions remain in red, revealing that Rh-PK-$Fe^{3+}$ is partially colocalized with mitochondria. FIG. 18F is a DIC image of FIG. 18A and fluorescence images of FIG. 18B and FIG. 18D merged together. Colocalization regions are in purple and non-overlapping regions remain in red, revealing that Rh-PK-$Fe^{3+}$ is partially colocalized with lysosomes. FIG. 18G is an image of FIG. 18 A to FIG. 18D merged together. Colocalization regions are in yellow or purple exclusively; no non-overlapping regions were found, suggesting that chelatable $Fe^{3+}$ is still localized in mitochondria and lysosomes under the conditions. FIG. 18H is an image of FIG. 18A, FIG. 18C and FIG. 18D merged together showing no overlapping region between lysosome and mitochondria.

Example 6. Synthesis of RhHPA

RhHPA was synthesized according to Scheme 2.

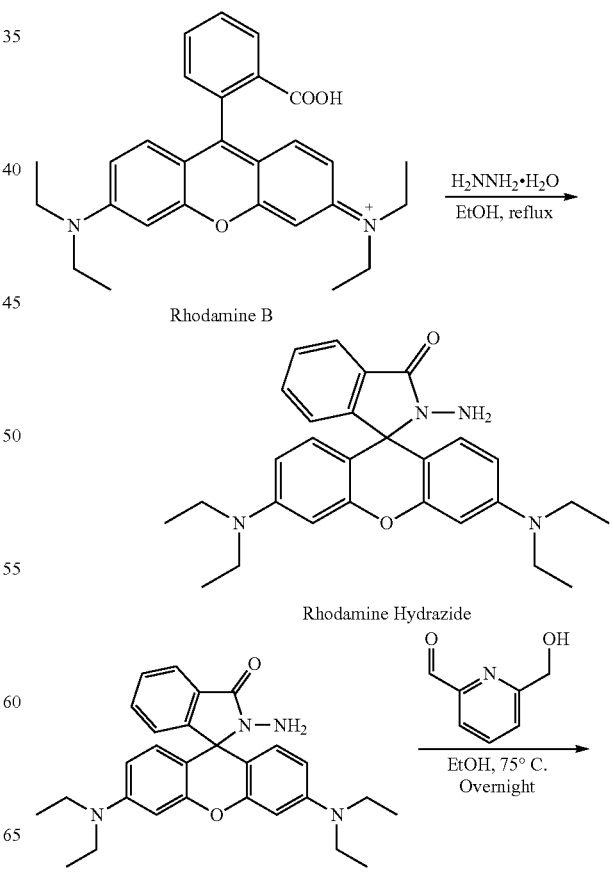

Scheme 2

Rhodamine B

Rhodamine Hydrazide

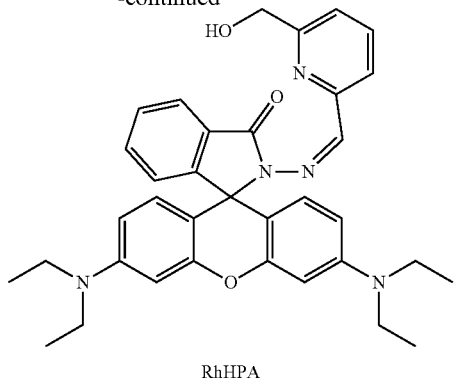

RhHPA

To a stirred ethanolic solution of Rhodamine hydrazide (912 mg, 2 mmol), 6-hydroxymetyl-pyridine-2-aldehyde (274 mg, 2 mmol) in ethanol was added slowly. The mixture was stirred and refluxed overnight. The crude product was evaporated under the reduced pressure and purified by silica gel column chromatography using $CH_2Cl_2/CH_3OH$ (20:1, v/v) as eluent. A colorless precipitate was obtained and dried in vacuum. Yield: 747 mg (66%). $^1H$ NMR ($CDCl_3$-d): 8.42 (s, 1H, —CH=N—), 8.02 (d, 1H, meta-py-H), 7.83 (d, 1H, meta-py-H), 7.58 (t, 1H, para-Py-H), 7.44-7.51 (m, 4H, Ar—H), 7.27 (s, 1H, solvent-H), 6.53 (d, 2H, xanthene-H), 6.46 (d, 2H, xanthene-H), 6.24 (dd, 2H, xanthene-H), 5.29 (s, 1H, py-$CH_2$—), 4.66 (s, 1H, py-OH), 3.32 (q, 8H, —N—$CH_2$—), 2.17 (s, 1H, solvent), 1.15 (t, 12H, —N—$CH_3$); $^{13}C$ NMR ($CDCl_3$-d): 165.43 (C27), 158.03 (C35), 153.19, 152.97, 152.31, 149.02, 145.67 (C36, C38, C39, C40, C41), 136.79, 133.79, 128.33, 128.25, 127.78 (C20, C21, C22, C23, C24, C25), 123.83, 123.59, 120.33, 119.35, 108.04, 105.43, 98.05 (C1, C2, C3, C4, C5, C6, C13, C14, C16, C17, C18, C19), 77.36-77.73 (solvent), 65.91 (C12), 63.59 (C42), 44.32 (C33), 12.60 (C34).

ESI-MS: Fragments at m/z=575.29 (base peak) is attributed to molecular ion peak $[C_{35}H_{37}N_5O_3]^+$. The fragment at m/z=576.6 is attributed to $[C_{35}H_{37}N_5O_3+H]^+$. The fragment at m/z=598.2 is attributed to $[C_{35}H_{37}N_5O_3+Na]^+$.

Example 7. Cell Culture and Imaging

Primary cultured Bovine aortic endothelial cells (BAEC) were passaged in Endothelial Basal Medium (Lonza) containing 5% fetal bovine serum. Before the experiment, the cells were cultured to about 8th generation. For experiment preparation, the cells were routinely subcultured using 0.05% trypsin-EDTA solution. The cells were seeded on the 25 $cm^2$ flask and medium change every two days until a 70% confluency before transferring into disks. The cells were seeded on the 1 $cm^2$ disk and a medium change the next day. Confocal microscopy images (with DIC) of BAEC with prior iron depletion by 100 µM cell permeable $Fe^{3+}$-chelator ethylene diamine tetra acetic acid (EDTA) for overnight and then treated with RhHPA (10 µM) in 1:1 mixture of Eagles Minimal Essential medium (ATCC) and Ham's F12 medium (ATCC). (a) DIC image of cells with 10 µm scale bar (b) 10 µM RhHPA sensor after 30 min incubation (c) 100 µM cell permeable $Fe^{3+}$-chelator ethylene diamine tetra acetic acid (EDTA) for overnight and then treated with RhHPA, Fluorescence intensity was collected at 540-700 nm (for RhHPA).

Example 8. Determination of Complexation Ratio and Binding Constant

The stoichiometry of RhHPA-$Fe^{3+}$ was measured using Job's plot and mole ratio plots methods. B. Valeur, Molecular Fluorescence: Principles and Applications, Wiley-VCH. Weinheim, 2002. To determine the binding constant of chemosensor, a fluorescence titration of different amounts of $Fe^{3+}$ into the acetonitrile solution of sensor was carried out. It exhibits the fluorescence spectra of the RhHPA upon addition of various amounts $Fe^{3+}$. After titration, the fluorescent intensity of chemosensor made gradually increase by the addition of $[Fe^{3+}]$J. T. Hou, et al., Tetrahedron Letters, 52 (2011) 4927-4930. The determination of the binding constant of RhHPA was calculated using the following equation:

$$F-F_{min}=[Cd^{2+}](F_{max}-F_{min})/K_d$$

where F is the observed fluorescence, $F_{max}$ is the maximum fluorescence for the RhHPA-$Fe^{3+}$ complex at concentration of the equal reacted between sensor and metal cation, $F_{min}$ is the fluorescence intensity for occurring RhHPA-$Fe^{3+}$.

Absorption enhancement observation at 558 nm was plotted against the molar value of the $[Fe^{3+}]/[Fe^{3+}]+RhHPA$ and $[Fe^{3+}]/RhHPA$. The maximum absorption enhancements were obtained at 0.0375 (Job's plot calculation) and 1.1 (mole ratio plots) showing that RhHPA coordinated $Fe^{3+}$ with 1:1 ratio. Binding constant of fluorescent sensor "RhHPA" was calculated and it was found as $K=1.27\times10^7$ $M^{-1}$.

To demonstrate the sensing nature RhHPA, the recognition between sensor and metal cations was conducted using fluorescence and UV-Vis. spectroscopy in ACN/Tris-HCl buffer (10 mM, pH 7.3, v/v 2:1). The stock solution of sensor and metal ions were prepared at the concentration of 1 mM. M. P. Walkees, Mutat. Res., 2003, 533, 107; M. Waisberg, et al., Toxicology, 2003, 192, 95.

Figure 5:
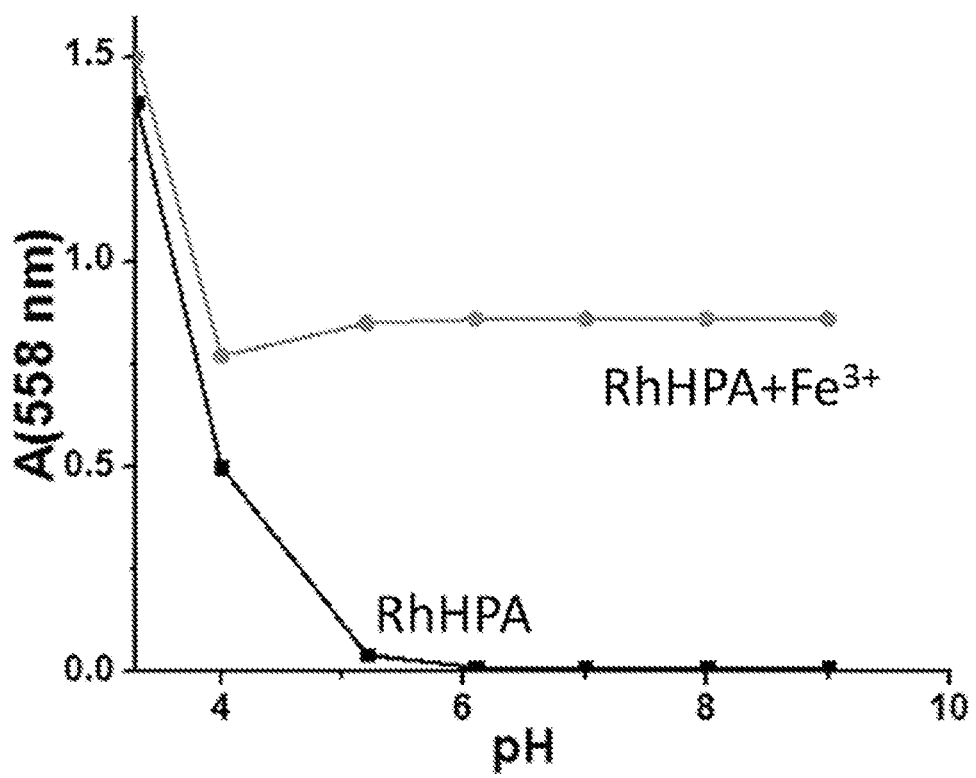
FIG. 5 is a graph showing the effect of pH on the absorbance value of the sensor RhHPA and its $Fe^{3+}$-complex.

Upon addition of $Fe^{3+}$ to a colorless solution of RhHPA, fluorescent and colorimetric characteristics of rhodamine B appeared. See Scheme 3. This indicated that the hydroxide group in compound RhHPA indeed played an important role in the course of binding with $Fe^{3+}$. And these changes can be attributed to the structure transformation from spirolactam (non-fluorescence) to ring-opened amide fluorescence), due to the complexation of $Fe^{3+}$. Further, the optimum pH conditions for successful application of sensor "RhHPA" were investigated. The effects of pH on the fluorescence intensity of chemosensor measured in the absence and presence $Fe^{3+}$ in ACN/Tris-HCl buffer were carried out. See FIG. 5, which shows the effect of pH on the absorbance value of the sensor "RhHPA" (50 µM) and its $Fe^{3+}$-complex (50 µM) in ACN/Tris-HCl buffer (10 mM, pH 7.3, v/v 2:1). At the acidic conditions (pH<5), for RhHPA and RhHPA-$Fe^{3+}$ complex, spirolactam formation of the chemosensor replaced with ring opening situation due to highly protonation. There was no significant changes in the fluorescent profile of the sensor at pH 5 to 9. In the presence of $Fe^{3+}$, a significant fluorescent enhancement ("turn-on") was observed in the pH range 5 to 9. Hence, the sensor "RhHPA" can be used for the detection of iron(III) cation at the physiological pH range.

Scheme 3

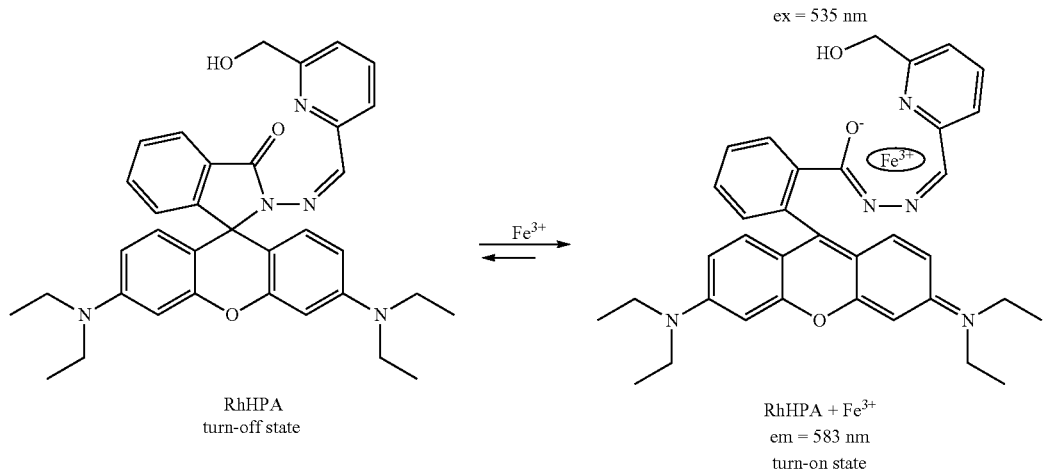

RhHPA
turn-off state

RhHPA + Fe$^{3+}$
ex = 535 nm
em = 583 nm
turn-on state

Example 9. Selectivity Studies

Figure 6:
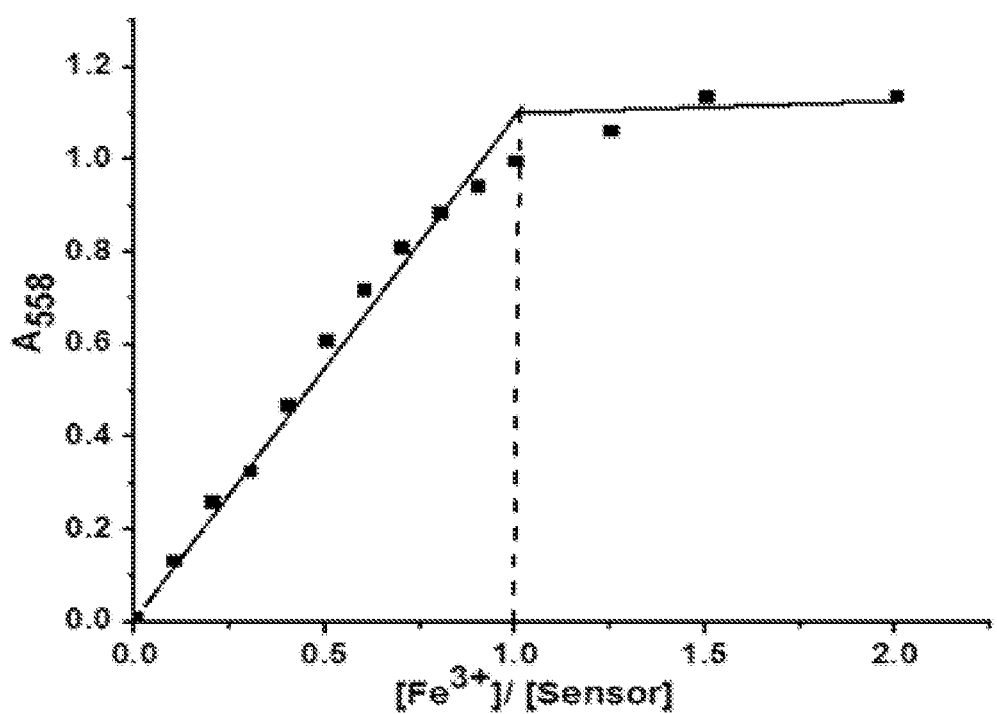
FIG. 6 is a plot of absorbance of RhHPA dependent on the concentration of $Fe^{3+}$ in the range from 0 to 2 equivalents.
Figure 7:
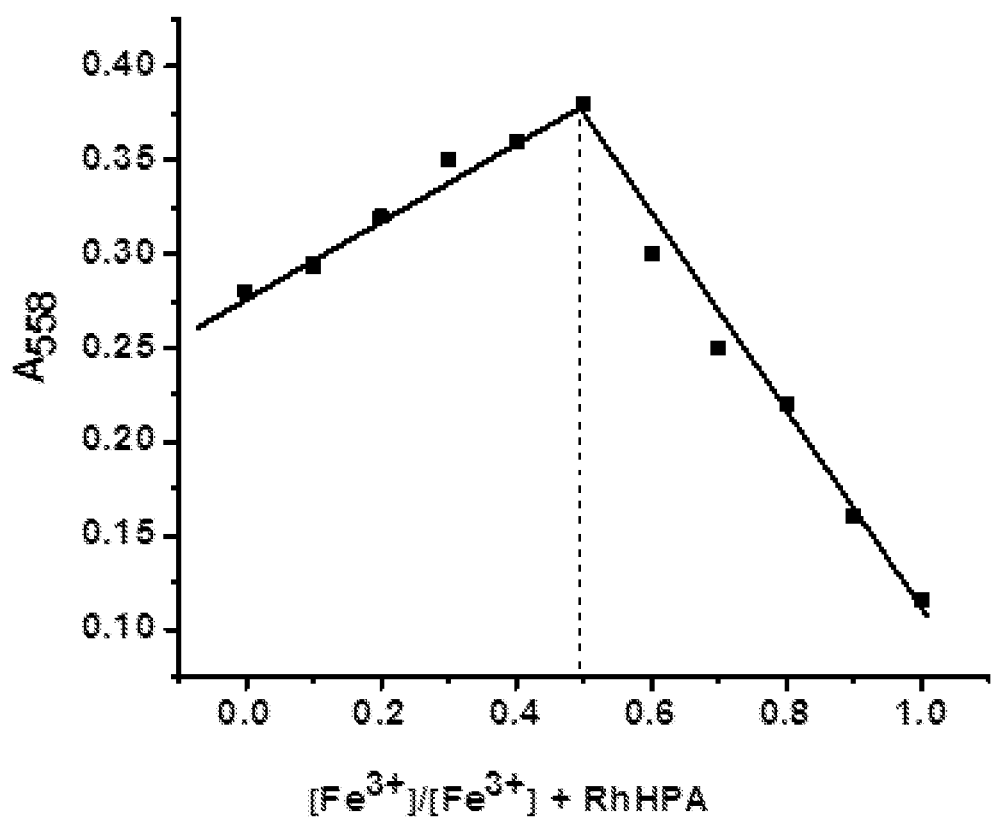
FIG. 7 is a Job's plot between $Fe^{3+}$ and RhHPA.
Figure 8:
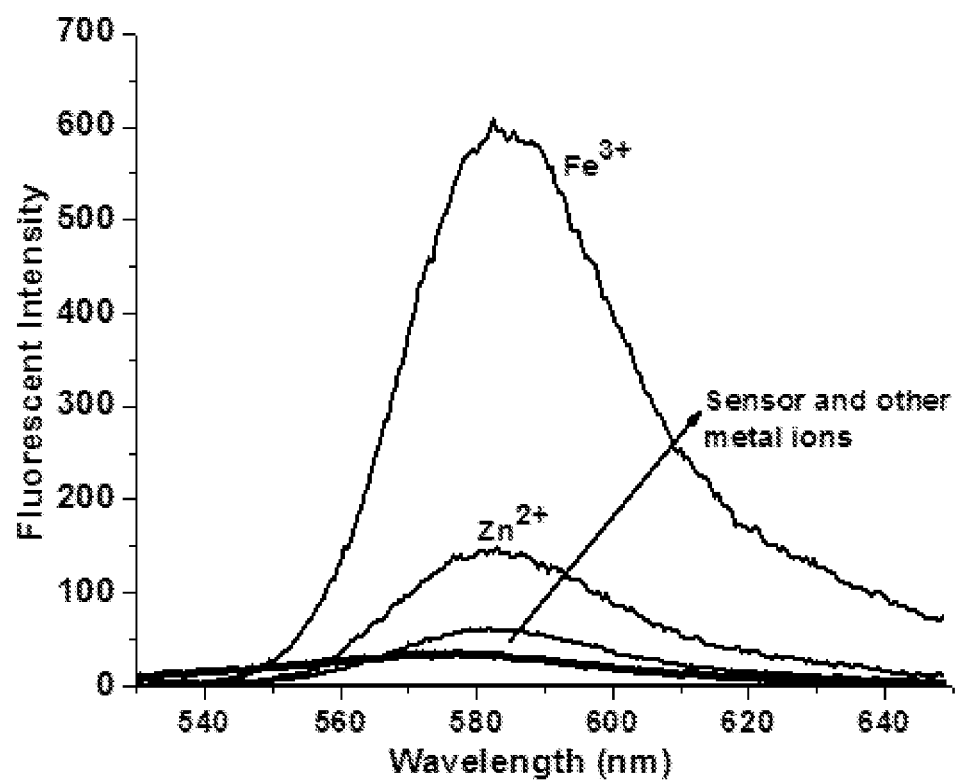
FIG. 8 shows fluorescence emission spectra of sensor RhHPA (50 µM) observed upon addition of 1 equivalent metal ions.
Figure 9:
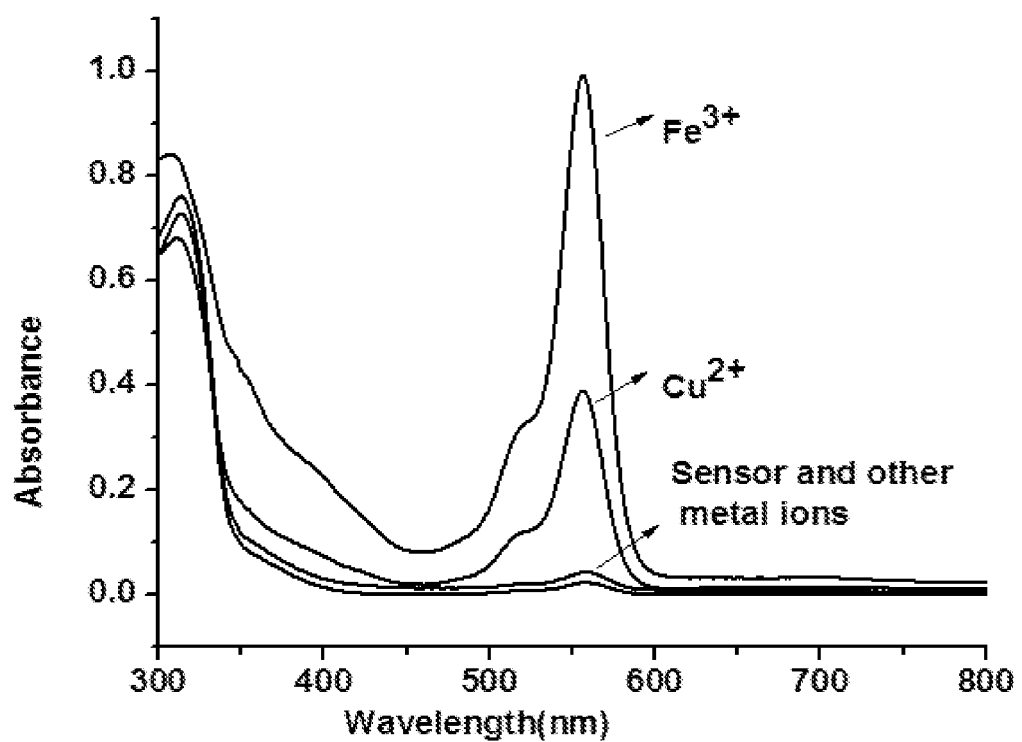
FIG. 9 shows UV-vis absorption spectra of sensor RhHPA (50 µM) observed upon addition of 1 equivalent metal ions.

The UV-vis. and fluorescence spectra of RhHPA to various possible interfering metal ions and its selectivity for Fe$^{3+}$ were examined. See FIG. 6, which is a plot of absorbance dependent on the concentration of Fe$^{3+}$ in the range from 0 to 2 equivalents in ACN/Tris-HCl buffer (10 mM, pH 7.3, v/v 2:1); FIG. 7, which is a Job's plot between Fe$^{3+}$ and RhHPA, indicating the 1:1 binding mode for sensor and iron(III). Fe$^{3+}$ induced a notable color change in buffer solution, which can be ascribed to the spirolactam bond cleavage of rhodamine group (V. Bhalla, et al., Sensors and Actuators B 178 (2013) 228-232), while the over other metal ions did not show any obvious absorbance response. Addition of Na$^+$, K$^+$, Ca$^{2+}$, Mg$^{2+}$, Cr$^{3+}$, Fe$^{3+}$, Hg$^{2+}$, Cu$^{2+}$, Pb$^{2+}$, Zn$^{2+}$, Fe$^{2+}$, Co$^{2+}$, Ni$^{2+}$, and Ag$^+$ exerted little or no effect on the emission of RhHPA, while remarkable fluorescence enhancement was detected upon the addition of Fe$^{3+}$ by excitation of the rhodamine fluorophore at 535 nm. See FIG. 8, which shows fluorescence emission spectra, and FIG. 9, which shows UV-vis absorption spectra of sensor RhHPA (50 NM) observed upon addition of 1 equivalent metal ions (chloride or nitrate salts of Na$^+$, K$^+$, Ca$^{2+}$, Mg$^{2+}$, Cr$^{3+}$, Fe$^{3+}$, Hg$^{2+}$, Cu$^{2+}$, Pb$^{2+}$, Zn$^{2+}$, Fe$^{2+}$, Co$^{2+}$, Ni$^{2+}$, Cd$^{2+}$, and Ag$^+$) in ACN/Tris-HCl buffer (10 mM, pH 7.3, v/v 2:1). RhHPA showed a highly fluorescence selectivity towards Fe$^{+3}$ over other metal ions except a little of fluorescence enhancement for Zn(II) and Cu(II).

Figure 10:
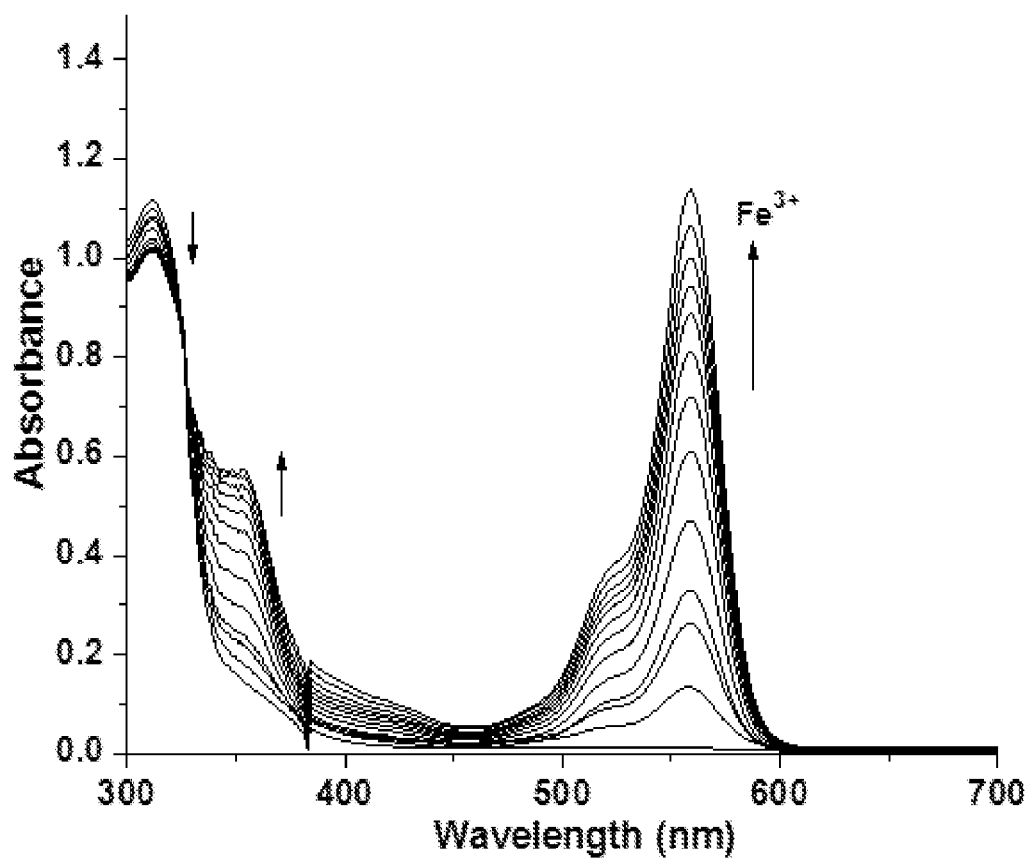
FIG. 10 shows the $Fe^{3+}$ concentration dependent variations in the absorbance (0-100 µM of $Fe^{3+}$ ions) spectra of RhHPA.
Figure 11:
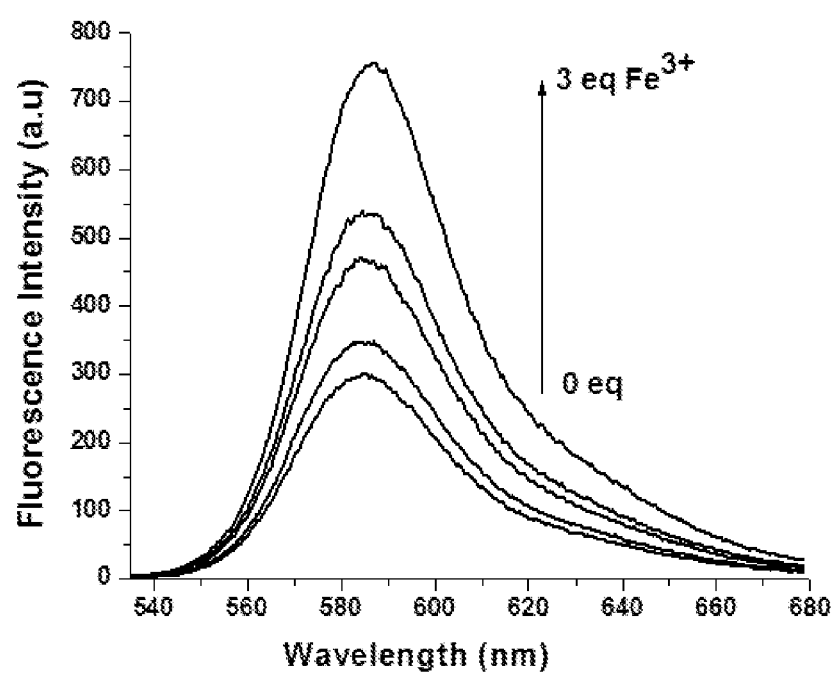
FIG. 11 shows the $Fe^{3+}$ concentration dependent variations in the fluorescence (0-150 µM of $Fe^{3+}$ ions) spectra of RhHPA.

RhHPA exhibited non-fluorescent property as it shows no absorption at visible region and is colorless. Fe$^{3+}$ concentration dependent variations in the (FIG. 10) absorbance (0-100 μM of Fe$^{3+}$ ions) and (FIG. 11) Fluorescence (0-150 μM of Fe$^{3+}$ ions) spectra of RhHPA in ACN/Tris-HCl buffer (10 mM, pH 7.3, v/v 2:1) (50 μM); excitation wavelength: 510 nm. Upon addition of Fe$^{3+}$ metal ion, a pink color was observed due to a specific absorption at around 558 nm. When the iron(III) in acetonitrile was much more added into the acetonitrile solution of chemosensor, a strong fluorescence and absorption appeared.

Figure 12:
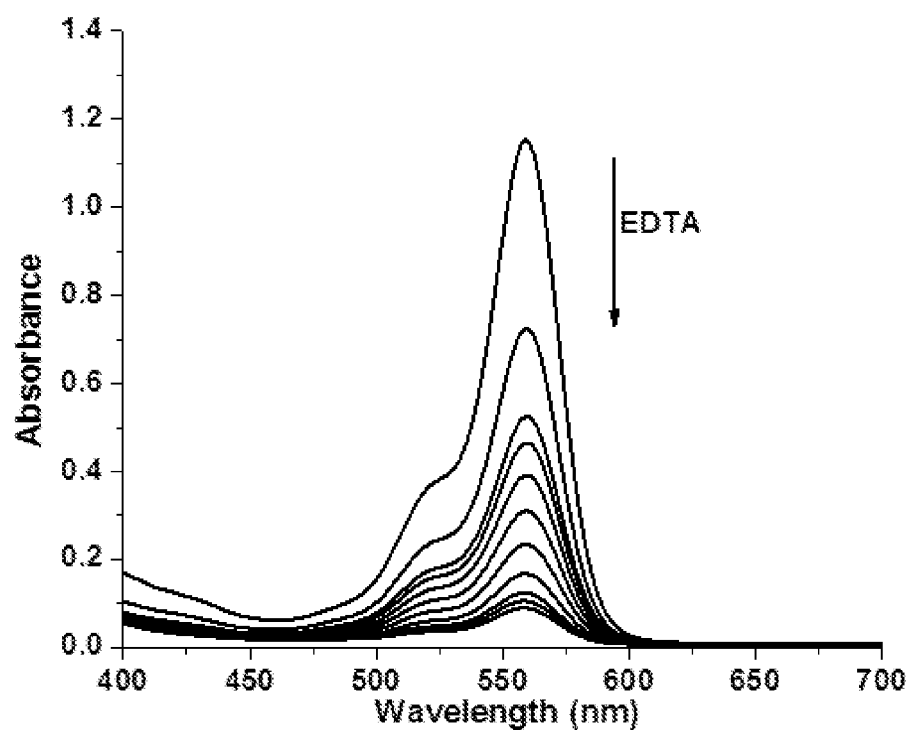
FIG. 12 shows absorbance spectra of RhHPA-$Fe^{3+}$ complex with increasing concentration of EDTA.
Figure 13:
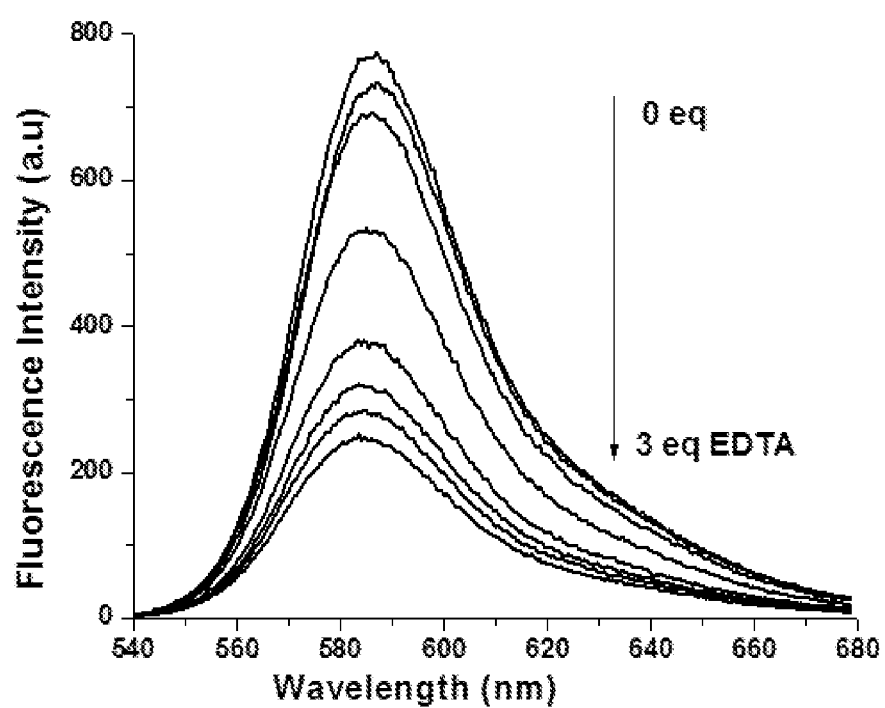
FIG. 13 shows fluorescence spectra of RhHPA-$Fe^{3+}$ complex with increasing concentration of EDTA.

The coordination between RhHPA and Fe$^{3+}$ is a reversible process as can be seen in FIG. 12, FIG. 13 and Scheme 3. FIG. 12 and FIG. 13 show the changes of the absorbance and fluorescence emission, respectively, of RhHPA-Fe$^{3+}$ (50 μM complex with increasing concentration of EDTA 3 eq, 0 to 150 μM, from bottom to top; in ACN/Tris-HCl buffer (10 mM, pH 7.3, v/v 2:1)). The pink solution of fluorescent chemosensor-Fe$^{3+}$ complex turned back to the colorless form when treated with 0.1 mM EDTA. Thus, it demonstrates that the coordination of this fluorescent probe with Fe$^{3+}$ is reversible by the chemical processes.

Figure 14:
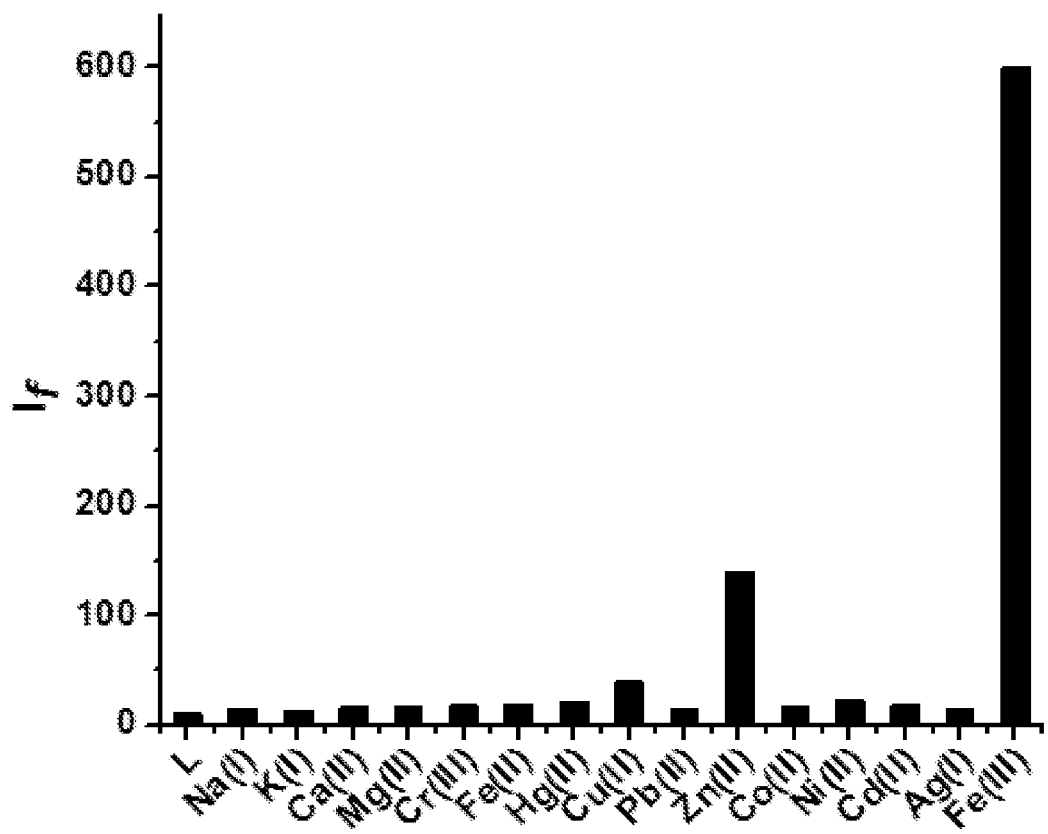
FIG. 14 is a graph showing the fluorescence intensity of RhHPA at 583 nm in the presence of different metal ions.
Figure 15:
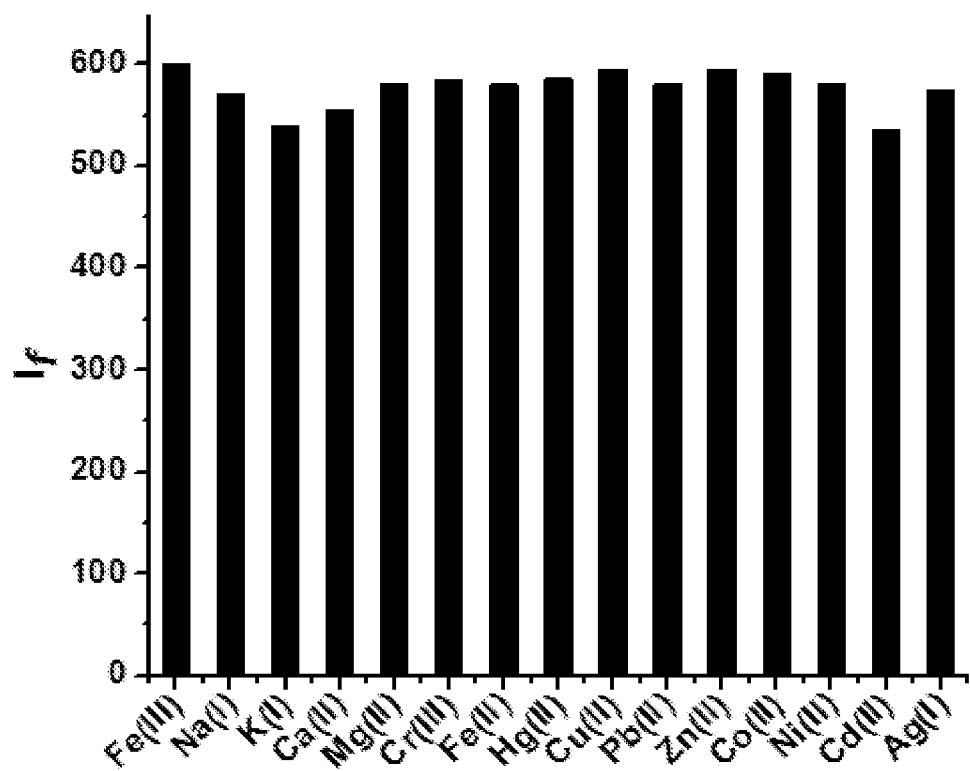
FIG. 15 is a graph showing the fluorescence intensity of RhHPA at 583 nm with 75 µM $Mn^+$, followed by 75 µM $Fe^{3+}$.

Experiments of iron(III) with other metal ions were investigated by means of the fluorescence response of RhHPA toward Fe$^{3+}$ in the presence of various other metal ions such as Na$^+$, K$^+$, Ca$^{2+}$, Mg$^{2+}$, Cr$^{3+}$, Hg$^{2+}$, Cu$^{2+}$, Pb$^{2+}$, Zn$^{2+}$, Fe$^{2+}$, Co$^{2+}$, Ni$^{2+}$, Cd$^{2+}$, and Ag$^+$. A reduced selectivity for Fe$^{3+}$ had no changes with addition of other metal ions. Cu(II) and Zn(II) increased the fluorescence intensity slightly. FIG. 14 shows the fluorescence intensity of RhHPA (L) (25 μM) at 583 nm in the presence of different metal ions (75 μM) in Tris-HCl/ACN solution (pH 7.3). FIG. 15 shows the fluorescence intensity of RhHPA at 583 nm with 75 μM Mn+, followed by 75 μM Fe$^{3+}$. FIG. 14 and FIG. 15 demonstrate that some alkaline, alkaline-earth or transition metal ions do not interfere with the iron(III)-induced fluorescence increase, showing that the chemosensor RhHPA has is selective for Fe$^{3+}$.

Example 10. Cell Imaging Assays

To evaluate the ability of RhHPA to capture Fe$^{3+}$ ions in cells, BAEC cells were incubated with the sensor (10 μM) for 30 min. RhHPA was cell permeable, and it exhibited 4-fold fluorescence enhancement. To demonstrate that this fluorescent enhancement was due to the complexication between Fe$^{3+}$ and the sensor, two control experiments were carried out.

BAEC cells were incubated with 10 μM of ferric chloride (FeCl$_3$) at 37° C. for overnight, then 10 μM of RhHPA was added to BAEC cells and was incubated at 37° C. for 30 min. The Fe$^{3+}$-treated BAEC cells showed significant increase in fluorescent intensity (~8-fold, two times higher than the signal from non-iron loaded cells) (FIG. 19C) compared to that without Fe$^{3+}$ supplementation (FIG. 19B), suggesting a positive response RhHPA to increased labile Fe$^{3+}$ in Fe$^{3+}$-treated cells.

Figure 19A:
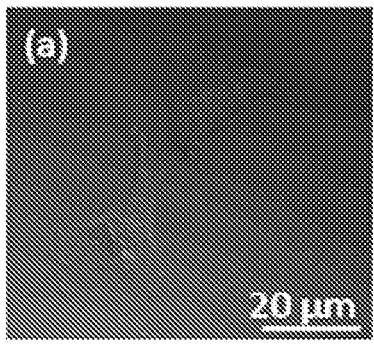
FIG. 19A to FIG. 19E are representative confocal microscopy images (with DIC) of BAEC (Bovine aortic endothelial cells) studies with RhHPA.
Figure 19B:
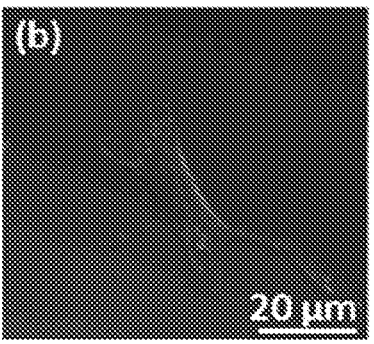
Figure 19C:
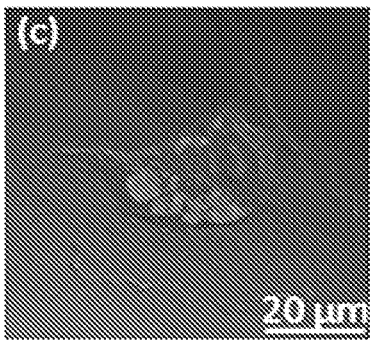
Figure 19D:
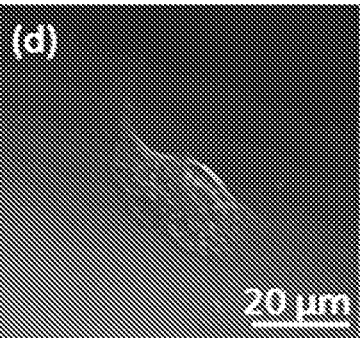
Figure 19E:
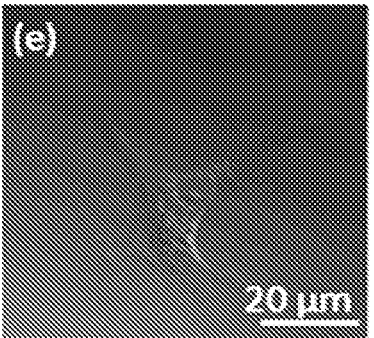
Figure 19F:
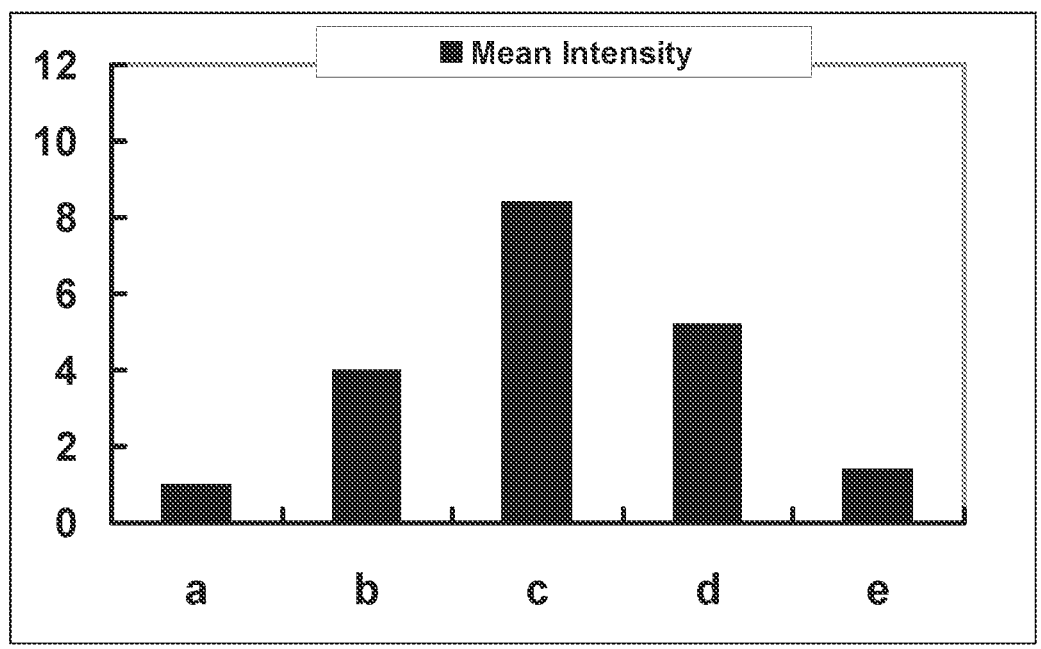
FIG. 19F is a bar chart of the mean intensity of FIG. 19A to FIG. 19E.

FIG. 19A to FIG. 19E are representative confocal microscopy images (with DIC) of BAEC studies with RhHPA. FIG. 19A is the image of cell only. FIG. 19B is image where the cells were treated with the sensor after 30 min incubation. FIG. 19C is the image where the cells were incubated with 10 μM $Fe^3$ for 30 min and then the sensor was added. FIG. 19D is the image where the cells were incubated with 10 μM $Fe^3$ for 30 min and then SIH was added, and incubated overnight. FIG. 19E is the image of the cells incubated with SIH ($Fe^{3+}$-chelator, 100 μM) overnight and then sensor was added. FIG. 19F is a bar chart of the mean intensity of FIG. 19A to FIG. 19E.

For the second control experiment, an $Fe^{3+}$-chelator SIH was added to iron-loaded and non-iron-loaded cells with RhHPA. As seen in FIG. 19C, BAEC cells treated with 100 μM of SIH showed small decrease in fluorescence signal which is lower than that of signals of RhHPA-treated cells (FIG. 20E), suggesting RhHPA can detect the decrease in $Fe^{3+}$ levels as well as basal level of labile $Fe^{3+}$ in BAEC cells. The BAEC cells treated with 20 μM of $Fe^{3+}$ overnight first followed then treated with 100 μM of SIH and subsequent addition of 10 μM of RhHPA showed large decrease in fluorescence signal (FIG. 20D) compare to that of cells with Fe(III) supplement and is almost at the same level as that of the signal of cells without $Fe^{3+}$ and SIH. This indicates that RhHPA has the ability to detect endogenous level of labile $Fe^{3+}$ as well as the dynamic changes in $Fe^{3+}$ in BAEC cells.

FIG. 20A to FIG. 20H are representative confocal images of intracellular colocalization studies of 10 μM RhHPA incubated with live BAEC cells co-labeled with MitoTracker Green (100 nM) and LysoTracker Blue DND-22 (50 nM). FIG. 20A is a DIC image of cells with 10 μm scale bar. FIG. 20B is the RhHPA-$Fe^{3+}$ fluorescence collected at 547-703 nm (red). FIG. 20C is the MitoTracker fluorescence collected at 492-548 nm (green). FIG. 20D is the LysoTracker fluorescence collected at 409-484 nm (blue). FIG. 20E is a DIC image of FIG. 20A and fluorescence images of FIG. 20B and FIG. 20C merged together. Colocalization regions are in yellow and non-overlapping regions remain in red. FIG. 20F is a DIC image of FIG. 20A and fluorescence images of FIG. 20B and FIG. 20D merged together. Overlapping regions are in purple and non-overlapping regions remain in red. FIG. 20G is an image of FIG. 20A to FIG. 20D merged together, revealing that the RhHPA-$Fe^{3+}$ images are 100% colocalized with the sum of those of MitoTracker and LysoTracker. FIG. 20H is an image of FIG. 20A, FIG. 20C and FIG. 20D merged together, showing no overlapping region between lysosomes and mitochondria.

The fluorescent signals detected by RhHPA in BAEC cells suggest that labile $Fe^{3+}$ ions are located in certain subcellular compartments in the cells. BAEC cells (without $Fe^{3+}$ treatment) were treated with RhHPA, MitoTracker Green FM and LysoTracker blue DND-22. As shown in FIG. 20A to FIG. 20H, there are partial colocalization between RhHPA-$Fe^{3+}$ and the MitoTracker (FIG. 20E) as well as that between RhHPA-$Fe^{3+}$ and the LysoTracker (FIG. 20F); however, a complete colocalization was observed among RhHPA-$Fe^{3+}$, MitoTracker and LysoTracker (FIG. 20G). These data suggest that the exchangeable $Fe^{3+}$ pools in BAEC cells detectable by RhHPA are localized in mitochondria and endosomes/lysosomes, not in cytosol. Additional experiments with RhHPA and the trackers under $Fe^{3+}$ supplement conditions revealed again elevated levels of cellular chelatable $Fe^{3+}$ and that the labile $Fe^{3+}$ pools are still localized in mitochondria and endosomes/lysosomes (FIG. 21A to FIG. 21H).

Figures 21A, 21B, 21C, 21D, 21E, 21F, 21G, 21H:
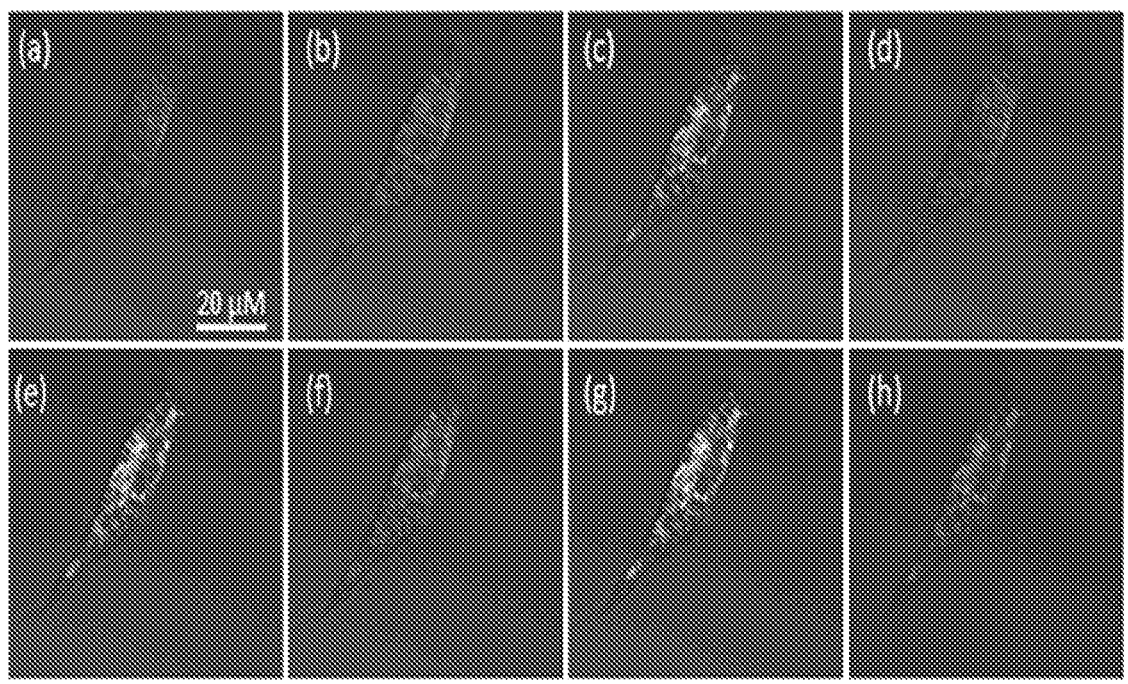
FIG. 21A to FIG. 21H are representative confocal microscopy images of intracellular colocalization studies of 10 μM RhHPA incubated with $Fe^{3+}$-loaded BEAC cells co-labeled with MitoTracker Green FM and LysoTrackerBlue DND-22.

FIG. 21A to FIG. 21H are representative confocal microscopy images of intracellular colocalization studies of 10 μM RhHPA incubated with $Fe^{3+}$-loaded BAEC cells (pre-implemented with 10 μM$Fe^{3+}$) co-labeled with MitoTracker Green FM (100 nM, incubated for 30 min) and LysoTrackerBlue DND-22 (50 nM, incubated for 120 min). FIG. 21A is a DIC image of cells with 10 μm scale bar. FIG. 21B is the RhHPA-$Fe^3$ fluorescence collected at 547-703 nm (red). FIG. 21C is the MitoTracker fluorescence collected at 492-548 nm (green). FIG. 21D is the LysoTracker fluorescence collected at 409-484 nm (blue). FIG. 21E is a DIC image of FIG. 21A and fluorescence images of FIG. 21B and FIG. 21C merged together. Colocalization regions are in yellow and non-overlapping regions remain in red. FIG. 21F is a DIC image of FIG. 21A and fluorescence images of FIG. 21B and FIG. 21D merged together. Overlapping regions are in purple and non-overlapping regions remain in red. FIG. 21G is an image of FIG. 21A to FIG. 21D merged together, revealing that the RhHPA-$Fe^{3+}$ images are colocalized with the sum of those of MitoTracker and LysoTracker. FIG. 21H is an image of FIG. 21A, FIG. 21C, and FIG. 21D merged together, showing no overlapping region between lysosomes and mitochondria.

Example 11. Synthesis of Rh6GD

General Information

Rhodamine 6G, N, N-dimethylaminocinnamaldehyde (DMACA) were purchased from Sigma-Aldrich. The other chemicals and the solvents used in the experiments were purchased commercially and were used without further purification. Tetrahydrofuran (Sigma-Aldrich), Ethanol, and double-distilled water were used as solvents. MitoTracker Green FM, LysoTracker Deep Red were purchased from Life Technologies and used in accordance with the manufacturer's protocols.

ESI-MS analyses were performed using a PerkinElmer API 150EX LC-MS mass spectrometer or a Waters ACQUITY UPLC Q-TOF mass spectrometer. UV/Vis spectra were recorded on a Perkin-Elmer Lambda 25 spectrometer at 293 K. Fluorescence spectra was recorded on a Perkin-Elmer LS55 luminescence spectrometer at 293 K. Excitation and emission slits were 5 nm and emission spectra were collected 530 nm-700 nm after excited at 510 nm. The pH measurements were carried out on a Corning pH meter equipped with a Sigma-Adrich micro combination electrode calibrated with standard buffer solutions. $^1H$ and $^{13}C$ NMR spectra were recorded on a Bruker Ascend 400 NMR spectrometer at ambient temperature (298 K). Chemical shifts are reported in delta (δ) unit per million (ppm) downfield tetramethylsilane. Splitting patterns are abbreviated as follows: s, singlet; d, doublet; t, triplet; q, quartet; m, multiplet; br, broad.

Synthesis of Rhodamine 6G Hydrazide

The rhodamine 6G hydrazide was synthesized by a reported procedure in good yield (H. Li, et al., Chem. Commun., 2009, 45, 5904)

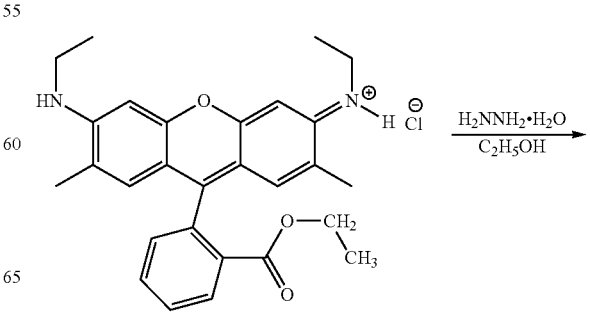

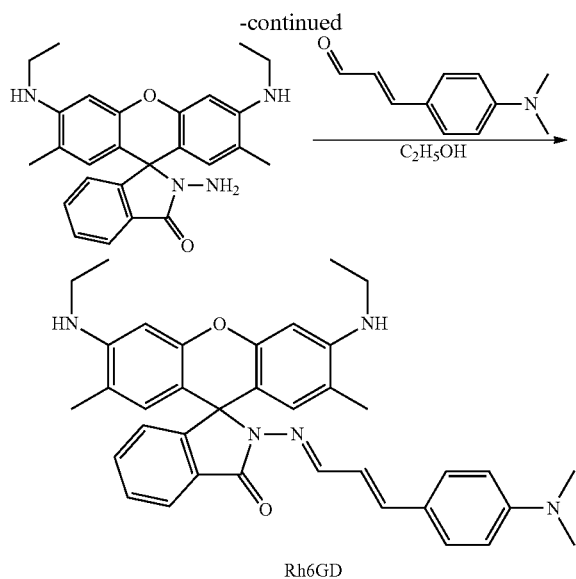

Rh6GD

Condensation of Rhodamine 6G hydrazide with N, N-dimethylaminocinnamaldehyde: Based on a reported similar condensation reaction [35], a mixture of Rhodamine 6G hydrazide (0.12 g, 0.21 mmol) and N,Ndimethylcinnamaldehyde (0.04 g, 0.26 mmol) in absolute ethanol was refluxed for 12 h. After the completion of the reaction, solvent was evaporated to give Rh6GD in 66% yield. $^1$H NMR (400 MHz, DMSO) δ 8.63 (d, J=9.3 Hz, 1H), 7.89-7.80 (m, 1H), 7.62-7.37 (m, 4H), 7.35 (s, 1H), 7.16-6.85 (m, 2H), 6.75-6.42 (m, 5H), 6.36-6.24 (m, 3H), 6.19 (d, J=13.5 Hz, 2H), 5.06 (s, 2H), 3.30-2.91 (m, 10H), 1.85 (d, J=8.2 Hz, 6H), 1.21 (t, J=7.1 Hz, 6H). $^{13}$C NMR (100 MHz, DMSO) δ 163.63, 151.95, 150.75, 147.70, 128.65, 126.90, 123.42, 118.24, 111.94, 105.23, 95.92, 65.43, 40.21, 40.00, 36.75, 17.08, 14.26. TOF-MS ES$^+$: calctd 585.3104. found 586.3206 (M+H)$^+$.

Example 12. Metal Ion Sensing of Rh6GD

Selectivity and spectroscopic properties of the Rh6GD sensor were investigated to evaluate the performance of the fluorescence sensor in solution. The solution of metal ions were prepared from chloride salts of $Ni^{2+}$, $Fe^{3+}$, $Cu^{2+}$, $Mn^{2+}$, $Hg^{2+}$, $Na^+$, $Ca^{2+}$, $Zn^{2+}$, $Ag^+$, and nitrate salts of $Mg^{2+}$, $K^+$, $Co^{2+}$ (1 mM) in deionized water, except for $Cu^{2+}$ and $Co^{2+}$, which were dissolved in acetonitrile anhydrous. Solution of $Cu^+$ was freshly prepared by dissolving tetrakis(acetonitrile) copper(I) (Sigma-Aldrich) into double-distilled water. $Fe^{3+}$, $Fe^{2+}$ solutions were prepared freshly from ferric chloride, ferrous ammonium sulfate (FAS, Fe $(NH_4)_2(SO_4)_2$, respectively in 0.01 M HCl. A stock solution of Rh6GD (1 mM) was prepared in THF. The solution of Rh6GD was diluted to 25 μM with $H_2O$/THF (pH 7.3, v/v, 4:1). Before spectroscopic measurements, solutions were freshly prepared by diluting the corresponding high-concentration stock solution. For each spectrum, 1 mL of a probe solution was added to a 1-cm quartz cell, to which different stock solutions of cations were gradually added. All spectroscopic measurements were done under simulated physiological pH, and measurements were performed at least triplicate and resulting averages are reported.

Figure 22:
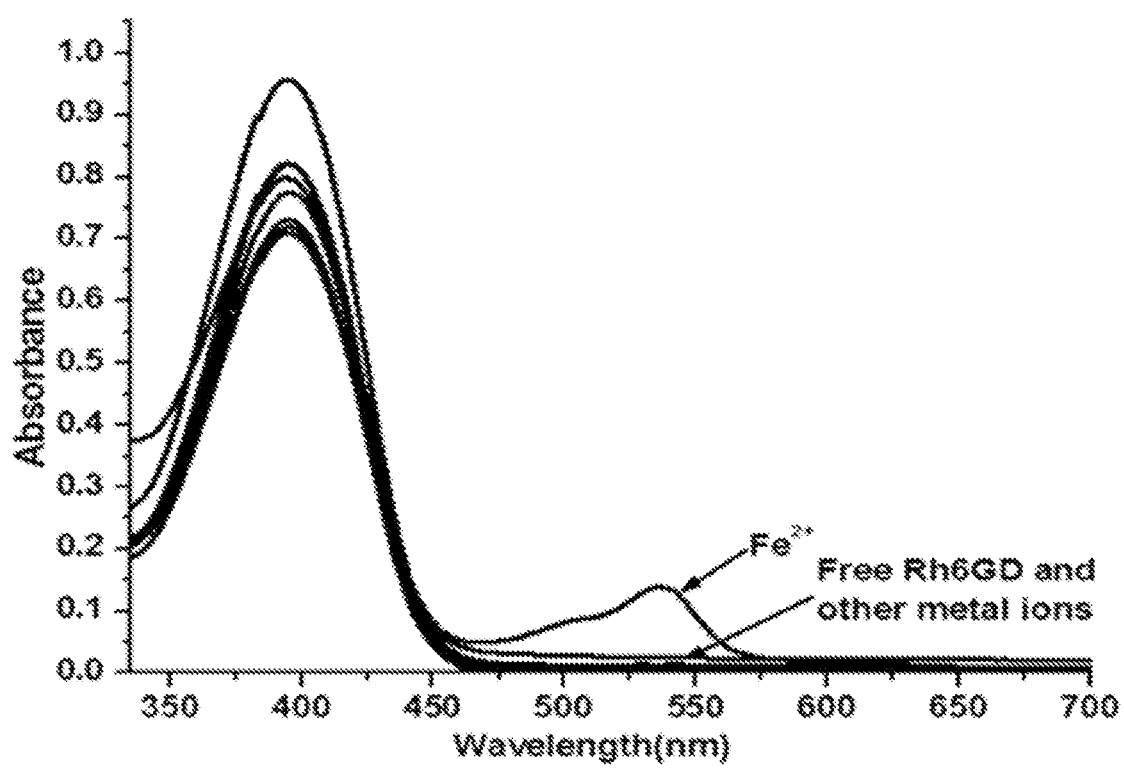
FIG. 22 shows absorbance spectra of 25 μM Rh6GD to various metal ions in $H_2O$/THF (pH 7.3, v/v 4:1).

The changes in UV-Vis spectra after the addition of various metal ions are shown in FIG. 22. The addition of $Fe^{2+}$ to the solution of Rh6GD showed an obvious pink color with an absorption peak at 536 nm in $H_2O$/THF (pH 7.32, v/v 4:1). The color change for $Fe^{2+}$ is readily detected visually. The new absorption band appeared at 536 nm is assigned to the ring-opened form of the rhodamine (Scheme 4) (Y. Wei, et al., Chem. Commun., 2010, 46, 4417; Z. Aydin, et al, Inorg. Chem. Commun., 2012, 20, 93). Compared with that of $Fe^{2+}$, other metal ions tested did not induce significant changes in UV-Vis absorption except $Cu^{2+}$ which showed a bit absorbance response to Rh6GD, presumably due to the binding of $Cu^{2+}$ to the O=C—N—N part of the sensor in the ground state.

Figure 23:
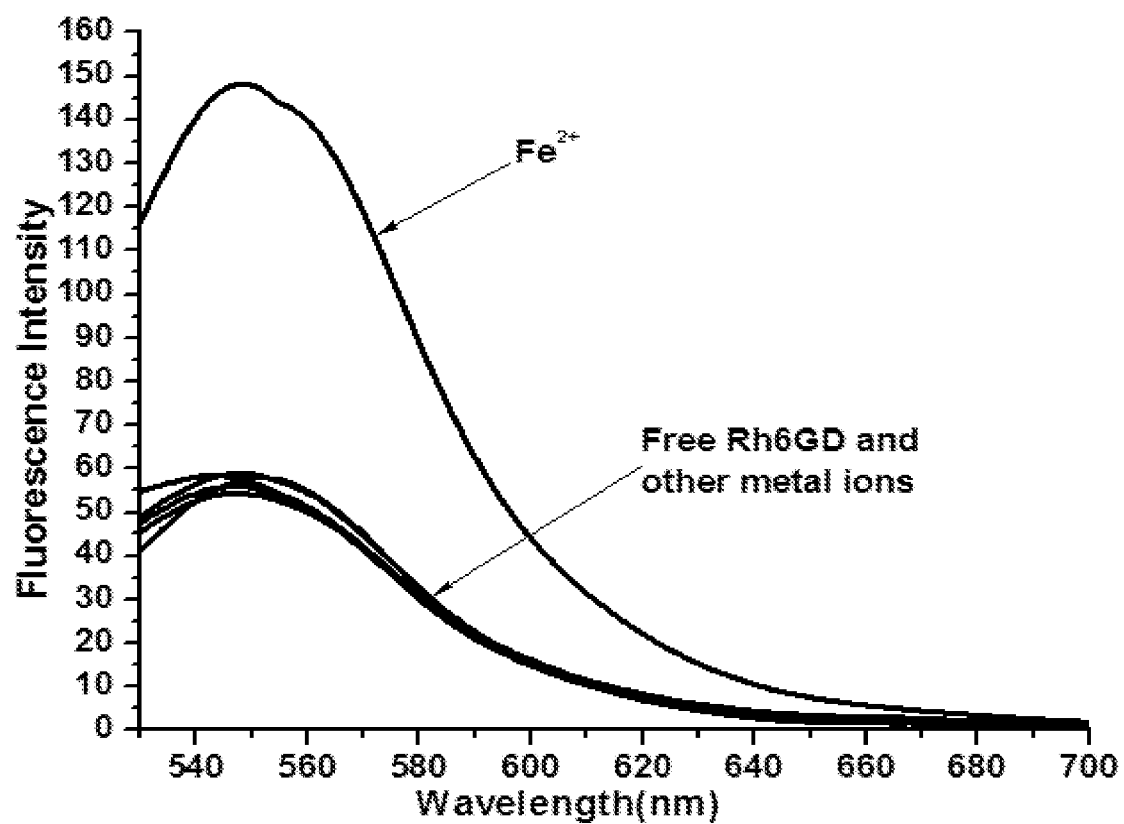
FIG. 23 shows the fluorescence response ($\lambda_{Ex}/\lambda_{Em}$ 510/549 nm) of 25 μM Rh6GD to 25 μM various metal ions in $H_2O$/THF (pH 7.3, v/v 4:1).

The changes in fluorescence spectra of Rh6GD with the addition of different metal ions in $H_2O$/THF (pH 7.32, v/v 4:1) are shown in FIG. 23. When $Fe^{2+}$ was added into the solution of Rh6GD, a large fluorescence enhancement at 549 nm was observed, induced by the complexation of $Fe^{2+}$. The emission intensity enhancement at 549 nm is around 3 times with 1.0 equiv of $Fe^{2+}$, suggesting that Rh6GD is a good turn-on fluorescent sensor for $Fe^{2+}$ (FIG. 23).

Figure 24:
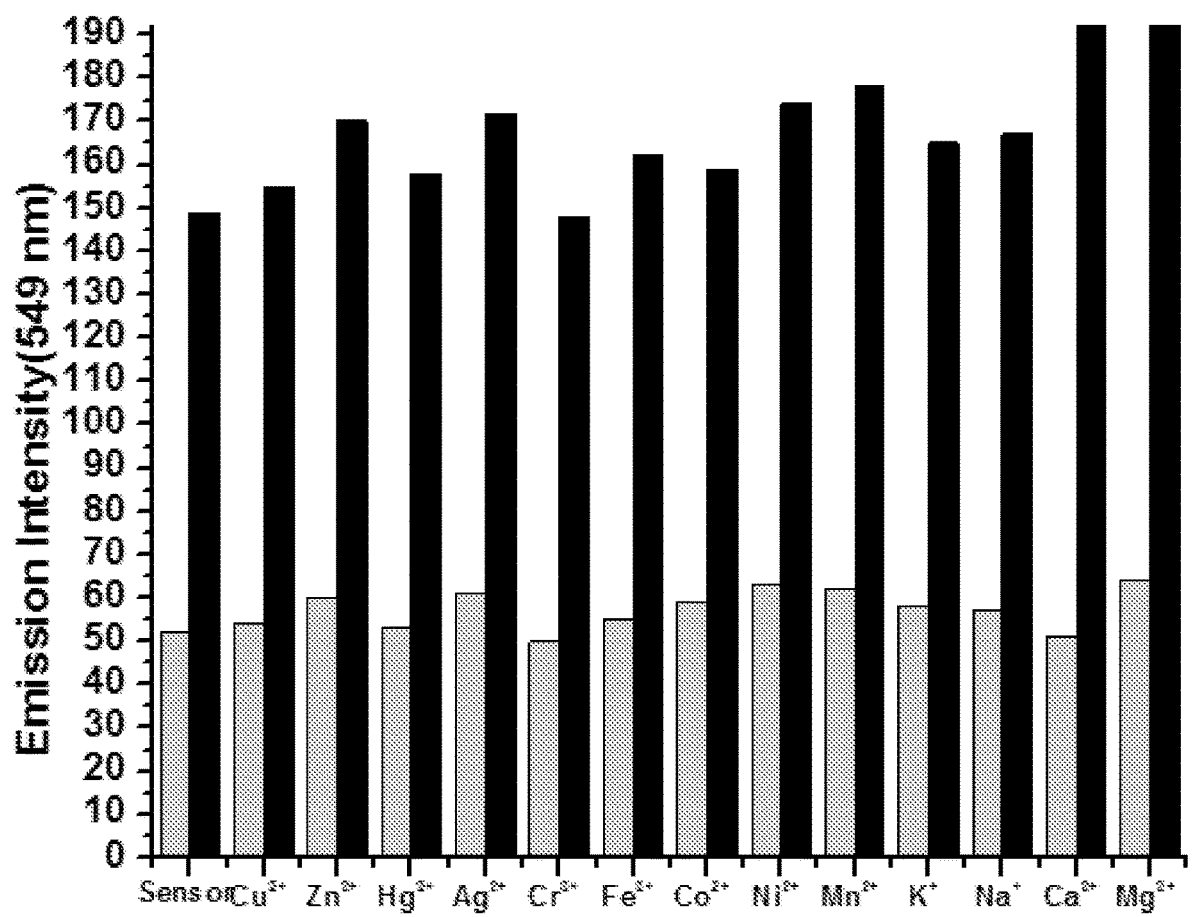
FIG. 24 shows the fluorescence responses of 25 μM Rh6GD to the presence of 25 μM various metal ions (light grey bar) and the subsequent addition of $Fe^{2+}$ (black bar) in the H2O/THF (pH 7.3, v/v 4:1); the bars represent the fluorescence intensity at 549 nm.

Rh6GD displayed an excellent selective turn-on fluorescent response to $Fe^{2+}$ only (FIG. 24). In the presence of any other bio-relevant metal ions including $Fe^{3+}$, $Ni^{2+}$, $Cu^+$, $Cu^{2+}$, $Zn^{2+}$, $Pb^{2+}$, $Cr^{3+}$, $Hg^{2+}$, $Mn^{2+}$, $Ag^+$, $Co^{2+}$, $K^+$, $Na^+$, $Ca^{2+}$ and $Mg^{2+}$, Rh6GD did not trigger fluorescence enhancements under the same conditions (the light grey bars in FIG. 24). Moreover, upon the addition of 1 equiv of $Fe^{2+}$ into solutions containing one of the other metal ions tested, the fluorescence was activated and the intensity increased to a level similar to that observed in the presence of $Fe^{2+}$ only (the black bars in FIG. 24). This demonstrates that these metal ions did not interfere with the fluorescence response of $Fe^{2+}$ to Rh6GD.

Figure 25:
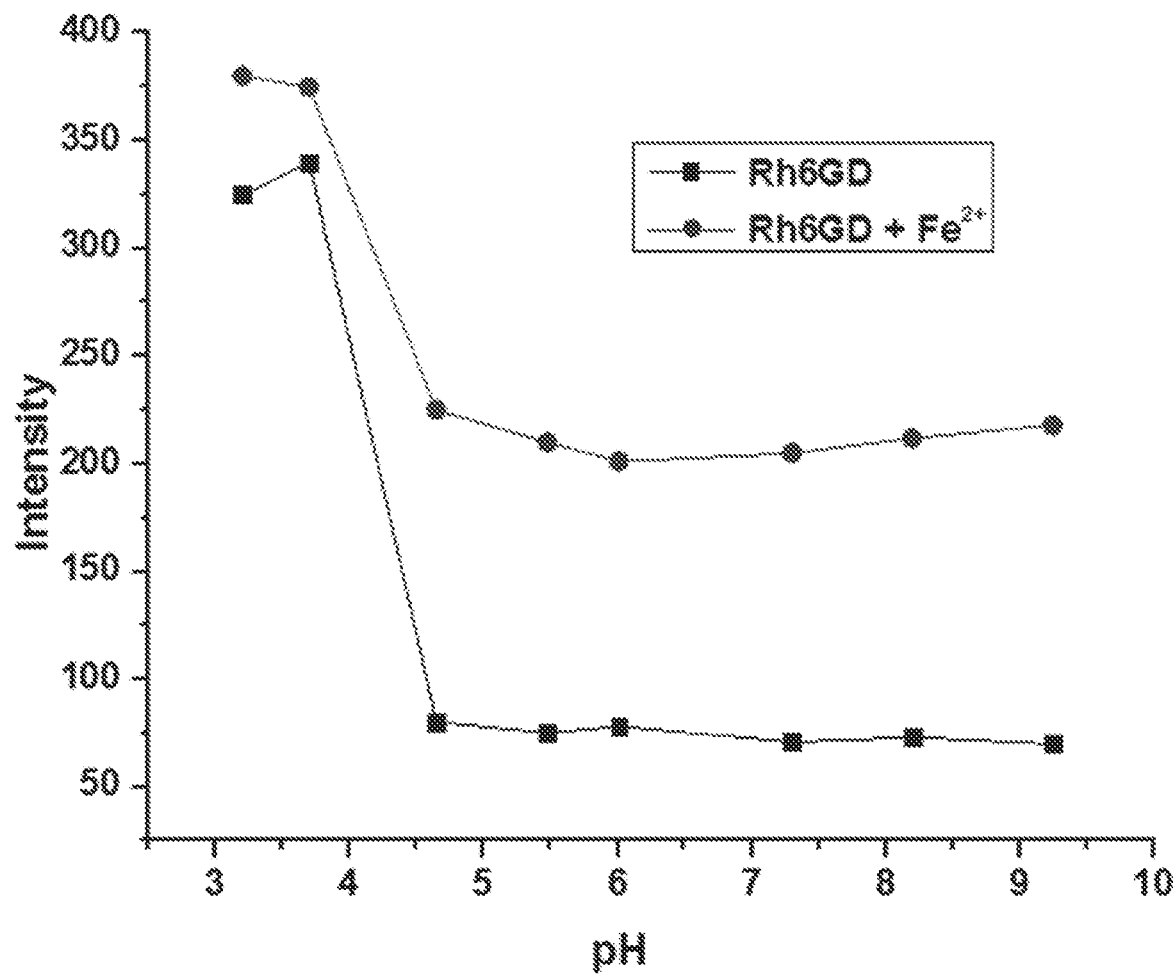
FIG. 25 shows the fluorescence intensity (549 nm) of Rh6GD and Rh6GD+Fe (II) (25 μM each at various pH values in $H_2O$/THF (pH 7.3, v/v 4:1) solution.

As rhodamine-based sensors give response to hydrogen ions, we tested the stability of Rh6GD sensor in the biological pH range. The effect of pH on the stability of the sensor was investigated at different pHs and monitored by fluorescence spectroscopy (FIG. 25). The pH of the solutions was adjusted by adding HCl/NaOH into the solutions. As seen from the FIG. 3.4, the fluorescence of the Rh6GD sensor itself and that of its Fe (II)-complex are stable over the pH range of 9.3 to 4.5, covering the biologically relevant pH range. Thus, Rh6GD may be applied as a fluorescence sensor for imaging in biological systems.

Example 13. Cell Culture and Confocal Imaging

Human primary fibroblast ws1 cells were grown at 37° C. in a humid atmosphere of 5% $CO_2$ atmosphere in eagle's minimum essential medium (EMEM, ATCC) supplemented with 10% fetal bovine serum (FBS, ATCC). Cultures were divided into 1:2 every 48 h to an approximate cell density of 1.21 million cells/ml and used for experiments after 24 h.

A Zeiss LSM 710 laser-scanning confocal microscope system was used for cell imaging experiments. 40× oil-immersion objective lens were used to perform all the experiments. For imaging with the Rh6GD sensor, excitation wavelength of the laser was 543 nm and emissions were collected over the range 545-625 nm. For images with MitoTracker Green FM, LysoTracker Deep Red, excitation wavelengths recommended by the manufacturer were 488 nm for MitoTracker, 633 nm for LysoTracker. Emissions were integrated at 492-535 nm (MitoTracker), 650-800 nm (LysoTracker), respectively.

Ws1 cells, at an approximately density of 1.2 million/ml in complete EMEM medium, were incubated with 100 μM ferrous ammonium sulfate (FAS, Fe $(NH_4)_2(SO_4)_2$ from a 10 mM stock solution) for overnight at 37° C. in a humid atmosphere of 5% $CO_2$ and then the cells were washed with fresh EMEM medium to remove excess $Fe^{2+}$. Then cells were incubated with Rh6GD (10 µM, from 500 µM stock solution in DMF) at 37° C. for 30 min and then cells were washed with EMEM media and then imaged. In addition, some cells were treated firstly with 100 µM $Fe^{2+}$ overnight and then the cells were washed with fresh EMEM medium. For chelation experiments, $Fe^{2+}$-loaded cells or untreated cells were incubated with 1 mM 2,2'-bipyridyl (Bpy) at 37° C. for 30 min, then sensor was added followed by washing with the media, and then imaging was done. Controls were imaged without incubation with $Fe^{2+}$ or 2,2'-bipyridyl.

Example 14. Binding Studies: Stoichiometry, Affinity and Reversibility

Figure 26:
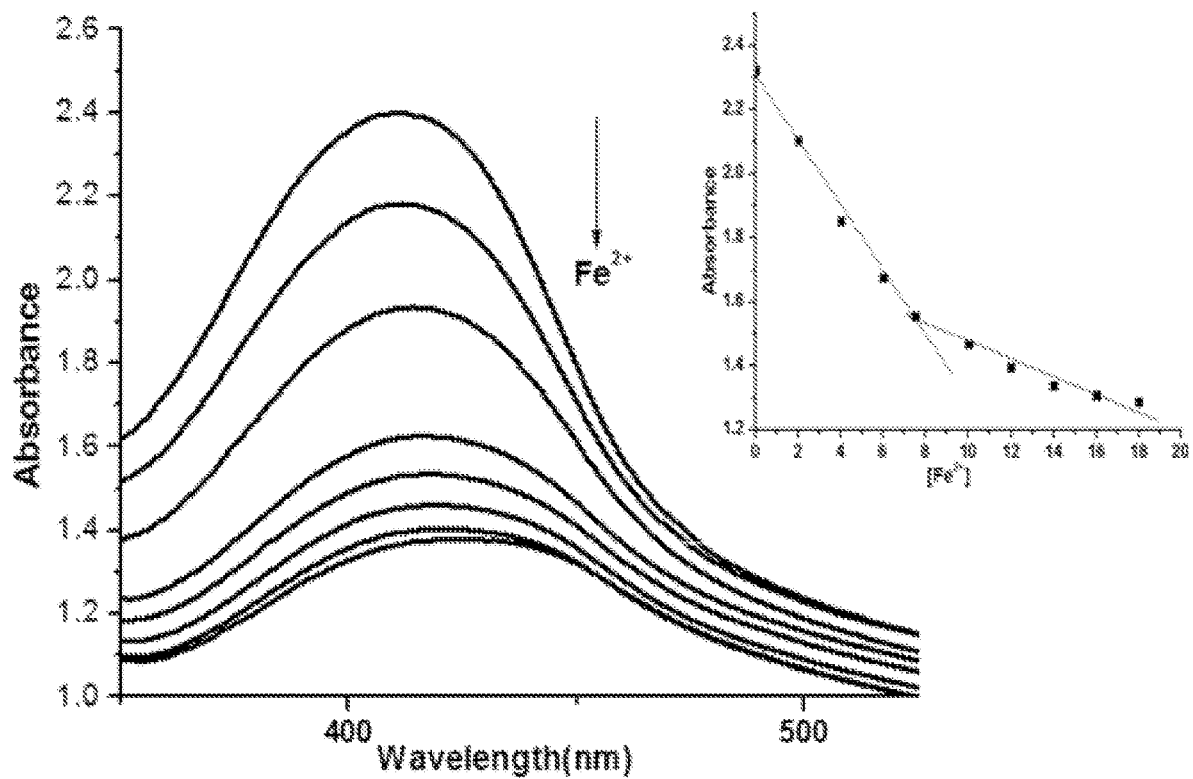
FIG. 26 shows the absorbance spectra of titration of 15 μM Rh6GD with increasing concentrations of $Fe^{2+}$ (0, 2, 4, 6, 7.5, 10, 12, 14, 16, 18 μM, respectively) in $H_2O$/THF (pH 7.3, v/v 4:1) solution. Inset is a plot of absorbance at 420 nm versus [$Fe^{2+}$].

The binding stoichiometry between the sensor Rh6GD and $Fe^{2+}$ was investigated by absorption and fluorescence titrations first. The sensor, Rh6GD has an absorption band at ~420 nm (FIG. 26) which is due to the transition from S0 to S1 states (A. Chakraborty, et al., N. Chem. Phys., 2006, 324, 733) of the dimethylaminocinnamaldehyde moiety. Upon addition of $Fe^{2+}$ ions, the band at 420 nm decreases in intensity and the titration curve (a plot of absorption versus $Fe^{2+}$) decreased (FIG. 26) linearly and the curve changed its slope at 2:1 ratio of the sensor and $Fe^{2+}$, suggesting the formation of a 2:1 of Rh6GD-$Fe^{2+}$ complex. Similar titrations were performed and were monitored by fluorescence spectroscopy.

Figure 27:
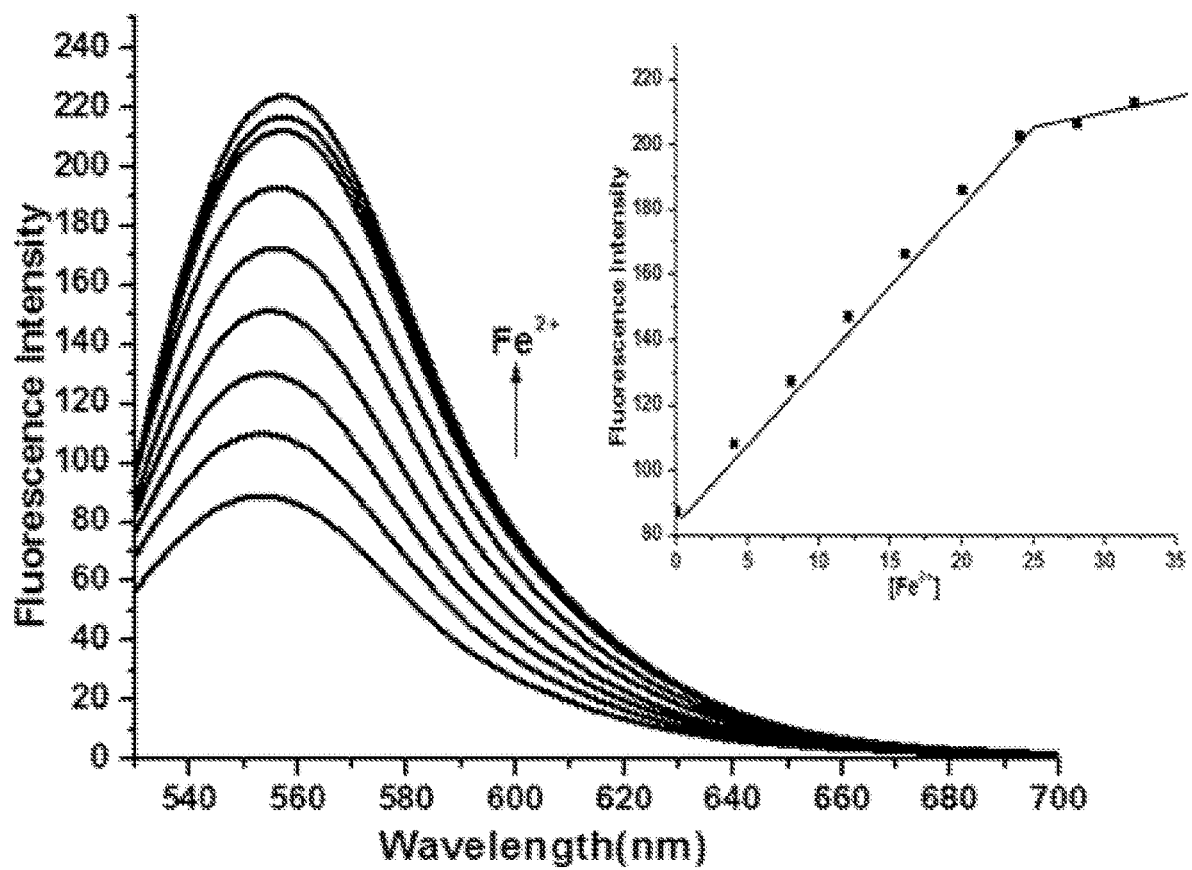
FIG. 27 shows the fluorescence intensity of the titration of 50 μM Rh6GD with increasing concentration of $Fe^{2+}$ (0, 4, 8, 12, 16, 20, 24, 28, 32 μM, from bottom to top) in $H_2O$/THF (pH 7.3, v/v 4:1). Inset, a plot of fluorescence at 550 nm versus [$Fe^{2+}$].

As shown in FIG. 27, the fluorescence band increased in intensity linearly and plateaued at 2:1 ratio of the sensor and $Fe^{2+}$, supporting the formation of a 2:1 of Rh6GD-$Fe^{2+}$ complex.

The binding constant was estimated by using the absorption titration results. The equations below were used to calculate the binding constant for 2:1 complexes following a reported procedure (M. Guo, et al., Dalton Trans., 2007, 102, 4951).

$$S + 2L \rightleftharpoons SL_2 \tag{1}$$

The complex apparent binding constant is given by $$K = \frac{[SL_2]_e}{[S]_e [L]_e^2} \tag{2}$$

The subscript e means concentrations at equilibrium. The ratio of the equilibrium between the complex, $[LS]_e$, and the initial concentration of the ligand, $[L]_o$, can be derived from the absorbance of the ligand at a chosen wavelength when the system is at equilibrium. The result of the derivation is shown in eq. (3).

$$F_c = \frac{A_u - A_m}{2A_u - 2A_c} = \frac{[SL_2]_e}{[L]_o} \tag{3}$$

$F_c$ is the fraction of L that formed a complex; the subscripts e and o stand for equilibrium and initial concentrations, respectively. $A_u$, $A_m$, and $A_c$ are the absorbances of solutions of L (before any $Fe^{2+}$ was added), during the titration, and at saturation, respectively. The concentration of free $Fe^{2+}$ at equilibrium, $[S]_e$, is found with the following identity:

$$[S]_e = [S]_o - [SL_2]_e = [S]_o - F_c[L]_o \tag{4}$$

Finally, the integrated apparent binding constant equation is shown in equation (5).

$$K = \frac{F_C}{2[L]_o [S]_e (1 - F_c)^2} \tag{5}$$

Using the above equation, the binding affinity was calculated based on the titration studies and was determined to be $1.8 \times 10^{11}$ $M^{-2}$.

Figure 28:
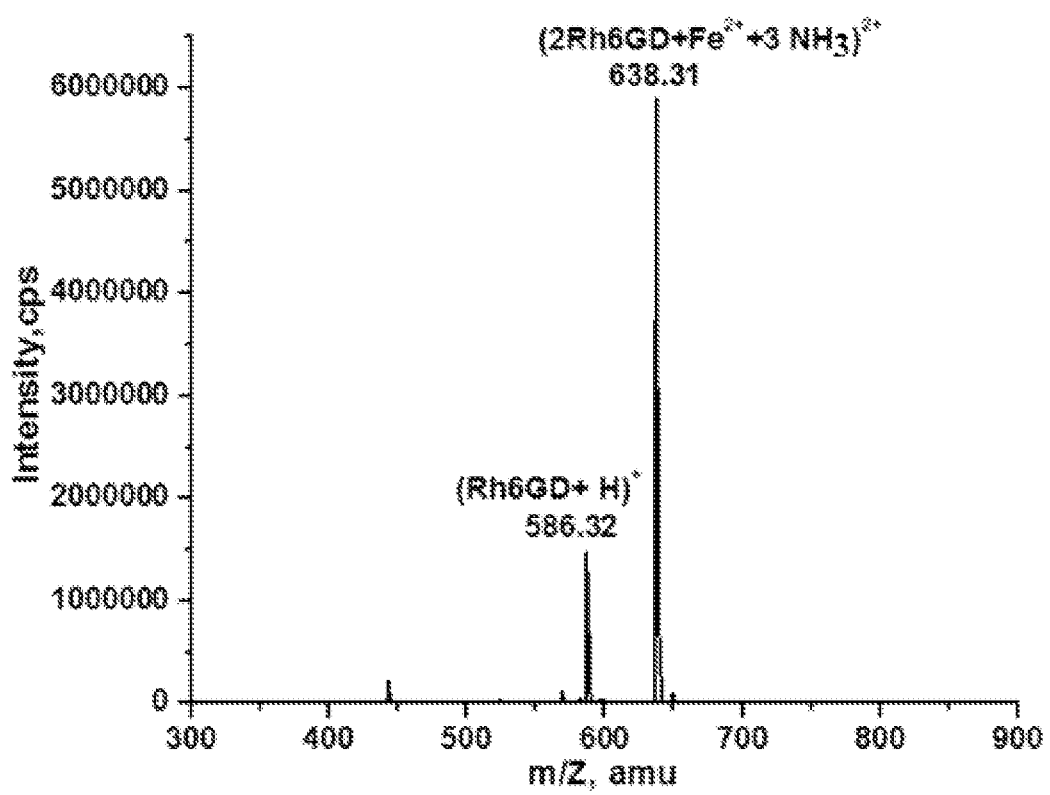
FIG. 28 shows an ESI-MS spectrum of the solution of Rh6GD with $Fe^{2+}$ (10 μM sensor and excess FAS (ferrous ammonium sulfate) in $H_2O$/THF (pH 7.3, v/v 4:1).

The species formed between Rh6GD and $Fe^{2+}$ was more accurately determined by ESI-MS. Upon the mixing of $Fe^{2+}$ and the sensor (10 µM sensor and excess of FAS in $H_2O$/THF (pH 7.32, v/v 4:1), one major species with m/z=638.31, assignable to a 2:1 complex (Rh6GD:$Fe^{2+}$=2:1) with three ammonia molecules attached, was detected by ESI-MS (FIG. 28), corroborating the 2:1 stoichiometry established by spectroscopic titrations.

Figure 29:
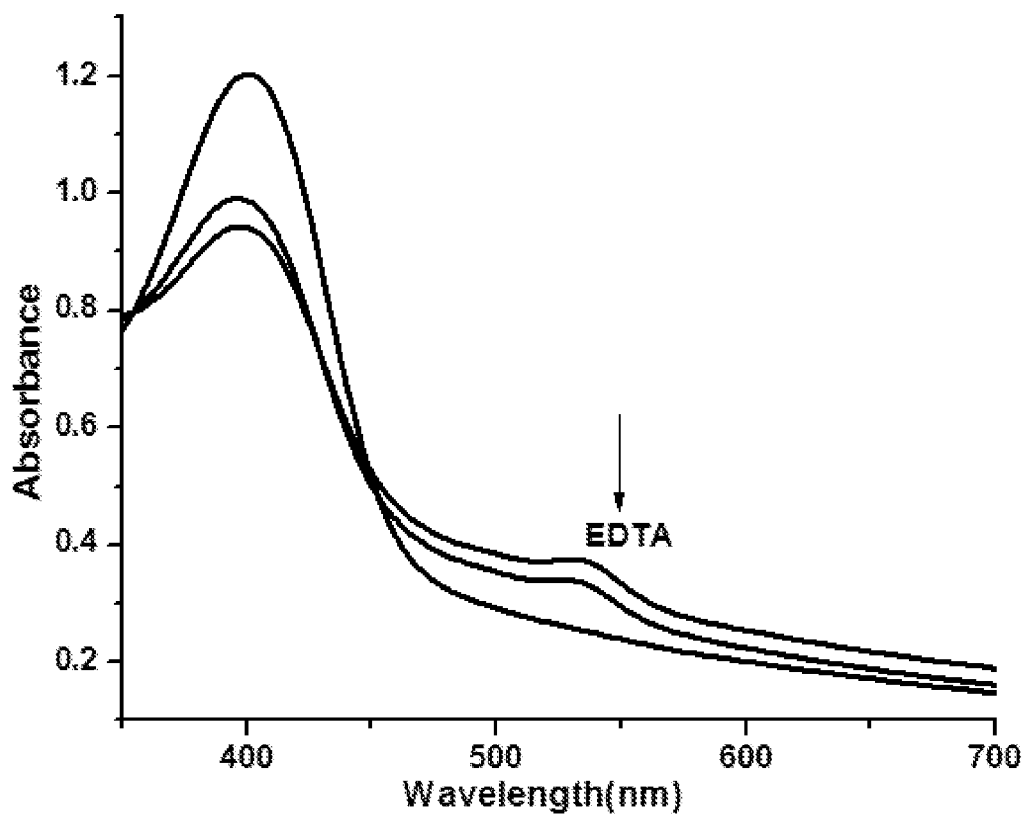
FIG. 29 shows the absorbance spectra of 40 μM Rh6GD-$Fe^{2+}$ complex with increasing concentration of EDTA in $H_2O$/THF (pH 7.3, v/v 4:1).

Reversibility experiments were carried out by adding the metal chelator EDTA to the Rh6GD-$Fe^{2+}$ complex in $H_2O$/THF (pH 7.3, v/v 4:1). In the absence of EDTA, the complex was colorful pink. After adding EDTA, the absorption of the complex decreased in intensity and finally, disappeared (FIG. 29), suggesting a reversible binding between Rh6GD and $Fe^{2+}$.

Example 15. Binding Site of $Fe^{2+}$ on the Rh6GD Sensor

Figure 30:
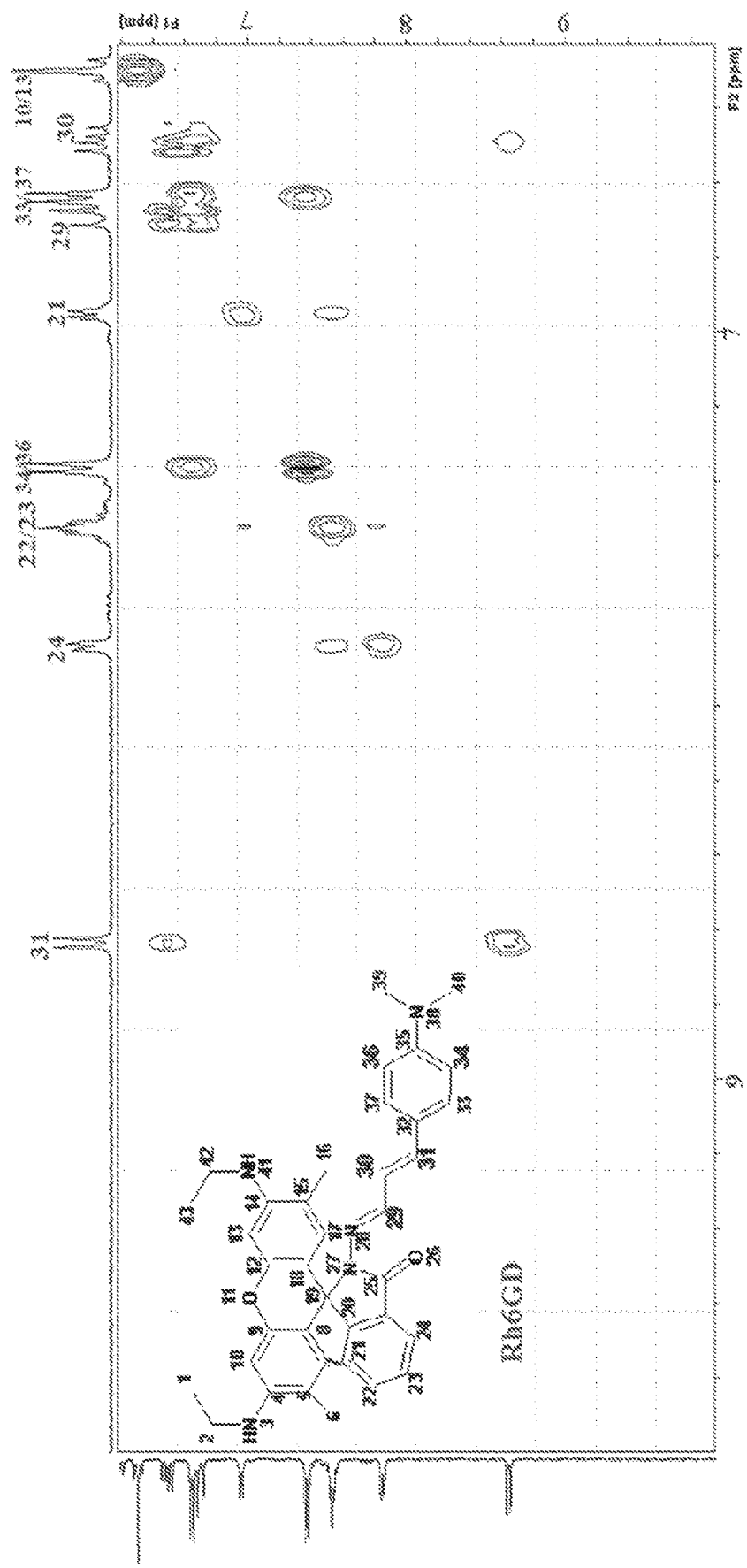
FIG. 30 shows a 2D-COSY NMR spectrum (magnified portion from 6 to 10 ppm) of the sensor Rh6GD in DMSO.

In order to probe the binding site of $Fe^{2+}$ on the Rh6GD sensor and structure of the complex, 1D and 2D $^1H$ NMR of the sensor Rh6GD was investigated first. A complete assignment of the $^1H$ NMR peaks of the the Rh6GD sensor was achieved by 2D $^1H$-$^1H$ COSY and $^1H$-$^1H$ NOESY NMR studies. FIG. 30 shows the aromatic region of the 2D $^1H$-$^1H$ COSY spectra with the peak assignments shown in the inset.

Figure 31:
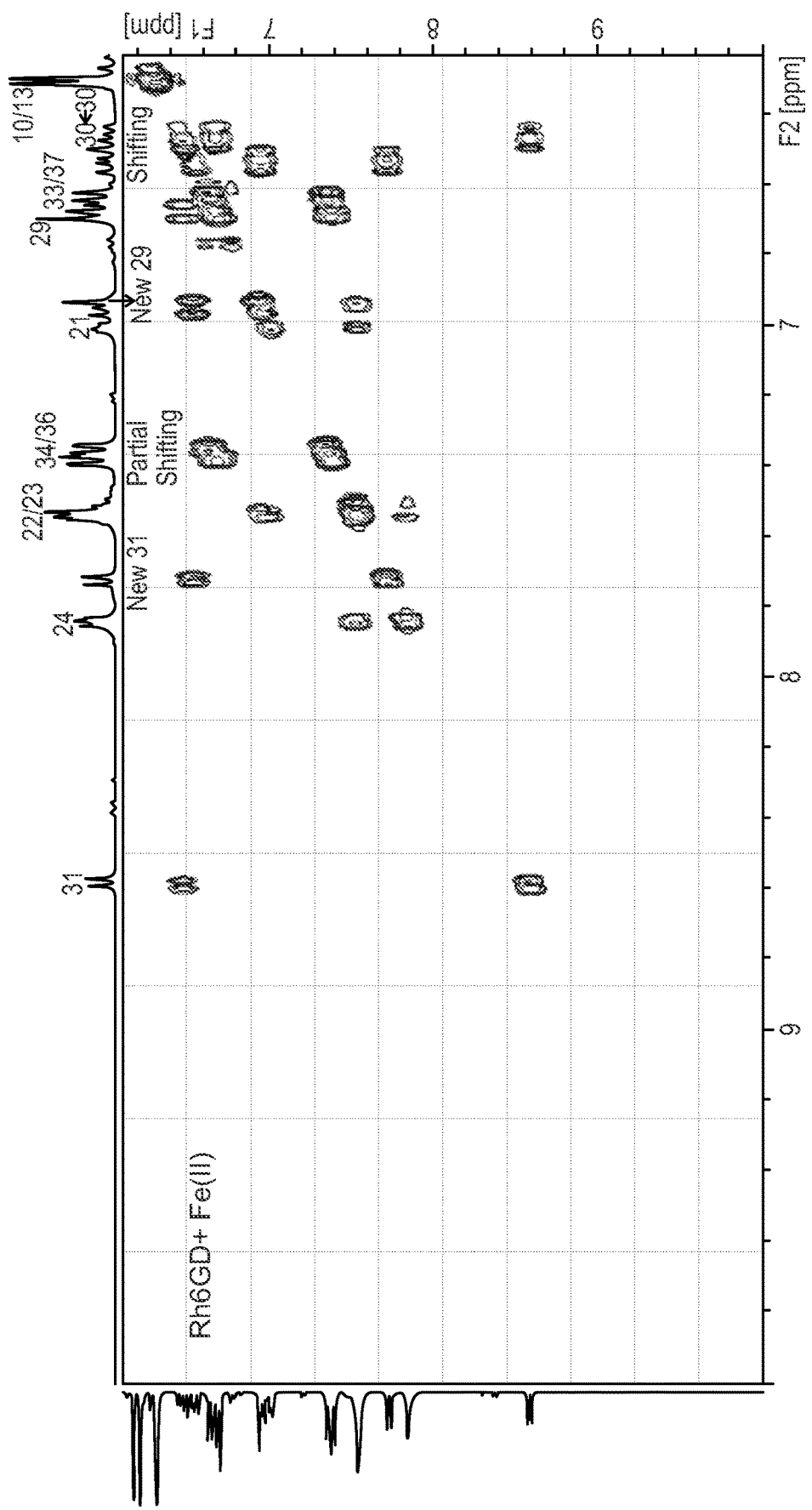
FIG. 31 shows a 2D-COSY NMR spectrum of (Rh6GD+$Fe^{2+}$) in DMSO.
Figure 32:
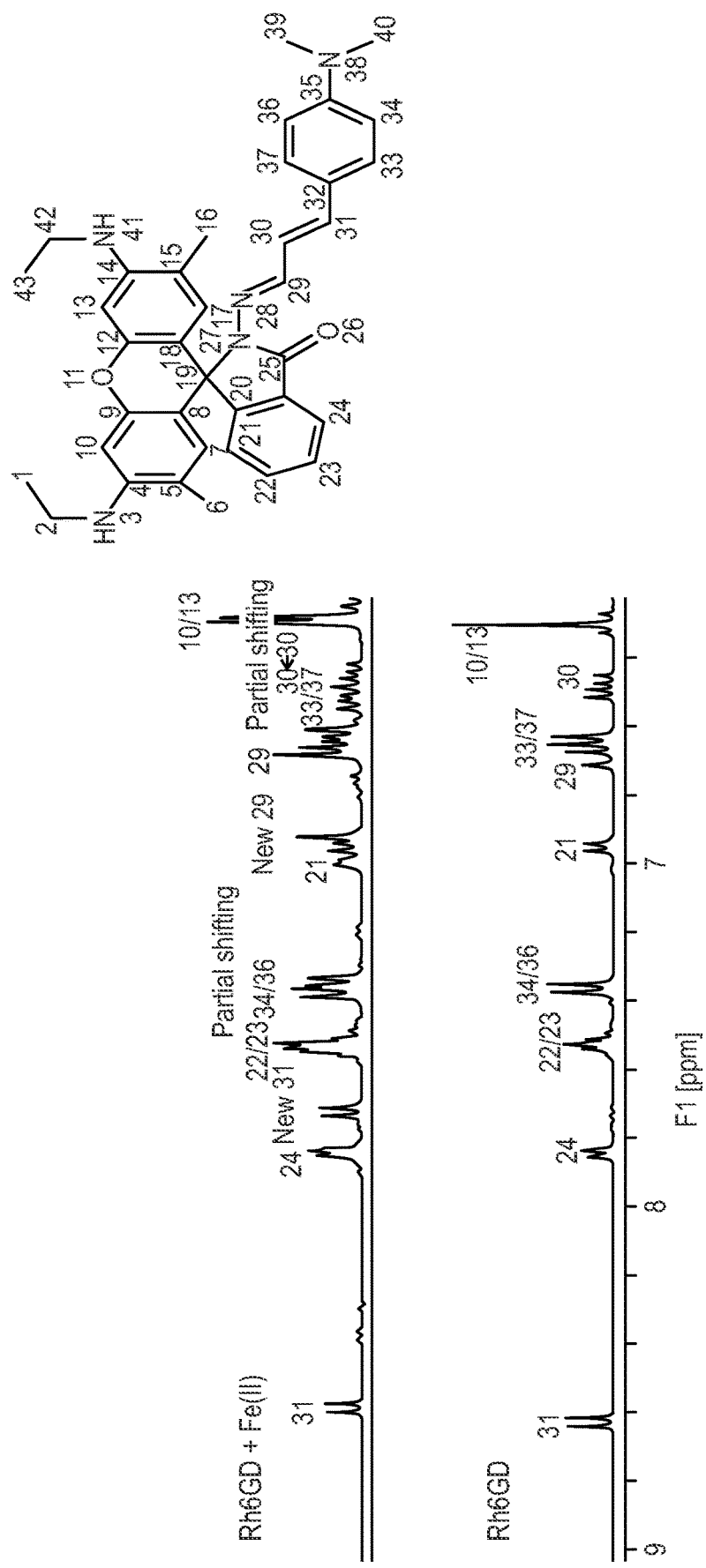
FIG. 32 shows a $^1H$ NMR spectrum of Rh6GD and (Rh6GD+$Fe^{2+}$) in DMSO.

After adding $Fe^{2+}$ (FAS, only partially soluble in the DMSO solution) to the Rh6GD in the NMR tube, the solution turned to reddish pink, suggesting the formation of the sensor-$Fe^{2+}$ complex. However, the NMR peaks of Rh6GD were not significantly broadened or shifted, suggesting that the formation of diamagnetic low-spin $Fe^{2+}$ species. The notable changes in the $^1H$ and 2D COSY spectra (FIGS. 31 and 32) are some upfield and downfield shifts of conjugated diene protons of Rh6GD, such as up-field shift of 31, minor up-field shifting of 33/37 and 34/36, downfield shifting of 29 and minor downfield shifting of 30 numbered protons. The most significant change in the NMR spectra is that the #31 $^1H$ doublets (~8.6 ppm, dimethylaminocinnamo moiety, numbering see FIG. 30 inset) decreased in intensity while a new #31 $^1H$ doublet appeared upfield at ~7.7 ppm (FIG. 31). Such a large upfield shift (~0.9 ppm) in $^1H$ NMR peak suggests a $Fe^{2+}$-coordination to the π-bond involving carbon 31. π-bond coordination is well known in transition metal alkene complexes and upfield shift of similar NMR peaks has been observed in π-coordinated $Fe^{2+}$-diene complexes (O. Seinosuke, T. Yoshid, et al., Inorg. Chem., 1967, 6, 20). Carbon 32 does not have an attached proton, however, small upfield shifts of the #33/37 and #34/36 $^1H$ peaks were also observed, suggesting that $Fe^{2+}$-coordination to the π-bond involving carbons 31 and 32. Another significant change in the NMR spectra is a downfield shifting of #29 proton from ~6.7 ppm to ~6.9 ppm. This, together with the minor downfield shift of the #30 proton, suggests the coordination of N28 to $Fe^{2+}$. Another donor site is usually the O26 from the rhodamine moiety, which is a common site for metal binding. Though O26-coordination is not expected to induce any obvious $^1$H NMR shift as the closest proton is 4-bond away. The slight broadening of #24, 22/23 peaks and shift of #21 proton peak after the addition of $Fe^{2+}$ support such binding. FIG. 32 shows the aromatic region of the $^1$H NMR spectra of Rh6GD and (Rh6GD+$Fe^{2+}$) to show the notable changes in the $^1$H NMR peaks with the peak assignments shown in the inset.

Figure 33:
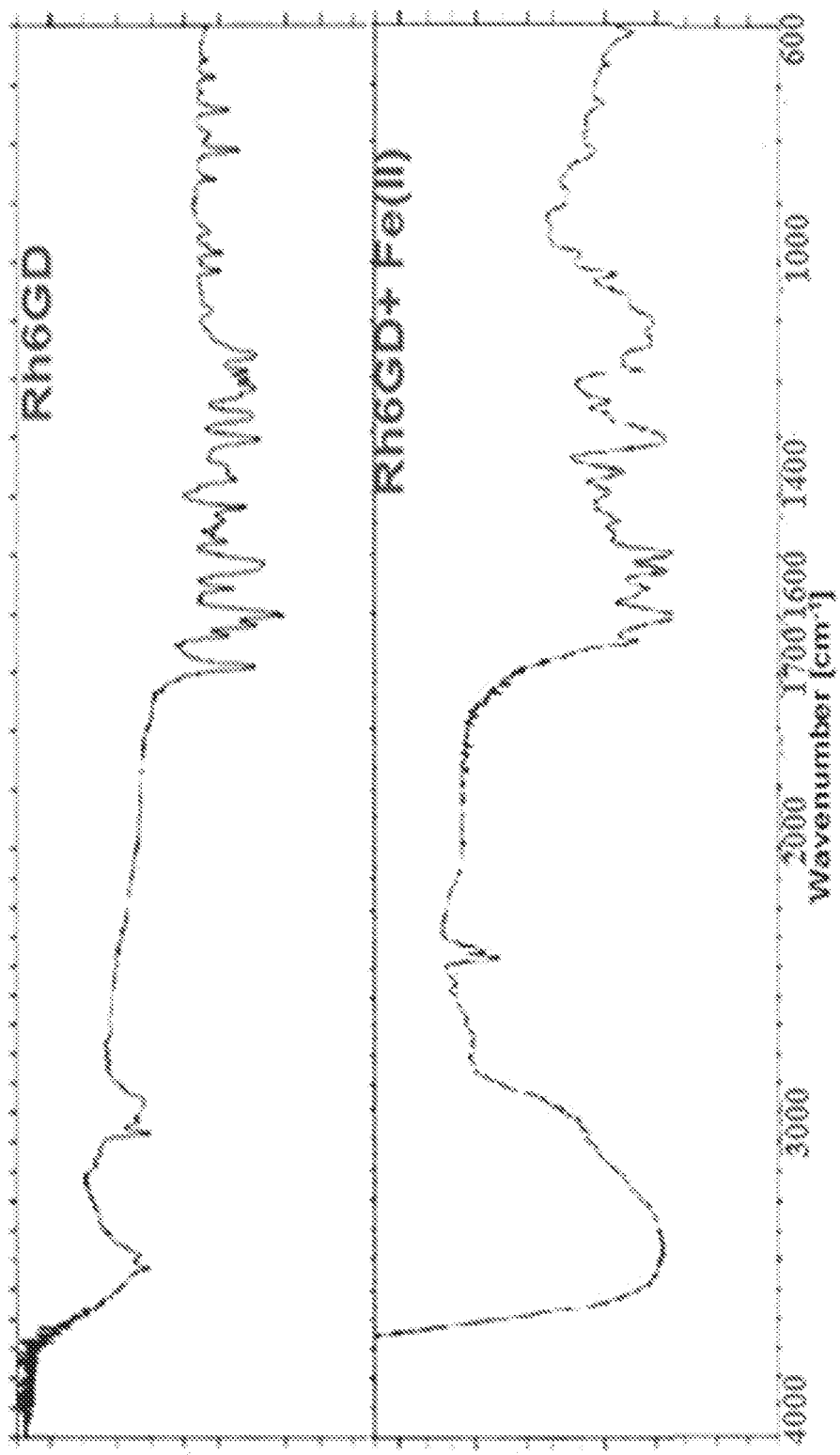
FIG. 33 shows a FTIR spectrums of Rh6GD and (Rh6GD+$Fe^{2+}$) in $H_2O$/THF (pH 7.3, v/v 4:1).

More direct evidence on O26 coordination came from evidences in FT-IR spectra. The FT-IR spectra of Rh6GD and Rh6GD-$Fe^{2+}$ were taken in KBr pellets and the results were shown in FIG. 33. The strong peak at ~1690 cm$^{-1}$, which corresponds to characteristic amide carbonyl (C=O) stretch absorption of Rh6GD, was disappeared; meanwhile, a strong broad peak, assignable to C—O stretch, appeared at ~1300 cm$^{-1}$, indicating that $Fe^{2+}$-binding induced a ring-opened form of the rhodamine and the binding with $Fe^{2+}$ takes place in this C—O. Other significant changes induced by $Fe^{2+}$-binding in the IR spectra include broadening of peak ~3000 cm$^{-1}$ (=C—H stretch), shift of peak at ~1640 cm$^{-1}$ (C=N, —C=C— stretch), broadening of peak at ~1600 cm$^{-1}$ (C—C stretch in aromatic ring) and splitting of the peak at ~1500 cm$^{-1}$ (C—C stretch in aromatic ring). Taken together, these NMR and FT-IR changes clearly indicates that O26, N28 and C31=C32 are involved in binding with $Fe^{2+}$, with the formation of a 5-membered chelating ring and a 5.5-membered chelating ring with a η-2 π-coordination. A possible structure of the complex is proposed in Scheme 4. Such a novel coordination involving a η-2 π-binding is unlikely to occur with $Fe^{3+}$ or other physiologically relevant metal ions, which may explain its excellent selectivity for $Fe^{2+}$.

Figures 34A, 34B, 34C:
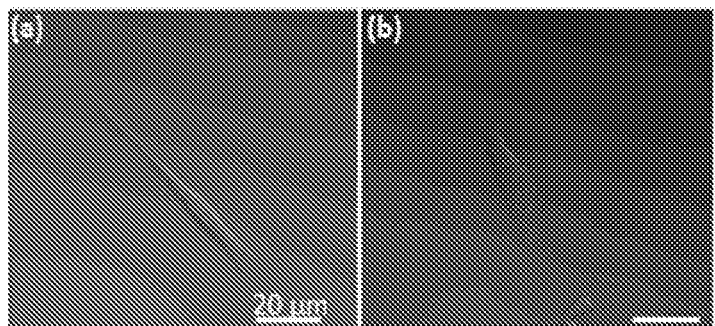
FIG. 34A to FIG. 34E are confocal microscopy images (with DIC) of live human ws1 fibroblast cells.
Figures 34D, 34E:
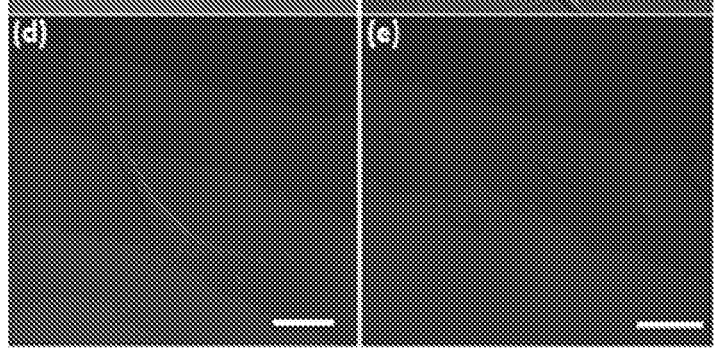
Figure 34F:
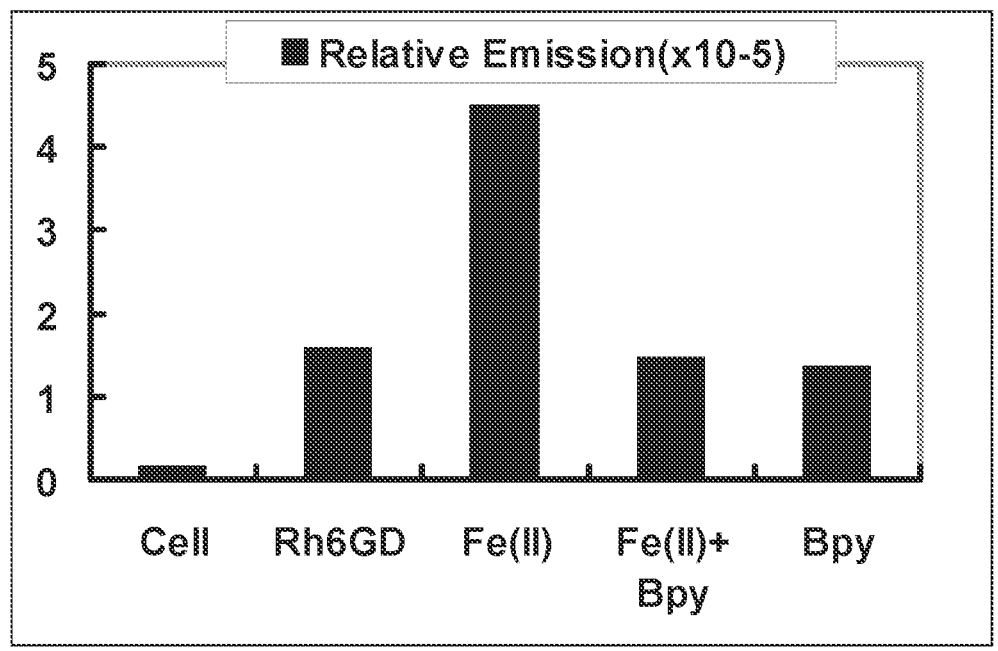
FIG. 34F is a graph showing the relative emission.

A possible mechanism for the reaction and the binding mode are shown in Scheme 4 ferrous ammonium sulfate (Fe $(NH_4)_2(SO_4)_2$) at 37° C. for overnight followed by washing with EMEM medium to remove excess $Fe^{2+}$ and then 10 μM of Rh6GD was added to the culture media and was incubated at 37° C. for 30 min. The $Fe^{2+}$-treated ws1 cells showed significant increase in fluorescent signals (FIG. 34C) compare to the ws1 cells without $Fe^{2+}$ supplementation (FIG. 34B), suggesting a positive response of Rh6GD to increased labile $Fe^{2+}$ levels in $Fe^{2+}$-treated cells. For $Fe^{2+}$-depleting conditions, 2,2-bipyridyl (Bpy) which is known to be a selective $Fe^{2+}$-chelator was used to chelate $Fe^{2+}$ (W. Breuer, et al., *J. Biol. Chem.*, 1995, 270, 24209; A. M. Romeo, et al., *J. Biol. Chem.*, 2001, 276, 24301). ws1 cells treated with 10 mM of Bpy showed significantly decrease in fluorescence signal (FIG. 34E) and it is weaker than that of the control cells (cells with sensor only, FIG. 34B); suggesting Rh6GD can detect basal level of labile $Fe^{2+}$ in ws1 cells as well as the dynamic change in cellular $Fe^{2+}$ levels. The ws1 cells treated with 100 μM of $Fe^{2+}$ overnight first followed by washing with EMEM medium and then treated with 10 mM of Bpy and subsequent addition of 10 μM of Rh6GD showed marked decrease in fluorescent intensity (FIG. 34D) compare to that of cells with $Fe^{2+}$ supplement (FIG. 34C). This fluorescent intensity is almost the same as that of cells without $Fe^{2+}$ or Bpy treatment (FIG. 34B). These data clearly demonstrate that Rh6GD has the ability to detect endogenous level of labile $Fe^{2+}$ as well as its dynamic changes in ws1 cells.

The discrete confocal fluorescence images revealed by Rh6GD in both the untreated and the $Fe^{2+}$-loaded ws1 cells imply that the labile $Fe^{2+}$ in ws1 cells may be localized in certain subcellular compartments (organelles) and that Rh6GD may be capable of imaging $Fe^{2+}$ at subcellular resolution. To explore this, the distribution of exchangeable

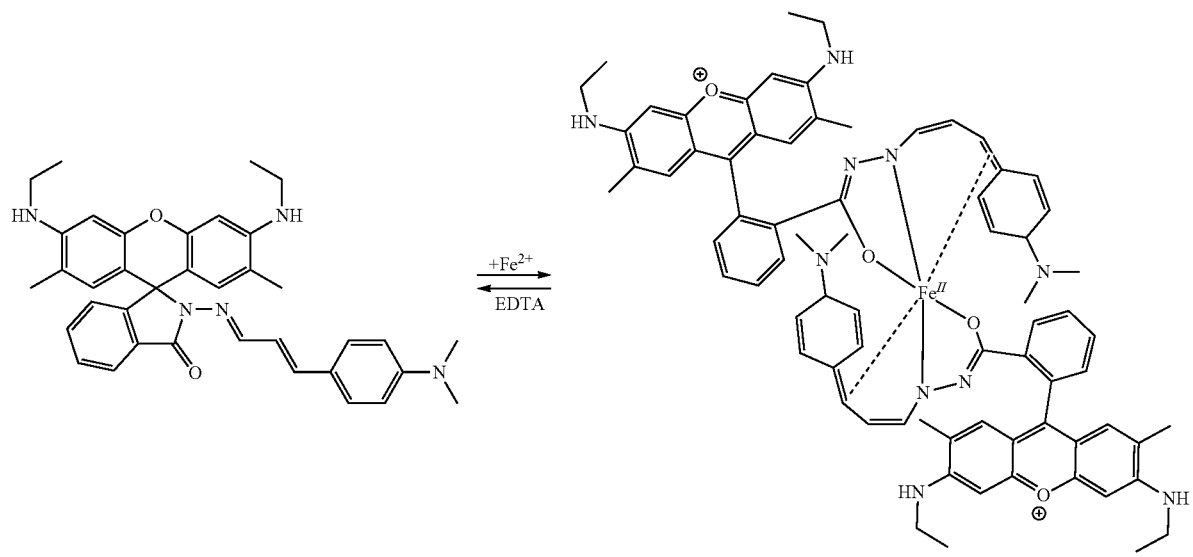

Scheme 4. Proposed 2:1 binding mode of Rh6GD with $Fe^{2+}$ in $H_2O$/THF (pH 7.3, v/v 4:1).

Example 16. Biological Imaging Studies

The ability of Rh6GD to detect $Fe^{2+}$ in primary human fibroblast cells (ws1) was investigated by using confocal microscopy. Live ws1 cells incubated with 10 μM Rh6GD showed weak fluorescence (FIG. 34B). For $Fe^{2+}$ repleting conditions, live ws1 cells were incubated with 100 μM of $Fe^{2+}$ pools in live ws1 cells were further investigated using Rh6GD, together with colocalization experiments using other dyes such as MitoTracker Green FM (a green fluorescent dye which localizes to mitochondria in live cells regardless of mitochondrial membrane potential) and LysoTracker Deep Red (a fluorescent dye that stains acidic compartments such as endosomes and lysosomes in live cells). Human ws1 cells (without $Fe^{2+}$ treatment) were treated with Rh6GD, MitoTracker Green FM, and LysoTracker Red DND-100. As illustrated in FIG. 35, partial colocalization between Rh6GD-$Fe^{2+}$ and the MitoTracker (FIG. 35E) as well as between Rh6GD-$Fe^{2+}$ and the LysoTracker (FIG. 35F) occurred whereas complete colocalization of Rh6GD-$Fe^{2+}$, MitoTracker and LysoTracker (FIG. 35G) was observed. These data suggest that the exchangeable $Fe^{2+}$ pools in ws1 cells detectable by Rh6GD are localized in mitochondria and endosomes/lysosomes, not in the cytosol.

Example 17. Synthesis of Rh101D

General Information

Rhodamine 101, N, N-dimethylaminocinnamaldehyde (DMACA) were purchased from Sigma-Aldrich. The other chemicals and the solvents used in the experiments were purchased commercially and were used without further purification. Tetrahydrofuran (Sigma-Aldrich), ethanol, and double-distilled water were used as solvents. MitoTracker Green FM, LysoTracker Deep Red were purchased from Life Technologies and used in accordance with the manufacturer's protocols.

ESI-MS analyses were performed using a Waters ACQUITY UPLC mass spectrometer. UV/Vis spectra were recorded on a Perkin-Elmer Lambda 25 spectrometer at 293 K. Fluorescence spectra was recorded on a Perkin-Elmer LS55 luminescence spectrometer at 293 K. Excitation and emission slits were 5 nm and emission spectra were collected 570 nm-800 nm after excited at 550 nm. The pH measurements were carried out on a Corning pH meter equipped with a Sigma-Aldrich micro combination electrode calibrated with standard buffer solutions. $^1H$ and $^{13}C$ NMR spectra were recorded on a Bruker Ascend 400 NMR spectrometer at ambient temperature (298 K). Chemical shifts are reported in delta (δ) unit per million (ppm) downfield tetramethylsilane. Splitting patterns are abbreviated as follows: s, singlet; d, doublet; t, triplet; q, quartet; m, multiplet; br, broad.

Preparation of Rh101D

Rh101D was developed by adding a coordination site for $Fe^{2+}$ ions to the rhodamine 101 moiety. Rh101D was synthesized via a two-step procedure as outlined in Scheme 5. The rhodamine 101 hydrazide was synthesized using a procedure similar to a reported one in good yield (H. Li, et al., Chem. Commun., 2009, 45, 5904).

Condensation of Rhodamine 101 hydrazide with N, N-dimethylaminocinnamaldehyde: Using a procedure similar to a reported one (M. Kumar, et al., Tetrahedron Lett., 2011, 52, 4333), a mixture of Rhodamine 101 hydrazide (0.106 g, 0.21 mmol) and N, N-dimethylcinnamaldehyde (0.04 g, 0.26 mmol) in absolute ethanol were refluxed for 12 h. After the completion of the reaction, solvent was evaporated to give Rh101D in 58% yield.

$^1H$ NMR (400 MHz, DMSO) δ 7.72 (m, 1H), 7.57-7.35 (m, 2H), 7.12 (d, 1H), 7.04-6.66 (m, 6H), 6.60 (d, 4H), 5.91 (s, 3H), 4.23 (s, 3H), 3.39 (s, 1H), 3.23-3.16 (m, 4H), 2.93-2.88 (m, 8H), 2.84-2.79 (m, 6H), 2.42-2.37 (m, 4H), 2.02-1.93 (m, 6H). $^{13}C$ NMR (100 MHz, DMSO) δ 189.7, 160.57, 150.70, 147.37, 146.97, 144.85, 142.65, 140.83, 134.75, 132.57, 132.14, 129.67, 127.22, 126.79, 125.77, 124.27, 121.4, 120.58, 112.89, 108.99, 65.6, 42.01, 26.66, 23.04, 22.40, 16.1. TOF-MS $ES^+$: formula $C_{43}H_{43}N_5O_2$ calctd 661.34. found 662.5 $(M+H)^+$.

Scheme 5 Synthesis route for Rh101D.

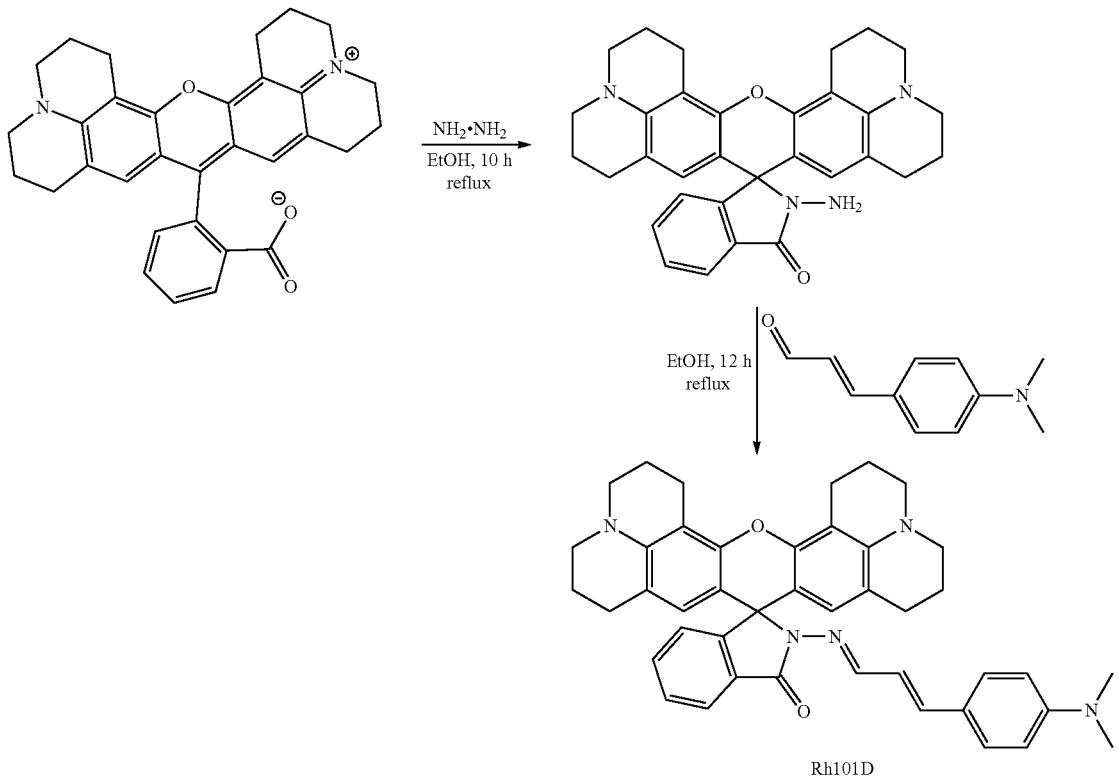

Rh101D

Example 18. Metal Ion Sensing for Rh101D

Metal ion selectivity and spectroscopic properties of the sensor were investigated to evaluate the performance of the fluorescence sensor Rh101D. The solution of metal ions were prepared from chloride salts of $Ni^{2+}$, $Fe^{3+}$, $Cu^{2+}$, $Mn^{2+}$, $Hg^{2+}$, $Na^+$, $Ca^{2+}$, $Zn^{2+}$, $Ag^+$, and nitrate salts of $Mg^{2+}$, $K^+$, $Co^{2+}$ (1 mM) in deionized water, except for $Co^{2+}$, which were dissolved in acetonitrile anhydrous. Solution of $Cu^+$ was freshly prepared by dissolving tetrakis(acetonitrile) copper(I) (Sigma-Aldrich) into double-distilled water. $Fe^{3+}$, $Fe^{2+}$ solutions were prepared freshly from ferric chloride, ferrous ammonium sulfate (FAS, Fe $(NH_4)_2(SO_4)_2$, respectively in 0.01 M HCl. A stock solution of Rh101D (1 mM) was prepared in THF. The solution of Rh101D was diluted to 25 μM with $H_2O$/THF (pH 7.3, v/v, 4:1).

Before spectroscopic measurements, solutions were freshly prepared by diluting the corresponding high-concentration stock solution. For each spectrum, 1 mL of a probe solution was added to a 1-cm quartz cell, to which different stock solutions of cations were gradually added. All spectroscopic measurements were done under simulated physiological pH, and measurements were performed at least triplicate and resulting averages are reported.

Figure 36:
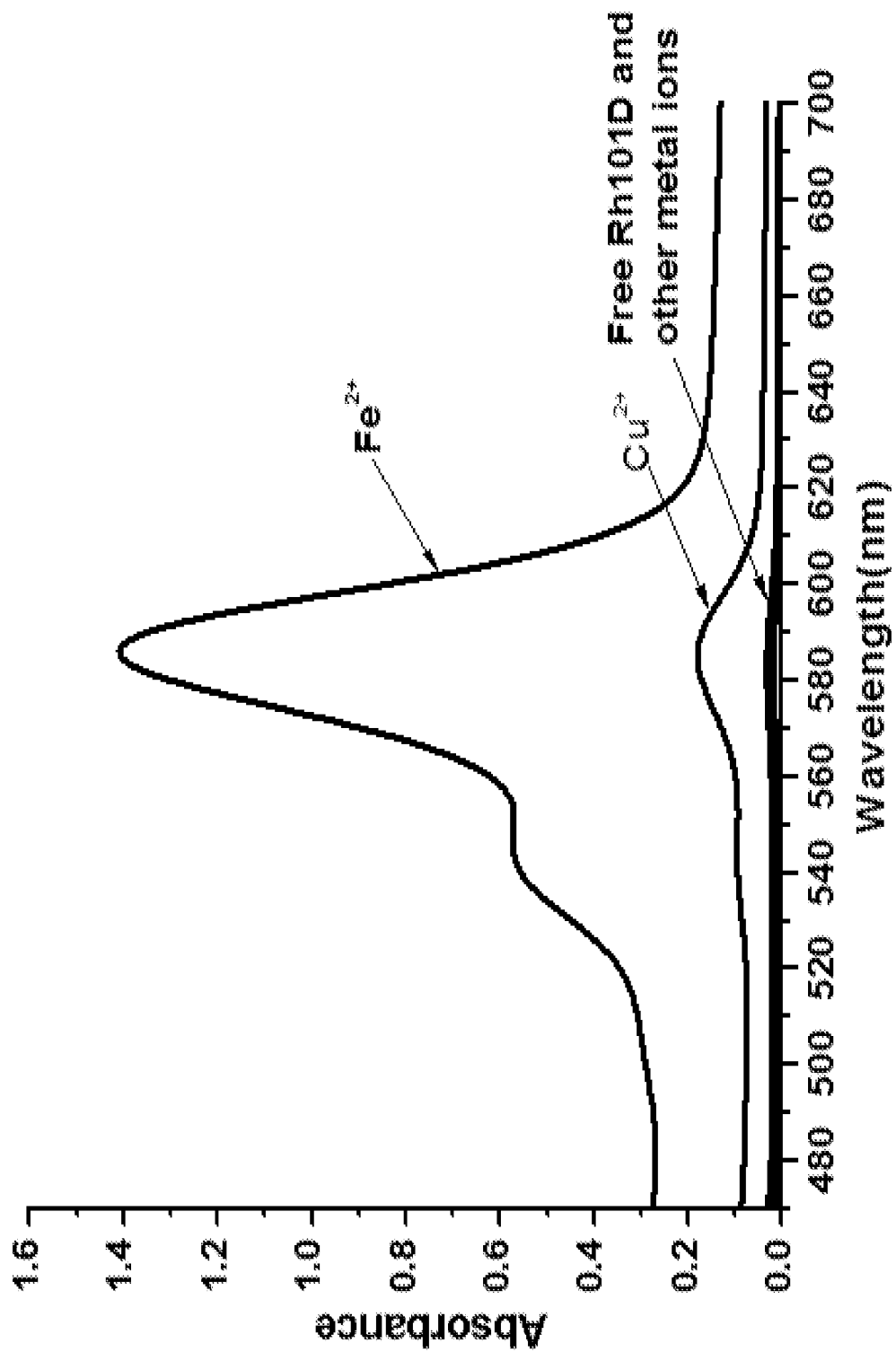
FIG. 36 shows the absorption spectra of 20 μM Rh101D to various metal ions in $H_2O$/THF (pH 7.3, v/v 1:1).

The changes in UV-Vis spectra after the addition of various metal ions into the sensor are shown in FIG. 36. The addition of $Fe^{2+}$ to the solution of Rh101D showed an obvious pink color with an absorption peak at 585 nm in $H_2O$/THF (pH 7.32, v/v 1:1) (FIG. 36). The color change for $Fe^{2+}$ is readily detected visually. Compared with that of $Fe^{2+}$, other metal ions did not induce significant changes in UV-Vis absorption while $Cu^{2+}$ induced a minor enhancement at this wavelength.

Figure 37:
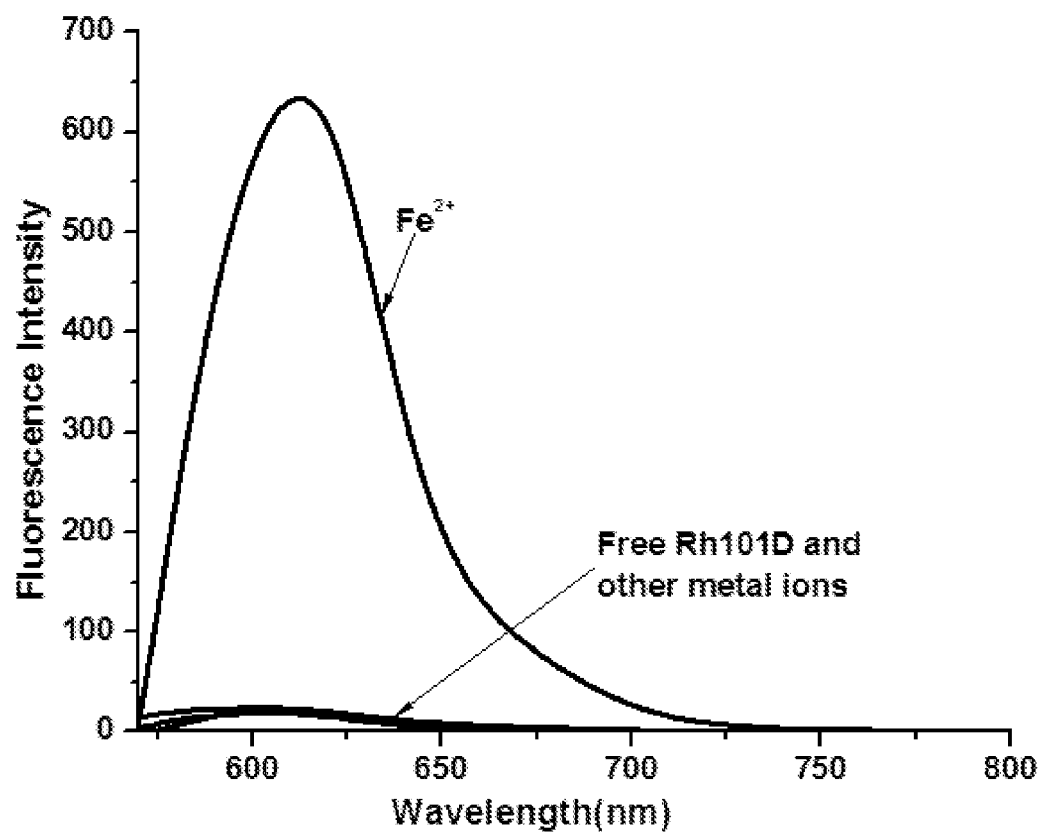
FIG. 37 shows the fluorescence intensity ($\lambda_{Ex}/\lambda_{Em}$ 550/605 nm) of 20 μM Rh101D to 20 μM various metal ions in $H_2O$/THF (pH 7.3, v/v 1:1).
Figure 38:
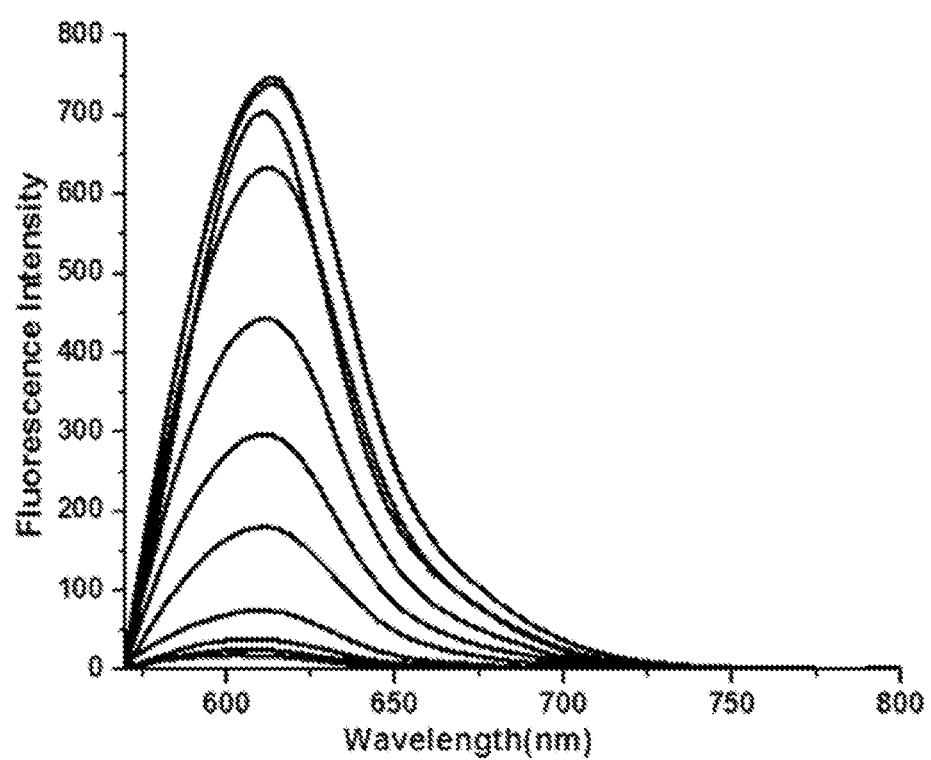
FIG. 38 shows the fluorescence intensity for the titration of 20 μM Rh101D with increasing concentration of $Fe^{2+}$ (0, 2, 4, 6, 8, 10, 12, 16, 20, 24, 28 μM from bottom to top) in $H_2O$/THF (pH 7.3, v/v 1:1).

The changes in fluorescence spectra of Rh101D with the addition of different metal ions in $H_2O$/THF (pH 7.32, v/v 1:1) are shown in FIG. 37. When $Fe^{2+}$ was added into the solution of Rh101D, a large fluorescence enhancement at 613 nm was observed, induced by the complexation of $Fe^{2+}$. The emission intensity enhancement at 613 nm suggesting that Rh101D is a great turn-on fluorescent sensor for $Fe^{2+}$ (FIG. 37). Titration of 20 μM Rh101D with increasing concentration of $Fe^{2+}$ is shown in FIG. 38.

Figure 39:
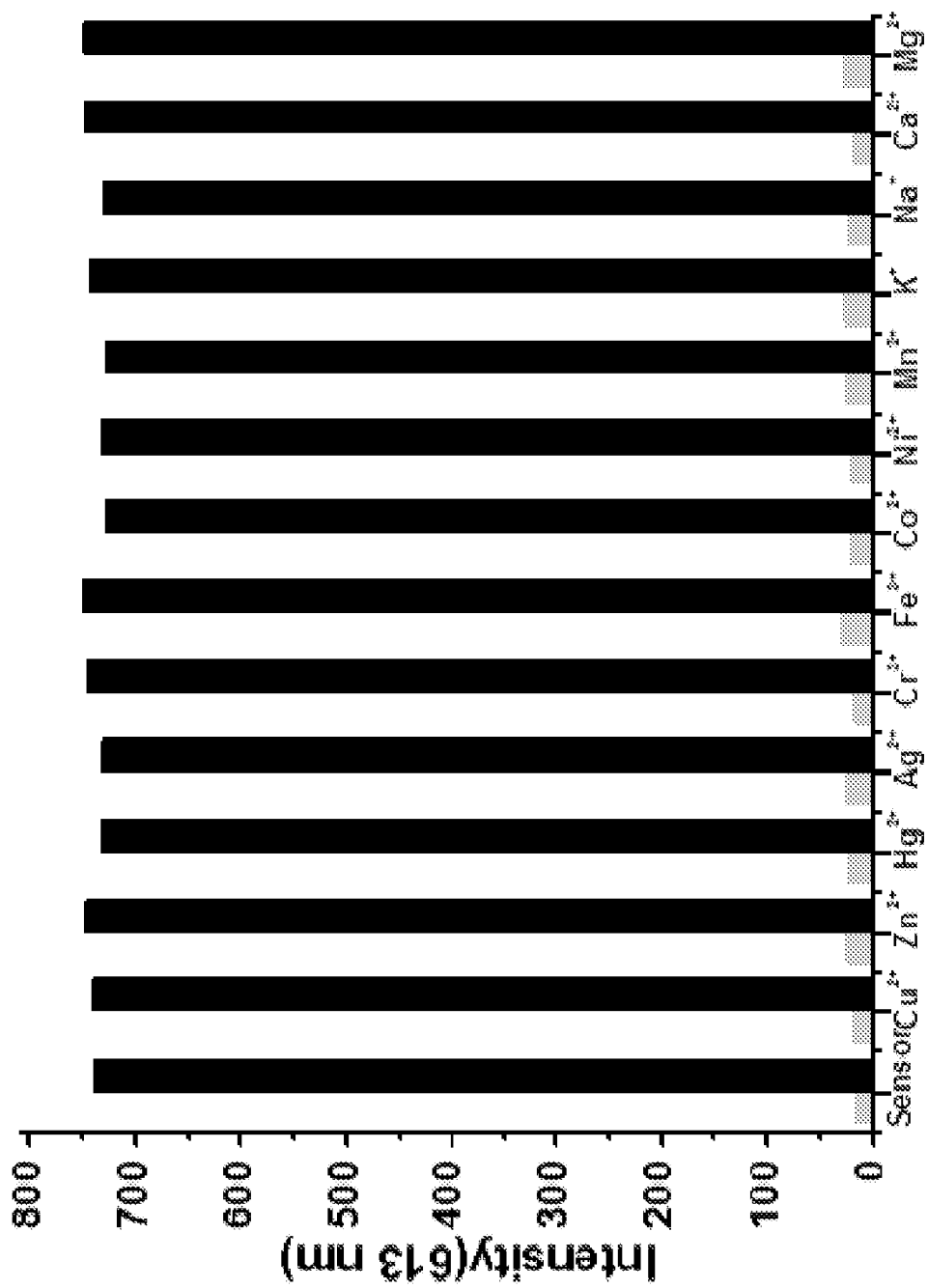
FIG. 39 shows the fluorescence intensity of 20 μM Rh101D to the presence of 20 μM various metal ions (light grey bar) and the subsequent addition of $Fe^{2+}$ (black bar) in the $H_2O$/THF (pH 7.3, v/v 1:1); the bars represent the fluorescence intensity at 613 nm.

Excitingly, Rh101D displayed an excellent selective turn-on fluorescent response at 613 nm to $Fe^{2+}$ (FIG. 39). In the presence of other bio-relevant metal ions including $Fe^{3+}$, $Ni^{2+}$, Cut, $Cu^{2+}$, $Zn^{2+}$, $Pb^{2+}$, $Cr^{3+}$, $Hg^{2+}$, $Mn^{2+}$, $Ag^+$, $Co^{2+}$, $K^+$, $Na^+$, $Ca^{2+}$ and $Mg^{2+}$; Rh101D did not trigger fluorescence enhancements under the same conditions (the light grey bars in FIG. 39). Moreover, upon the addition of 1 equiv. of $Fe^{2+}$ into solutions containing one of the other metal ions tested, the fluorescence was activated and the intensity increased to a level similar to that observed in the presence of $Fe^{2+}$ only (the black bars in FIG. 39). This demonstrated that these metal ions did not interfere with the response of $Fe^{2+}$ to Rh101D.

Figure 40:
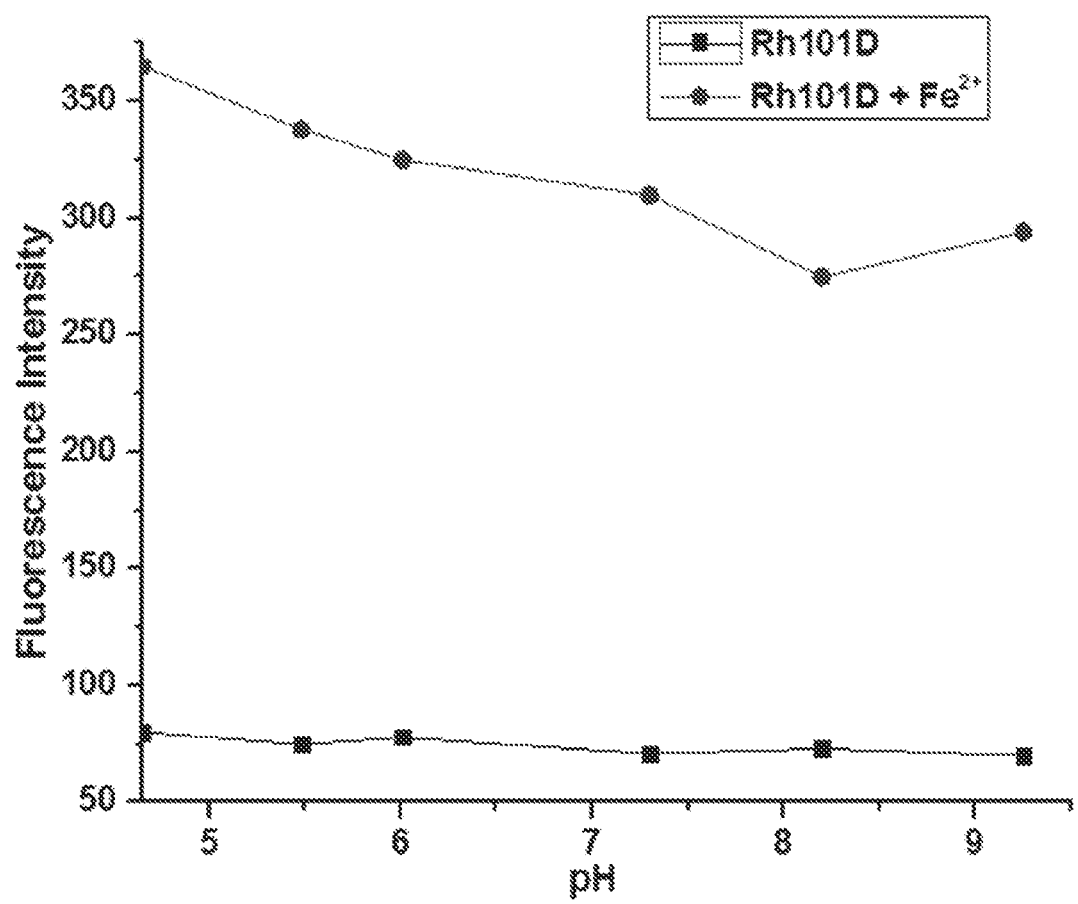
FIG. 40 shows the fluorescence intensity (613 nm) of Rh101D and Rh101D+Fe (II) (10 μM each) at various pH values in H2O/THF (pH 7.3, v/v 1:1) solution.

As rhodamine-based sensors give response to hydrogen ions, the stability of Rh101D sensor in biological pH range was tested. The effect of pH on the stability of the sensor was investigated at different pHs and monitored by fluorescence spectra (FIG. 40). The pH of the solution was adjusted by adding HCl or NaOH into the solution. The fluorescence of Rh101D at different pH values was plotted. As shown in FIG. 40, the sensor and the Fe (II)-complex is stable over the biological pH range from 9.5 to 4.5. Thus, Rh101D may be suitable to be used in biological systems.

Example 19. Cell Culture and Confocal Imaging for Rh101D

Bovine aortic endothelial cells BAEC cells, at an approximately density of 1.3 million/ml in complete EBM medium, were incubated with 100 μM ferrous ammonium sulfate (FAS, Fe $(NH_4)_2(SO_4)_2$ from a 10 mM stock solution) for overnight at 37° C. in a humid atmosphere of 5% $CO_2$ and then the cells were washed with fresh EBM medium to remove excess $Fe^{2+}$. Then cells were incubated with Rh101D (10 μM, from 500 μM stock solution in DMF) at 37° C. for 30 min and then cells were washed with EBM media and then imaged. In addition, some cells were treated firstly with 100 μM $Fe^{2+}$ overnight and then the cells were washed with fresh EBM medium. For chelation experiments, $Fe^{2+}$-loaded cells or untreated cells were incubated with 1 mM 2,2'-bipyridyl (Bpy) at 37° C. for 30 min, then sensor was added followed by washing with the media, and then imaging was done. Controls were imaged without incubation with $Fe^{2+}$ or 2,2'-bipyridyl. HCT-116, a human colon adenocarcinoma cell line were used for concentration determination of $Fe^{2+}$ with the help of the ratiometric sensor Rh101D. HCT-116 were maintained in McCoy's 5A medium supplemented with 10% fetal bouvine serum and 5% antibiotic antimycotic in a 5% $CO_2$ atmosphere at 37° C. Cultures were divided 1:2 every 48 h to an approximate cell density of 1.21 million cells/ml and used for experiments after 24 h. All experiments were performed with cells in the logarithmic growth phase.

A Zeiss LSM 710 laser-scanning confocal microscope system was used for cell imaging experiments in collaboration with Mr Bing Yan in the lab. 40× oil-immersion objective lens were used to perform all the experiments. For imaging with the Rh101D sensor, excitation wavelength of the laser was 543 nm and emissions were collected over the range 545-625 nm. For images with MitoTracker Green FM, LysoTracker Deep Red, excitation wavelengths recommended by the manufacturer were 488 nm for MitoTracker, 633 nm for LysoTracker. Emissions were integrated at 492-535 nm (MitoTracker), 650-800 nm (LysoTracker), respectively.

Figure 41:
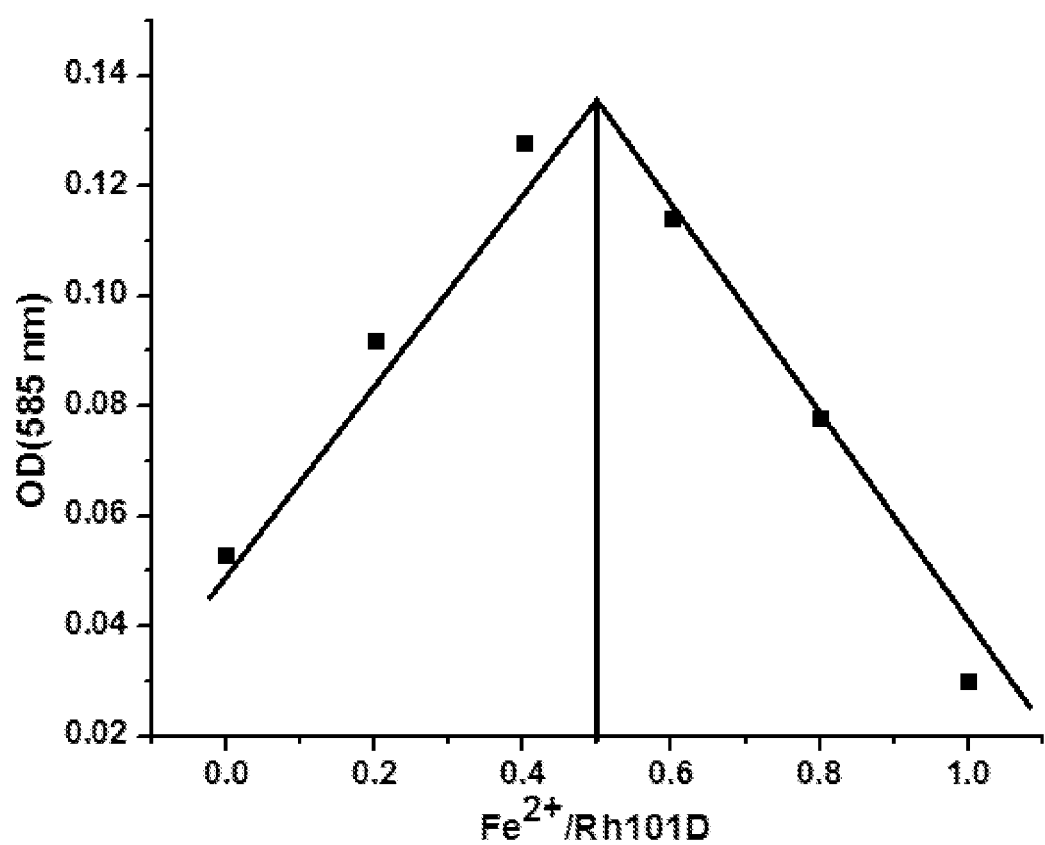
FIG. 41 shows a Job's plot, where the total concentrations of Rh101D and $Fe^{2+}$ were kept constant at 20 μM and the absorption intensity was measured at 585 nm in the $H_2O$/THF (pH 7.3, v/v 1:1) solution.

Example 20. Binding Studies: Stoichiometry, Binding Constant and Reversibility for Rh101D Besides metal-selectivity, the binding constant, which describes the strength of binding between the sensor and metal cations, is also an important factor to be considered in bio-imaging. The sensor should have an appropriate binding constant with the metal ions in study in biological systems (F. J. C. Rossotti, H. Rossotti, Series in Advanced Chemistry, McGraw-Hill Book Company, Water Street, N.Y., 1961; I. Johnson, Histochem. J., 1998, 30, 123; M. A. Cooper, Anal. Bioanal. Chem., 2003, 377, 834). The stoichiometry between the probes (sensor) and the metal ions should be examined first before determining the binding constants. Researchers used several methods to determine the stoichiometry between sensors and metal cations (Y. Kwon, et al., J. Am. Chem. Soc., 2005, 127, 10107; X. Zhang, et al., Tetrahedron Lett., 2007, 48, 5455; M. Zhang, et al., Tetrahedron Lett., 2007, 48, 3709; Y. Xiang, et al., Org. Lett., 2006, 8, 1549). The binding property of Rh101D to $Fe^{2+}$ was investigated with Job's method (Id.) and absorption titration. EDTA titration experiments were carried out to determine the reversibility of Rh101D-$Fe^{2+}$ binding. Job's method was applied to study the binding stoichiometry between Rh101D and $Fe^{2+}$ and monitored by the absorbance at 585 nm. The Job's plot (FIG. 41) using a total concentration of 20 μM Rh101D and $Fe^{2+}$ in $H_2O$/THF (pH 7.3, v/v 1:1) solution exhibited a maximum absorbance when the molecular fractions of $Fe^{2+}$ and Rh101D were close to 50%, suggesting a 1:1 stoichiometry for the binding of Rh101D and $Fe^{2+}$.

The binding constants were estimated by using the fluorescence titration results (FIG. 38). The equations below were used to calculate the binding constant for 1:1 complexes following a reported procedure (M. Guo, et al. Dalton Trans., 2007, 102, 4951).

$$L + S \rightleftharpoons LS$$

where L=sensor, S=$Fe^{2+}$ and LS=sensor+$Fe^{2+}$
The complex apparent binding constant is given by $$K = \frac{[LS]}{[L][S]}$$

Here, the concentrations at equilibrium:

$$Fc = \frac{(Au - Am)}{(Au - Af)} = K = \frac{[LS]}{[L]}$$

Fc is the fraction of L that formed a complex, [LS] is concentration at equilibrium; [L] is initial concentration. Au, Am, and Ac are the absorbances of solutions of L (before any $Fe^{2+}$, during the titration and at saturation. The concentration of free $Fe^{2+}$ at equilibrium, $[S]_e$, is found with the following identity.

$$[S]_e = [S]_o - [LS]_e = [S]_o - F_c[L]_o$$

Using the above equation, the binding affinity was calculated based on the titration studies and was determined to be $1.2 \times 10^5$ $M^{-1}$.

Figure 42:
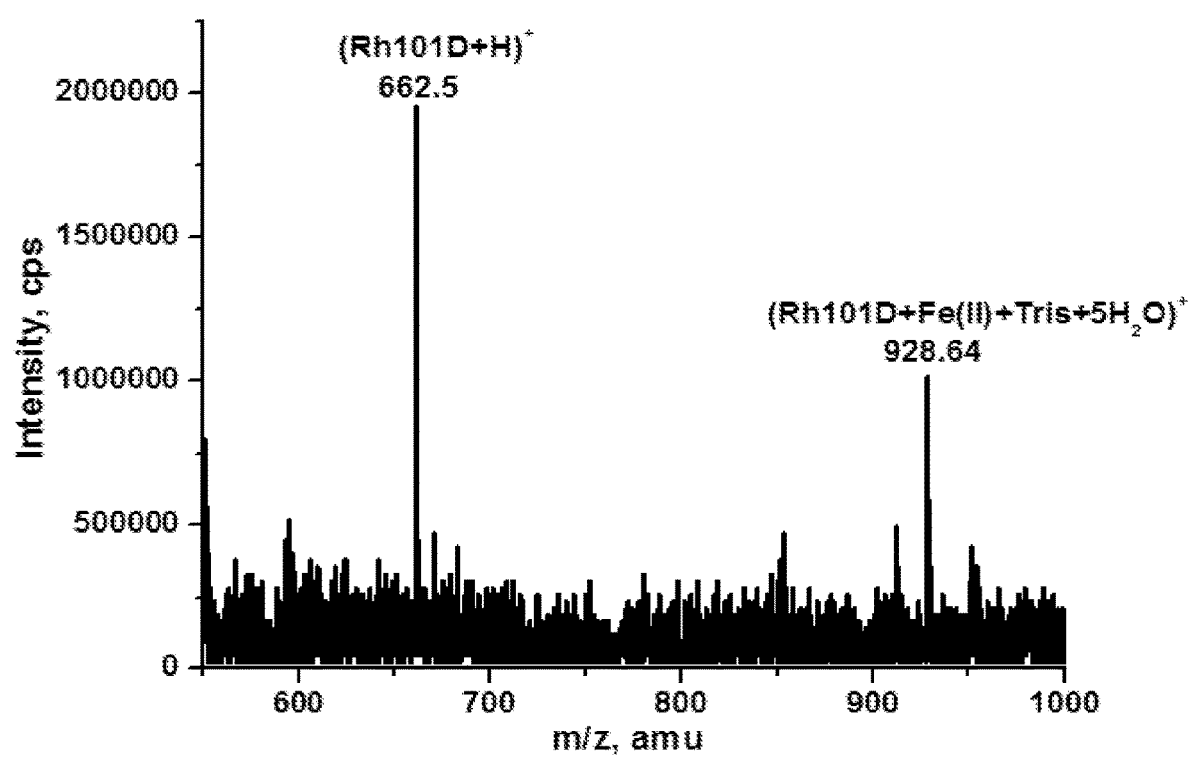
FIG. 42 shows an ESI-MS spectrum of the solution of Rh101D with $Fe^{2+}$ (10 μM sensor and excess FAS in Tris-Cl buffer (pH 7.3). The net charge of [Rh101D-Fe (II)-Tris-$5H_2O$] species is 1+.

The species formed between Rh101D and $Fe^{2+}$ was more accurately determined by ESI-MS. Upon the mixing of $Fe^{2+}$ and the sensor (10 μM sensor and excess of FAS in Tris buffer (pH 7.32), one major species with m/z=928.64, assignable to a 1:1 complex (Rh101D:$Fe^{2+}$=1:1) with one Tris, five water molecules attached, were detected by ESI-MS (FIG. 42), corroborating the 1:1 stoichiometry established by spectroscopic titrations.

Figure 43:
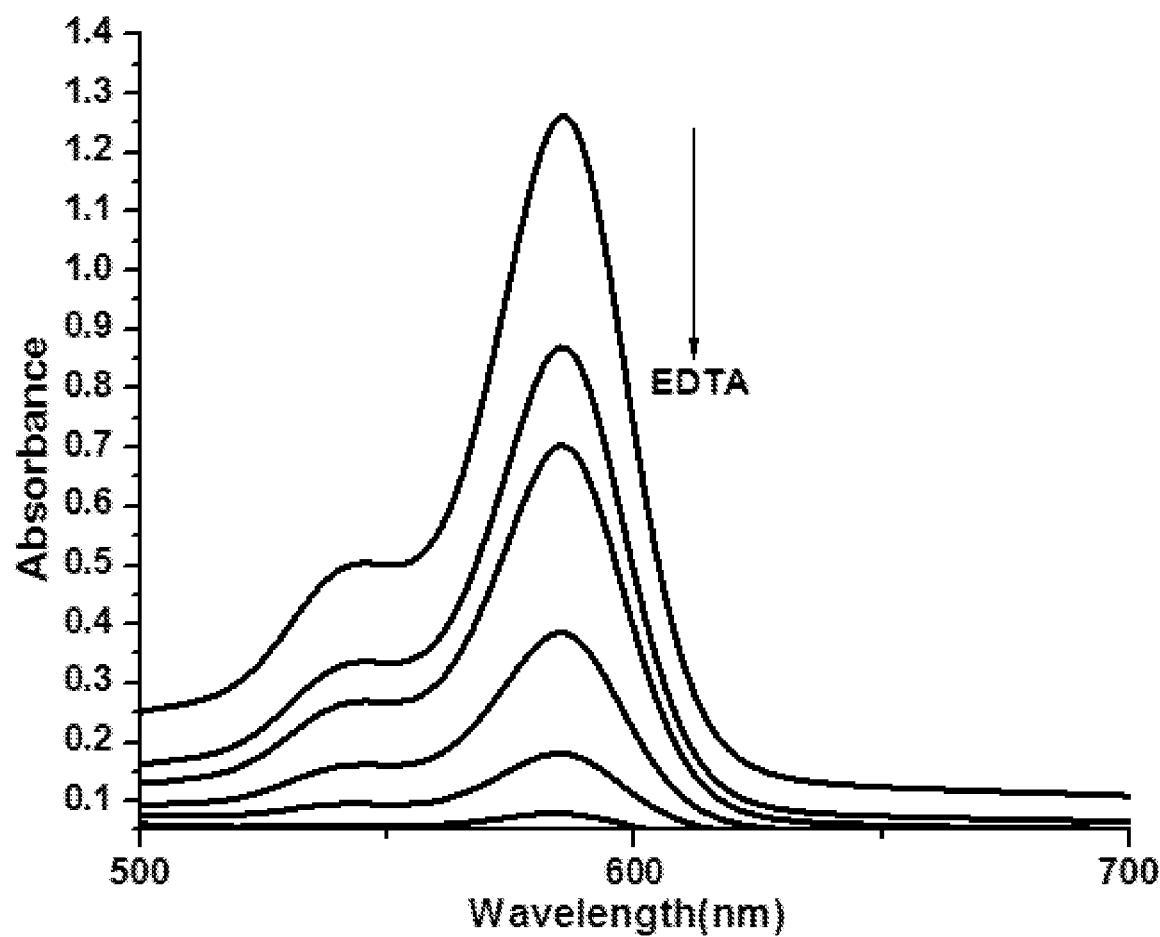
FIG. 43 shows the absorbance spectra for the treatment of 20 μM Rh101D-$Fe^{2+}$ complex with increasing concentration (0, 4, 8, 12, 16, 20 μM, from top to bottom) of EDTA in $H_2O$/THF (pH 7.3, v/v 1:1).

Reversibility experiments were carried out by adding EDTA to the Rh101D-$Fe^{2+}$ complex in $H_2O$/THF (pH 7.3, v/v 1:1). In the absence of EDTA, the complex was colorful and fluorescent. After adding EDTA, the absorption of the complex decreased in intensity and finally, disappeared (FIG. 43), suggesting a reversible binding between Rh101D and $Fe^{2+}$.

Example 21. Binding Site of $Fe^{2+}$ on Rh101D

Figure 44:
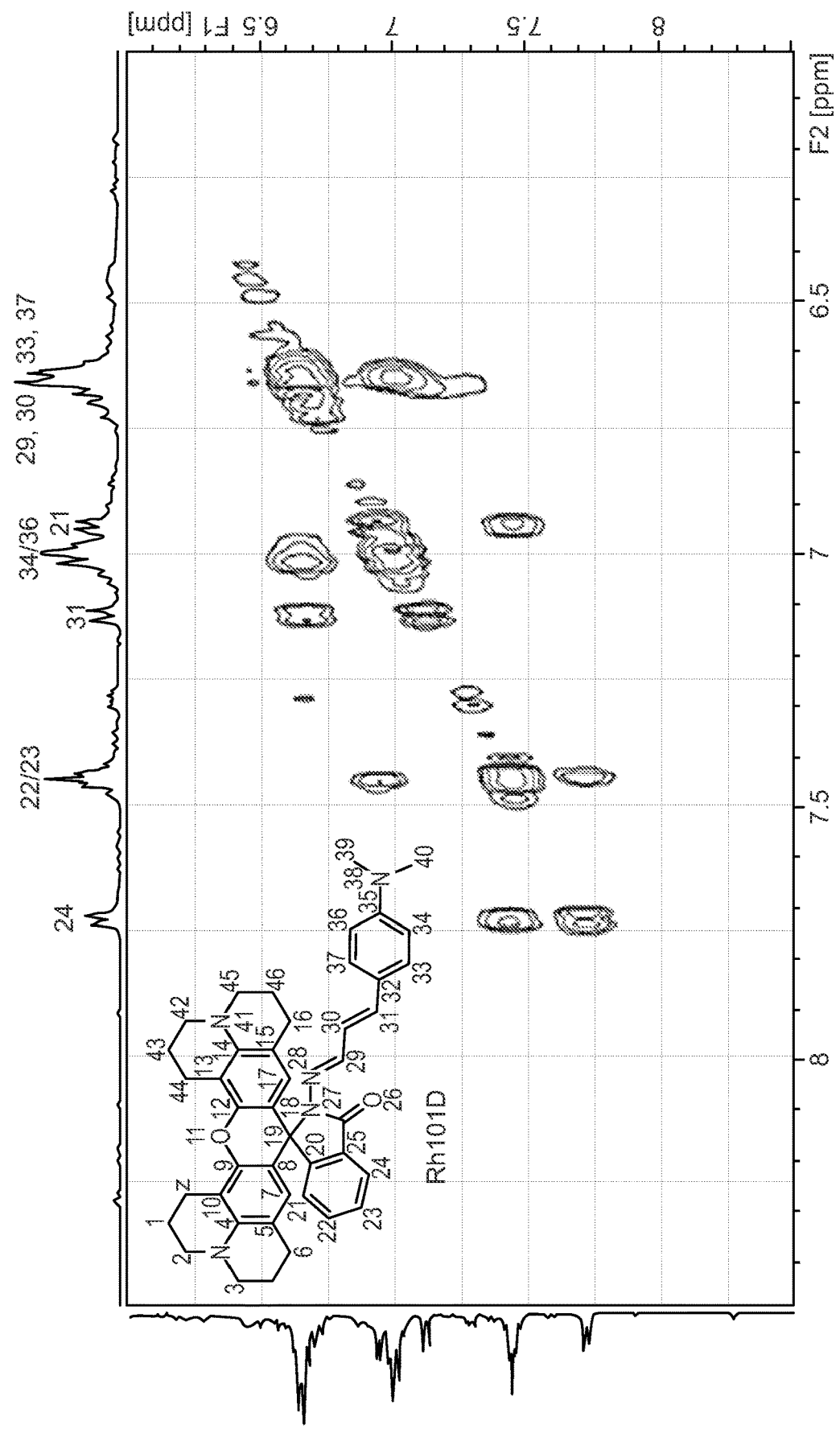
FIG. 44 shows the 2D-COSY NMR of the sensor Rh101D in DMSO.

The binding site of $Fe^{2+}$ on Rh101D was investigated by 2D NMR. Due to limited solubility of the sensor in solution, the $^1H$ NMR signals are relatively weak however the 2D [$^1H$, $^1H$] COSY NMR spectra are of sufficient resolution for the assignment of the peaks in the aromatic region (FIG. 44). After adding $Fe^{2+}$ to Rh101D, all the $^1H$ NMR signals were broadened. This result suggests that Fe (II) in this case may be at least partially in paramagnetic high spin state and thereby broadening of the peaks occurs instead of shifting of peaks.

Figure 45:
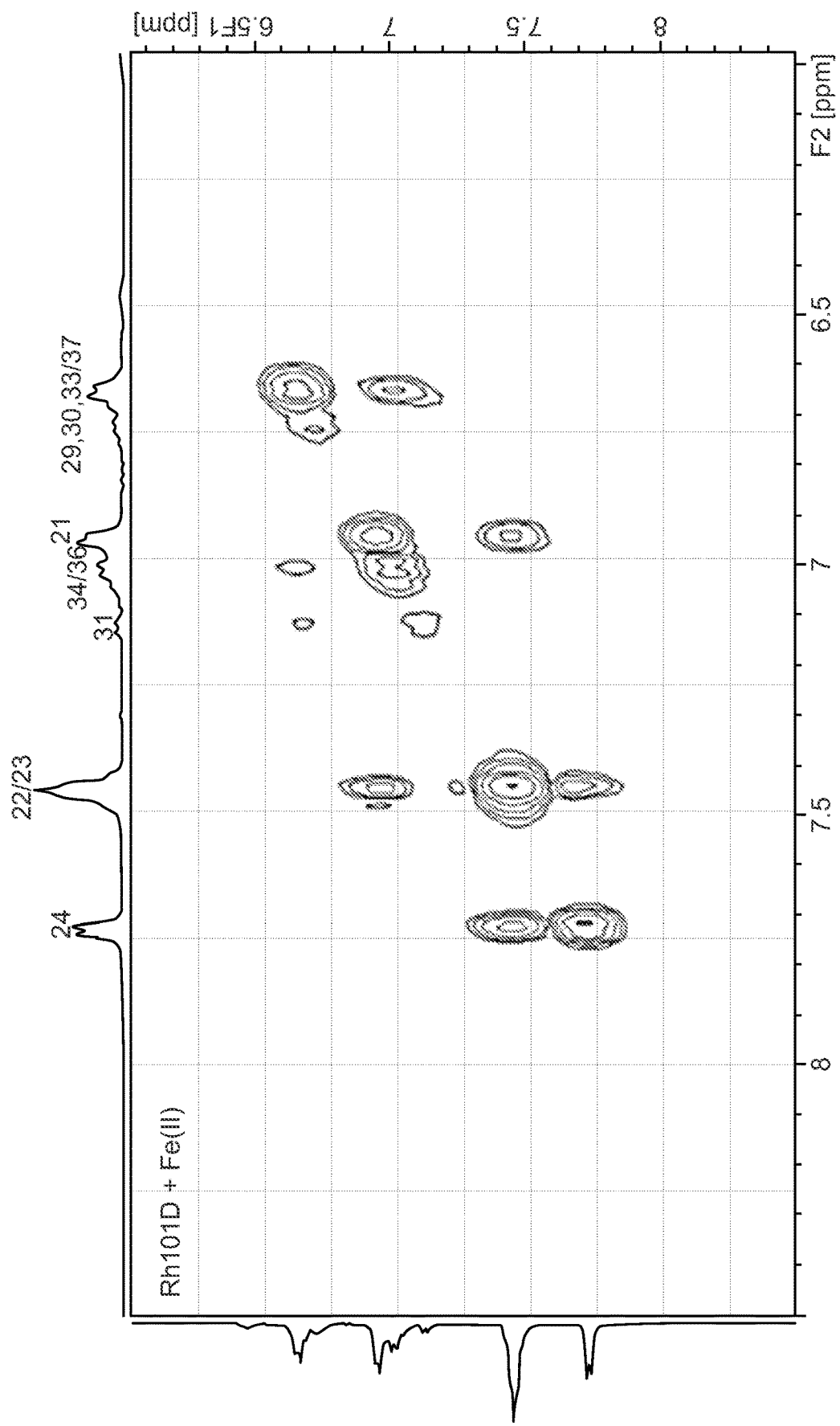
FIG. 45 shows the 2D-COSY NMR of (Rh101D+$Fe^{2+}$) in DMSO.

A closer look at the COSY NMR spectra (FIG. 44 and FIG. 45) reveals that the 29, 30 and 31 numbered proton peaks in the NMR spectra greatly decrease in intensity and the majority of them are beyond detection. Meanwhile, the 33/37 and 34/36 numbered proton peaks in the NMR spectra also decreased in intensity significantly however the 24, 22/23 and 21 numbered proton peaks did not decrease in intensity. This phenomenon clearly indicates that the paramagnetic $Fe^{2+}$ ion is located at the region close to the 29, 30, 31, and 32 numbered protons and is nearby the benzene ring on the DMACA moiety. As this region has the same chemical structure as that of the sensor Rh6GD, it is reasonable to adopt the same coordination mode with $Fe^{2+}$, i.e., the $Fe^{2+}$ coordination involves O26, N28 and C31=C32, with the formation of a 5-membered chelating ring and a 5.5-membered chelating ring with a η-2 pi-coordination at C31=C32. Such a novel coordination mode is unlikely to occur with $Fe^{3+}$ or other physiologically relevant metal ions, which may explain its excellent selectivity for $Fe^{2+}$.

In contrast to the 2:1 (sensor to Fe) stoichiometry found in the low-spin $Fe^{II}$-complex with Rh6GD, the $Fe^{II}$-complex of Rh101D is 1:1 (sensor to Fe) stoichiometry. It is likely that the bulky ring system in the Rh101 moiety prevents it from forming a 2:1 complex and the remaining coordination sites on $Fe^{II}$ is filled with small ligands (DMSO, Tris, $NH_{4+}$, $H_2O$, $OH^-$, etc) from the solution. These oxygen/nitrogen-based small ligands are not able to provide a strong enough ligand field as that from the pair of N and C=C ligands in the Rh6GD sensor, the $Fe^{II}$ thus could adopt a paramagnetic high-spin state. A possible structure of the $Fe^{II}$-Rh101D complex is proposed in Scheme 6, which also shows a possible mechanism for the reaction and the binding mode.

Scheme 6 Proposed 1:1 binding mode of Rh101D with $Fe^{2+}$ in $H_2O$/THF (pH 7.3, v/v 1:1).

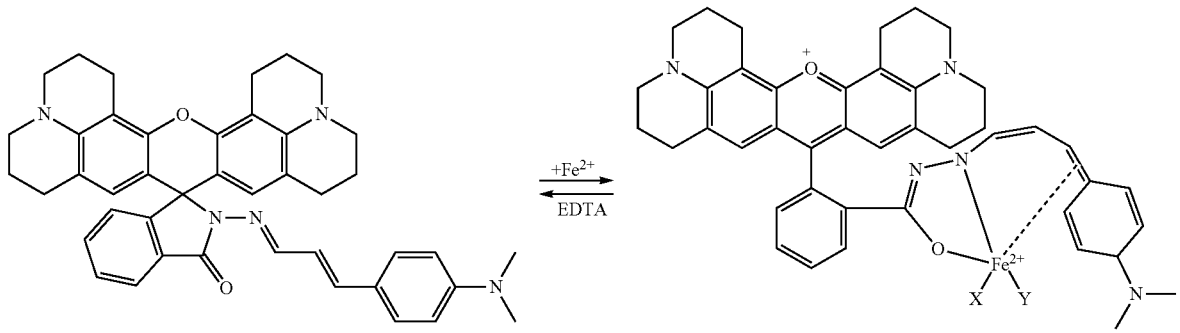

X, Y = Tris or $H_2O$

Example 22. Biological Imaging Studies

Figure 46F:
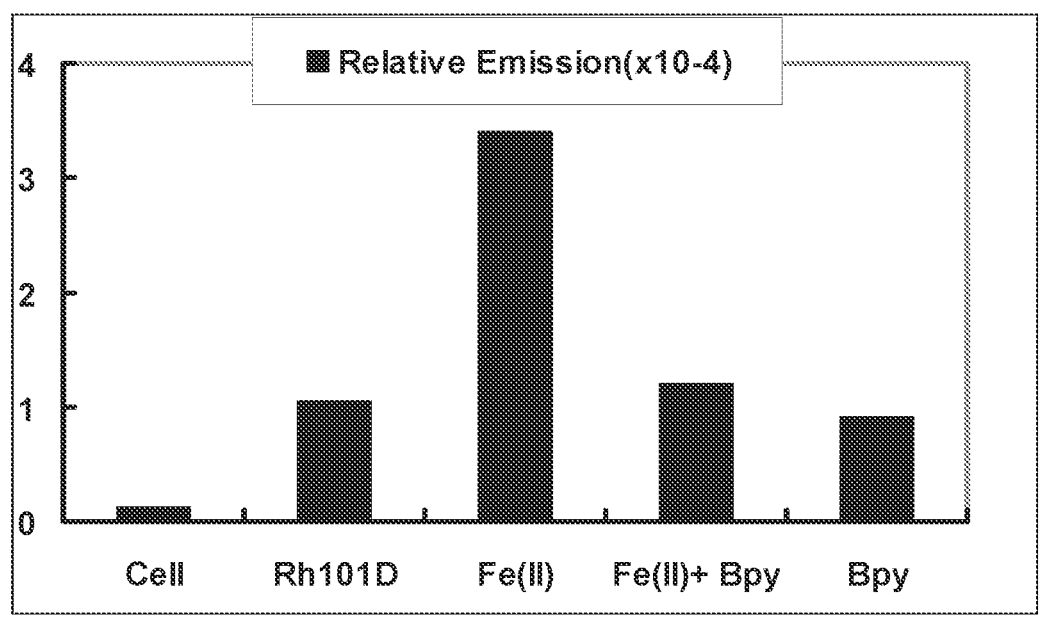
FIG. 46F is a graph showing the relative emission from the treatments in FIGS. 46A-E.

The ability of Rh101D to detect $Fe^{2+}$ in live bovine aortic endothelial cells (BAEC) was investigated by confocal microscopy. Live BAEC cells incubated with 10 μM Rh101D showed weak fluorescence (FIG. 46B). For $Fe^{2+}$ repleting conditions, live BAEC cells were incubated with 100 μM of ferrous ammonium sulfate (Fe $(NH_4)_2(SO_4)_2$) at 37° C. for overnight followed by washing with EBM medium to remove excess $Fe^{2+}$ and then 10 μM of Rh101D was added to the culture media and was incubated at 37° C. for 30 min. The $Fe^{2+}$-treated BAEC cells showed significant increase in fluorescent signals (FIG. 46C) w.r.t the BAEC cells without $Fe^{2+}$ supplementation (FIG. 46B), suggesting a positive response of Rh101D to increased labile $Fe^{2+}$ levels in $Fe^{2+}$-treated cells. For $Fe^{2+}$-depleting conditions, 2,2-bipyridyl (Bpy) which is known to be a selective $Fe^{2+}$-chelator was used to chelate $Fe^{2+}$+[33]. BAEC cells treated with 1 mM of Bpy showed decrease in fluorescence signal and it is weaker than that of the control cells (FIG. 46E); suggesting Rh101D can detect basal level of labile $Fe^{2+}$ in BAEC cells. The BAEC cells treated with 100 μM of $Fe^{2+}$ overnight first followed by washing with EBM medium and then treated with 1 mM of Bpy and subsequent addition of 10 μM of Rh101D showed marked decrease in fluorescent intensity (FIG. 46D) compare to that of cells with $Fe^{2+}$ supplement. This fluorescent intensity is almost the same as that of cells without $Fe^{2+}$ or Bpy treatment. These data clearly demonstrate that Rh101D has the ability to detect endogenous level of labile $Fe^{2+}$ as well as its dynamic changes in BAEC cells.

The discrete confocal fluorescence images revealed by Rh101D in both the untreated and the $Fe^{2+}$-loaded BAEC cells imply that the labile $Fe^{2+}$ in BAEC cells may be localized in certain subcellular compartments (organelles) and that Rh101D may be capable of imaging $Fe^{2+}$ at subcellular resolution. To explore this, the distribution of exchangeable $Fe^{2+}$ pools in live BAEC cells were further investigated using Rh101D, together with colocalization experiments using other dyes—MitoTracker Green FM (a green fluorescent dye which localizes to mitochondria in live cells regardless of mitochondrial membrane potential) and LysoTracker Deep Red (a fluorescent dye that stains acidic compartments such as endosomes and lysosomes in live cells). BAEC cells (without $Fe^{2+}$ treatment) were treated with Rh101D, MitoTracker Green FM, and LysoTracker Red DND-100. As illustrated in FIG. 47, partial colocalization between Rh101D-$Fe^{2+}$ and the MitoTracker (FIG. 47E) as well as between Rh101D-$Fe^{2+}$ and the LysoTracker (FIG. 47F) occurred whereas complete colocalization of Rh101D-$Fe^{2+}$, MitoTracker and LysoTracker (FIG. 47G) was observed. These data suggest that the exchangeable $Fe^{2+}$ pools in BAEC cells detectable by Rh101D are localized in mitochondria and endosomes/lysosomes, not in the cytosol.

Example 23. Determination of Labile $Fe^{2+}$ Concentration in Live Cells

Figure 48:
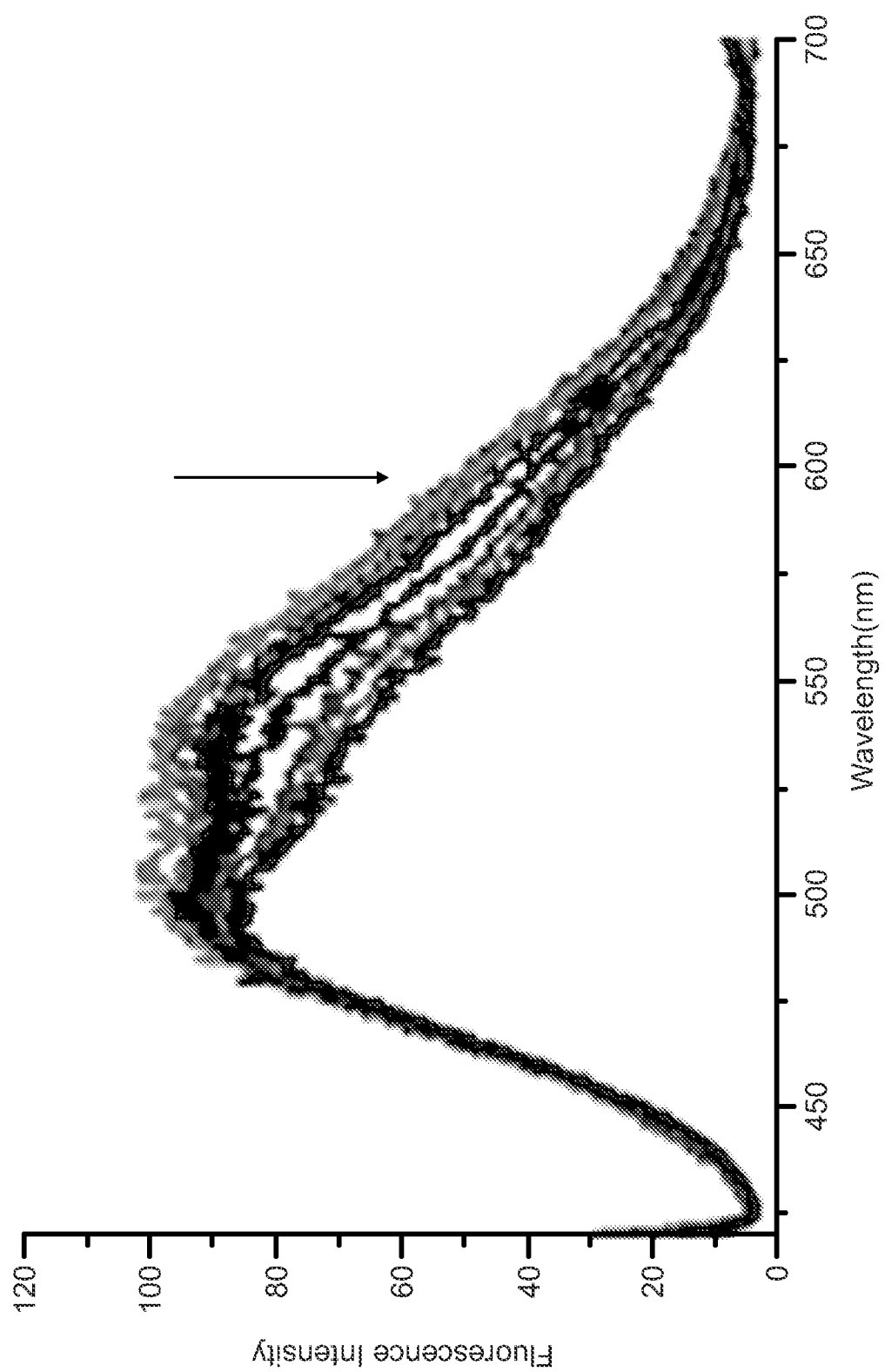
FIG. 48 shows the fluorescence intensity of 20 μM Rh101D to increasing concentration of $Fe^{2+}$ ($\lambda_{Ex}$ 405 nm).
Figure 49:
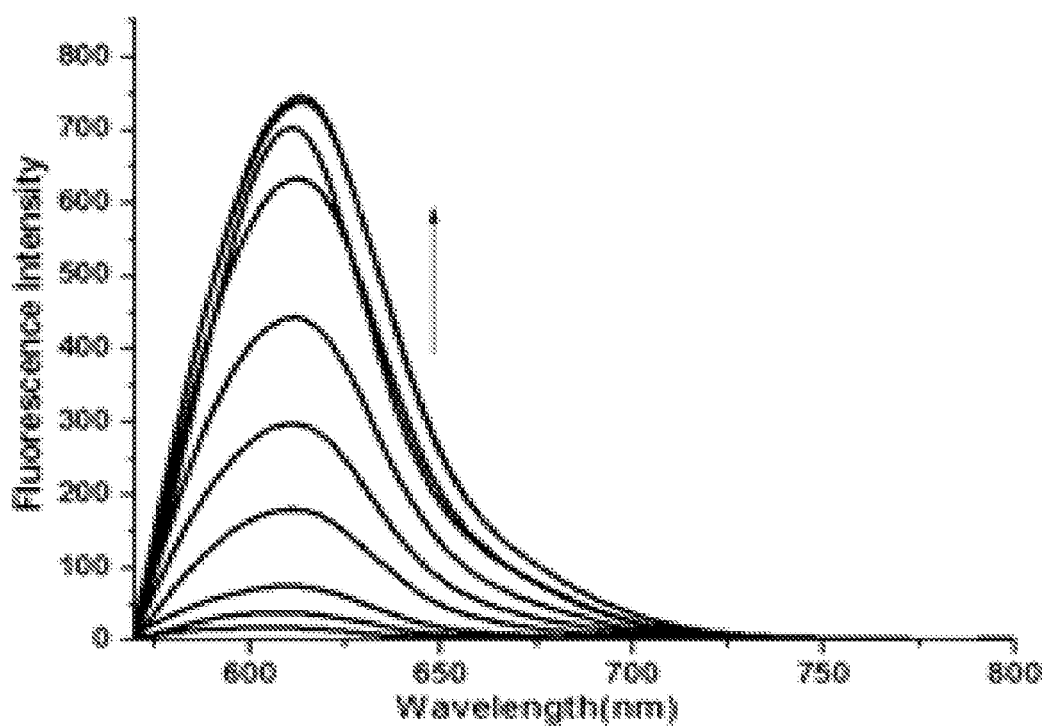
FIG. 49 shows the fluorescence intensity of 20 μM Rh101D to increasing concentration of $Fe^{2+}$ ($\lambda_{Ex}$ 550 nm).

To determine the concentration of labile $Fe^{2+}$ in cells, the ratiometric $Fe^{2+}$ sensor Rh101D has been developed. The two-band absorption/fluorescence nature of the ratiometric sensor enables the tracing of the cellular distribution of the sensor itself as well as detecting the labile $Fe^{2+}$ pools. When $Fe^{2+}$ was added to Rh101D solution, a decrease in fluorescence intensity at ~500-550 nm (FIG. 48) and an increase in intensity of the fluorescence at ~625 nm were observed (FIG. 49).

Figure 50:
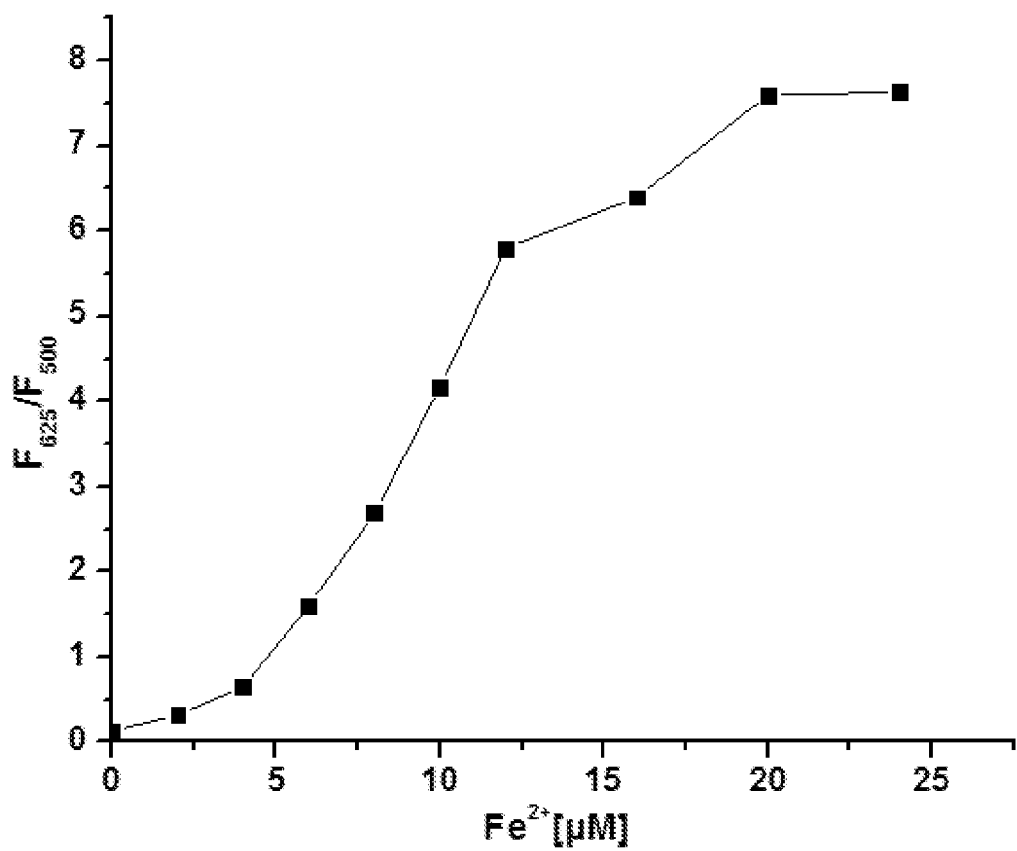
FIG. 50 is a plot of the ratio of fluorescence intensities at 625 nm to 500 nm versus [$Fe^{2+}$] for the in-vitro calibration of 20 μM Rh101D with [$Fe^{2+}$].

To determine the cellular concentration of $Fe^{2+}$, an in-vitro calibration curve was obtained by titrating the sensor, Rh101D (20 μM), with different concentrations of $Fe^{2+}$ and a calibration curve was obtained by plotting $[Fe^{2+}]$ versus fluorescent ratio ($F_{625}/F_{500}$) (FIG. 50).

The in vitro solution studies have shown that Rh101D can detect $Fe^{2+}$ with excellent selectivity and the $Fe^{2+}$ concentration is correlated with the ratio of fluorescence intensities at 625 nm to 500 nm (FIG. 50). To examine whether it can detect $Fe^{2+}$ concentration in living systems, HCT-116, a human colon adenocarcinoma cell line was used to test its ability in determining endogenous $Fe^{2+}$ ions in live cells. Since Rh101D is cell permeable, after being treated with 10 μM of Rh101D for 30 min at 37° C., the cells exhibited a strong fluorescence in the yellow channel (FIG. 51C) but very weak fluorescence in the red channel (FIG. 51G). It is obvious that Rh101D (yellow color) was located almost everywhere in the cytosol of the cells but not in the nucleus, indicating that the Rh101D sensor is located in all region in the cytosol. However, in FIG. 51B, red color images are located in limited areas (certain organelles) in the cells, indicating $Fe^{2+}$ ions are in certain organelles. FIGS. 51D, H, and L are the ratiometric images of Rh101D at yellow and red channels. Fitting the ratiometric imaging data to the calibration curve gives $Fe^{2+}$ concentration in HCT-116 cells, with a value of ~10±1 μM determined in the mitochondria of untreated cells, 14±1 μM in the mitochondria of Fe (II) treated cells, and 7±1 μM in the mitochondria of Fe(II)-chelator Bpy treated cells and ~8±1 μM determined in the lysosomes of untreated cells, 11±1 μM in the lysosomes of Fe (II) treated cells, and 5±1 μM in the lysosomes of Bpy treated cells and the results were summarized in Table 1.

TABLE 1

Free $Fe^{2+}$ concentration in the HCT-cells.

| Cell Type | Fe(II) concentration in Mitochondria | | | Fe(II) concentration in Lysosome | | |
|---|---|---|---|---|---|---|
| | Untreated cells | Fe (II) treated cells | Bpy treated cells | Untreated cells | Fe (II) treated cells | Bpy treated cells |
| HCT-116 | 10 ± 1 μM | 14 ± 1 μM | 7 ± 1 μM | 8 ± 1 μM | 11 ± 1 μM | 5 ± 1 μM |

Example 24. Synthesis of NIRh-Fret

General Information

Acetonitrile anhydrous (99.8% Sigma-Aldrich), $H_2SO_4$ (98% Fisher), Ethanol, dichloromethane (99.8% TCI America) and double-distilled water were used as solvents. 2-(1,3,3-Trimetylindolin-2-ylidene) acetaldehyde was purchased from OChem Incorporation. 2-(4-Diethylamino-2-hydroxybenzoyl)benzoicacid and benzotriazol-1-yloxytris (dimethylamino)-phosphoniumhexafluorophosphate (BOP) were purchased from TCI America. N, N-dimethylamino-cinnamaldehyde (DMACA) were purchased from Sigma- Aldrich. Tetrahydrofuran (Sigma-Aldrich), ethanol, and double-distilled water were used as solvents. All the reagents and solvents were of the highest commercial quality and were used without further purification. MitoTracker Green FM, LysoTracker Red DND-100 were purchased from Life Technologies and used in accordance with the manufacturer's protocols.

ESI-MS analyses were performed using a PerkinElmer API 150EX mass spectrometer or a Waters ACQUITY UPLC Q-Tof mass spectrometer. UV/Vis spectra were recorded on a Perkin-Elmer Lambda 25 spectrometer at 293 K. Fluorescence spectra was recorded on a Perkin-Elmer LS55 luminescence spectrometer at 293 K. Excitation and emission slits were 5 nm and emission spectra were collected 720 nm-850 nm after excited at 700 nm.

The pH measurements were carried out on a Corning pH meter equipped with a Sigma-Adrich micro combination electrode calibrated with standard buffer solutions. $^1$H and $^{13}$C NMR spectra were recorded on a Bruker Ascend 400 digital NMR spectrometer at ambient temperature (298 K). Chemical shifts are reported in delta (δ) unit per million (ppm) downfield tetramethylsilane. Splitting patterns are abbreviated as follows: s, singlet; d, doublet; t, triplet; q, quartet; m, multiplet; br, broad.

Preparation of NIRh-Fret

NIRh-Fret was synthesized via a two-step procedure as outlined in Scheme 6 with an overall yield of 32%. It was characterized by $^1$H NMR, $^{13}$C NMR, and ESI-MS.

$^1$H NMR (400 MHz, DMSO) δ 8.63 (d, J=9.3 Hz, 1H), 7.89-7.80 (m, 1H), 7.62-7.37 (m, 4H), 7.35 (s, 1H), 7.16-6.85 (m, 2H), 6.75-6.42 (m, 5H), 6.36-6.24 (m, 3H), 6.19 (d, J=13.5 Hz, 2H), 5.06 (s, 2H), 3.30-2.91 (m, 10H), 1.85 (d, J=8.2 Hz, 6H), 1.21 (t, J=7.1 Hz, 6H). $^{13}$C NMR (100 MHz, DMSO) δ 163.63, 151.95, 150.75, 147.70, 128.65, 126.90, 123.42, 118.24, 111.94, 105.23, 95.92, 65.43, 40.21, 40.00, 36.75, 17.08, 14.26. TOF-MS ES$^+$: calctd 729.40. found 730.4183 (M+H)$^+$.

Scheme 6 Synthesis route for NIRh-Fret

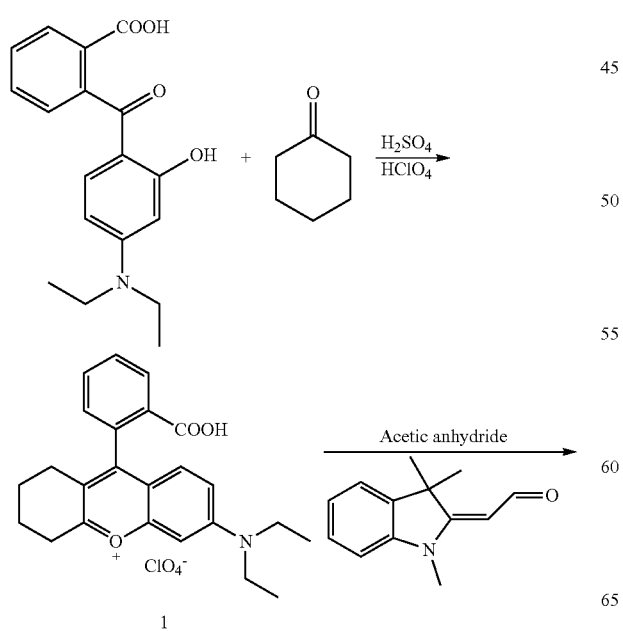

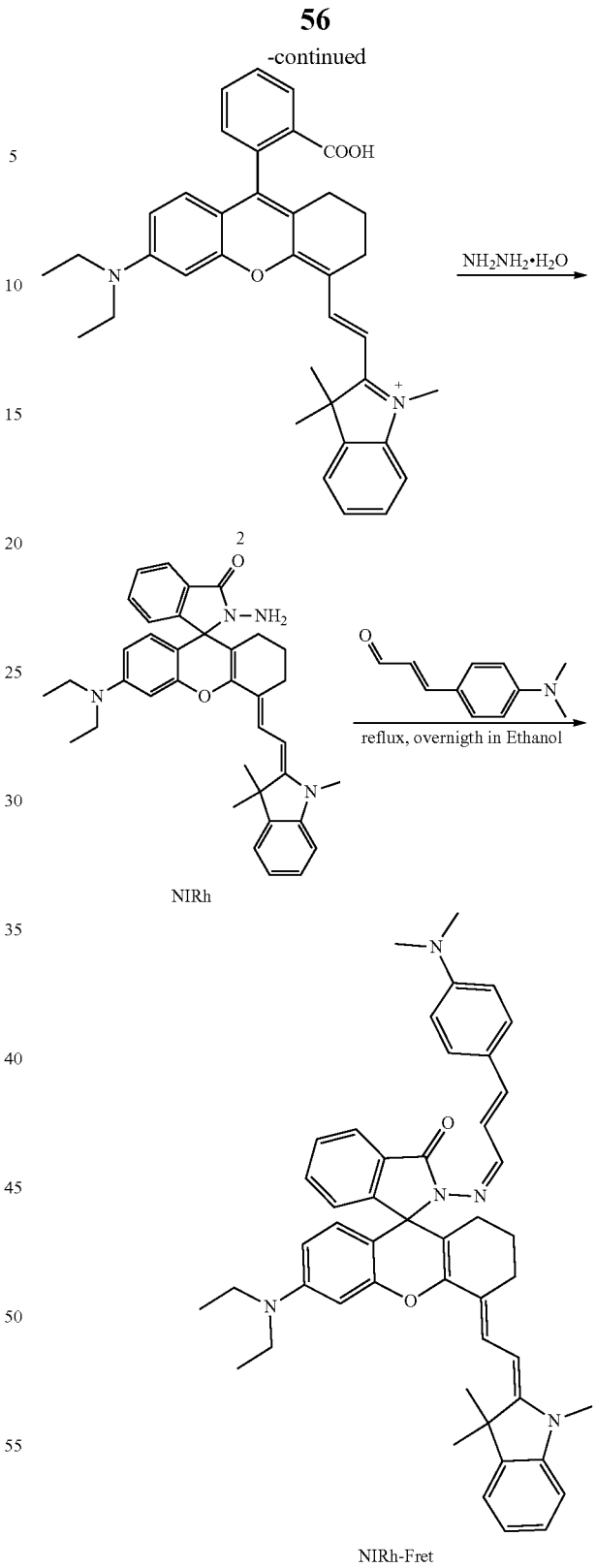

Preparation of 6-(N, N Diethylamino)-9-(2-Carboxyphenyl)-1,2,3,4-tetra-Hydroxantylium Perchlorate (1): Freshly distilled cyclohexanone (3.3 mL, 31.9 mmol) was added drop-wisely to concentrated H$_2$SO$_4$ (35 mL) and cooled down to 0° C. Then, 2-(4-Diethylamino-2-hydroxybenzoyl) benzoic acid (5 g, 16 mmol) was added in portions with vigorous stirring. The reaction mixture was heated at 90° C. for 1.5 h, then cooled down, and poured onto ice (150 g). Perchloric acid (70%, 4 mL) was then added, and the resulting precipitate was filtered off and washed with cold water (100 mL) to obtain a red solid. 1 was used for the next step without further purification.

Preparation of 3H-Indolium,2-[2-[9-(2-carboxyphenyl)-6-(diethylamino)-2,3-dihydro-1H-xanthen-4-yl]ethenyl]-1,3,3-trimethyl-, perchlorate (2): 1 (1 g, 2.1 mmol) and 2-(1,3,3-Trimetylindolin-2-ylidene) acetaldehyde (0.44 g, 2.2 mmol) were dissolved in acetic anhydride (12 mL), and the reaction mixture was heated to 50° C. and further stirred at 50° C. for 75 min. Then, water (12 mL) was added to the reaction mixture to quench the reaction. The solvent was removed under reduced pressure to give the crude product, which was purified by alumina gel chromatography using $CH_2Cl_2$ to $CH_2Cl_2$/methanol (200:1 to 20:1) as eluent to afford the compound 2 (0.45 g, yield 33%). $^1$H NMR ($CDCl_3$, 300 MHz δ(ppm)): 8.68 (d, 1H), 8.15 (d, 1H), 7.80-7.11 (m, 8H), 6.92-6.60 (m, 3H), 5.50 (s, 1H), 3.62 (d, 3H), 2.71 (t, 2H), 2.46-2.30 (m, 4H), 1.82 (s, 8H), 1.28 (t, 6H). ESI-MS. found: m/z=559.6 $[M]^+$, calcd for $C_{37}H_{39}N2O_3^+$=559.3.

Preparation of Spiro[1H-isoindole-1,9'-[9H]xanthen]-3(2H)-one,2-amino-6'-(diethylamino)-4'-[2-(1,3-dihydro-1,3,3-trimethyl-2H-indol-2-ylidene)ethylidene]-1',2',3',4'-tetrahydro-(NIRh): To a solution of 2 (0.76 mmol, 500.1 mg) in dry $CH_2Cl_2$ was successively added $NH_2NH_2 \cdot H_2O$ (7.6 mmol, 380.2 mg) and BOP (0.80 mmol, 360.9 mg). The mixture was stirred at room temperature for 2 h, and the solvent was evaporated under reduced pressure. The residue was purified by an alumina gel column using $CH_2Cl_2$/methanol (V/V, 20:0 to 20:1) to afford compound NIRh as a yellow solid (212 mg, 38%).

Condensation of NIRh with N, N-dimethylaminocinnamaldehyde (NIRh-Fret): A mixture of NIRh (0.123 g, 0.21 mmol) and N,Ndimethylcinnamaldehyde (0.04 g, 0.26 mmol) in absolute ethanol was refluxed for 12 h. After the completion of the reaction, solvent was evaporated to give NIRh-Fret in 32% yield by a reported procedure [23].

Example 25. Metal Ion Sensing, Spectroscopic and Selectivity Studies

A solution of metal ions was prepared from chloride salts of $Ni^{2+}$, $Fe^{3+}$, $Cu^{2+}$, $Mn^{2+}$ $Hg^{2+}$, $Na^+$, $Ca^{2+}$, $Zn^{2+}$, $Ag^+$, and nitrate salts of $Mg^{2+}$, $K^+$, $Co^{2+}$ (1 mM) in deionized water, except for $Co^{2+}$, which was dissolved in acetonitrile anhydrous. Solution of $Cu^+$ was freshly prepared by dissolving tetrakis(acetonitrile)copper(I) (Sigma-Aldrich) into double-distilled water. $Fe^{3+}$, $Fe^{2+}$ solutions were prepared freshly from ferric chloride, ferrous ammonium sulfate (FAS, Fe $(NH_4)_2(SO_4)_2$, respectively in 0.01 M HCl.

A stock solution of NIRh-Fret (1 mM) was prepared in THF. The solution of NIRh-Fret was diluted to 20 μM with $H_2O$/THF (pH 7.3, v/v, 1:1). Before spectroscopic measurements, solutions were freshly prepared by diluting the corresponding high-concentration stock solution. For each spectrum, 1 mL of a probe solution was added to a 1-cm quartz cell, to which different stock solutions of cations were gradually added. All spectroscopic measurements were done under simulated physiological pH, and measurements were performed at least triplicate and resulting averages are reported.

Figure 52:
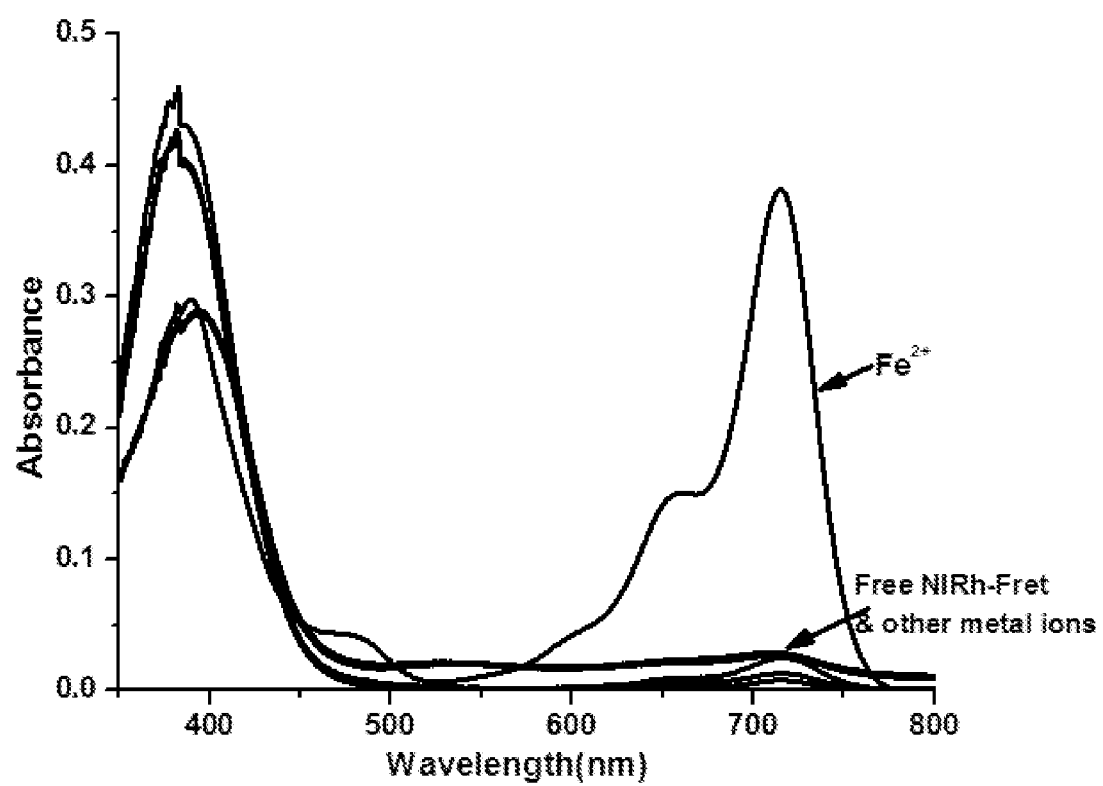
FIG. 52 shows the absorption spectra of 20 μM NIRh-Fret to various metal ions in $H_2O$/THF (pH 7.3, v/v 1:1).

Selectivity and spectroscopic properties of the sensor were investigated to evaluate the performance of the fluorescence sensor. The changes in UV-Vis spectra after the addition of various metal ions are shown in FIG. 52. The addition of $Fe^{2+}$ to the solution of NIRh-Fret showed an obvious green color with an absorption peak at 722 nm in $H_2O$/THF (pH 7.32, v/v 1:1). The color change for $Fe^{2+}$ is readily detected visually. Compared with that of $Fe^{2+}$, other metal ions did not induce significant changes in UV-Vis absorption.

Figure 53:
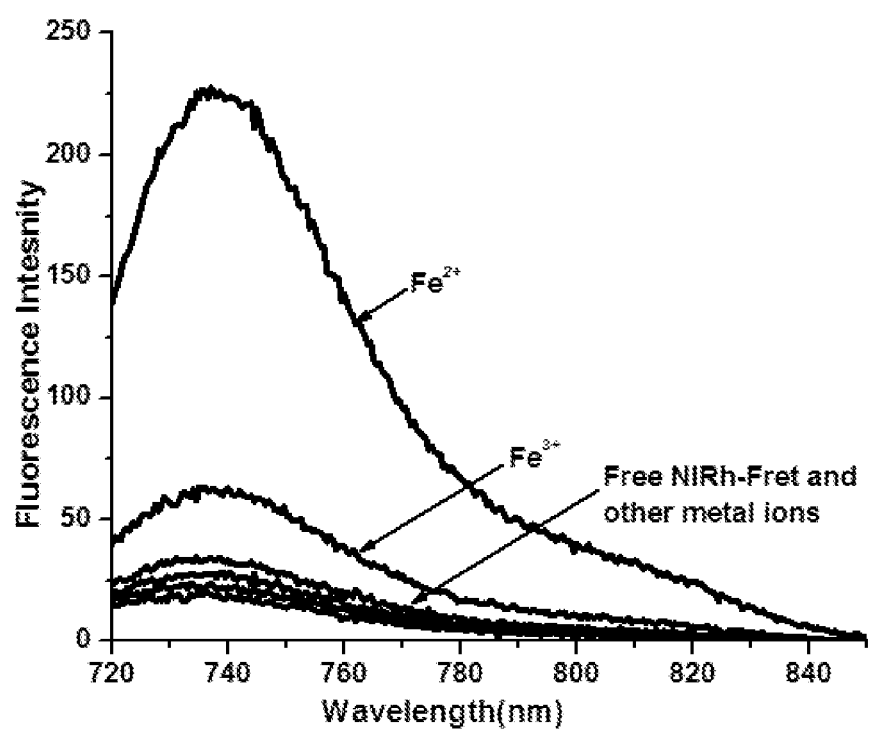
FIG. 53 shows the fluorescence spectra ($\lambda_{Ex}/\lambda_{Em}$ 700/743 nm) of 20 μM NIRh-Fret to 20 μM various metal ions in $H_2O$/THF (pH 7.3, v/v 1:1).
Figure 54:
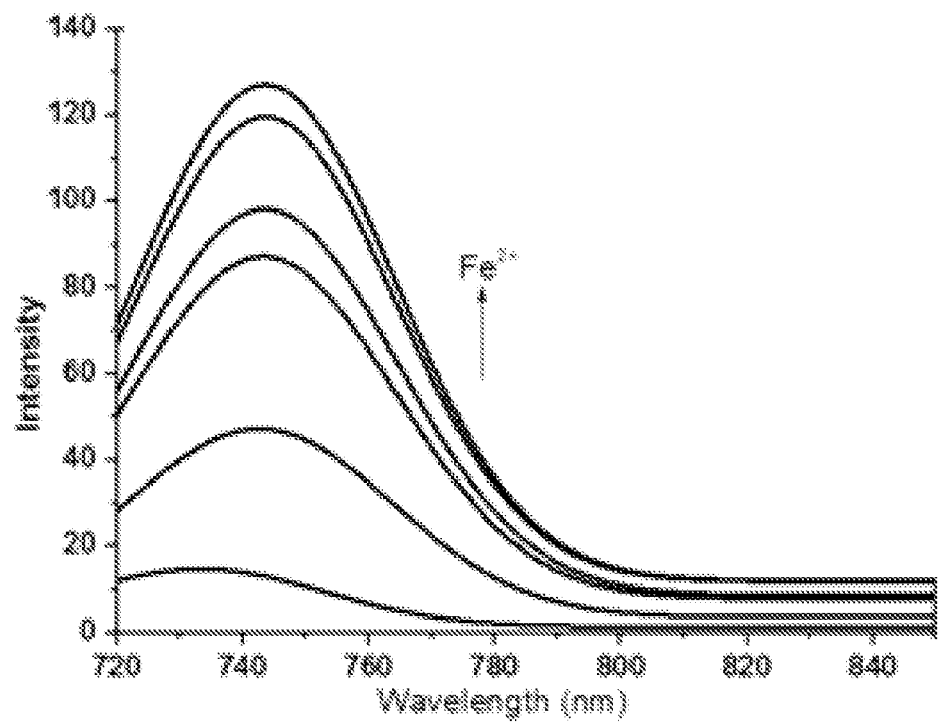
FIG. 54 shows the intensity spectra for the titration of 20 μM NIRh-Fret with increasing concentration of $Fe^{2+}$ (0, 4, 8, 12, 16, 20 μM from bottom to top) in $H_2O$/THF (pH 7.3, v/v 1:1).

The changes in fluorescence spectra of NIRh-Fret with the addition of different metal ions in $H_2O$/THF (pH 7.32, v/v 1:1) are shown in FIG. 53. When $Fe^{2+}$ was added into the solution of NIRh-Fret, a large fluorescence enhancement at 743 nm was observed, induced by the complexation of $Fe^{2+}$. The emission intensity enhancement at 743 nm is around 10 times with 1.0 equiv of $Fe^{2+}$, suggesting that NIRh-Fret is a great turn-on fluorescent sensor for $Fe^{2+}$ (FIG. 53). Titration of 20 μM NIRh-Fret with increasing concentration of $Fe^{2+}$ is shown in FIG. 54.

Figure 55:
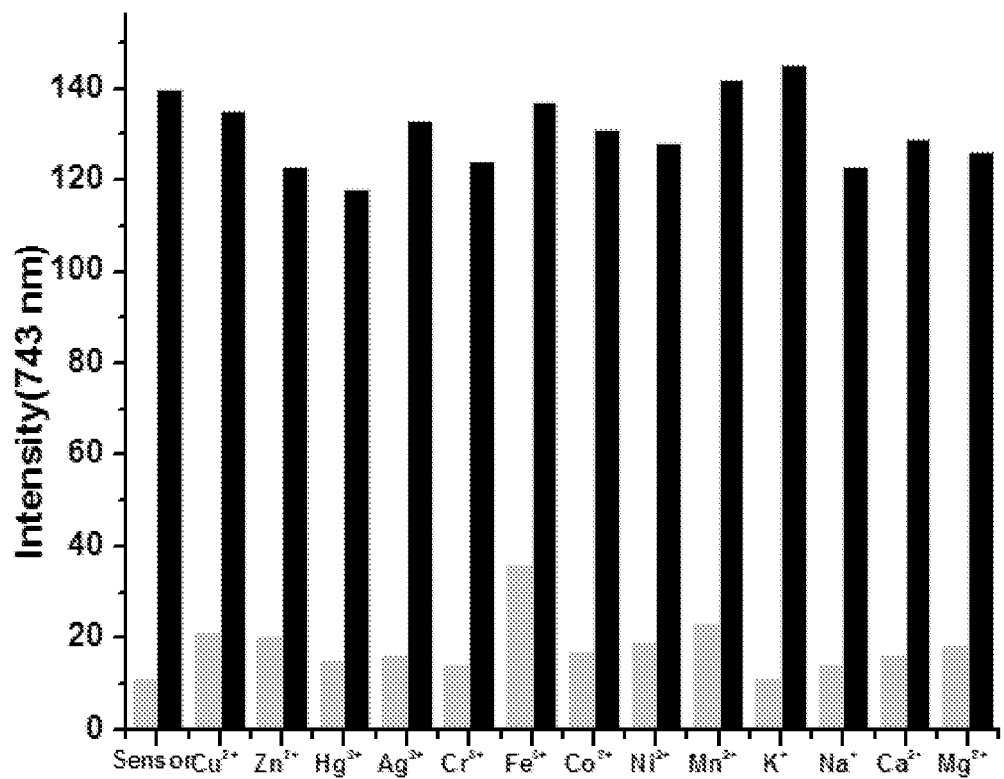
FIG. 55 shows the graph of fluorescence responses of 20 μM NIRh-Fret to the presence of 20 μM various metal ions (light grey bar) and the subsequent addition of $Fe^{2+}$ (black bar) in the $H_2O$/THF (pH 7.3, v/v 1:1); the bars represent the fluorescence intensity at 743 nm.

NIRh-Fret displayed an excellent selective turn-on fluorescent response to $Fe^{2+}$ (FIG. 55). In the presence of other bio-relevant metal ions including $Fe^{3+}$, $Ni^{2+}$, $Cu^+$, $Cu^{2+}$, $Zn^{2+}$, $Pb^{2+}$, $Cr^{3+}$, $Hg^{2+}$, $Mn^{2+}$, $Ag^+$, $Co^{2+}$, $K^+$, $Na^+$, $Ca^{2+}$ and $Mg^{2+}$; NIRh-Fret did not trigger fluorescence enhancements under the same conditions (the light grey bars in FIG. 55). Moreover, upon the addition of 1 equiv of $Fe^{2+}$ into solutions containing one of the other metal ions tested, the fluorescence was activated and the intensity increased to a level similar to that observed in the presence of $Fe^{2+}$ only (the black bars in FIG. 55). This demonstrated that these metal ions did not interfere with the response of $Fe^{2+}$ to NIRh-Fret.

Figure 56:
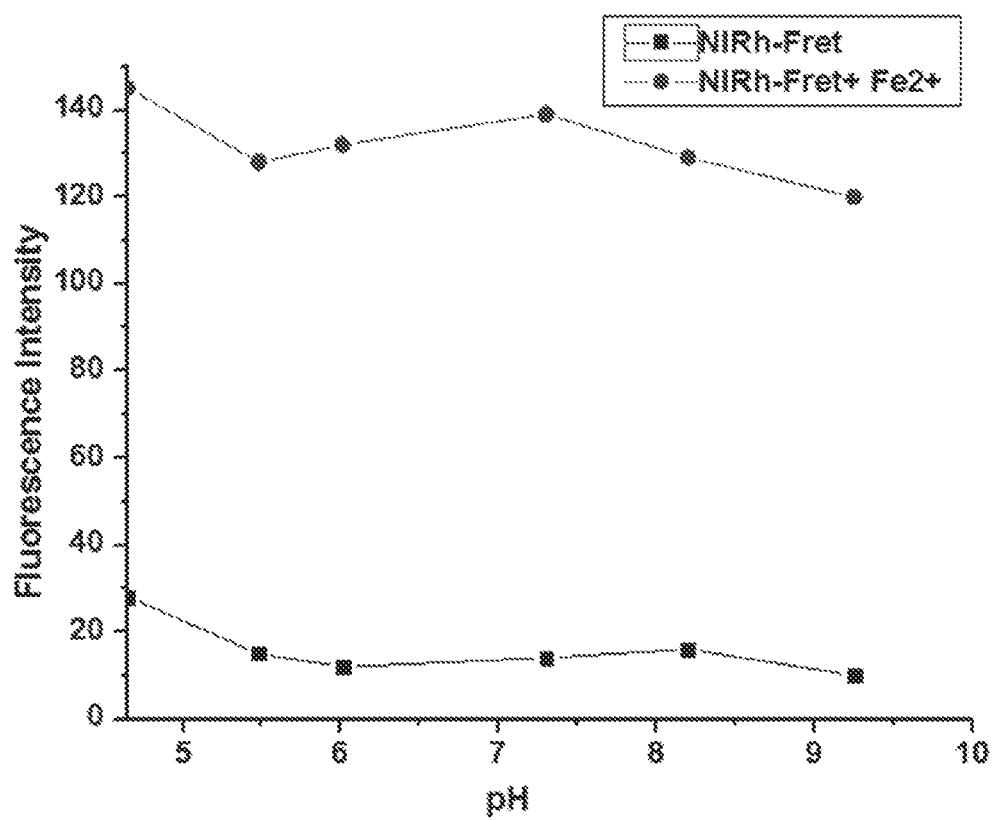
FIG. 56 shows the fluorescence intensity (743 nm) of NIRh-Fret and NIRh-Fret+$Fe^{2+}$ (20 μM each) at various pH values in $H_2O$/THF (pH 7.3, v/v 1:1) solution.

As rhodamine-based sensors give response to hydrogen ions, the stability of NIRh-Fret sensor in biological pH range was tested. The effect of pH on the stability of the sensor was investigated at different pH values and monitored by fluorescence spectra (FIG. 56). The pH of the solutions was adjusted by adding HCl or NaOH into the solutions. The fluorescence of NIRh-Fret at different pH values was plotted in FIG. 56, which shows that the sensor and Fe (II)-complex is stable over the biological pH range down to pH 4.5. Thus, NIRh-Fret may be applied in biological systems.

Example 26. Cell Culture and Confocal Imaging

Bovine aortic endothelial cells (BAEC) were grown at 37° C. in a humid atmosphere of 5% $CO_2$ atmosphere in Endothelial Basal Medium (EBM, Lonza) supplemented with 5% fetal bovine serum (FBS, ATCC). Cultures were divided into 1:2 every 48 h to an approximate cell density of 1.3 million cells/ml and used for experiments after 24 h.

For kinetic experiment, Caco-2 cells (ATCC) were maintained in Dulbecco's minimal essential medium (DMEM, ATCC) supplemented with 10% fetal bovine serum (FBS, ATCC), 100 U/ml penicillin G, and 100 μg/ml streptomycin at 37° C. in a humid atmosphere of 5% $CO_2$ atmosphere. The culture medium was replaced with a fresh medium every 2-3 days. After being nearly confluent, the cells were used for experiment.

For concentration determination, human primary fibroblast ws1 cells were grown at 37° C. in a humid atmosphere of 5% $CO_2$ atmosphere in eagle's minimum essential medium (EMEM, ATCC) supplemented with 10% fetal bovine serum (FBS, ATCC). Cultures were divided into 1:2 every 48 h to an approximate cell density of 1.21 million cells/ml and used for experiments after 24 h. In addition, the human colon adenocarcinoma cell line HT29 (ATCC) was routinely grown in Dulbecco's modified Eagle's medium (DMEM) supplemented with 10% fetal bovine serum (FBS, ATCC).

A Zeiss LSM 710 laser-scanning confocal microscope system was used for cell imaging experiments in collaboration with Mr. Bing Yan in the lab. 40× oil-immersion objective lens were used to perform all the experiments. For imaging with the NIRh-Fret sensor, excitation wavelength of the laser was 633 nm and emissions were collected over the range 650-850 nm. For images with MitoTracker Green FM, LysoTracker Red DND-100, excitation wavelengths recommended by the manufacturer were 488 nm for MitoTracker, 543 nm for LysoTracker. Emissions were integrated at 492-535 nm (MitoTracker), 550-625 nm (LysoTracker), respectively.

Example 27. Zebrafish Experiments

Embryos were collected from natural spawning and raised up in embryo medium (M. Santra, et al. *Chem. Commun.*, 2009, 10, 2115). Zebrafish mutant strain Casper was utilized because it lacks pigment, allowing better visualization (J. A. Lister, et al., Development, 1999, 126, 3757). Zebrafish embryos at 6 days post fertilization (dpf) were incubated with 10 µM NIRh-Fret in embryo media for 1 h at 28° C. In addition, iron (II) loaded zebrafish (100 µM Fe $(NH_4)_2$ $(SO_4)_2$ for 8 hours incubation) were incubated with 10 µM NIRh-Fret in embryo media for 1 h at 28° C. The treated zebrafish were imaged by a LSM710 confocal microscope.

Figures 74A, 74B, 74C:
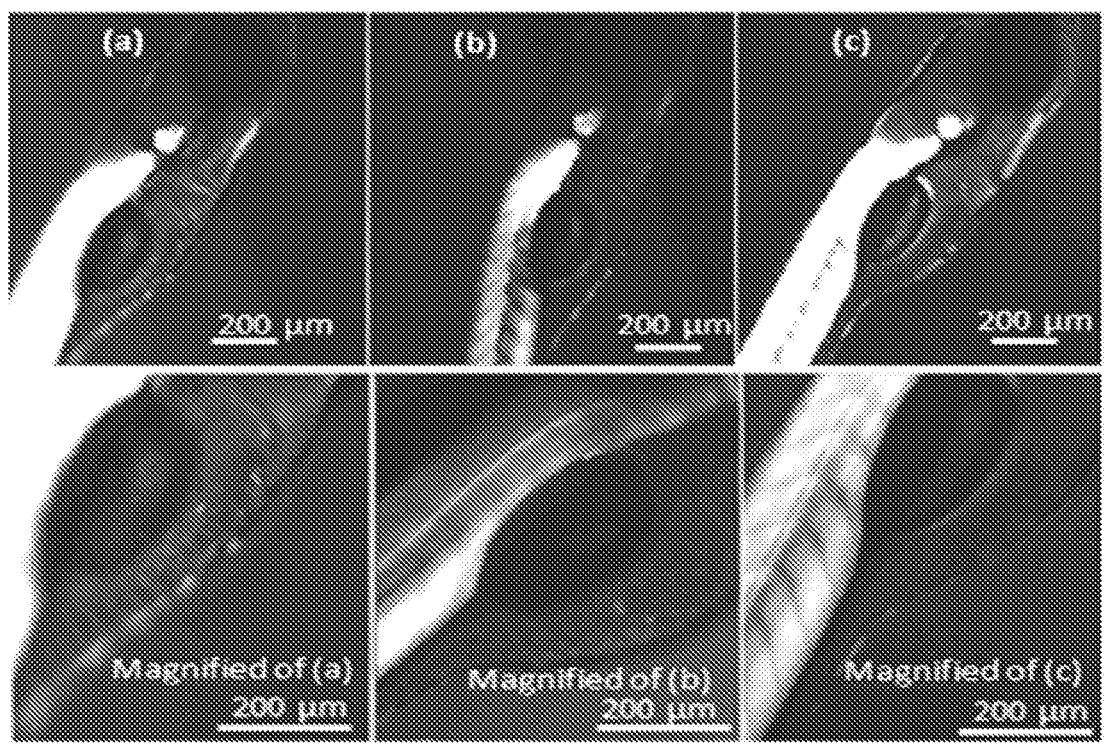
FIGS. 74A-D show confocal microscopy images 6-day old zebra fish larvaes (a) Zebrafish only (b) Zebrafish larva was incubated with 10 μM NIRh-Fret for 30 min (c) Zebrafish larva incubated with 100 μM $Fe^{2+}$ for 8 h and then 10 μM NIRh-Fret was added and incubated for 30 min; (d) is a bar chart of the relative intensities of (a), (b) and (c).
Figure 74D:
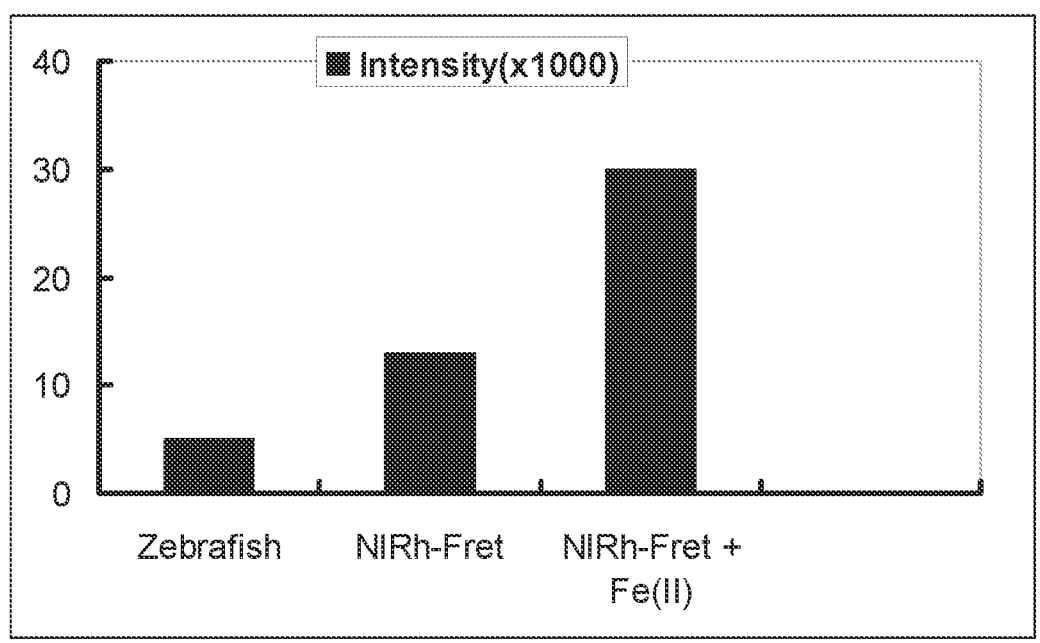

The ability of NIRh-Fret to detect free $Fe^{2+}$ in zebrafish was further investigated using confocal microscopy. 6-days-old zebrafishes were incubated with 10 µM NIRh-Fret showed weak fluorescence (FIG. 74B). For $Fe^{2+}$ replete conditions, live zebrafish were incubated with 100 µM of ferrous ammonium sulfate (Fe $(NH_4)_2(SO_4)_2$) at 28° C. for 8 h followed by washing with E3 medium to remove excess $Fe^{2+}$ and then 10 µM of NIRh-Fret was added to the culture media and was incubated at 28° C. for 30 min.

The $Fe^{2+}$-treated zebrafish showed significant increase in fluorescent signals (FIG. 74C) w.r.t the zebrafish without $Fe^{2+}$ supplementation (FIG. 74B), suggesting a positive response of NIRh-Fret to increased labile $Fe^{2+}$ levels in $Fe^{2+}$-treated zebrafish. In addition, the red-colored region was observed as a well-localized red round spot, being the intestine region of the 6-days-old zebrafish.

Figure 57:
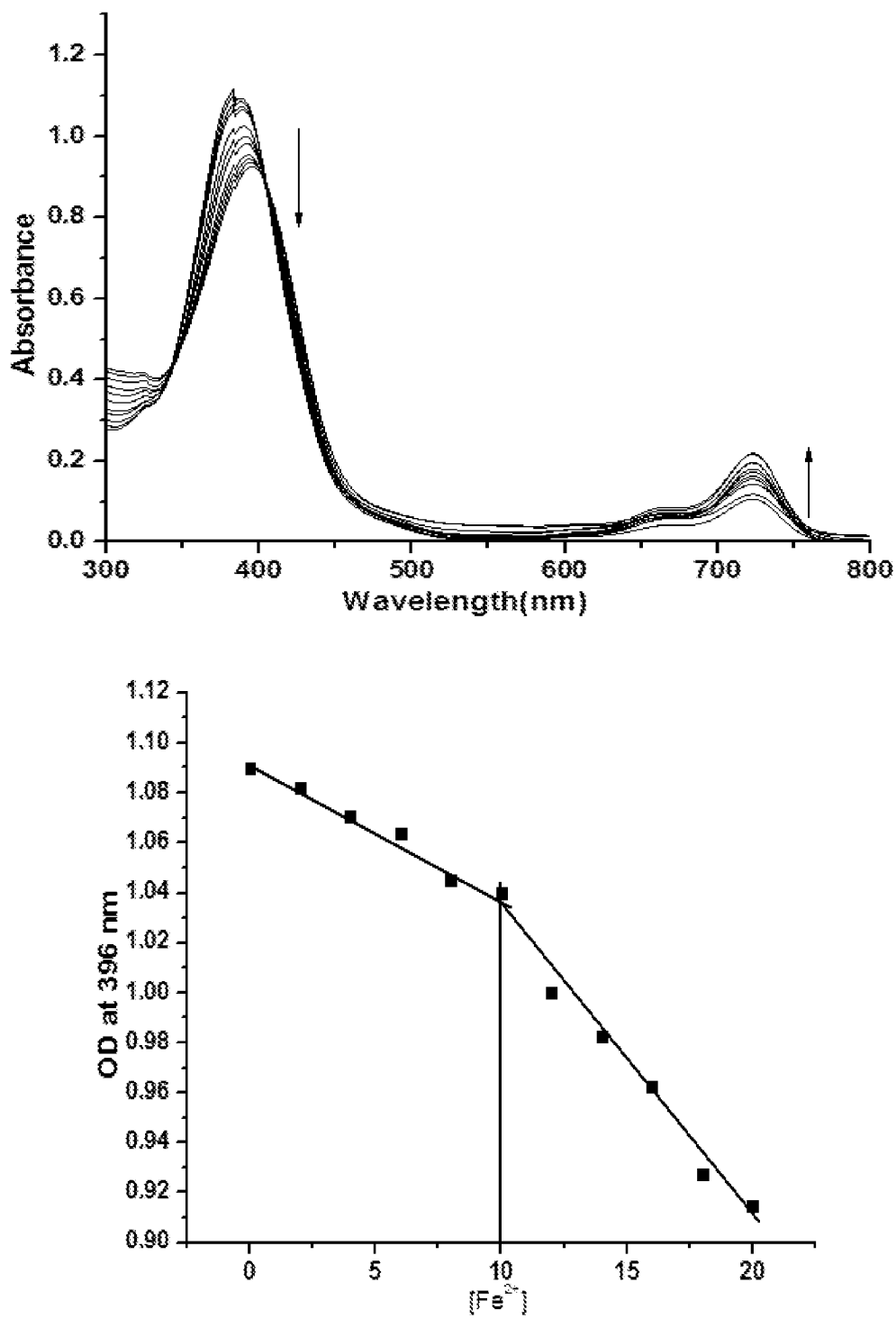
FIG. 57 shows the absorbance spectra for the titration of 10 μM NIRh-Fret with increasing concentrations of $Fe^{2+}$ (0, 2, 4, 6, 8, 10, 12, 14, 16, 18, 20 μM, respectively) in $H_2O$/THF (pH 7.3, v/v 1:1) solution. The bottom panel is a plot of absorbance at 396 nm versus [$Fe^{2+}$].

Example 28. Binding Studies: Stoichiometry, Affinity and Reversibility for NIRh-Fret The binding stoichiometry and the affinity between the sensor NIRh-Fret and $Fe^{2+}$ were investigated by UV-vis absorption titration. The titration curve (a plot of absorption versus $Fe^{2+}$) decreased (FIG. 57) linearly at 396 nm and changed slope at 1:1 ratio of the sensor and $Fe^{2+}$, suggesting the formation of a 1:1 of NIRh-Fret-$Fe^{2+}$ complex. The binding constant for the formation of this complex was determined to be $2.9 \times 10^6$ $M^{-1}$ using a reported procedure (C. A. Perez, et al., *J. Inorg. Biochem.*, 2009, 103, 326).

Figure 58:
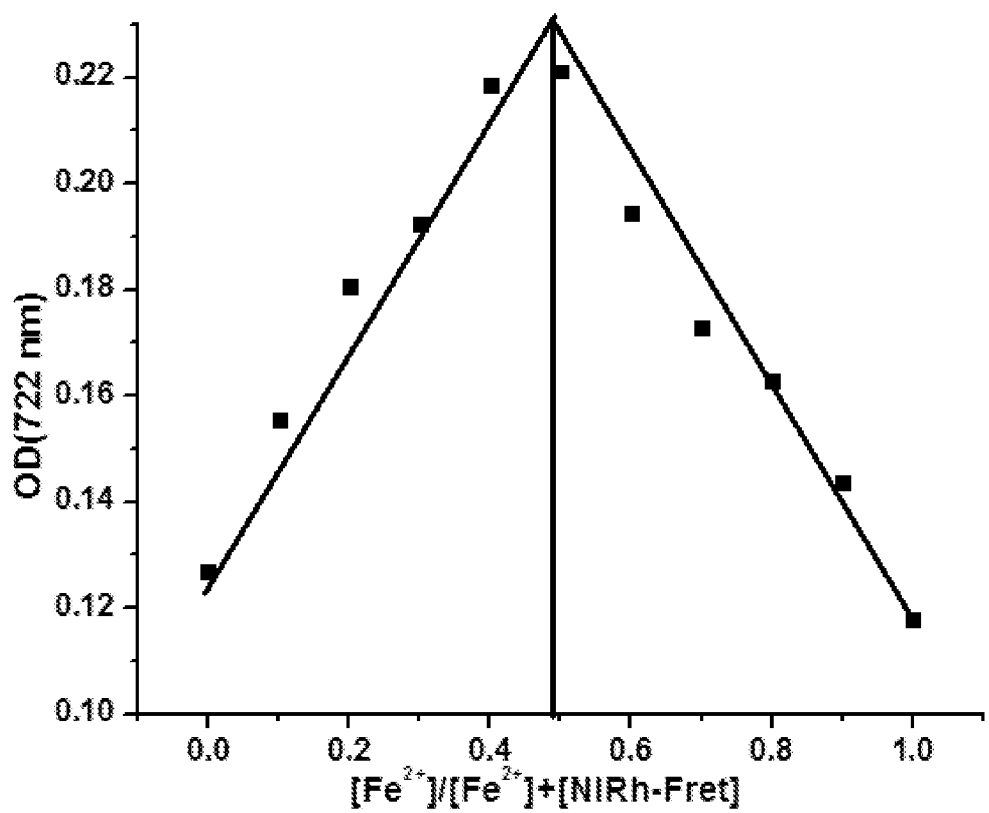
FIG. 58 is a Job's plot. The total concentrations of NIRh-Fret and $Fe^{2+}$ were kept at constant 20 μM and the absorption intensity was measured at 722 nm in $H_2O$/THF (pH 7.3, v/v 1:1) solution.

The Job's plot (FIG. 58) using a total concentration of 20 µM NIRh-Fret and $Fe^{2+}$ in $H_2O$/THF (pH 7.3, v/v 1:1) solution exhibited a maximum absorbance when the molecular fractions of $Fe^{2+}$ and NIRh-Fret were close to 50%, corroborating the 1:1 stoichiometry for the binding of NIRh-Fret and $Fe^{2+}$.

Figure 59:
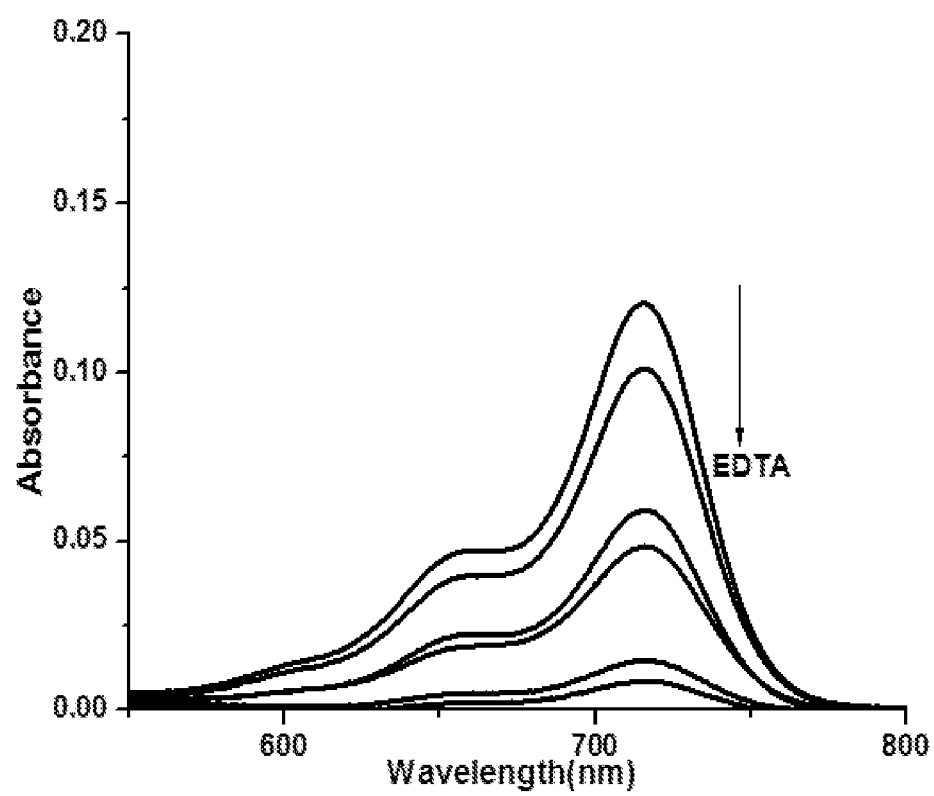
FIG. 59 shows the absorbance spectra for the treatment of 10 μM NIRh-Fret-$Fe^{2+}$ complex with increasing concentration of EDTA (0, 4, 8, 12, 16, 20 μM, from top to bottom) in $H_2O$/THF (pH 7.3, v/v 1:1).

Reversibility experiments were carried out by adding EDTA to the NIRh-Fret-$Fe^{2+}$ complex in $H_2O$/THF (pH 7.3, v/v 1:1). In the absence of EDTA, the complex was colorful and fluorescent. After adding EDTA, the absorption of the complex decreased in intensity and finally, disappeared (FIG. 59), suggesting a reversible binding between NIRh-Fret and $Fe^{2+}$.

Figure 60:
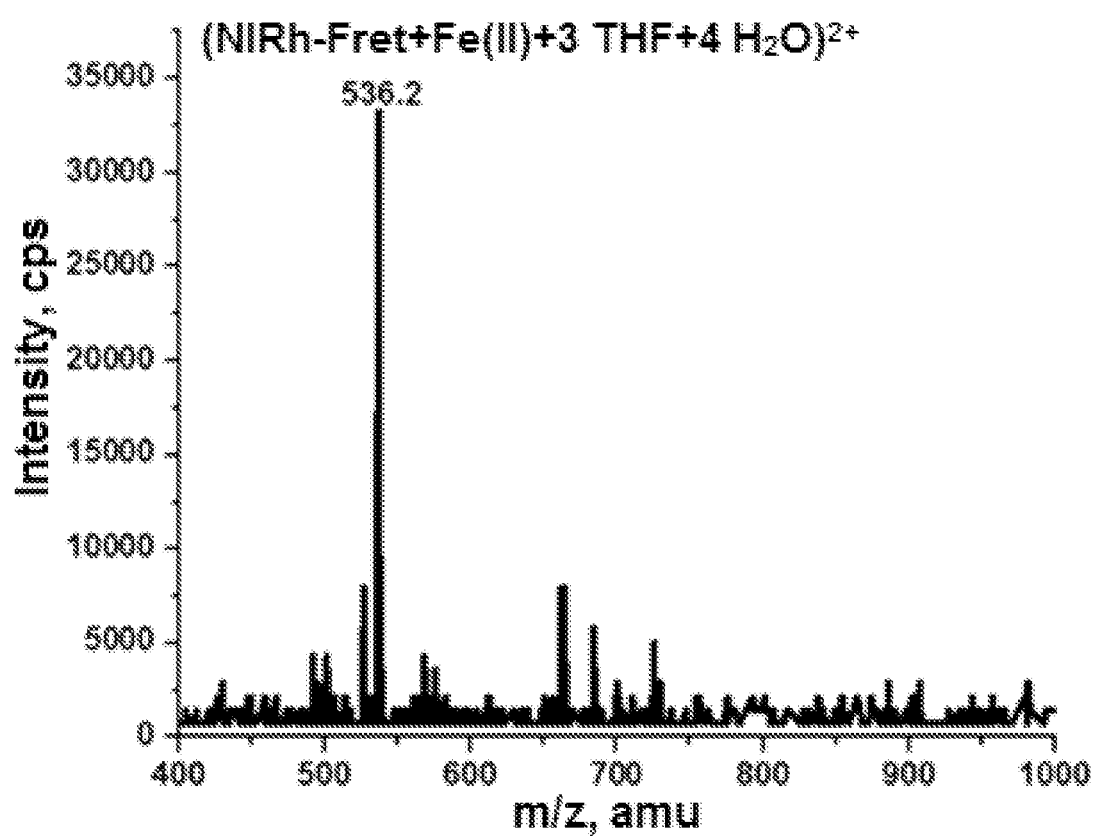
FIG. 60 shows the ESI-MS spectrum of the solution of NIRh with $Fe^{2+}$ (10 μM sensor and excess $Fe^{2+}$ in H2O/THF (pH 7.3, v/v 1:1).

The species formed between NIRh-Fret and $Fe^{2+}$ was more accurately determined by ESI-MS. Upon the mixing of $Fe^{2+}$ and the sensor (10 µM sensor and excess of $Fe^{2+}$ in $H_2O$/THF (pH 7.3, v/v 1:1)), one major species was detected by ESI-MS, corresponding to NIRh-Fret+Fe(II) with four water, three tetrahydrofuran molecules, attached (m/z=536.2, assignable to a 1:1 complex) (FIG. 60).

Example 29. Binding Site of $Fe^{2+}$ on the NIRh-Fret Sensor

Figure 61:
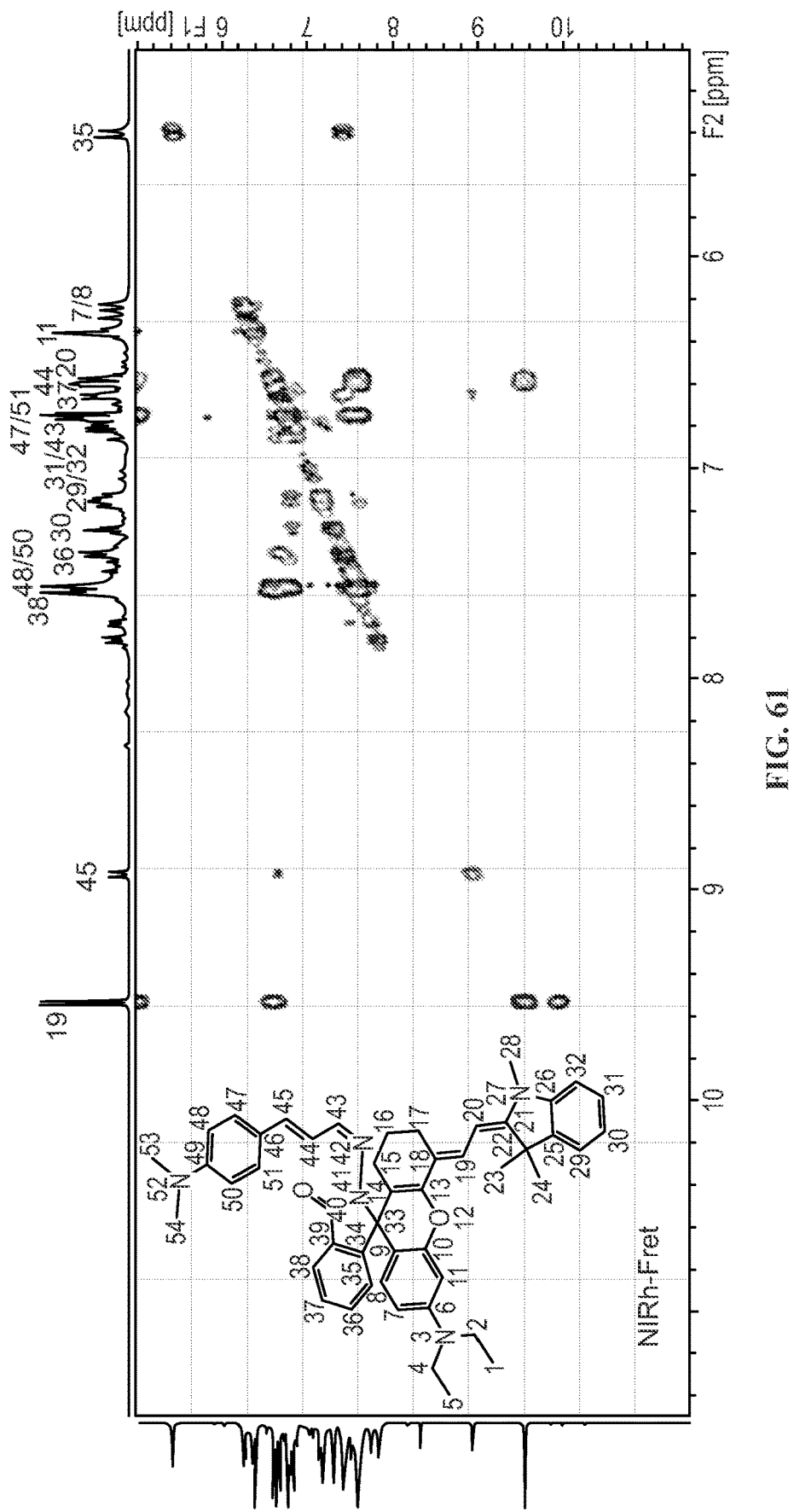
FIG. 61 shows a 2D-COSY NMR of the sensor NIRh-Fret in DMSO.

In order to probe the binding site of $Fe^{2+}$ on the NIRh-Fret sensor, 1D and 2D $^1H$ NMR of the sensor NIRh-Fret was investigated first. Due to limited solubility and the extensive aromatic ring systems in the NIRh-Fret sensor, there are severe overlaps of the peaks in the aromatic region of the NMR spectra. The assignment of the $^1H$ NMR peaks was based on 2D $^1H$-$^1H$ COSY spectra. FIG. 61 shows the aromatic region of the 2D $^1H$-$^1H$ COSY spectra with the peak assignments shown in the inset.

Figure 62:
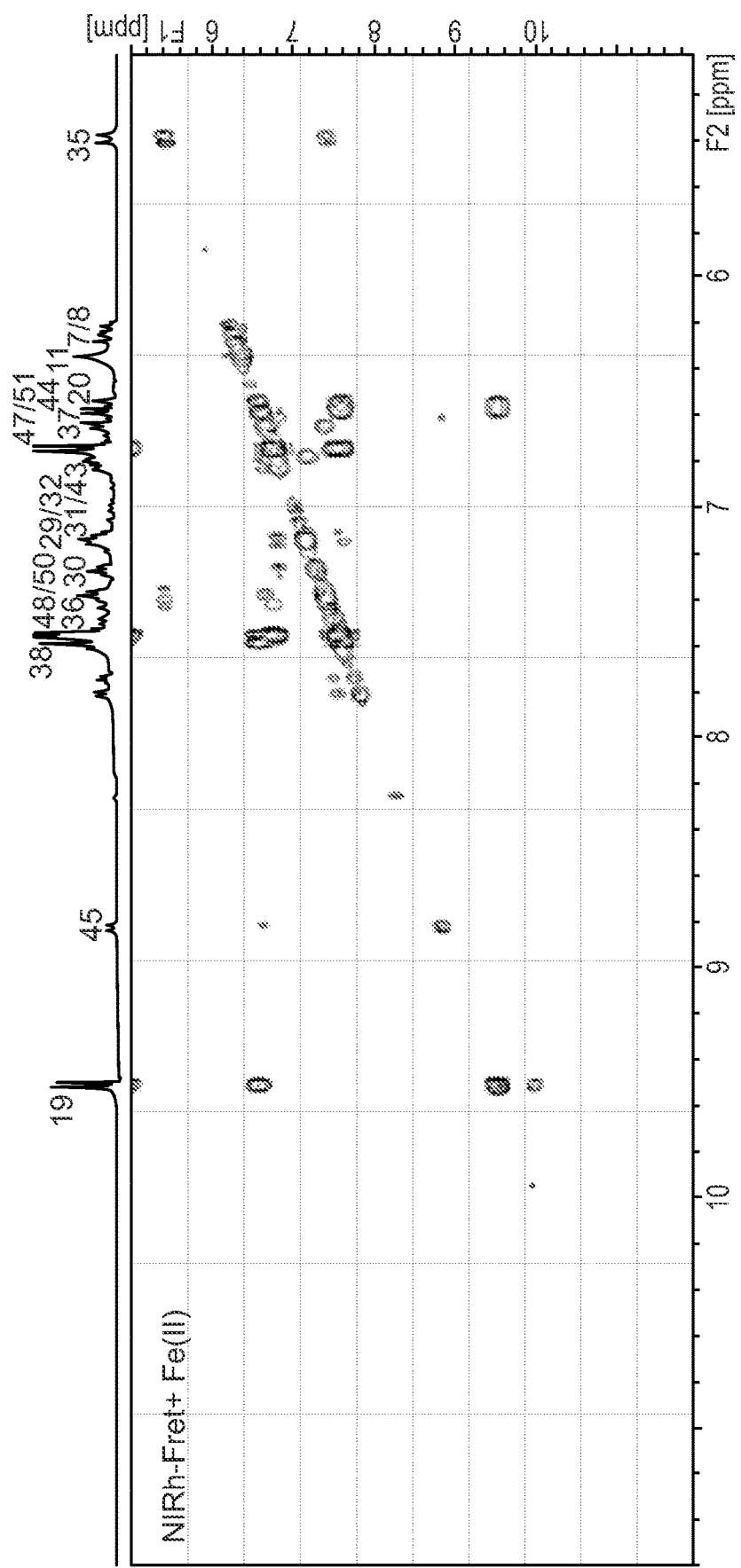
FIG. 62 shows a 2D-COSY NMR of (NIRh-Fret+$Fe^{2+}$) in DMSO.

After adding $Fe^{2+}$ to NIRh-Fret, the NMR spectra still clearly show a diamagnetic feature (FIG. 62), indicating that Fe (II) is in low-spin state. A careful comparison of the spectra patterns in the absence and presence of $Fe^{2+}$ revealed that $Fe^{2+}$-induced some upfield shifts of conjugated diene protons of NIRh-Fret in $^1H$ and COSY NMR spectra. The notable changes in the $^1H$ and COSY spectra are such as up-field shift of 45 numbered proton (8.96 to 8.72 ppm), up-field shifts of 48/50 and 47/51 numbered protons (by ~0.13 ppm) as well as minor downfield shift of the 44 numbered proton and diminish in intensity of the 43 numbered proton. These changes in NMR peaks indicate that Fe (II) is in low spin state, coordinating at the region close to these protons on the sensor. The most likely donor atoms involved in binding with $Fe^{2+}$ are O40, N42 and C44=C45, forming a 5-membered chelating ring and a 5.5-membered chelating ring with a η-2 pi-coordination.

This is a similar binding mode as those in the Rh6GD and Rh101D sensors. A possible structure of the complex is proposed in Scheme 7. Such a novel coordination mode is unlikely to occur with $Fe^{3+}$ or other physiologically relevant metal ions, which may explain its excellent selectivity for $Fe^{2+}$. A possible mechanism for the reaction and the binding mode are shown in Scheme 7.

Scheme 7 Proposed 1:1 binding mode of NIRh-Fret with $Fe^{2+}$ in $H_2O$/THF (pH 7.3, v/v 1:1).

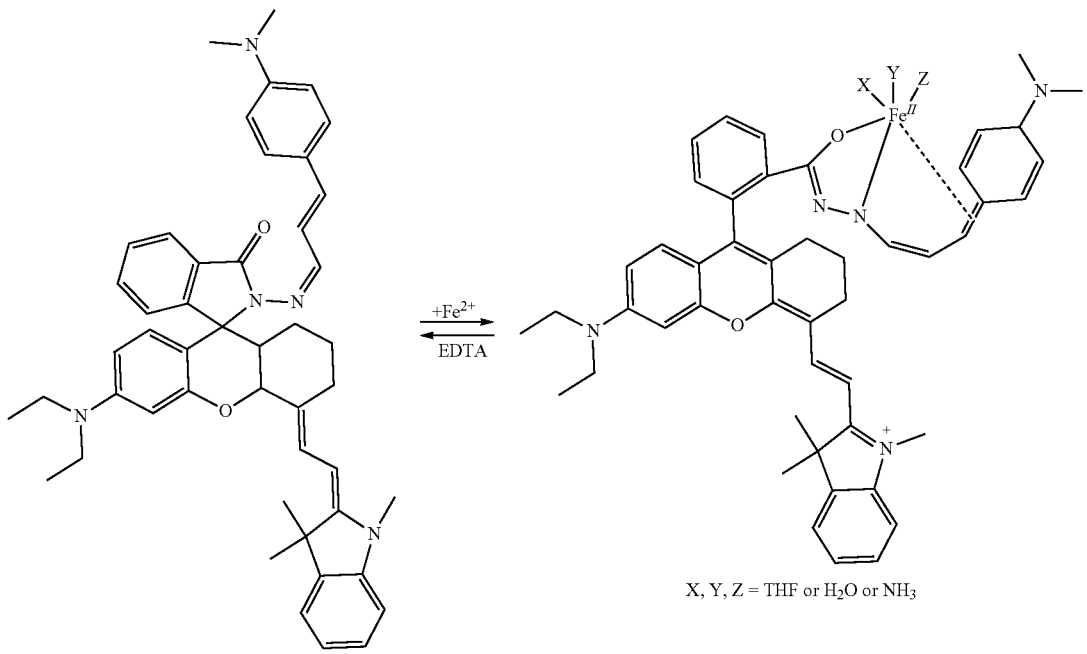

X, Y, Z = THF or $H_2O$ or $NH_3$

Example 30. Biological Imaging Studies

Figure 63F:
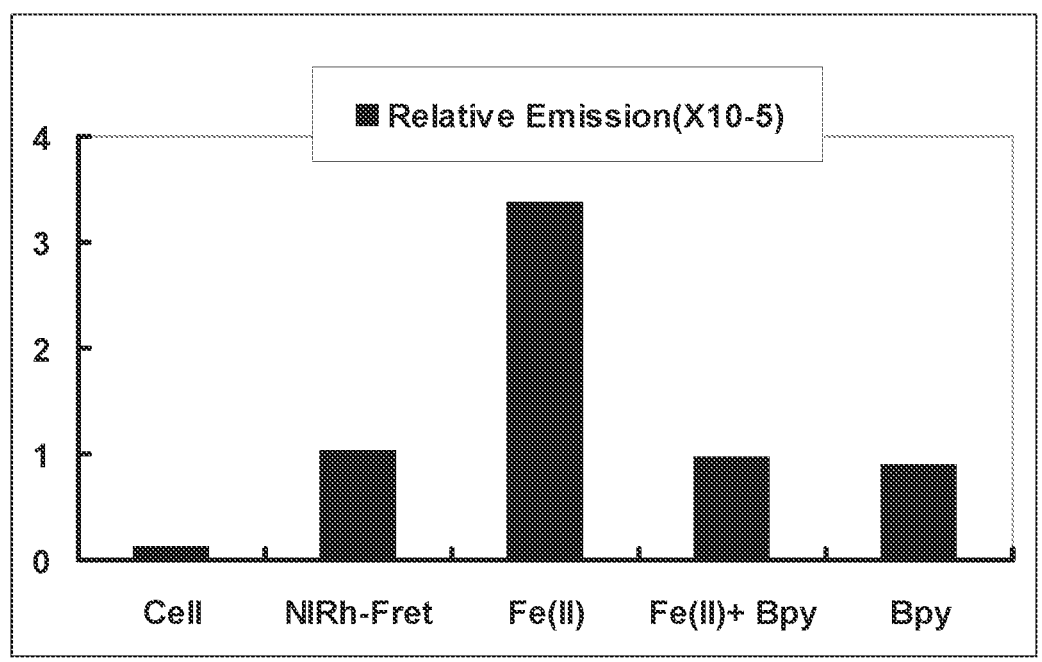
FIG. 63F is bar chart of the relative intensities of FIGS. 63A, B, C, D, and E.
Figures 64A, 64B, 64C, 64D, 64E, 64F, 64G, 64H:
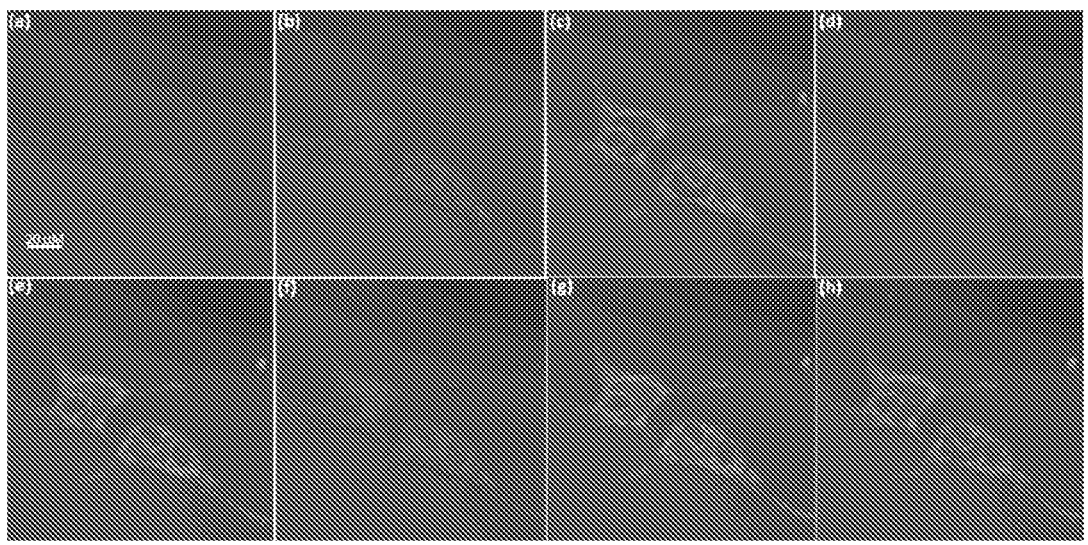
FIGS. 64A-H show representative confocal images of intracellular colocalization studies of 10 μM NIRh-Fret incubated with live bovine aortic endothelial cells (BAEC) co-labeled with MitoTracker Green (100 nM) and LysoTracker Red DND-100 (50 nM).

The ability of NIRh-Fret to detect $Fe^{2+}$ in live bovine aortic endothelial cells (BAEC) was investigated by using confocal microscopy. Live BAEC cells incubated with 10 μM NIRh-Fret showed weak fluorescence (FIG. 63B). For $Fe^{2+}$ replete conditions, live BAEC cells were incubated with 100 μM of ferrous ammonium sulfate (Fe $(NH_4)_2$ $(SO_4)_2$) at 37° C. for overnight followed by washing with EBM medium to remove excess $Fe^{2+}$ and then 10 μM of NIRh-Fret was added to the culture media and was incubated at 37° C. for 30 min. The $Fe^{2+}$-treated BAEC cells showed significant increase in fluorescent signals (FIG. 63C) w.r.t the BAEC cells without $Fe^{2+}$ supplementation (FIG. 63B), suggesting a positive response of NIRh-Fret to increased labile $Fe^{2+}$ levels in $Fe^{2+}$-treated cells. For $Fe^{2+}$-depleting conditions, 2,2-bipyridyl (Bpy) which is known to be a selective $Fe^{2+}$-chelator was used to chelate $Fe^{2+}$ (Y. Katayama, et al. Chem. Lett., 2000, 29, 1152; J. L. Chen, et al. Microchim. Acta, 2007, 156, 307). BAEC cells treated with 1 mM of Bpy showed decrease in fluorescence intensity of the signals and they were weaker than those of the control cells (FIG. 63E); suggesting NIRh-Fret can detect basal level of labile $Fe^{2+}$ in BAEC cells. The BAEC cells treated with 100 μM of $Fe^{2+}$ overnight first followed by washing with EBM medium and then treated with 1 mM of Bpy and subsequent addition of 10 μM of NIRh-Fret showed marked decrease in fluorescent intensity (FIG. 63D) compare to that of cells with $Fe^{2+}$ supplement.

This fluorescent intensity is almost the same as that of cells without $Fe^{2+}$ or Bpy treatment. These data clearly demonstrate that NIRh-Fret has the ability to detect endogenous level of labile $Fe^{2+}$ as well as its dynamic changes in BAEC cells.

The discrete confocal fluorescence images revealed by NIRh-Fret in both the untreated and the $Fe^{2+}$-loaded BAEC cells imply that the labile $Fe^{2+}$ in BAEC cells may be localized in certain subcellular compartments (organelles) and that NIRh-Fret may be capable of imaging $Fe^{2+}$ at subcellular resolution. To explore this, the distribution of exchangeable $Fe^{2+}$ pools in live BAEC cells were further investigated using NIRh-Fret, together with colocalization experiments using other dyes-MitoTracker Green FM (a green fluorescent dye which localizes to mitochondria in live cells regardless of mitochondrial membrane potential) and LysoTracker Red DND-100 (a fluorescent dye that stains acidic compartments such as endosomes and lysosomes in live cells). Human BAEC cells (without $Fe^{2+}$ treatment) were treated with NIRh-Fret, MitoTracker Green FM and LysoTracker Red DND-100. As illustrated in FIGS. 64A-H, partial colocalization between NIRh-Fret-$Fe^{2+}$ and the MitoTracker (FIG. 64E) as well as between NIRh-Fret-$Fe^{2+}$ and the LysoTracker (FIG. 64F) occurred whereas complete colocalization of NIRh-Fret-$Fe^{2+}$, MitoTracker and LysoTracker (FIG. 64G) was observed. These data suggest that the exchangeable $Fe^{2+}$ pools in BAEC cells detectable by NIRh-Fret are localized in mitochondria and endosomes/lysosomes.

Figure 65F:
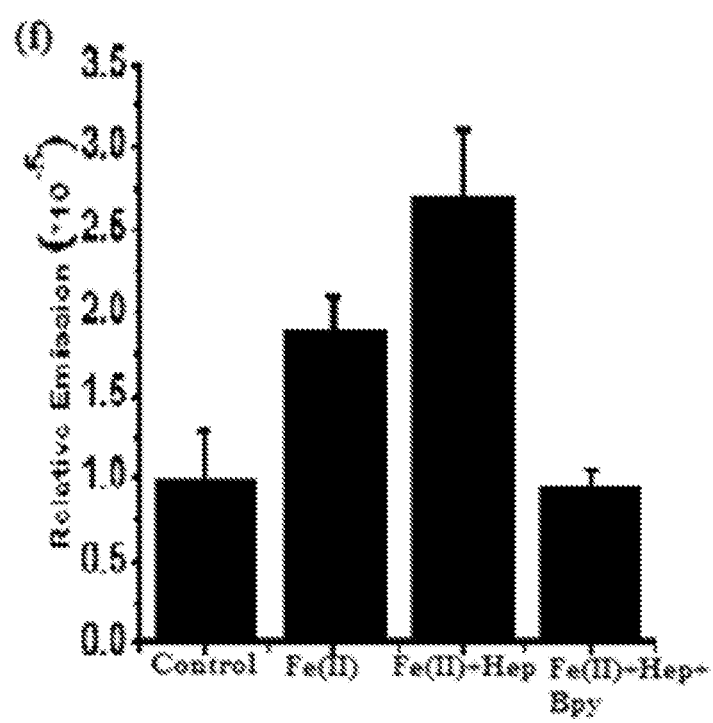
FIG. 65F is a bar chart of the relative intensities of FIGS. 65A, B, C, D, and E.

Example 31. Imaging Labile Iron Pools in Hepcidin-Stimulated Caco-2 Cells with NIRh-Fret The ability of NIRh-Fret to monitor the changes in cellular labile $Fe^{2+}$ stores triggered by hepcidin stimulation, a key iron regulatory hormone produced by the liver which controls iron homeostasis was studied (C. H. Park, et al., J. Biol. Chem., 2001, 276, 7806; G. Nicolas, et al, Blood Cells Mol. Dis., 2002, 29, 327; and T. Ganz, Blood, 2003, 102, 783). Live Caco-2 cells incubated with 10 μM NIRh-Fret showed weak fluorescence (FIG. 65B). For $Fe^{2+}$ replete conditions, live Caco-2 cells were incubated with 100 μM of ferrous ammonium sulfate (Fe $(NH_4)_2(SO_4)_2$) at 37° C. for 6 h followed by washing with DMEM medium to remove excess $Fe^{2+}$ and then 10 μM of NIRh-Fret was added to the culture media and was incubated at 37° C. for 30 min. For hepcidin stimulated condition, Cells was treated first with 100 μM of ferrous ammonium sulfate (Fe $(NH_4)_2(SO_4)_2$) for 1 h, followed by addition of 0.5 μM hepcidin and then incubated for another 5 h. The hepcidin-treated, iron supplemented Caco-2 cells showed significant increase in fluorescent signals (FIG. 65C) w.r.t the Caco-2 cells with $Fe^{2+}$ supplementation only (FIG. 65B), suggesting a positive response of NIRh-Fret to increased labile $Fe^{2+}$ levels in hepcidin-treated cells. For $Fe^{2+}$-depleting conditions, Caco-2 cells were treated with (Fe $(NH_4)_2(SO_4)_2$) and hepcidin for 6 and 5 h, respectively followed by a 40 min treatment with 1 mM of 2,2-bipyridyl (Bpy) showed decrease in fluorescence signal and it is weaker than that of Caco-2 cells with $Fe^{2+}$ supplementation only (FIG. 65E); suggesting fluorescence increase detected by NIRh-Fret was due to increase in labile iron level.

Example 31. Kinetics of $Fe^{2+}$ Transport in Caco-2 Cells

To explore the possibility of NIRh-Fret sensor to trace the $Fe^{2+}$ transport process in cells, a few kinetic experiments using Caco-2 cells were performed. Caco-2 cells were incubated with ferrous ammonium sulfate (Fe $(NH_4)_2$ $(SO_4)_2$) (100 μM) at different incubation time (2 h, 6 h, 8 h and 18 h) followed by addition of NIRh-Fret (10 μM), MitoTracker Green FM (100 nM) and LysoTracker Red DND-100 (50 nM) to detect the subcellular locations of $Fe^{2+}$. Briefly, in a typical experiment (for example, for 2 h); Caco-2 cells were incubated with 100 μM $Fe(NH_4)_2(SO_4)_2$ for 1.5 h and then excess $Fe(NH_4)_2(SO_4)_2$ was removed by changing to fresh DMEM medium and cells were further incubated with NIRh-Fret, Mito Tracker, and Lyso Tracker for another 30 min followed by washing with fresh DMEM medium to remove extracellular dyes. Then cells were imaged by a confocal microscopy immediately.

Figure 66:
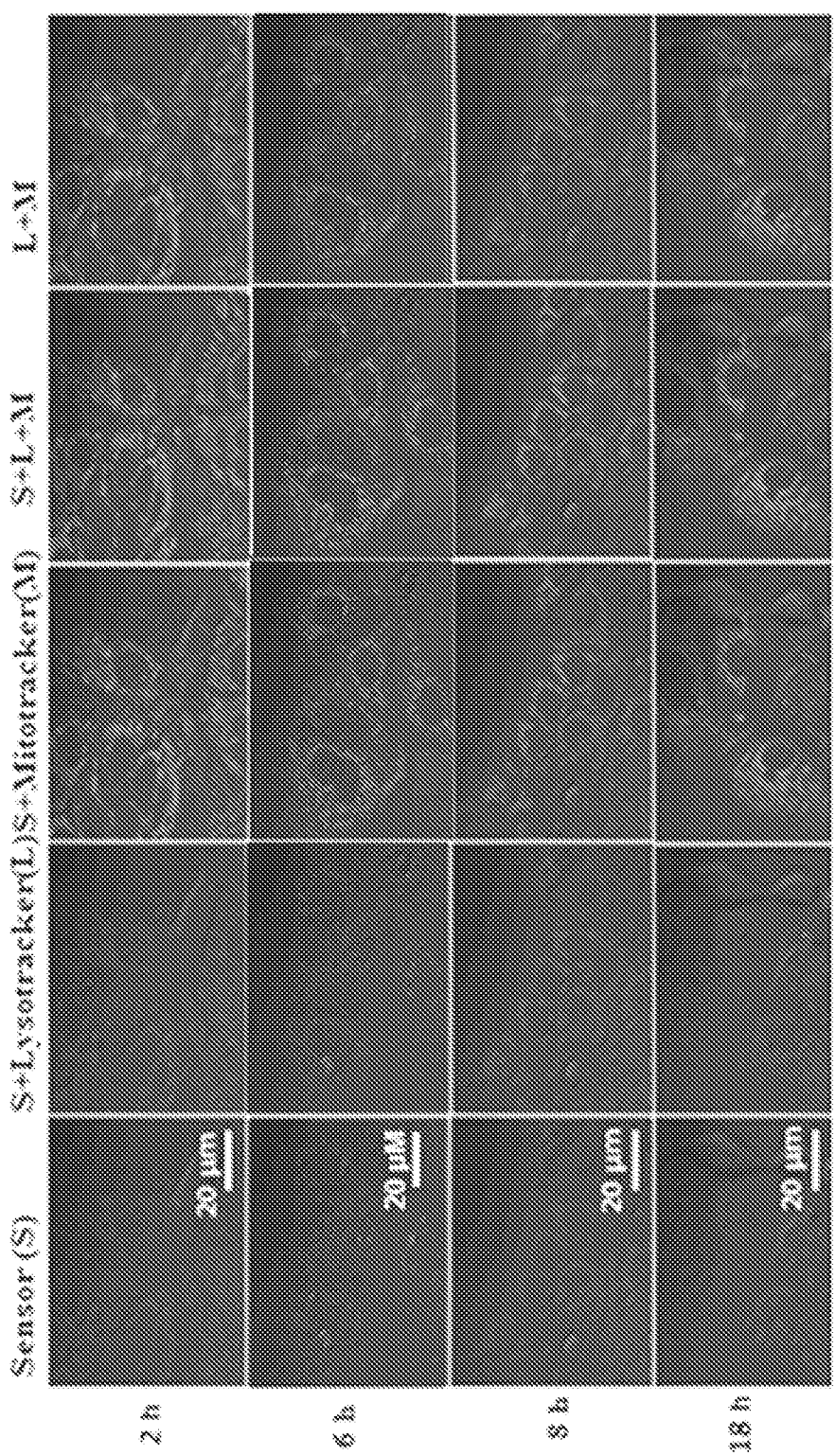
FIG. 66 shows images of the subcellular kinetic experiments for NIRh-Fret-$Fe^{2+}$ in caco-2 cells performed by incubation the cells with Fe2+.

The results from the kinetic experiment were represented in FIG. 66 in five columns: signals from the NIRh-Fret sensor (1st column), sensor and lysotracker (2nd column), sensor and mitotracker (3rd column), sensor and both trackers (4th column), mito- and lyso-trackers (5th column).

Figure 67:
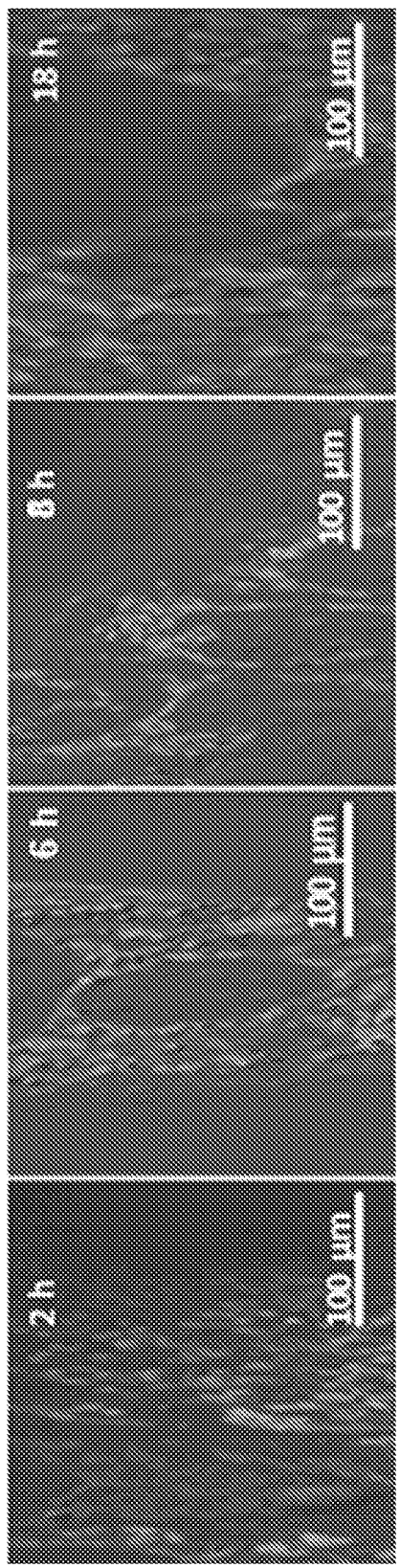
FIG. 67 represents magnified portion of 4th column of FIG. 66.

The multichannel confocal capability allowed us to monitor several colors simultaneously in cells and the color changing at different time was shown in FIG. 67, which represents magnified portion of 4th column of FIG. 66 to better understand the docking process. Separate red, blue, purple, green colored dots are visible in the images at 2 h. At 6 h, much of the red, purple-colored dots (endo/lyso) were merged together with green/yellow-colored dots (mito), while blue colored lysosomes were separated, suggesting that the Fe-loaded lysosomes were docked with mitochondria. Red colored dots belong to the regions where free $Fe^{2+}$ ions are located. Images shown in green colors belong to mito-tracker and yellow (red+green) indicates that free $Fe^{2+}$ ions are in mitochondria. Blue colors imply lyso-tracker and purple indicates that free $Fe^{2+}$ ions are in lysosomes.

At 2 hr incubation with $Fe^{2+}$, when images from all channels were merged (the 4th column), it can be seen that several spots like red, blue, some part purple and green and very trace amount of yellow spots are in the image (FIG. 67). The red colored dots in FIG. 66 and FIG. 67 are likely to be the freshly formed early endosomes containing $Fe^{2+}$—after the internalization of $Fe^{2+}$ in Caco-2 cells. When the ATP-dependent proton pumps on endosomal membrane lower the lumen pH of the endosomes (J. V. Renswoude, et al., Proc. Natl. Acad. Sci. (USA), 1982, 79, 6186; A. Dautry-Varsat, et al., Proc. Natl. Acad. Sci. (USA), 1983, 80, 2258; S. Paterson, et al., J. Cell. Physio., 1984, 120, 225; and D. J. Yamashiro, et al., Cell, 1984, 37, 789), endosomes gradually mature into lysosomes and are stained into blue by the LysoTracker. Purple color (red+blue=purple) indicates free $Fe^{2+}$ ions are in lysosomes. Green color implies the free $Fe^{2+}$ ions are still not loaded into mitochondria at this stage.

Figure 68:
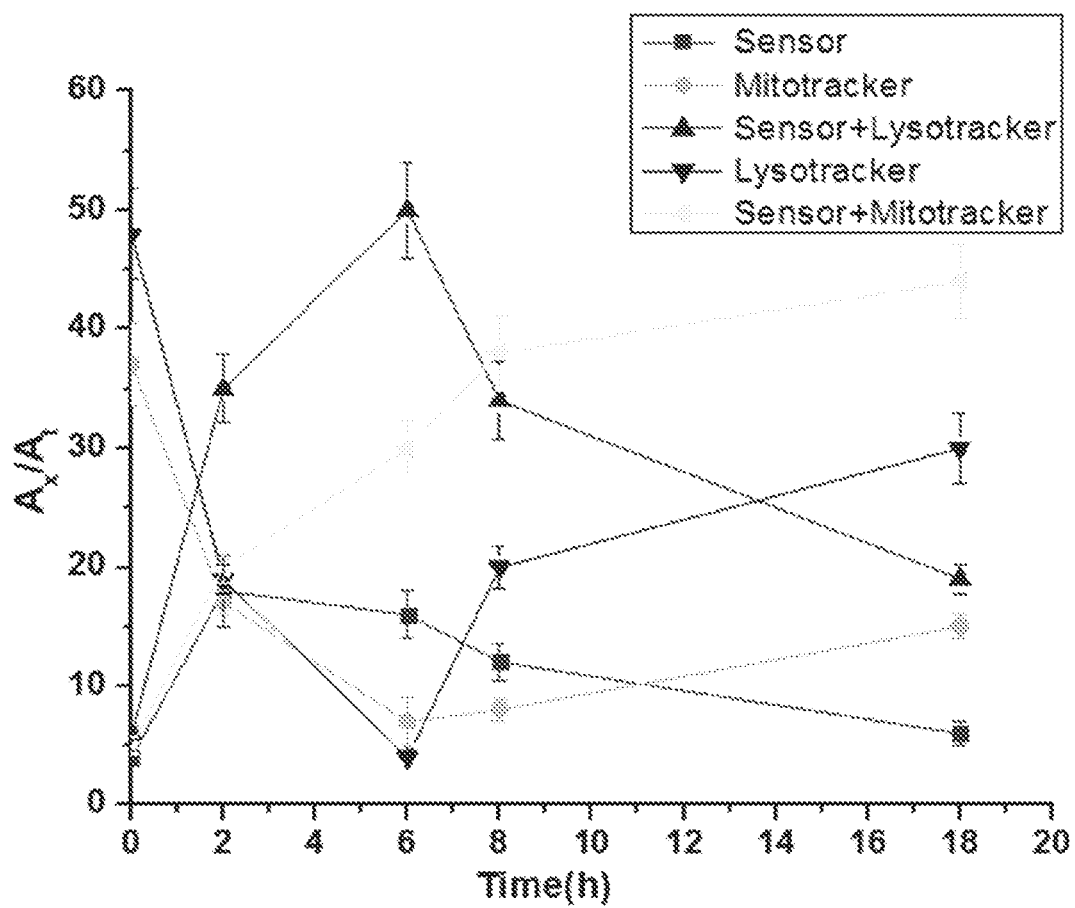
FIG. 68 is a graph showing color areas changing at different time in FIG. 66.

At 6 hr incubation with $Fe^{2+}$, the number of red-colored dots ($Fe^{2+}$-containing early endosomes) as well as green colored mitochondria significantly decreased ($4^{th}$ column in FIG. 66, FIG. 67 and the red line in FIG. 68) and were almost invisible in the image. Meanwhile, blue-colored lysosomes decreased in number, but purple-colored lysosomes ($Fe^{2+}$-loaded) ($2^{nd}$ column in FIG. 66 and the purple line in FIG. 68) and yellow-colored mitochondria dominated the images (3rd and 4th columns in FIG. 66 and the yellow line in FIG. 68). Moreover, at 6 hrs, the images (FIG. 66 and FIG. 67) of much of the mitochondria and lysosomes were not distinguishable: almost all mitochondria showed a unified green-yellowish-purple (column 4) or greenish-blue (column 5) colors, indicating mitochondria and the Fe-loaded lysosomes were docked at this stage. There were a small number of blue-colored lysosomes still visible (column 4) in the cells, suggesting that the Fe-free lysosomes were not docked with mitochondria. FIG. 68 is a graph showing color areas changing at different time in FIG. 66 (area of the all color dots were measured and assumed that the total area is 100%, then each color area was calculated as a percentage (Ax/At). Red-color indicates $Fe^{2+}$ in early endosomes; yellow-color indicates $Fe^{2+}$ in mitochondria; purple-color indicates $Fe^{2+}$ in lysosomes; green color indicates mitochondria without $Fe^{2+}$-loading; blue-color indicates lysosomes without $Fe^{2+}$-loading).

At 8 hr, purple-colored lysosomes ($Fe^{2+}$-loaded) ($2^{nd}$ column in FIG. 66 and the purple line in FIG. 68), and yellow-colored mitochondria dominated the images (3rd and 4th columns in FIG. 66 and the yellow line in FIG. 68), but more distinct blue-colored lysosomes were observed (FIG. 67), indicating mitochondria and lysosomes were getting separated (~10% separation).

At 18 hr, yellowish-green-colored mitochondria clearly dominated over blue or purple-colored lysosomes. The images of lysosomes and mitochondria became re-distinguishable (FIG. 67), showing separate yellowish-green and blue colors (column 4) or green and blue (column 5) colors, suggesting more separation of mitochondria and lysosomes than those at 8 hrs. $Fe^{2+}$ was mostly in mitochondria, and the lysosomes had dropped off the $Fe^{2+}$, indicating $Fe^{2+}$ was transferred from lysosomes into mitochondria and the Mito-Lyso docking occurs only when $Fe^{2+}$ is being transferred between these two organelles. No significant level of free $Fe^{2+}$ was detected in cytosol in the whole $Fe^{2+}$ trafficking process as monitored by the sensor. At 24 hrs (data not shown), green-colored mitochondria and blue-colored lysosomes dominated the images, presumably due to that the free $Fe^{2+}$ ions have been utilized (e.g., incorporated into Fe-containing proteins) by the normal cellular metabolism.

Figure 69:
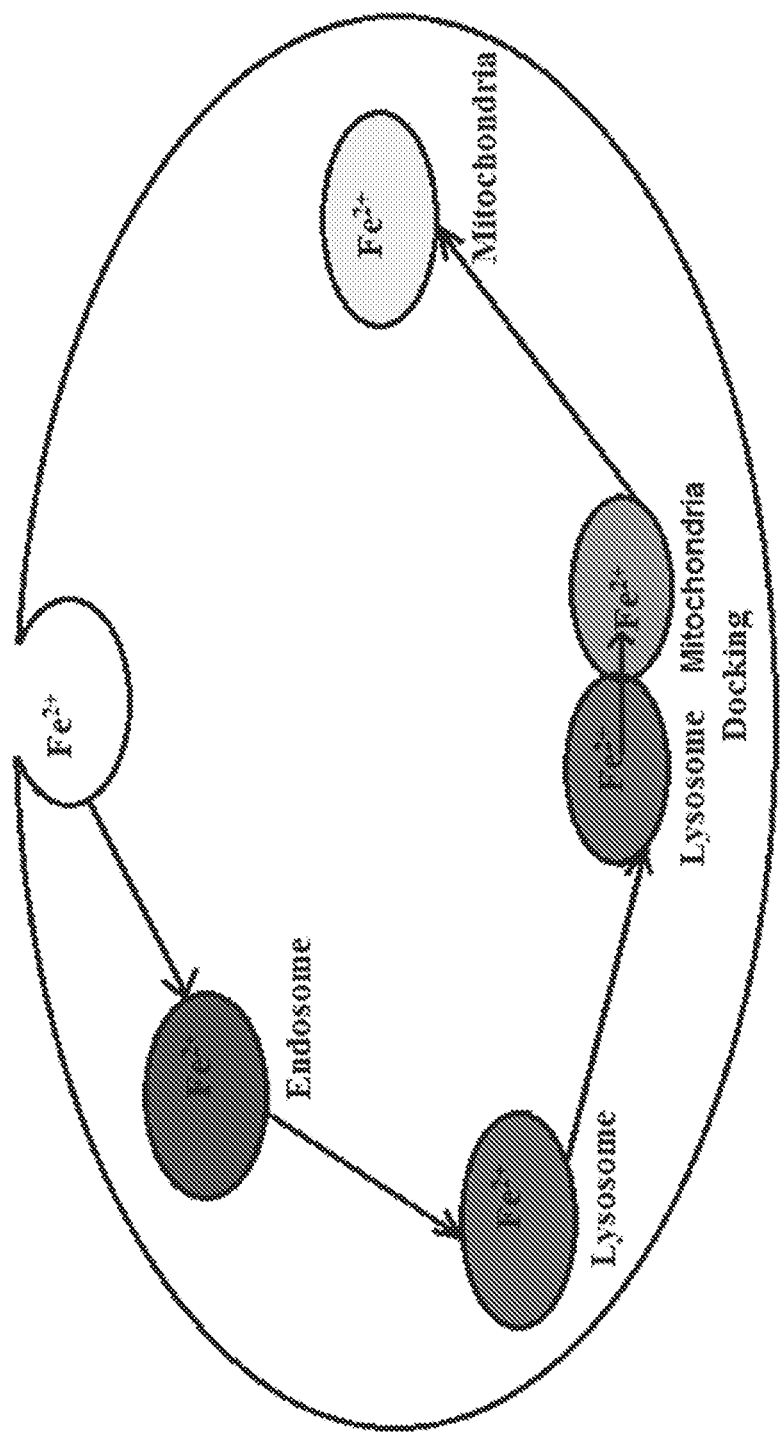
FIG. 69 shows a hypothetical schematic of one possible cellular distribution process of free $Fe^{2+}$ in Caco-2 cells.

The pictures of the kinetic process traced by the imaging of the iron sensors and the other organelle trackers suggest that after the intake of $Fe^{2+}$ by endocytosis, transport pathway starts from endosomes to lysosomes and then $Fe^{2+}$ was transferred from endo/lysosomes into mitochondria through a Mito-Endo/Lyso docking mechanism, bypassing the cytosol as shown in the cartoon in FIG. 69. This may be one of the efficient routes (like "high way") for iron transport in cells. The detailed mechanism for the $Fe^{2+}$ transfer during the lysosome-mitochondria docking process needs further investigation but is beyond the scope of this thesis research.

Example 32. Determination of Labile $Fe^{2+}$ Concentration in Cells

Figure 70A:
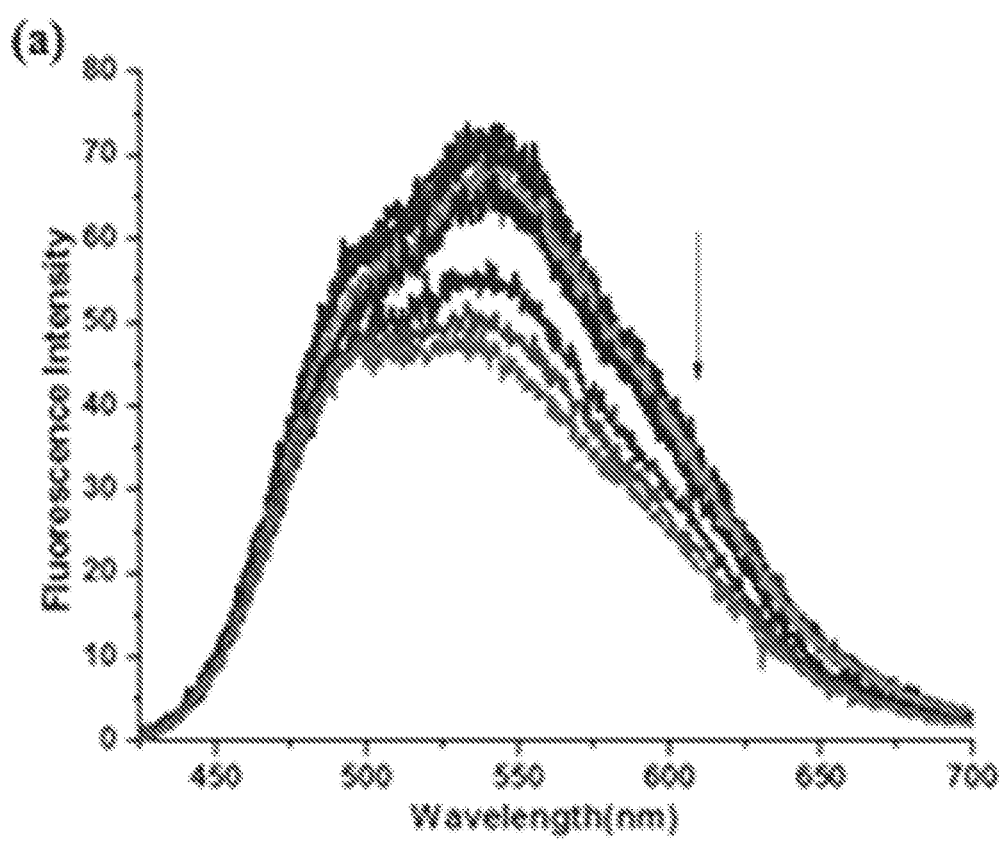
FIG. 70A shows fluorescence spectra of 20 μM NIRh-Fret to increasing concentration of $Fe^{2+}$ (λEx 405 nm).
Figure 70B:
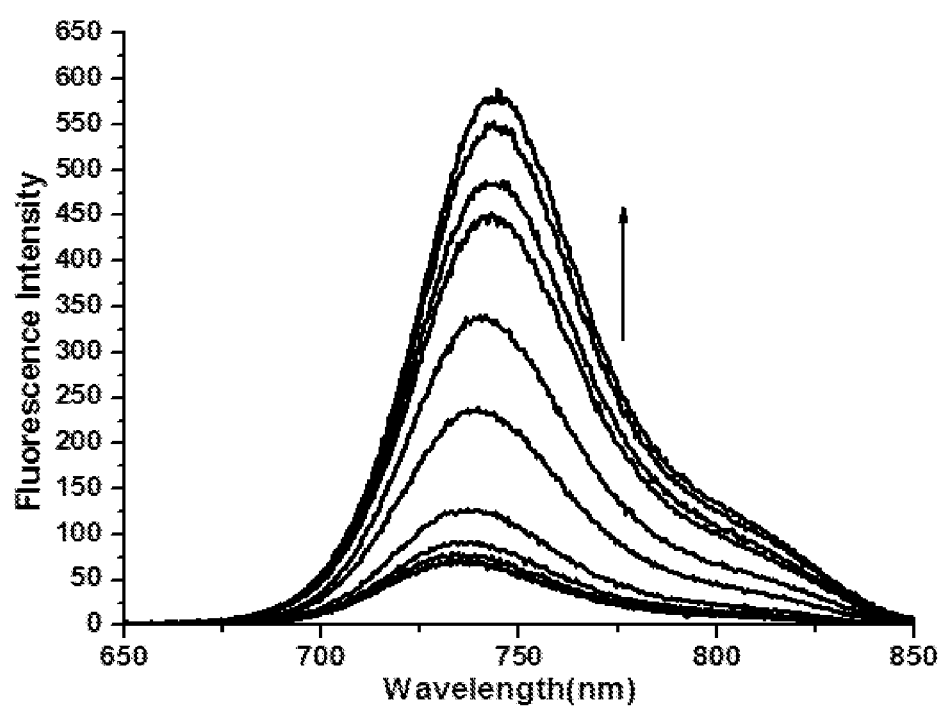
FIG. 70B shows fluorescence spectra of 20 μM NIRh-Fret to increasing concentration of $Fe^{2+}$ ($\lambda_{Ex}$ 633 nm) (0, 1, 3, 5, 7, 9, 11, 13, 15, 17, 20 μM, from bottom to top) in H2O/THF (pH 7.3, v/v 1:1).

To determine the concentration of labile $Fe^{2+}$, the ratiometric $Fe^{2+}$ sensor, NIRh-Fret, has been developed. The two-bands absorption/fluorescence nature of the ratiometric sensor enables the tracing of the cellular distribution of the sensor itself as well as detecting the labile $Fe^{2+}$ pools. When $Fe^{2+}$ was added to NIRh-Fret solution, a decrease in intensity at 540 nm of the fluorescence and an increase in intensity at 735 nm were observed (FIGS. 70A-B).

Figure 71:
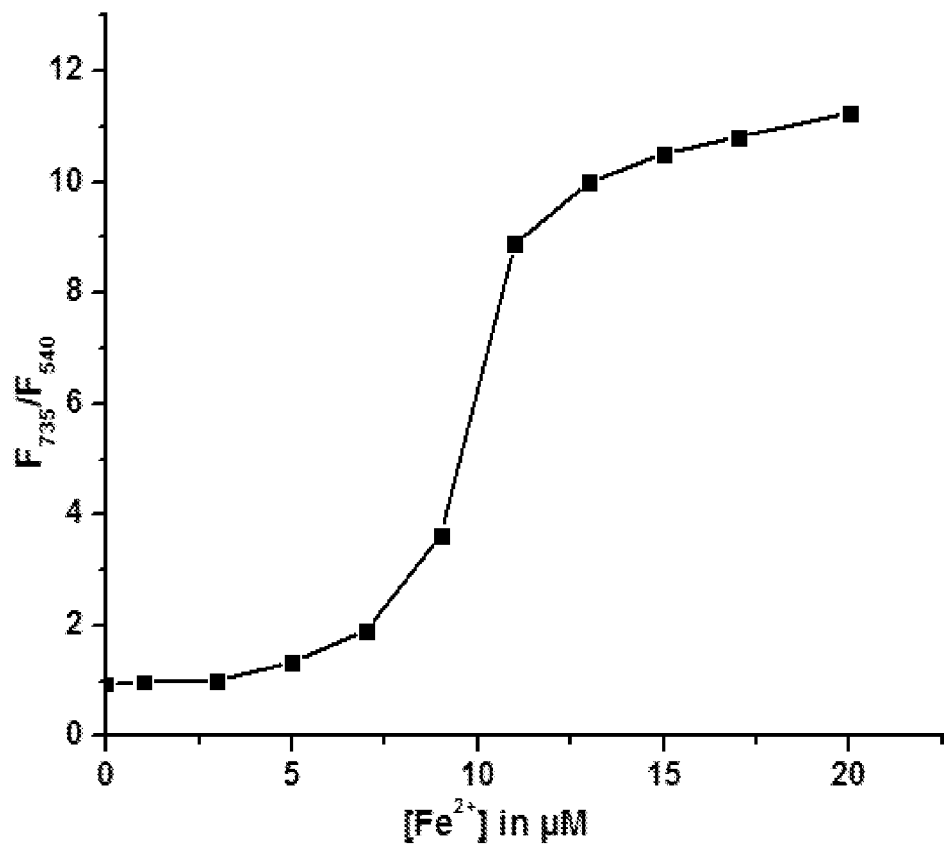
FIG. 71 shows a plot of the ratio of fluorescence intensities at 735 nm to 540 nm versus [$Fe^{2+}$].

To determine the cellular concentration of $Fe^{2+}$, an in-vitro calibration curve was obtained by titrating the sensor, NIRh-Fret (20 μM), with different concentrations of $Fe^{2+}$ and a calibration curve was obtained by plotting [$Fe^{2+}$] versus fluorescent ratio ($F_{735}/F_{540}$) (FIG. 71). Ratiometric imaging was performed with 2 different cell lines, HT29 cells and WS1 cells and with iron replete and depleting conditions. The images (FIGS. 72A-L and FIGS. 73A-L) clearly show that the fluorescent signals of the sensor itself (yellow images) are evenly distributed in the cells except the nucleus, revealing the true location of the sensor in the cells. However, the $Fe^{2+}$ images (red images) displayed discrete images, confirming that the labile $Fe^{2+}$ in cells are localized in certain subcellular compartments (organelles). Moreover, the ratiometric images clearly show 2 distinct colors (one purple and one cyan) of the organelles and they change in color under iron replete and depleting conditions, suggesting that the two organelles (i.e., lysosomes and mitochondria) have different free $Fe^{2+}$ concentrations and both respond to iron replete and depleting conditions.

Fitting the ratiometric imaging data to the calibration curve gives $Fe^{2+}$ concentration for the first time in ws1 cells, with a value of ~8±1 μM determined in the mitochondria of untreated cells, 12±1 μM in the mitochondria of Fe (II) treated cells, and 5±1 μM in the mitochondria of the Fe(II)-chelator Bpy treated cells, 71 μM determined in the lysosomes of untreated cells, 10±1 μM in the lysosomes of Fe (II) treated cells, and 5±1 μM in the lysosomes of Bpy treated cells. Cytosol $Fe^{2+}$ levels are low which were not readily observed by the imaging pictures. However, the ratios of the two channels are significantly higher than those of the backgrounds and the ratios respond well with iron depleting and replete conditions. By fitting the ratios to the calibration curve, $Fe^{2+}$ concentration was determined to be below 1 μM in the cytosol of untreated cells, 3-4 μM in the cytosol of Fe (II) treated cells, and 0 μM in the cytosol of Bpy treated cells. Also $Fe^{2+}$ concentrations in HT-29 cells determined to be ~11±1 μM in the mitochondria of untreated cells, 15±1 μM in mitochondria of Fe (II)-treated cells, and 9±1 μM in mitochondria of Bpy-treated cells and 9±1 μM determined in the lysosomes of untreated cells, 13±1 μM in the lysosomes of Fe (II) treated cells, and 6±1 μM in the lysosomes of Bpy treated cells, below 1 μM determined in the cytosol of untreated cells, 4-5 μM in the cytosol of Fe (II) treated cells, and 0 μM in the cytosol of Bpy treated cells and the results are summarized in Table 2.

TABLE 2

| | Free $Fe^{2+}$ concentration in the mitochondria, lysosome and cytosol of ws1 and HT-29 cells | | | | | | | | |
|---|---|---|---|---|---|---|---|---|---|
| | Fe(II) concentration in mitochondria | | | Fe(II) concentration in lysosome | | | Fe(II) concentration in cytosol | | |
| Cell type | Untreated cells | Fe(II) treated cells | Bpy treated cells | Untreated cells | Fe(II) treated cells | Bpy treated cells | Untreated cells | Fe(II) treated cells | Bpy treated cells |
| ws1 | 8 ± 1 μM | 12 ± 1 μM | 5 ± 1 μM | 7 ± 1 μM | 10 ± 1 μM | 5 ± 1 μM | Below 1 μM | 3-4 μM | 0 μM |
| HT-29 | 11 ± 1 μM | 15 ± 1 μM | 9 ± 1 μM | 9 ± 1 μM | 13 ± 1 μM | 6 ± 1 μM | Below 1 μM | 4-5 μM | 0 μM |

What is claimed is:

1. A compound of Formula III:

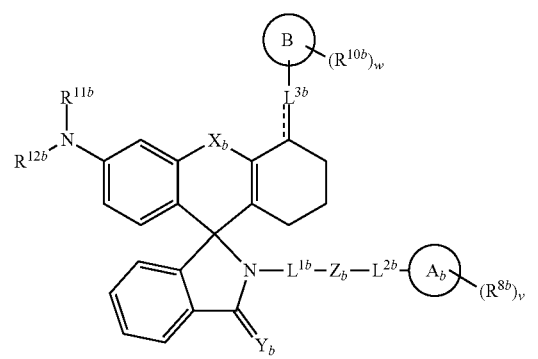

III or a salt thereof, wherein

═════ is a single or double bond;

$X_b$ is O;

$Y_b$ is O;

$L^{1b}$ is a bond;

$L^{3b}$ is $(CR^z)_u$;

u is 2;

$L^{2b}$ is $(CH)_3$;

$Z_b$ is N;

ring B is selected from $C_{6-10}$ aryl and 5-10 membered heteroaryl;

ring $A_b$ is selected from $C_{6-10}$ aryl and 5-10 membered heteroaryl;

each $R^z$ is independently selected from H and $C_{1-6}$ alkyl;

each $R^{8b}$ is independently $NR^{c1}R^{d1}$;

each $R^{10b}$ is independently $C_{1-6}$ alkyl;

$R^{11b}$ and $R^{12b}$ are each $C_{1-6}$ alkyl;

$R^{c1}$ and $R^{d1}$ are each independently selected from $C_{1-6}$ alkyl;

v is 1, 2, or 3; and w is 1, 2, or 3.

2. The compound of claim 1, wherein ring $A_b$ is $C_{6-10}$ aryl.

3. The compound of claim 1, wherein the compound is
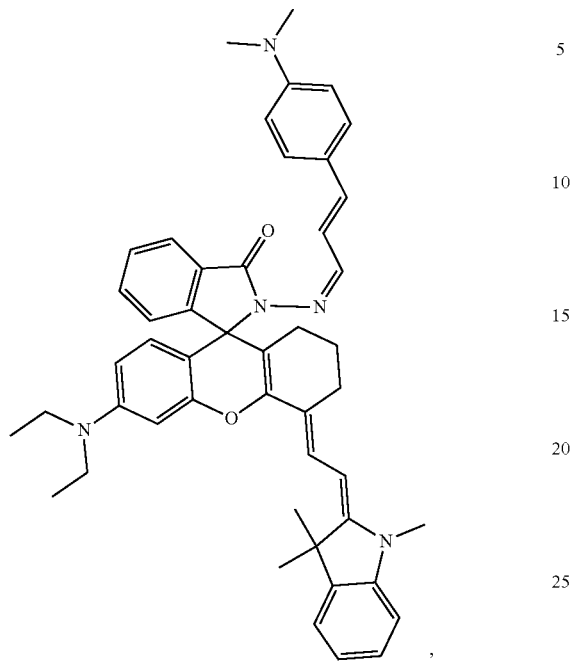
or a salt thereof.